US012403186B2

(12) United States Patent
Borriello

(10) Patent No.: US 12,403,186 B2
(45) Date of Patent: *Sep. 2, 2025

(54) ALLOGENEIC TUMOR CELL VACCINE

(71) Applicant: ALLOPLEX BIOTHERAPEUTICS, INC., Woburn, MA (US)

(72) Inventor: Frank Borriello, Winchester, MA (US)

(73) Assignee: Alloplex Biotherapeutics, Inc., Woburn, MA (US)

(*) Notice: Subject to any disclaimer, the term of this patent is extended or adjusted under 35 U.S.C. 154(b) by 384 days.

This patent is subject to a terminal disclaimer.

(21) Appl. No.: 17/233,124

(22) Filed: Apr. 16, 2021

(65) Prior Publication Data

US 2021/0236610 A1 Aug. 5, 2021

Related U.S. Application Data

(62) Division of application No. 15/821,105, filed on Nov. 22, 2017, now Pat. No. 11,058,752.

(60) Provisional application No. 62/425,424, filed on Nov. 22, 2016.

(51) Int. Cl.
A61K 39/00 (2006.01)
A61P 35/00 (2006.01)
C07K 14/525 (2006.01)
C07K 14/535 (2006.01)
C07K 16/44 (2006.01)
C12N 5/09 (2010.01)

(52) U.S. Cl.
CPC .. *A61K 39/0011* (2013.01); *A61K 39/001129* (2018.08); *A61K 39/001138* (2018.08); *A61K 39/001139* (2018.08); *A61P 35/00* (2018.01); *C07K 14/525* (2013.01); *C07K 14/535* (2013.01); *C07K 16/44* (2013.01); *C12N 5/0693* (2013.01); *A61K 2039/5152* (2013.01); *A61K 2039/5156* (2013.01); *C07K 2317/524* (2013.01); *C07K 2317/53* (2013.01); *C07K 2317/56* (2013.01); *C07K 2317/622* (2013.01); *C07K 2317/72* (2013.01); *C12N 2501/25* (2013.01); *C12N 2501/52* (2013.01)

(58) Field of Classification Search
CPC .................................................. C12N 5/0693
USPC ....................................................... 424/185.1
See application file for complete search history.

(56) References Cited

U.S. PATENT DOCUMENTS

| 5,882,654 | A | 3/1999 | Morton |
| 10,731,128 | B2 | 8/2020 | Borriello |
| 11,058,752 | B2* | 7/2021 | Borriello ............... A61P 35/00 |
| 11,185,586 | B2 | 11/2021 | Borriello |
| 2002/0006413 | A1 | 1/2002 | Sobol et al. |
| 2003/0100074 | A1 | 5/2003 | Yu et al. |
| 2007/0243159 | A1 | 10/2007 | Selvaraj |
| 2009/0162404 | A1 | 6/2009 | Podack |
| 2010/0150950 | A1 | 6/2010 | Coccia et al. |
| 2010/0297189 | A1 | 11/2010 | Dobric et al. |
| 2011/0014162 | A1 | 1/2011 | Lowdell |
| 2011/0039916 | A1 | 2/2011 | Federoff et al. |
| 2013/0071403 | A1 | 3/2013 | Rolland et al. |
| 2018/0126014 | A1 | 5/2018 | Zhou et al. |
| 2018/0185463 | A1 | 7/2018 | Borriello |
| 2018/0267024 | A1 | 9/2018 | Deml et al. |
| 2019/0038671 | A1 | 2/2019 | Fan et al. |
| 2020/0102538 | A1 | 4/2020 | Borriello |
| 2020/0123566 | A1* | 4/2020 | Canton ............. C07K 14/4748 |
| 2020/0330596 | A1 | 10/2020 | Borriello |
| 2022/0040328 | A1* | 2/2022 | Canton ................ C07K 14/475 |
| 2022/0096631 | A1* | 3/2022 | Borriello ............ A61K 31/7088 |

FOREIGN PATENT DOCUMENTS

| JP | H07502987 A | 3/1995 |
| JP | 2001517206 A | 10/2001 |
| JP | 2011-5011772 A | 4/2011 |
| JP | 2011511772 A | 4/2011 |
| WO | 9928349 A2 | 6/1999 |
| WO | WO 0109303 * | 2/2001 |
| WO | 03045428 A2 | 6/2003 |
| WO | 2009/095261 A2 | 8/2009 |
| WO | 2011004201 A1 | 1/2011 |
| WO | 2018/098279 A1 | 5/2018 |
| WO | 2018098279 A9 | 7/2018 |
| WO | 2021251975 A1 * | 12/2021 |

OTHER PUBLICATIONS

Varghese et al (Cancer Immunology, Immunotherapy (2022) 71:2943-2955).*

(Continued)

Primary Examiner — Lynn A Bristol
(74) Attorney, Agent, or Firm — Bochner PLLC; Beverly W. Lubit

(57) ABSTRACT

The described invention provides a tumor cell vaccine comprising genetically modified tumor cell line of a particular tumor type that stably expresses high levels of two or more immunomodulators. According to some embodiments, an immunogenic amount of the tumor cell line variants may be selected for concomitant expression of two or more of recombinant membrane expressed IgG1, CD40L, TNF-alpha, as well as membrane and soluble forms of GM-CSF, and Flt-3L peptides that are effective to elicit an anti-tumor immune response compared to the parent unmodified tumor cell line as measured in vitro by a one-way mixed lymphocyte tumor reaction assay using human peripheral blood mononuclear cells and the genetically modified allogeneic cell vaccine candidate. According to some embodiments, the tumor cell vaccine candidate will induce an immune response in the recipient cancer patient that cross reacts with the patient's own (autologous) tumor cells, the effects of which will be sufficient to result in enhanced anti-tumor immunity contributing to the increased survival of a vaccinated patient cohort compared to a matched unvaccinated patient cohort.

5 Claims, 45 Drawing Sheets
Specification includes a Sequence Listing.

(56) References Cited

OTHER PUBLICATIONS

Jiang et al (Adv Drug Deliv Rev Jan. 2022; 180:114046 doi: 10.1016/j.addr.2021.114046. Epub Nov. 9, 2021).*
Accolla et al (J Neuroimmune Pharmacol Mar. 2013;8(1):28-36. doi: 10.1007/s11481-012-9423-7. Epub Dec. 7, 2012).*
Liu et al. Journal of Hematology & Oncology (2022) 15:28.*
Tresker (Studies in History and Philosophy of Science Part C: Studies in History and Philosophy of Biological and Biomedical Sciences vol. 82, Aug. 2020 101249).*
Tresker (Studies in History and Philosophy of Science Part C: Studies in History and Philosophy of Biological and Biomedical Sciences vol. 83, Oct. 2020, 101291).*
ClinicalTrials.gov Identifier: NCT05237206 ("Study of Suplexa in Patients With Metastatic Solid Tumours and Haematologic Malignancies"; First Posted: Feb. 14, 2022; Sponser: Alloplex Biotherapeutics Inc).*
U.S. Appl. No. 16/899,318, filed Jun. 11, 2020, US-2020-0330596-A1, Published.
O'Hare, K., et al., Transformation of mouse fibroblasts to methotrexate resistance by a recombinant plasmid expressing a prokaryotic dihydrofolate reductase. Proc Natl Acad Sci USA 1981, 78:1527.
Oliver, K.G., et al. Multiplexed Analysis of Human Cytokines by Use of the FlowMetrix System. Clin Chem 1998;44(9):2057-2060.
Ornitz, D.M., et al., Elastase I Promoter Directs Expression of Human Growth Hormone and SV40 T Antigen Genes to Pancreatic Acinar Cells in Transgenic Mice. Cold Spring Harbor Symp Quant Biol 1986, 50:399-409.
Palucka K. et al., Cancer immunotherapy via dendritic cells. Nature Reviews Cancer (Apr. 2012) 12: 265-276.
Panicali. D., et al., Construction of poxviruses as cloning vectors: Insertion of the thymidine kinase gene from herpes simplex virus into the DNA of infectious vaccinia virus. Proc Natl Acad Sci USA 1982, 79:4927-4931.
Pardoll, D., The blockade of immune checkpoints in cancer immunotherapy, Nature Reviews: Cancer, vol. 12, Apr. 2012, 253.
PCT/US2017/063016 International Search Report and Written Opinion, Apr. 30, 2018, 13 pgs.
Pearson, W. R., et al, "Improved tools for biological sequence comparison", (1988), Proc. Natl. Acad. Sci. 85:2444-2448.
Pinkert, C.A., et al. An albumin enhancer located 10 kb upstream functions along with its promoter to direct efficient, liver-specific expression in transgenic mice. Genes Devel, 1987, 1:268-276.
Plasterk, R.H.A., et al., Resident Aliens. The Tc1/mariner superfamily of transposable elements. TIG 15:326-332, 1999.
Qian, F., et al. Pivotal Role of Mitogen-Activated Protein Kinase-Activated Protein Kinase 2 in Inflammatory Pulmonary Diseases. Curr Protein Pept Sci. 2016 ; 17(4): 332-342.
Rabinovitch A. et al. Roles of cytokines in the pathogenesis and therapy of type 1 diabetes. Cell Biochem Biophys, vol. 48(2-3): 159-63, (2007).
Raker, V. K. et al. Tolerogenic Dendritic Cells for Regulatory T Cell Induction in Man. Front Immunol, vol. 6(569): 1-11, (2015).
Readhead, C., et al., Expression of a myelin basic protein gene in transgenic shiverer mice: Correction of the dysmyelinating phenotype, Cell 1987, 48:703-712.
Rieger, R., et al., Chimeric form of tumor necrosis factor-alpha has enhanced surface expression and antitumor activity, Cancer Gene Therapy, 2009, 16, 53-64.
Rossi, D. et al. The biology of chemokines and their receptors. Annu Rev Immunol,, vol. 18: 217-242, (2000).
Rossowska, J., et al. Temporary elimination of IL-10 enhanced the effectiveness of cyclophosphamide and BMDC-based therapy by decrease of the suppressor activity of MDSCs and activation of antitumour immune response. Immunobiology 220 (2015) 389-398.
Sadowski, J., Site-Specific Recombinases: Changing Partners and Doing the Twist. Bacteriol., 165:341-357, 1986.
Saenger, Y.M., et al. Immunomodulatory Molecules of the Immune System, H.L. Kaufman and J.D. Wolchok (eds.) General Principles of Tumor Immunotherapy, Chapter 5, 67-121.
Salmons, B., et al. Targeting of Retroviral Vectors for Gene Therapy. Human Gene Ther 1993, 4:129-141.
Santerre, R.F., et al., Expression of prokaryotic genes for hygromycin B and G418 resistance as dominant-selection markers in mouse L cells. Gene 1984, 30:147.
Schrum S. et al. Synthesis of the CC-chemokines MIP-1alpha, MIP-1beta, and RANTES is associated with a type 1 Immune response. J Immunol, vol. 157: 3598-3604, (1996).
Schwartz, R. H., "T cell anergy", Annu. Rev. Immunol., vol. 21: 305-334 (2003).
Shani, M., Tissue-specific expression of rat myosin light-chain 2 gene in transgenic mice, Nature 1985, 314:283-286.
Shi Y et al., Granulocyte-macrophage colony-stimulating factor (GM-CSF) and T-cell responses: what we do and don't know, Cell Research (2006) 16: 126-133.
Shirota, H., et al. CpG-conjugated apoptotic tumor cells elicit potent tumor-specific immunity, Cancer Immunol Immunother (2011) 60:659-669.
Shortman, K., et al., Steady-state and inflammatory dendritic-cell development, Nature Reviews Immunology, vol. 7. 19-30 (2007).
Smith and Waterman, Comparison of Biosequences. Adv. Appl. Math. 2:482 (1981).
Spickofsky, N., et al., Procedures for constructing cDNA expression libraries in Epstein-Barr virus shuttle vectors capable of stable episomal replication. DNA Prot Eng Tech 1990, 2:14-18.
Sprent J. et al. The thymus and central tolerance. Philos Trans R Soc Lond B Biol Sci, vol. 356(1409): 609-616, (2001).
Stahl, P. H. et al. "Handbook of Pharmaceutical Salts: Properties, Selection, and Use" (Wiley VCH, Zurich, Switzerland: 2002).
Studier, F.W. et al., Use of T7 RNA polymerase to direct expression of cloned genes. Methods Enzymol 1990, 185:60-89.
Swift, G. H., et al., Tissue-specific expression of the rat pancreatic elastase I gene in transgenic mice. Cell 1984, 38:639-646.
Szybalska, E.H., et al., Genetics of Human Cell Lines, IV. DNA-Mediated Heritable Transformation of a Biochemical Trait. Proc Natl Acad Sci USA 1962, 48:2026.
Taams, L. S. et al., "Human anergic/suppressive CD4+CD25+ T cells: a highly differentiated and apoptosis-prone population", Eur. J. Immunol. vol. 31: 1122-1131 (2001).
Takahashi, H., et al., Induction of CD8+ cytotoxic T cells by immunization with purified HIV-1 envelope protein in ISCOMs. Nature 1990, 344:873-875.
Taub D.D. et al. Recombinant human interferon-inducible protein 10 is a chemoattractant for human monocytes and T lymphocytes and promotes T cell adhesion to endothelial cells . . . J Exp Med., vol. 177:1809-1814, (1993).
Taylor, I. C.A., et al., Factor Substitution in a Human HSP70 Gene Promoter: TATA-Dependent and TATA-Independent Interactions. Mol Cell Biol 1990, 10:165-75.
Ueno H, et al., Harnessing Human Dendritic Cell Subsets for Medicine. Immunol. Rev. (2010) 234: 199-212.
Underwood, K.W., et al., Catalytically Active MAP KAP Kinase 2 Structures in Complex with Staurosporine and ADP Reveal Differences with the Autoinhibited Enzyme. Structure, vol. 11, 627-636, Jun. 2003.
Van Doren, K., et al., Efficient Transformation of Human Fibroblasts by Adenovirus Simian Virus 40 Recombinants. Mol Cell Biol 1984, 4:1653-1656.
Van Kooten C et al., CD40-CD40 ligand. J. Leukoc Biol. Jan. 2000; 67(1): 2-17.
Vollmer, J., et al. Immunotherapeutic applications of CpG oligodeoxynucleotide TLR9 agonists. Advanced drug delivery reviews. 61 (3): 195-204.
Wagner, E., et al., Transferrin-polycation conjugates as carriers for DNA uptake into cells. Proc. Natl. Acad. Sci. USA 87, 3410-3414 (1990).
Wakkach, A., et al. Characterization of IL-10-Secreting T Cells Derived from Regulatory CD4+CD25+ Cells by the TIRC7 Surface Marker. The Journal of Immunology, 2008, 180: 6054-6063.
Warren, HS., et al., Future prospects for vaccine adjuvants. Critical Reviews in Immunology 1988, 8:83.
Whiteside, T. L., The tumor microenvironment and its role in promoting tumor growth, Oncogene (2008) 27, 5904-5912.

(56) References Cited

OTHER PUBLICATIONS

Wigler, M., et al., Transfer of purified herpes virus thymidine kinase gene to cultured mouse cells. Cell 1977, 11:223-232.
Wigler, M., et al., Transformation of mammalian cells with an amplifiable dominant acting gene. Proc Natl Acad Sci USA 1980, 77:3567.
Williams, K.J. et al., Correlation between the Induction of Heat Shock Protein 70 and Enhanced Viral Reactivation in Mammalian Cells Treated with Ultraviolet Light and Heat Shock. Cancer Res 1989, 49:2735-42.
U.S. Appl. No. 17/517,632, filed Nov. 2, 2021, Pending.
Japanese Office Action for Application No. 2019-547602, dated Nov. 10, 2021, 4 pages and partial translation.
Adams, J.M., et al. The c-myc oncogene driven by immunoglobulin enhancers induces lymphoid malignancy in transgenic mice. Nature 1985, 318:533-538.
Alexander, W., et al., Expression of the c-myc Oncogene under Control of an Immunoglobulin Enhancer in E[L-myc Transgenic Mice. Mol Cell Biol 1987, 7:1436-1444.
Alexandraki K. et al. Inflammatory Process in Type 2 Diabetes. The Role of Cytokines. Annals of the New York Academy of Sciences, 1084: 89-117, (2006).
Altschul, P., et al. Gapped BLAST and PSI-BLAST: a new generation of protein database search programs. Nucleic Acids Res. 25:3389-3402 (1997).
Battaglia, M. et al., "Rapamycin promotes expansion of functional CD4+CD25+Foxp3+ regulator T cells of both healthy subjects and type 1 diabetic patients", J. Immunol., vol. 177: 8338-8347, (2006).
Bendall, S.C., et al. Single-Cell Mass Cytometry of Differential Immune and Drug Responses Across a Human Hematopoietic Continuum. Science, vol. 332:687-696; May 6, 2011.
Bendall, S.C., et al., From single cells to deep phenotypes in cancer. Nature Biotechnology, vol. 30 No. 7:639-647; Jul. 2012.
Bestor, T.H., Transposons Reanimated in Mice. Cell, 122(3):322-325, 2005.
Bitter, G.A., et al., Expression and Secretion Vectors for Yeast. Meth Enzymol 1987, 153:516-544.
Bode, C., CpG DNA as a vaccine adjuvant, Expert Rev Vaccines. Apr. 2011; 10(4): 499-511).
Boesen, J.J.B., et al., Circumvention of chemotherapy-induced myelosuppression by transfer of themdr1 gene. Biotherapy 1994, 6:291-302.
Bonifant CL, et al., Toxicity and management in CAR T-cell therapy, Molecular Therapy—Oncolytics (2016) 3, 16011; doi:10.1038/mto.2016.11.
Bradley L.M. et al. Islet-Specific Th1, But Not Th2, Cells Secrete Multiple Chemokines and Promote Rapid Induction of Autoimmune Diabetes. J Immunol, vol. 162:2511-2520, (1999).
Broach, J.R., et al., Recombination within the yeast plasmid 2μ circle is site-specific. Cell, 29:227-234, 1982.
Browning, M., Antigen presenting cell/tumor cell fusion vaccines for cancer, Human Vaccines & Immunotherapeutics 9:7, 1545-1548; Jul. 2013;DOI: 10.4161/hv.24235.
Butterfield, L., Dendritic Cells in Cancer Immunotherapy Clinical Trials: Are We Making Progress?, Frontiers of Immunology, 2013 4: 454.
Cai, G., The CD160, BTLA, LIGHT/HVEM pathway: a bidirectional switch regulating T-cell activation, Immunol. Rev., May; 229(1):244-58 (2009).
Carbone E et al., A New Mechanism of NK Cell Cytotoxicity Activation: The CD40-CD40 Ligand Interaction. J Exp Med. Jun. 16, 1997; 185(12): 2053-60.
Carmi, Y, et al. Tumor-binding antibodies and tumor immunity. Oncotarget, vol. 6, No. 34, 35129-35130 (2015).
Carmi, Y., et al. Allogeneic IgG combined with dendritic cell stimuli induces anti-tumor T cell immunity. Nature. May 7, 2015; 521(7550): 99-104.
Chang, S., Overview of Prostate-Specific Membrane Antigen, Reviews in Urology, vol. 6 Suppl. 10, S13 (2004).
Choulika, A., et al., Transfer of Single Gene-Containing Long Terminal Repeats into the Genome of Mammalian Cells by a Retroviral Vector Carrying the cre Gene and the loxP Site. J Virol 1996, 70:1792-1798.
Clark, R.A. Resident memory T cells in human health and disease . . . Sci. Transl. Med., 7, 269rv1, (2015).
Colberre-Garapin, F., et al., A new dominant hybrid selective marker for higher eukaryotic cells. J Mol Biol 1981, 150:1-14.
Corpet, F., "Multiple sequence alignment with hierarchical clustering", (1988) Nucleic Acids Research 16:10881-90.
Croci, D. O., Dynamic cross-talk between tumor and immune cells in orchestrating the immunosuppressive network at the tumor microenvironment. Cancer Immunol Immunother (2007) 56:1687-1700.
Desai-Mehta, A. et al. Hyperexpression of CD40 Ligand by B and T Cells in Human Lupus and Its Role in Pathogenic Autoantibody Production. J. Clin. Invest. vol. 97(9), 2063-2073, (1996).
Drake, C.G., et al. Current status of immunological approaches for the treatment of prostate cancer. Curr Opin Urol. May 2010 ; 20(3): 241-246.
Dyall R., et al., Heteroclitic Immunization Induces Tumor Immunity, J. Exp. Med., vol. 188, No. 9, Nov. 2, 1998.
Eager, R. & Nemunaitis, J., GM-CSF Gene-Transduced Tumor Vaccines, Molecular Therapy, vol. 12, No. 1, 18 (Jul. 2005).
Earley, M.C., et al. Report from a Workshop on Multianalyte Microsphere Arrays. Cytometry 2002;50:239-242.
Elgueta R et al., Molecular mechanism and function of CD40/CD40L engagement in the immune system. Immunological reviews. 2009; 229(1).
Elshal, M.F.,et al., Multiplex Bead Array Assays: Performance Evaluation and Comparison of Sensitivity to ELISA. Methods 38(4): 317-323, Apr. 2006.
Faas, M.M., et al. Monocyte intracellular cytokine production during human endotoxaemia with or without a second in vitro LPS challenge: effect of RWJ-67657, a p38 MAP-kinase inhibitor, on LPS-hyporesponsiveness. Clin Exp Immunol 2002; 127:337-343.
Frey, N.V., et al., The Promise of Chimeric Antigen Receptor T-Cell Therapy, Oncology (2016).
Fujiyama, K., et al, IgG H chain [*Homo sapiens*]. NCBI PDB Accession No. BAN63131. Submitted Jan. 13, 2013; downloaded from the internet< https://www.ncbi.nlm.nih.gov/protein/BAN63131> on Feb. 21, 2018; Genbank Supplement pp. 1-2 (cited in PCT/US2017/63016 International Search Report).
Gorman, C.M., Mammalian cell expression. Curr Op Biotechnol 1990, 1:36-47.
Graf D et al., A soluble form of TRAP (CD40 ligand) is rapidly released after T cell activation . Eur J Immunol. Jun. 1995; 25(6): 1749-54.
Grosschedl, R., et al. Introduction of a u immunoglobulin gene into the mouse germ line: Specific expression in lymphoid cells and synthesis of functional antibody. Cell 1984, 38:647-658.
Grossman, M., et al. Retroviruses: delivery vehicle to the liver. Curr Opin Genet Devel 1993, 3:110-114.
Groth, A.C., et al., Phage Integrases: Biology and Applications. J. Mol. Biol. 335:667-678, 2004.
Gulley, J.L. et al. Immunotherapy for Prostate Cancer: Recent Advances, Lessons Learned, and Areas for Further Research. Clin Cancer Res; 17(12) Jun. 15, 2011.
Hamer, D.H., et al., SV40 recombinants carrying rabbit beta-globin gene coding sequences. Cell 1979, 17:725-735.
Jammer, R.E., et al. Diversity of alpha-fetoprotein gene expression in mice is generated by a combination of separate enhancer elements. Science 1987, 235:53-58.
Hanahan, D. Heritable formation of pancreatic β-cell tumours in transgenic mice expressing recombinant insulin/simian virus 40 oncogenes. Nature 1985, 315:115-122.
Henikoff & Henikoff; "Amino acid substitution matrices from protein blocks"; Proc. Natl. Acad. Sci. USA vol. 89, pp. 10915-10919, Nov. 1992.
Higano C S, et al., Integrated Data From 2 Randomized, Double-Blind, Placebo Controlled, Phase 3 Trials of Active Cellular Immunotherapy With Sipuleucel-T in Advanced Prostate Cancer. Cancer (2009) 115: 3670-3679.

(56) References Cited

OTHER PUBLICATIONS

Higgins, D. G., et al, "Fast and sensitive multiple sequence alignments on a microcomputer", (1989) Cabios 5:151-153.
Higgins, D.G., et al, "Clustal: a package for performing multiple sequence alignment on a microcomputer", (1988), Gene 73:237-244.
Hoover, HC., et al., Adjuvant active specific immunotherapy for human colorectal cancer: 6.5-year median follow-up of a phase III prospectively randomized trial. J Clin Oncol 1993, 11:390.
Woodlock, TJ., et al., Active specific immunotherapy for metastatic colorectal carcinoma: phase I study of an allogeneic cell vaccine plus low-dose interleukin-1 alpha. J Immunother 1999, 22:251-259.
Wooten, J. and Federhen, S., Statistics of Local Complexity in Amino Acid Sequences and Sequence Databases. Comput. Chem., 17:149-163 (1993).
Wu, G.Y., et al., Receptor-mediated in Vitro Gene Transformation by a Soluble DNA Carrier System*. J. Biol. Chem. 262, 4429-4432 (1987).
Xu, L., et al. MMI-0100 inhibits cardiac fibrosis in myocardial infarction by direct actions on cardiomyocytes and fibroblasts via MK2 inhibition. J Mol Cell Cardiol. Dec. 2014; 77: 86-101.
Youn B. et al. Chemokines, chemokine receptors and hematopoiesis. Immunol Rev, vol. 177: 150-174, (2000).
Yu, H., et al.Crosstalk between cancer and immune cells: role of STAT3 in the tumour microenvironment. (2007) Nature Rev. Immunol. 7:41-51.
Zhao Y. et al., Identification of stem cells from human umbilical cord blood with embryonic and hematopoietic characteristics. Exp. Cell Res., 312, 2454 (2006).
Zinn, K., et al., Regulated expression of an extrachromosomal human p-interferon gene in mouse cells. Proc Natl Acad Sci USA 1982, 79:4897.
Pearson, Using the FASTA program to search protein and DNA sequence databases. Methods Mol Biol. 1994;24:307-31.
PCT/US2017/63016 International Preliminary Report on Patentability, Sep. 25, 2018, 5 pgs.
Krummel, MF and Allison, JP., CD28 and CTLA-4 have opposing effects on the response of T cells to stimulation. J Exp Med. 1995;182:459-465.
Park Jang-June et al: "Expression of anti-HVEM single-chain antibody on tumor cells induces tumor-specific immunity with long-term memory", Cancer Immunology, Immunotherapy, NIH Author Manuscript, Springer, Berlin/Heidelberg, vol. 61, No. 2, Aug. 30, 2011 (Aug. 30, 2011), pp. 203-214.
Mason et al., Science, "A Deletion Truncating the Gonadotropin-Releasing Hormone Gene Is Responsible for Hypogonadism in the hpg Mouse", 1986, 234:1366-1371.
Shani, Nature, "Tissue-specific expression of rat myosin light-chain 2 gene in transgenic mice", (1985), 314:283-286.
Wu et al., Journal of Biological Chemistry, "Receptor-mediated gene delivery and expression in vivo", 263:14621, 1988.
Voskoglou-Nomikos et al., "Clinical Predictive Value of the in Vitro Cell Line, Human Xenograft, and Mouse Allograft Preclinical Cancer Models1", 2003, Clinical Cancer Res. 9: 42227-4239.
Dennis, "Off By A Whisker", 2006, Nature 442:739-741.
Cespdes et al., "Mouse models in oncogenesis and cancer therapy", (Clin. Trans!. Oncol. 8(5):318-329 (2006)).
Talmadge et al., "Murine models to evaluate novel and conventional therapeutic strategies for cancer", (Am. J. Pathol 170(3):793-804 (2007)).
Borriello et al., First International Precision Vaccines Conference: Multidisciplinary Approaches to Next-Generation Vaccines, mSphere, Aug. 1, 2018;3(4): 1-12.
Crittenden et al., Current Clinical Trials Testing Combinations of Immunotherapy and Radiation, Semin Radiat Oncol Jan. 25, 2015(1): 54-64.
Encke et al., Genetic vaccination with Flt3-L and GM-CSF as adjuvants: Enhancement of cellular and humoral immune responses that results in protective immunity in a murine model of hepatitis C virus infection, World J Gastroenterol Nov. 28, 2006; 12(44): 7118-7125.
Xu et al., Comparative ability of various plasmid-based cyeokines and chemokines to adjuvant the activity of HIV plasmid DNA vaccines, Vaccine 26, 2008, 4819-4829.
De Corte et al., (epi information I "Assessment of Assertions of Synergy as a Basis for Inventive Step in Compositions Comprising Mixtures", 1: 1-12, Feb. 2019).
Berenbaum, Synergy, additivism and antagonism in immunosuppression, Clin. Exp. Immunol., 28: 1-18, 1977.
Berenbaum, What is Syergy?, Pharmacol. Rev., 41: 93-141, 1989.
Tallarida, Drug Synergism and Dose Effect Analysis, Ed. Chapman & Hall, pp. 1-71, 2002.
Correction International Search Report, PCT/US2020/37283, dated Nov. 24, 2020.
Nagaraj et al., Altered recognition of antigen is a mechanism of CD8+ T cell tolerance in cancer. Nat Med. Jul. 2007;13(7):828-35.
Nair et al., Natural Killer T Cells in Cancer Immunotherapy. Front Immunol. Sep. 22, 2017;8:1178, 18 pages.
Njau et al., The CD28/B7 pathway: a novel regulator of plasma cell function. Adv Exp Med Biol. 2013;785:67-75.
O'Konek et al., Immune Regulation of Tumor Immunity by NKT Cells. Natural Killer T Cells: Balancing the Regulation of Tumor Immunity. Springer, New York. Masaki Terabe (Ed.). Chapter 4, pp. 55-70, (2012).
O'Sullivan et al., Cancer immunoediting by the innate immune system in the absence of adaptive immunity. J Exp Med. Sep. 24, 2012;209(10):1869-82.
Obata et al., MAP kinase pathways activated by stress: the p38 MAPK pathway. Crit Care Med. Apr. 2000;28(4 Suppl):N67-77.
Ohshima et al., OX40 costimulation enhances interleukin-4 (IL-4) expression at priming and promotes the differentiation of naive human CD4(+) T cells into high IL-4-producing effectors. Blood. Nov. 1, 1998;92(9):3338-45.
Okkenhaug et al., Grb2 forms an inducible protein complex with CD28 through a Src homology 3 domain-proline interaction. J Biol Chem. Aug. 14, 1998;273(33):21194-202.
Ono et al., Plasmid DNAs directly injected into mouse brain with lipofectin can be incorporated and expressed by brain cells. Neurosci Lett. Sep. 18, 1990;117(3):259-63.
Pages et al., Binding of phosphatidylinositol-3-OH kinase to CD28 is required for T-cell signalling. Nature. May 26, 1994;369(6478):327-9.
Pardoll, Cancer Immunotherapy with Vaccines and Checkpoint Blockade. The Molecular Basis of Cancer. Elsevier Health Sciences, John Mendelsohn (Ed.). Chapter 52, pp. 709-738, (2015).
Paterson et al., Antigens of activated rat T lymphocytes including a molecule of 50,000 Mr detected only on CD4 positive T blasts. Mol Immunol. Dec. 1987;24(12):1281-90.
Paul et al., The Molecular Mechanism of Natural Killer Cells Function and Its Importance in Cancer Immunotherapy. Front Immunol. Sep. 13, 2017;8:1124, 15 pages.
Paul, The immune system: An Introduction. Fundamental Immunology, 4th Edition. Lippicott-Raven Publishers, Philadelphia. Chapter 1, pp. 1-18, (1999).
Pauza et al., Gamma Delta T Cell Therapy for Cancer: It Is Good to be Local. Front Immunol. Jun. 8, 2018;9:1305, 11 pages.
Peterfalvi et al., Invariant Valpha7.2-Jalpha33 TCR is expressed in human kidney and brain tumors indicating infiltration by mucosal-associated invariant T (MAIT) cells. Int Immunol. Dec. 2008;20(12):1517-25.
Prasad et al., T-cell antigen CD28 interacts with the lipid kinase phosphatidylinositol 3-kinase by a cytoplasmic Tyr (P)-Met-Xaa-Met motif. Proc Natl Acad Sci U S A. Mar. 29, 1994;91(7):2834-8.
Qian et al., Regulation of Toll-like receptor signaling pathways in innate immune responses. Ann N Y Acad Sci. Apr. 2013;1283:67-74.
Raab et al., p56Lck and p59Fyn regulate CD28 binding to phosphatidylinositol 3-kinase, growth factor receptor-bound protein GRB-2, and T cell-specific protein-tyrosine kinase ITK: implications for T-cell costimulation. Proc Natl Acad Sci USA. Sep. 12, 1995;92(19):8891-5.

(56) References Cited

OTHER PUBLICATIONS

Richards et al., Monocytes and macrophages in cancer: development and functions. Cancer Microenviron. Aug. 2013;6(2):179-91.
Ricklin et al., Complement: a key system for immune surveillance and homeostasis. Nat Immunol. Sep. 2010;11(9):785-97.
Rozanski et al., Sustained antibody responses depend on CD28 function in bone marrow-resident plasma cells. J Exp Med. Jul. 4, 2011;208(7):1435-46.
Rudd et al., Unifying concepts in CD28, ICOS and CTLA4 co-receptor signalling. Nat Rev Immunol. Jul. 2003;3(7):544-56.
Sallusto et al., Two subsets of memory T lymphocytes with distinct homing potentials and effector functions. Nature. Oct. 14, 1999;401(6754):708-12.
Salomon et al., B7/CD28 costimulation is essential for the homeostasis of the CD4+CD25+ immunoregulatory T cells that control autoimmune diabetes. Immunity. Apr. 2000;12(4):431-40.
Santiago-Schwarz et al., Distinct characteristics of lymphokine-activated killer (LAK) cells derived from patients with B-cell chronic lymphocytic leukemia (B-CLL). A factor in B-CLL serum promotes natural killer cell-like LAK cell growth. Blood. Oct. 1, 1990;76(7):1355-60.
Saraiva et al., The regulation of IL-10 production by immune cells. Nat Rev Immunol. Mar. 2010;10(3):170-81.
Seaman, Natural killer cells and natural killer T cells. Arthritis Rheum. Jun. 2000;43(6):1204-17.
Sharma et al., Failure of Immunological Cells to Eradicate Tumor and Cancer Cells: an overview. Turkish Journal of Biology. 2014;38:786-799.
Sharpe et al., The B7-CD28 superfamily. Nat Rev Immunol. Feb. 2002;2(2):116-26.
Shojaei et al., G-CSF-initiated myeloid cell mobilization and angiogenesis mediate tumor refractoriness to anti-VEGF therapy in mouse models. Proc Natl Acad Sci U S A. Apr. 21, 2009;106(16):6742-7.
Shouval et al., Interleukin-10 receptor signaling in innate immune cells regulates mucosal immune tolerance and anti-inflammatory macrophage function. Immunity. May 15, 2014;40(5):706-19.
So et al., Cutting edge: OX40 inhibits TGF-beta- and antigen-driven conversion of naive CD4 T cells into CD25+Foxp3+ T cells. J Immunol. Aug. 1, 2007;179(3):1427-30.
So et al., Immune regulation and control of regulatory T cells by OX40 and 4-1BB. Cytokine Growth Factor Rev. Jun.-Aug. 2008;19(3-4):253-62.
Soghoian et al., Cytolytic CD4(+) T cells in viral immunity. Expert Rev Vaccines. Dec. 2010;9(12):1453-63.
Souza-Fonseca-Guimaraes et al., The Emergence of Natural Killer Cells as a Major Target in Cancer Immunotherapy. Trends Immunol. Feb. 2019;40(2):142-158.
Spear et al., NKG2D ligands as therapeutic targets. Cancer Immun. May 1, 2013;13:8, 14 pages.
Stein et al., The cytoplasmic domain of CD28 is both necessary and sufficient for costimulation of interleukin-2 secretion and association with phosphatidylinositol 3'-kinase. Mol Cell Biol. May 1994;14(5):3392-402.
Steinman, The dendritic cell system and its role in immunogenicity. Annu Rev Immunol. 1991;9:271-96.
Sternberg et al., Bacteriophage P1 site-specific recombination. I. Recombination between loxP sites. J Mol Biol. Aug. 25, 1981;150(4):467-86.
Stjernsward et al., Tumour-distinctive cellular immunity to renal carcinoma. Clin Exp Immunol. Jun. 1970;6(6):963-8.
Straubinger et al., Liposomes as carriers for intracellular delivery of nucleic acids. Methods Enzymol. 1983;101:512-27.
Tartour et al., Angiogenesis and immunity: a bidirectional link potentially relevant for the monitoring of antiangiogenic therapy and the development of novel therapeutic combination with immunotherapy. Cancer Metastasis Rev. Mar. 2011;30(1):83-95.
Thompson et al., CD28 activation pathway regulates the production of multiple T-cell-derived lymphokines/cytokines. Proc Natl Acad Sci U S A. Feb. 1989;86(4):1333-7.

Torina et al., The Janus Face of NKT Cell Function in Autoimmunity and Infectious Diseases. Int J Mol Sci. Feb. 1, 2018;19(2):440, 11 pages.
Uchida et al., Autologous mixed lymphocyte-tumor reaction and autologous mixed lymphocyte reaction. II. Generation of specific and non-specific killer T cells capable of lysing autologous tumor. Int J Cancer. May 15, 1988;41(5):651-6.
Van Acker et al., CD56 in the Immune System: More Than a Marker for Cytotoxicity? Front Immunol. Jul. 24, 2017;8:892, 9 pages.
Van Kaer et al., Invariant natural killer T cells: bridging innate and adaptive immunity. Cell Tissue Res. Jan. 2011;343(1):43-55.
Venuprasad et al., Human Neutrophil-Expressed CD28 Interacts with Macrophage B7 to Induce Phosphatidylinositol 3-Kinase-Dependent IFN-gamma Secretion and Restriction of Leishmania Growth. The Journal of Immunology. 2002;136:920-928.
Vivier et al., Targeting natural killer cells and natural killer T cells in cancer. Nat Rev Immunol. Mar. 22, 2012;12(4):239-52.
Voo et al., Targeting of TLRs inhibits CD4+ regulatory T cell function and activates lymphocytes in human peripheral blood mononuclear cells. J Immunol. Jul. 15, 2014;193(2):627-34.
Vu et al., OX40 costimulation turns off Foxp3+ Tregs. Blood. Oct. 1, 2007;110(7):2501-10.
Wahl et al., Molecular hybridization of immobilized nucleic acids: theoretical concepts and practical considerations. Methods Enzymol. 1987;152:399-407.
Walunas et al., CTLA-4 can function as a negative regulator of T cell activation. Immunity. Aug. 1994;1(5):405-13.
Wang et al., Expression of heat-stable antigen on tumor cells provides co-stimulation for tumor-specific T cell proliferation and cytotoxicity in mice. Eur J Immunol. May 1995;25(5):1163-7.
Watanabe et al., Grb2 and Gads exhibit different interactions with CD28 and play distinct roles in CD28-mediated costimulation. J Immunol. Jul. 15, 2006;177(2):1085-91.
Watkins et al., IL-12 rapidly alters the functional profile of tumor-associated and tumor-infiltrating macrophages in vitro and in vivo. J Immunol. Feb. 1, 2007;178(3):1357-62.
Weinberg et al., OX-40: life beyond the effector T cell stage. Semin Immunol. Dec. 1998;10(6):471-80.
Weiss et al., Synergy between the T3/antigen receptor complex and Tp44 in the activation of human T cells. J Immunol. Aug. 1, 1986;137(3):819-25.
Woerly et al., CD28 and secretory immunoglobulin A-dependent activation of eosinophils: inhibition of mediator release by the anti-allergic drug, suplatast tosilate. Clin Exp Allergy. Sep. 2004;34(9):1379-87.
Wolff et al., Direct gene transfer into mouse muscle in vivo. Science. Mar. 23, 1990;247(4949 Pt 1):1465-8.
Wolint et al., Immediate cytotoxicity but not degranulation distinguishes effector and memory subsets of CD8+ T cells. J Exp Med. Apr. 5, 2004;199(7):925-36.
Wortham et al., TLR and NKG2D signaling pathways mediate CS-induced pulmonary pathologies. PLoS One. Oct. 9, 2013;8(10):e78735, 9 pages.
Wu et al., gammadelta T cells and their potential for immunotherapy. Int J Biol Sci. Jan. 10, 2014;10(2):119-35.
Wu et al., Targeting genes: delivery and persistent expression of a foreign gene driven by mammalian regulatory elements in vivo. J Biol Chem. Oct. 15, 1989;264(29):16985-7.
Xiu et al., Surface anchorage of superantigen SEA promotes induction of specific antitumor immune response by tumor-derived exosomes. J Mol Med (Berl). May 2007;85(5):511-21.
Yao et al., B7-h2 is a costimulatory ligand for CD28 in human. Immunity. May 27, 2011;34(5):729-40.
Zhao et al., A unique human blood-derived cell population displays high potential for producing insulin. Biochem Biophys Res Commun. Aug. 17, 2007;360(1):205-11.
International Search Report and Written Opinion for Application No. PCT/US2020/056698, dated Feb. 9, 2021, 11 pages.
Abel et al., Natural Killer Cells: Development, Maturation, and Clinical Utilization. Front Immunol. Aug. 13, 2018;9:1869, 23 pages.

(56) References Cited

OTHER PUBLICATIONS

Alberts et al., The Adaptive Immune System. Molecular Biology of the Cell, Fourth Edition. Garland Science, Chapter 24, pp. 1363-1420, (2002).
Alter et al., CD107a as a functional marker for the identification of natural killer cell activity. J Immunol Methods. Nov. 2004;294(1-2):15-22.
Andersen et al., Cytotoxic T cells. J Invest Dermatol. Jan. 2006;126(1):32-41.
Appay et al., Memory CD8+ T cells vary in differentiation phenotype in different persistent virus infections. Nat Med. Apr. 2002;8(4):379-85.
August et al., CD28 of T lymphocytes associates with phosphatidylinositol 3-kinase. Int Immunol. May 1994;6(5):769-74.
Ausubel et al., Informatics for Molecular Biologists. Current Protocols in Molecular Biology. John Wiley & Sons Inc. Chapter 19, pp. 19.0.1-19.5.24. (2003).
Balato et al., Natural killer T cells: an unconventional T-cell subset with diverse effector and regulatory functions. J Invest Dermatol. Jul. 2009;129(7):1628-42.
Benichou et al., Direct versus indirect allorecognition pathways: on the right track. Am J Transplant. Apr. 2009;9(4):655-6.
Bennstein et al., Unraveling Natural Killer T-Cells Development. Front Immunol. Jan. 9, 2018;8:1950, 7 pages.
Bhatia et al., Different cell surface oligomeric states of B7-1 and B7-2: implications for signaling. Proc Natl Acad Sci USA. Oct. 25, 2005;102(43):15569-74.
Bingle et al., The role of tumor-associated macrophages in tumor progression: implications for new anticancer therapies. J Pathol. 2002;196:254-265.
Bluestone et al., CTLA4Ig: bridging the basic immunology with clinical application. Immunity. Mar. 2006;24(3):233-8.
Boomer et al., An enigmatic tail of CD28 signaling. Cold Spring Harb Perspect Biol. Aug. 2010;2(8):a002436, 21 pages.
Bour-Jordan et al., Intrinsic and extrinsic control of peripheral T-cell tolerance by costimulatory molecules of the CD28/ B7 family. Immunol Rev. May 2011;241(1):180-205.
Brigham et al., In vivo transfection of murine lungs with a functioning prokaryotic gene using a liposome vehicle. Am J Med Sci. Oct. 1989;298(4):278-81.
Brutkiewicz, CD1d ligands: the good, the bad, and the ugly. J Immunol. Jul. 15, 2006; 177(2):769-75.
Cai et al., Selective CD28pYMNM mutations implicate phosphatidylinositol 3-kinase in CD86-CD28-mediated costimulation. Immunity. Oct. 1995;3(4):417-26.
Campbell et al., CCR7 expression and memory T cell diversity in humans. J Immunol. Jan. 15, 2001;166(2):877-84.
Campbell et al., Structure/function of human killer cell immunoglobulin-like receptors: lessons from polymorphisms, evolution, crystal structures and mutations. Immunology. Mar. 2011;132(3):315-25.
Cappuzzello et al., Cytokines for the induction of antitumor effectors: The paradigm of Cytokine-Induced Killer (CIK) cells. Cytokine Growth Factor Rev. Aug. 2017;36:99-105.
Carreno et al., The B7 family of ligands and its receptors: new pathways for costimulation and inhibition of immune responses. Annu Rev Immunol. 2002;20:29-53.
Casella et al., Autocrine-paracrine VEGF loops potentiate the maturation of megakaryocytic precursors through Flt1 receptor. Blood. Feb. 15, 2003;101(4):1316-23.
Chao et al., The CD47-SIRPa pathway in cancer immune evasion and potential therapeutic implications. Curr Opin Immunol. Apr. 2012;24(2):225-32.
Chapman et al., The inhibitory receptor LIR-1 uses a common binding interaction to recognize class I MHC molecules and the viral homolog UL18. Immunity. Nov. 1999;11(5):603-13.
Chen et al., Molecular mechanisms of T cell co-stimulation and co-inhibition. Nat Rev Immunol. Apr. 2013;13(4):227-42.
Chow et al., Innate Allorecognition Results in Rapid Accumulation of Monocyte-Derived Dendritic Cells. J Immunol. Sep. 1, 2016;197(5):2000-8.
Claverie et al., Information enhancement methods for large scale sequence analysis. Comput Chem. 1993;17(2):191-201.
Curotto De Lafaille et al., Natural and adaptive foxp3+ regulatory T cells: more of the same or a division of labor? Immunity. May 2009;30(5):626-35.
De Kouchkovsky et al., microRNA-17-92 regulates IL-10 production by regulatory T cells and control of experimental autoimmune encephalomyelitis. J Immunol. Aug. 15, 2013;191(4):1594-605.
De Matteis et al., Immunosuppressive Treg cells acquire the phenotype of effector-T cells in chronic lymphocytic leukemia patients. J Transl Med. Jun. 20, 2018;16(1):172, 9 pages.
De Smedt et al., Ox40 costimulation enhances the development of T cell responses induced by dendritic cells in vivo. J Immunol. Jan. 15, 2002;168(2):661-70.
Deroost et al., Gamma/Delta T Cells and Their Role in Protection Against Malaria. Front Immunol. Dec. 20, 2018;9:2973, 9 pages.
Dolfi et al., Late signals from CD27 prevent Fas-dependent apoptosis of primary CD8+ T cells. J Immunol. Mar. 1, 2008;180(5):2912-21.
Dondossola et al., Self-targeting of TNF-releasing cancer cells in preclinical models of primary and metastatic tumors. Proc Natl Acad Sci U S A. Feb. 23, 2016;113(8):2223-8.
Dong et al., MAP kinases in the immune response. Annu Rev Immunol. 2002;20:55-72.
Dunn et al., The three Es of cancer immunoediting. Annu Rev Immunol. 2004;22:329-60.
Ebihara et al., Induction of NKG2D ligands on human dendritic cells by TLR ligand stimulation and RNA virus infection. Int Immunol. Oct. 2007; 19(10):1145-55.
Esensten et al., CD28 Costimulation: From Mechanism to Therapy. Immunity. May 17, 2016;44(5):973-88.
Evans et al., Crystal structure of a soluble CD28-Fab complex. Nat Immunol. Mar. 2005;6(3):271-9.
Falschlehner et al., Following Trail's path in the immune system. Immunology. Jun. 2009;127(2):145-54.
Felgner et al., Lipofection: a highly efficient, lipid-mediated DNA-transfection procedure. Proc Natl Acad Sci U S A. Nov. 1987;84(21):7413-7.
Fraser et al., Regulation of interleukin-2 gene enhancer activity by the T cell accessory molecule CD28. Science. Jan. 18, 1991;251(4991):313-6.
Gabrilovich et al., Coordinated regulation of myeloid cells by tumours. Nat Rev Immunol. Mar. 22, 2012;12(4):253-68.
Gabrilovich, Myeloid-Derived Suppressor Cells. Cancer Immunol Res. Jan. 2017;5(1):3-8.
Galluzzi et al., Classification of current anticancer immunotherapies. Oncotarget. Dec. 30, 2014;5(24):12472-508.
Gao et al., Cytokine-Induced Killer Cells As Pharmacological Tools for Cancer Immunotherapy. Front Immunol. Jul. 6, 2017;8:774, 13 pages.
Gati et al., CD158 receptor controls cytotoxic T-lymphocyte susceptibility to tumor-mediated activation-induced cell death by interfering with Fas signaling. Cancer Res. Nov. 1, 2003;63(21):7475-82.
Girardi et al., Molecular basis of lipid antigen presentation by CD1d and recognition by natural killer T cells. Immunol Rev. Nov. 2012;250(1):167-79.
Godfrey et al., NKT cells: what's in a name? Nat Rev Immunol. Mar. 2004;4(3):231-7.
Huang, X., et al., "Parallelization of a local similarity algorithm", (1992) Computer Applications in the Biosciences 8:155-165.
Hunter TB, et al., An Agonist Antibody Specific for CD40 Induces Dendritic Cell Maturation and Promotes Autologous Anti-tumour T-cell Responses in an In vitro Mixed Autologous Tumour Cell/Lymph Node Cell Model (2007) Scandanavian J. Immunology 65, 479-486.
Jancey, J., et al., "Effective recruitment and retention of older adults in physical activity research: PALS study", Am J Health Behav, vol. 30(6): 626-635, (2009).
Janeway, CA, Jr., The priming of helper T cells . . . Semin. Immunol., vol. 1(1): 13-20 (1989).
Jensen, S.M. et al. Adoptive cellular immunotherapy of cancer: a three-signal paradigm for translating recent developments into

(56) References Cited

OTHER PUBLICATIONS improved treatment strategies. Springer Science & Business Media, 2007, Tumor Immunology and Cancer Vaccines, vol. 123, Chapter 13, 293-336.
Jiang T.T. Regulatory T Cells: New Keys for Further Unlocking the Enigma of Fetal Tolerance and Pregnancy Complications. J Immunol., vol. 192(11): 4949-4956, (2014).
Kantoff P W, et al., Sipuleucel-T Immunotherapy for Castration-Resistant Prostate Cancer. N. Engl. J. Med. (2010) 363: 411-422.
Karlin & Altschul; "Applications and statistics for multiple high-scoring segments in molecular sequences"; Proc. Natl. Acad. Sci. USA, vol. 90, pp. 5873-5877, Jun. 1993.
Karpusas M et al., 2 å crystal structure of an extracellular fragment of human CD40 ligand. Structure. Oct. 15, 1995;3(10):1031-9.
Kaufman and Wolchok (eds.), General Principles of Tumor Immunotherapy, Chapter 5, 67-121 (2007).
Kelsey, G.D., et al. Species- and tissue-specific expression of human alpha 1-antitrypsin in transgenic mice. Genes Devel 1987, 1:161-171.
Klein, L. Aire Gets Company for Immune Tolerance. Cell, vol. 163(4):794-795, (2015).
Kleinnijenhuis, J., et al. Innate Immune Recognition of *Mycobacterium tuberculosis*. (2011) Clin. Dev. Immunol. 105310 (12 pgs.).
Knapinska, A.M., et al. Chaperone Hsp27 Modulates AUF1 Proteolysis and AU-Rich Element-Mediated mRNA Degradation. Molecular and Cellular Biology, Apr. 2011, vol. 31., No. 7, 1419-1431.
Kollias, G., et al., Regulated expression of human A gamma-, beta-, and hybrid gamma beta-globin genes in transgenic mice: manipulation of the developmental expression patterns, Cell 1986, 46:89-94.
Kootstra, N.A. et al., Gene Therapy with Viral Vectors. Ann. Rev. Pharm. Toxicol., 43:413-439, 2003.
Kozlowska, A., et al. Therapeutic gene modified cell based cancer vaccines. Gene 525 (2013) 200-207.
Krieg, AM., et al. (1995). CpG motifs in bacterial DNA trigger direct B-cell activation. Nature. 374 (6522): 546-9.
Kronenberg, M. et al., "Regulation of immunity by self-reactive T cells", Nature, vol. 435: 598-604 (2005).
Krug, A., et al. Identification of CpG oligonucleotide sequences with high induction of IFN-alpha/beta in plasmacytoid dendritic cells . . . Eur. J. Immunol. 2001. 31: 2154-2163.
Krumlauf, R., et al. Developmental regulation of alpha-fetoprotein genes in transgenic mice . . . Mol Cell Biol 1985, 5:1639-1648.
Kumar N.P. et al. 2015. Coincident diabetes mellitus modulates Th1-, Th2-, and Th17-cell responses in latent tuberculosis in an IL-10- and TGF-beta-dependent manner. Eur J Immunol. 2016. 46:390-399. doi: 10.1002/eji.201545973.
Kumar, C, et al., AKT crystal structure and AKT-specific inhibitors. Oncogene (2005) 24, 7493-7501.
Leder, A., et al. Consequences of widespread deregulation of the c-myc gene in transgenic mice: Multiple neoplasms and normal development. Cell 1986, 45:485-495.
Lefebvre, E., et al. Antifibrotic Effects of the Dual CCR2/CCR5 Antagonist Cenicriviroc in Animal Models of Liver and Kidney Fibrosis. PLoS One 11(6): e0158156. doi:10.1371/ journal.pone.0158156, Jun. 2016.
Liu, Q., et al. Developing irreversible inhibitors of the protein kinase cysteinome. Chem Biol. Feb. 21, 2013; 20(2): 146-159.
Loetscher P. et al. The Ligands of CXC Chemokine Receptor 3, I-TAC, Mig, and IP10, Are Natural Antagonists for CCR3*. J. Biol. Chem., vol. 276: 2986-2991, (2001).
Logan, J., et al., Adenovirus tripartite leader sequence enhances translation of mRNAs late after infection. Proc Natl Acad Sci USA 1984, 81:3655-3659.
Lowy, I., et al., Isolation of transforming DNA: cloning the hamster aprt gene . . . Cell 1980, 22:817.
MacDonald, R.J. Expression of the pancreatic elastase I gene in transgenic mice. Hepatology 1987, 7:425-515.
Macey, Marion G., Flow cytometry: principles and applications, Humana Press, 2007.

Mackay C.R., Chemokines: immunology's high impact factors. Nat Immunol., vol. 2: 95-101, (2001).
Mackett, M., et al., General Method for Production and Selection of Infectious Vaccinia Virus Recombinants Expressing Foreign Genes. J Virol 1984, 49:857-864.
Mackett, M., et al., Vaccinia virus: A selectable eukaryotic cloning and expression vector. Proc Natl Acad Sci USA 1982, 79:7415-7419.
Magram, J. et al., Developmental regulation of a cloned adult beta-globin gene in transgenic mice, Nature 1985, 315:338-340.
Makaryan, V., et al., TCIRG1 associated Congenital Neutropenia. Hum Mutat. Jul. 2014; 35(7): 824-827.
Makrides, S.C., Strategies for achieving high-level expression of genes in *Escherichia coli*. Microbiol Rev 1996, 60:512-538.
Mason, AJ., et al., A deletion truncating the gonadotropin-releasing hormone gene is responsible for hypogonadism in the hpg mouse. Science 1986, 234:1366-1371.
Matsuzaki, H., et al., Chromosome engineering in Saccharomyces cerevisiae by using a site-specific recombination system of a yeast plasmid. J. Bacteriology, 172:610-618, 1990.
Mazzei GJ et al., Recombinant Soluble Trimeric CD40 Ligand Is Biologically Active. J Biol Chem. Mar. 31, 1995; 270(13):7025-8.
Mclachlin, J.R., et al. Retroviral-Mediated Gene Transfer. Prog Nucleic Acid Res Mol Biol 1990, 38:91-135.
Metzger T.C. et al., "Control of central and peripheral tolerance by Aire", Immunol. Rev. 2011, vol. 241: 89-103, (2011).
Meyers and Miller; "Optimal alignments in linear space"; Computer Applic. Biol. Sci., 4:11-17 (1988).
Morgenstern, J.P., et al., Advanced mammalian gene transfer: high titre retroviral vectors with multiple drug selection markers and a complementary helper-free packaging cell line. Nucleic Acids Res 1990, 18:3587-3596.
Mulligan, R.C., et al., Selection for animal cells that express the *Escherichia coli* gene coding for xanthine-guanine phosphoribosyltransferase. Proc Natl Acad Sci USA 1981, 78:2072.
Murphy, Kenneth. Janeway's Immunobiology: 8th ed. Chapter 15: Garland Science. (2012), pp. 611-668.
Nash, H.A., Purification of Bacteriophage lambda, Int Protein. Nature, 247, 543-545, 1974).
Needleman, S., et al., "A General Method Applicable to the Search for Similarities in the Amino Acid Sequence of Two Proteins", (1970), J. Mol. Biol. 48:443.
Nocentini, G., et al. Pharmacological modulation of GITRL/GITR system: therapeutic perspectives. British Journal of Pharmacology (2012) 165 2089-2099.
Nunes-Duby, S.E., et al., Similarities and differences among 105 members of the Int family of site-specific recombinases. Nucleic Acids Res. 26:391-406, 1998.
Gottschalk et al., The Role of Invariant Natural Killer T Cells in Dendritic Cell Licensing, Cross-Priming, and Memory CD8(+) T Cell Generation. Front Immunol. Jul. 28, 2015;6:379, 8 pages.
Gray Parkin et al., Expression of CD28 by bone marrow stromal cells and its involvement in B lymphopoiesis. J Immunol. Sep. 1, 2002;169(5):2292-302.
Grell et al., The transmembrane form of tumor necrosis factor is the prime activating ligand of the 80 kDa tumor necrosis factor receptor. Cell. Dec. 1, 1995;83(5):793-802.
Grohmann et al., CTLA-4-Ig regulates tryptophan catabolismin vivo. Nat Immunol. Nov. 2002;3(11):1097-101.
Guinn et al., 4-1BBL cooperates with B7-1 and B7-2 in converting a B cell lymphoma cell line into a long-lasting antitumor vaccine. J Immunol. Apr. 15, 1999;162(8):5003-10.
Gulley et al., Immunotherapy for prostate cancer: recent advances, lessons learned, and areas for further research. Clin Cancer Res. Jun. 15, 2011;17(12):3884-91.
Guo et al., Cytokine-induced killer (CIK) cells: from basic research to clinical translation. Chinese Journal of Cancer. 2015;34:6, 9 pages.
Gutgemann et al., Cytokine-induced killer cells are type II natural killer T cells. Ger Med Sci. 2007;5:1-4.
Hastings, Innate and Adaptive Immune Responses to Cancer. Fundamentals of Cancer Prevention. D.S. Alberts (Ed.), Springer-Verlag Berlin Heidelberg. pp. 79-108, (2008).

(56) References Cited

OTHER PUBLICATIONS

Holdorf et al., Proline residues in CD28 and the Src homology (SH)3 domain of Lck are required for T cell costimulation. J Exp Med. Aug. 2, 1999;190(3):375-84.
Huang et al., OX40L induces helper T cell differentiation during cell immunity of asthma through PI3K/AKT and P38 Mapk signaling pathway. J Transl Med. Mar. 20, 2018;16(1):74, 10 pages.
Huynh et al., Constructing and Screening cDNA Libraries of lambdagt10 and lambdagt11. DNA Cloning, vol. I, a practical approach. IRL Press, Oxford, D.M. Glover (Ed). Chapter 2, pp. 49-78, (1985).
Hwu et al., Cancer and the Celuular Immune Response. The Molecular Basis of Cancer. Elsevier Health Sciences, John Mendelsohn (Ed.). Chapter 51, pp. 695-708, (2015).
Ito et al., Regulation of the Induction and Function of Cytotoxic T Lymphocytes by Natural Killer T Cell. J Biomed Biotechnol. 2010;2010:641757, 8 pages.
June et al., T-cell proliferation involving the CD28 pathway is associated with cyclosporine-resistant interleukin 2 gene expression. Mol Cell Biol. Dec. 1987;7(12):4472-81.
Kaur et al., OX40/OX40 ligand interactions in T-cell regulation and asthma. Chest. Feb. 2012;141(2):494-499.
Kim et al., Growth factor receptor-bound protein 2 SH2/SH3 domain binding to CD28 and its role in co-signaling. J Biol Chem. Jan. 2, 1998;273(1):296-301.
Kimmel, Identification and characterization of specific clones: strategy for confirming the validity of presumptive clones. Methods Enzymol. 1987;152:507-11.
King et al., Analysis of CD28 cytoplasmic tail tyrosine residues as regulators and substrates for the protein tyrosine kinases, EMT and Lck. J Immunol. Jan. 15, 1997;158(2):580-90.
Kleiveland, Peripheral Blood Monuclear Cells. The Impact of Food Bioactives on Health, In Vitro and Ex Vivo Models. Springer Open. Chapter 15, pp. 161-167, (2015).
Koehn et al., GVHD-associated, inflammasome-mediated loss of function in adoptively transferred myeloid-derived suppressor cells. Blood. Sep. 24, 2015;126(13):1621-8.
Krovi et al., Invariant Natural Killer T Cell Subsets-More Than Just Developmental Intermediates. Front Immunol. Jun. 20, 2018;9:1393, 17 pages.
Kumar et al., Different subsets of natural killer T cells may vary in their roles in health and disease. Immunology. Jul. 2014;142(3):321-36.
Kumar et al., Natural Killer T Cells: An Ecological Evolutionary Developmental Biology Perspective. Front Immunol. Dec. 22, 2017;8:1858, 19 pages.
Lacy et al., Cytokine release from innate immune cells: association with diverse membrane trafficking pathways. Blood. Jul. 7, 2011;118(1):9-18.
Lanier, NKG2D Receptor and Its Ligands in Host Defense. Cancer Immunol Res. Jun. 2015;3(6):575-82.
Lenschow et al., Differential up-regulation of the B7-1 and B7-2 costimulatory molecules after Ig receptor engagement by antigen. J Immunol. Sep. 1, 1994;153(5):1990-7.
Levine et al., Antiviral effect and ex vivo CD4+ T cell proliferation in HIV-positive patients as a result of CD28 costimulation. Science. Jun. 28, 1996;272(5270):1939-43.
Levine et al., Effects of CD28 costimulation on long-term proliferation of CD4+ T cells in the absence of exogenous feeder cells. J Immunol. Dec. 15, 1997;159(12):5921-30.
Liao et al., The Functions of Type I and Type II Natural Killer I (NKT) Cells in Inflammatory Bowel Diseases. Inflamm Bowel Dis. May 2013;19(6):1330-1338.
Liu et al., The Regulation of CD1d+ and CD1d− Tumors by NKT Cells, The Roles of NKT Cells in Regulating CD1d+ and CD1d− Tumor Immunity. Natural Killer T Cells, Balancing the Regulation of Tumor Immunity. Springer, New York, 2012, Masaki Terabe (Ed.). Chapter 5, pp. 71-94, (2012).

Lopez et al., Perforin forms transient pores on the target cell plasma membrane to facilitate rapid access of granzymes during killer cell attack. Blood. Apr. 4, 2013;121(14):2659-68.
Lu et al., Tumor-infiltrating myeloid cells induce tumor cell resistance to cytotoxic T cells in mice. J Clin Invest. Oct. 2011;121(10):4015-29.
Lyddane et al., Cutting Edge: CD28 controls dominant regulatory T cell activity during active immunization. J Immunol. Mar. 15, 2006;176(6):3306-10.
Mak et al., NK, yo T and NKT Cells. Primer to the Immune Response, 2nd Edition. AP Cell Press. Chapter 11, pp. 247-268, (2014).
Mandal et al., Natural killer cells: In health and disease. Hematol Oncol Stem Cell Ther. Jun. 2015;8(2):47-55.
Marcus et al., Recognition of tumors by the innate immune system and natural killer cells. Adv Immunol. 2014;122:91-128.
Martin et al., A 44 kilodalton cell surface homodimer regulates interleukin 2 production by activated human T lymphocytes. J Immunol. May 1, 1986;136(9):3282-7.
McLaughlin et al., Adeno-associated virus general transduction vectors: analysis of proviral structures. J Virol. Jun. 1988;62(6):1963-73.
McNamara et al., Tamoxifen inhibits endothelial cell proliferation and attenuates VEGF-mediated angiogenesis and migration in vivo. Eur J Surg Oncol. Dec. 2001;27(8):714-8.
Meng et al., A dynamic transcriptomic atlas of cytokine-induced killer cells. J Biol Chem. Dec. 21, 2018;293(51):19600-19612.
Metzler et al., Solution structure of human CTLA-4 and delineation of a CD80/CD86 binding site conserved in CD28. Nat Struct Biol. Jul. 1997;4(7):527-31.
Molon et al., Chemokine nitration prevents intratumoral infiltration of antigen-specific T cells. J Exp Med. Sep. 26, 2011;208(10):1949-62.
Moore et al., Interleukin-10 and the interleukin-10 receptor. Annu Rev Immunol. 2001;19:683-765.
Moretta et al., A novel surface antigen expressed by a subset of human CD3− CD16+ natural killer cells. Role in cell activation and regulation of cytolytic function. J Exp Med. Mar. 1, 1990;171(3):695-714.
Moynihan et al., Roles for Innate Immunity in Combination Immunotherapies. Cancer Res. Oct. 1, 2017;77(19):5215-5221.
Murphy et al., Janeway's Immunobiology. 9th edition, Garland Science pp. 387-395, (2017).
Murphy et al., Janeways Immunobiology. 9th edition. Garland Science. pp. 128-130, (2017).
Murphy, T Cell-Mediated Immunity. Janeway's Immunobiology, 8th Edition. Chapter 9: Garland Science. Chapter 9, pp. 335-372, (2012).
Murphy, The Development and Survival of Lymphocytes. Janeway's Immunobiology: 8th Edition. Garland Sciences. Chapter 8, pp. 275-334, (2012).
Choi et al., Mechanism of EBV inducing anti-tumour immunity and its therapeutic use. Nature. Feb. 2021;590(7844):157-162.
Montagna et al., Ex vivo priming for long-term maintenance of antileukemia human cytotoxic T cells suggests a general procedure for adoptive immunotherapy. Blood. Dec. 1, 2001;98(12):3359-66.
U.S. Appl. No. 15/821,105, filed Nov. 22, 2017, U.S. Pat. No. 11,058,752, Issued.
U.S. Appl. No. 16/899,318, filed Jun. 11, 2020, U.S. Pat. No. 11,185,586, Issued.
U.S. Appl. No. 17/517,632, filed Nov. 2, 2021, 2022-0096631, Published.
U.S. Appl. No. 16/660,442, filed Oct. 22, 2019, U.S. Pat. No. 10,731,128, Issued.
Boczkowski et al., Induction of tumor immunity and cytotoxic T lymphocyte responses using dendritic cells transfected with messenger RNA amplified from tumor cells. Cancer Res. Feb. 15, 2000;60(4):1028-34.
Srivatsan et al., Allogeneic tumor cell vaccines: the promise and limitations in clinical trials. Hum Vaccin Immunother. 2014;10(1):52-63.

(56) References Cited

OTHER PUBLICATIONS

Funaki, Y. et al., "Studies on lymphocyte immune responses to soluble antigens from spontaneous mouse carcinomas," Iwate Medical University Dental Journal, vol. 12, Issue 1, pp. 24-34, 1987.
Office Action of the Japan Patent Office in related Japanese Appl. No. 2019-547602, dated Oct. 22, 2024, 23 pages.
Office Action of the Japan Patent Office in related Japanese Appl. No. 2022-524134, dated Dec. 23, 2024, 5 pages.

* cited by examiner

RIBBON STRUCTURE OF AN HLA CLASS I SURFACE ANTIGEN

RIBBON STRUCTURE OF AN HLA CLASS I SURFACE ANTIGEN

FIG. 3B
SEQ ID NO. 49

```
   1 AATGTAGTCT TATGCAATAC TCTTGTAGTC TTGCAACATG GTAACGATGA GTTAGCAACA
  61 TGCCTTACAA GGAGAGAAAA AGCACCGTGC ATGCCGATTG GTGGAAGTAA GGTGGTACGA
 121 TCGTGCCTTA TTAGGAAGGC AACAGACGGG TCTGACATGG ATTGGACGAA CCACTGAATT
 181 GCCGCATTGC AGAGATATTG TATTTAAGTG CCTAGCTCGA TACATAAACG GGTCTCTCTG
 241 GTTAGACCAG ATCTGAGCCT GGGAGCTCTC TGGCTAACTA GGGAACCCAC TGCTTAAGCC
 301 TCAATAAAGC TTGCCTTGAG TGCTTCAAGT AGTGTGTGCC CGTCTGTTGT GTGACTCTGG
 361 TAACTAGAGA TCCCTCAGAC CCTTTTAGTC AGTGTGGAAA ATCTCTAGCA GTGGCGCCCG
 421 AACAGGGACT TGAAAGCGAA AGGGAAACCA GAGGAGCTCT CTCGACGCAG GACTCGGCTT
 481 GCTGAAGCGC GCACGGCAAG AGGCGAGGGG CGGCGACTGG TGAGTACGCC AAAAATTTTG
 541 ACTAGCGGAG GCTAGAAGGA GAGAGATGGG TGCGAGAGCG TCAGTATTAA GCGGGGGAGA
 601 ATTAGATCGC GATGGGAAAA AATTCGGTTA AGGCCAGGGG GAAAGAAAAA ATATAAATTA
 661 AAACATATAG TATGGGCAAG CAGGGAGCTA GAACGATTCG CAGTTAATCC TGGCCTGTTA
 721 GAAACATCAG AAGGCTGTAG ACAAATACTG GGACAGCTAC AACCATCCCT TCAGACAGGA
 781 TCAGAAGAAC TTAGATCATT ATATAATACA GTAGCAACCC TCTATTGTGT GCATCAAAGG
 841 ATAGAGATAA AAGACACCAA GGAAGCTTTA GACAAGATAG AGGAAGAGCA AAACAAAAGT
 901 AAGACCACCG CACAGCAAGC GGCCGCTGAT CTTCAGACCT GGAGGAGGAG ATATGAGGGA
 961 CAATTGGAGA AGTGAATTAT ATAAATATAA AGTAGTAAAA ATTGAACCAT TAGGAGTAGC
1021 ACCCACCAAG GCAAAGAGAA GAGTGGTGCA GAGAGAAAAA AGAGCAGTGG GAATAGGAGC
1081 TTTGTTCCTT GGGTTCTTGG GAGCAGCAGG AAGCACTATG GGCGCAGCGT CAATGACGCT
1141 GACGGTACAG GCCAGACAAT TATTGTCTGG TATAGTGCAG CAGCAGAACA ATTTGCTGAG
1201 GGCTATTGAG GCGCAACAGC ATCTGTTGCA ACTCACAGTC TGGGGCATCA AGCAGCTCCA
1261 GGCAAGAATC CTGGCTGTGG AAAGATACCT AAAGGATCAA CAGCTCCTGG GGATTTGGGG
1321 TTGCTCTGGA AAACTCATTT GCACCACTGC TGTGCCTTGG AATGCTAGTT GGAGTAATAA
1381 ATCTCTGGAA CAGATTTGGA ATCACACGAC CTGGATGGAG TGGGACAGAG AAATTAACAA
1441 TTACACAAGC TTAATACACT CCTTAATTGA AGAATCGCAA AACCAGCAAG AAAAGAATGA
1501 ACAAGAATTA TTGGAATTAG ATAAATGGGC AAGTTTGTGG AATTGGTTTA ACATAACAAA
1561 TTGGCTGTGG TATATAAAAT TATTCATAAT GATAGTAGGA GGCTTGGTAG GTTTAAGAAT
1621 AGTTTTTGCT GTACTTTCTA TAGTGAATAG AGTTAGGCAG GGATATTCAC CATTATCGTT
1681 TCAGACCCAC CTCCCAACCC CGAGGGGACC CGACAGGCCC GAAGGAATAG AAGAAGAAGG
1741 TGGAGAGAGA GACAGAGACA GATCCATTCG ATTAGTGAAC GGATCTCGAC GGTATCGCTA
1801 GCTTTTAAAA GAAAAGGGGG GATTGGGGGG TACAGTGCAG GGGAAAGAAT AGTAGACATA
1861 ATAGCAACAG ACATACAAAC TAAAGAATTA CAAAAACAAA TTACAAAAAT TCAAAATTTT
1921 ACTAGTGATT ATCGGATCAA CTTTGTATAG AAAAGTTGGG CTCCGGTGCC CGTCAGTGGG
1981 CAGAGCGCAC ATCGCCCACA GTCCCCGAGA AGTTGGGGGG AGGGGTCGGC AATTGAACCG
2041 GTGCCTAGAG AAGGTGGCGC GGGGTAAACT GGGAAAGTGA TGTCGTGTAC TGGCTCCGCC
2101 TTTTTCCCGA GGGTGGGGGA GAACCGTATA TAAGTGCAGT AGTCGCCGTG AACGTTCTTT
2161 TTCGCAACGG GTTTGCCGCC AGAACACAGG TAAGTGCCGT GTGTGGTTCC CGCGGGCCTG
2221 GCCTCTTTAC GGGTTATGGC CCTTGCGTGC CTTGAATTAC TTCCACCTGG CTGCAGTACG
2281 TGATTCTTGA TCCCGAGCTT CGGGTTGGAA GTGGGTGGGA GAGTTCGAGG CCTTGCGCTT
2341 AAGGAGCCCC TTCGCCTCGT GCTTGAGTTG AGGCCTGGCC TGGGCGCTGG GGCCGCCGCG
2401 TGCGAATCTG GTGGCACCTT CGCGCCTGTC TCGCTGCTTT CGATAAGTCT CTAGCCATTT
2461 AAAATTTTTG ATGACCTGCT GCGACGCTTT TTTTCTGGCA AGATAGTCTT GTAAATGCGG
2521 GCCAAGATCT GCACACTGGT ATTTCGGTTT TTGGGGCCGC GGGCGGCGAC GGGGCCCGTG
2581 CGTCCCAGCG CACATGTTCG GCGAGGCGGG GCCTGCGAGC GCGGCCACCG AGAATCGGAC
2641 GGGGGTAGTC TCAAGCTGGC CGGCCTGCTC TGGTGCCTGG TCTCGCGCCG CCGTGTATCG
2701 CCCCGCCCTG GGCGGCAAGG CTGGCCCGGT CGGCACCAGT TGCGTGAGCG GAAAGATGGC
2761 CGCTTCCCGG CCCTGCTGCA GGGAGCTCAA AATGGAGGAC GCGGCGCTCG GGAGAGCGGG
2821 CGGGTGAGTC ACCCACACAA AGGAAAAGGG CCTTTCCGTC CTCAGCCGTC GCTTCATGTG
2881 ACTCCACGGA GTACCGGGCG CCGTCCAGGC ACCTCGATTA GTTCTCGAGC TTTTGGAGTA
2941 CGTCGTCTTT AGGTTGGGGG GAGGGGTTTT ATGCGATGGA GTTTCCCCAC ACTGAGTGGG
3001 TGGAGACTGA AGTTAGGCCA GCTTGGCACT TGATGTAATT CTCCTTGGAA TTTGCCCTTT
```

FIG. 3B-1

```
3061 TTGAGTTTGG ATCTTGGTTC ATTCTCAAGC CTCAGACAGT GGTTCAAAGT TTTTTTCTTC
3121 CATTTCAGGT GTCGTGACAA GTTTGTACAA AAAAGCAGGC TGCCACCATG GAGTTCGGCC
3181 TGAGCTGGGT GTTCCTGGTG GCCCTGTTCA GAGGCGTGCA GTGCCACCTG AAGCTGCAGG
3241 AGAGCGGCCC CGGCCTGGTG GCCCCAGCC AGAGCCTGAG CATCACCTGC ACCGTGAGCG
3301 GCTTCAGCCT GACCGCCTAC GGCGTGGACT GGGTGAGACA GCCCCCGGC AAGTGCCTGG
3361 AGTGGCTGGG CGTGATCTGG GGCGGCGGCA GAACCAACTA CAACAGCGGC CTGATGAGCA
3421 GACTGAGCAT CAGAAAGGAC AACAGCAAGA GCCAGGTGTT CCTGACCATG AACAGCCTGC
3481 AGACCGACGA CACCGCCAAG TACTACTGCG TGAAGCACAC CAACTGGGAC GGCGGCTTCG
3541 CCTACTGGGG CCAGGGCACC ACCGTGACCG TGAGCAGCGG CGGCGGCGGC AGCGGCGGCG
3601 GCGGCAGCGG CGGCGGCGGC AGCGGCAGCC CCGGCCAGAG CGTGAGCATC AGCTGCAGCG
3661 GCAGCAGCAG CAACATCGGC AACAACTACG TGTACTGGTA CCAGCACCTG CCCGGCACCG
3721 CCCCCAAGCT GCTCATCTAC AGCGACACCA AGAGACCCAG CGGCGTGCCC GACAGAATCA
3781 GCGGCAGCAA GAGCGGCACC AGCGCCAGCC TGGCCATCAG CGGCCTGCAG AGCGAGGACG
3841 AGGCCGACTA CTACTGCGCC AGCTGGGACG ACAGCCTGGA CGGCCCCGTG TTCGGCTGCG
3901 GCACCAAGCT GACCGTGCTG CTGAAGACCC CCCTGGGCGA CACCACCCAC ACCTGCCCCA
3961 GATGCCCCGA GCCCAAGAGC TGCGACACCC CCCCCCCCTG CCCCAGATGC CCCGAGCCCA
4021 AGAGCTGCGA CACCCCCCCC CCCTGCCCCA GATGCCCCGA GCCCAAGAGC TGCGACACCC
4081 CCCCCCCCTG CCCCAGATGC CCCGCCCCCG AGCTGCTGGG CGGCCCCAGC GTGTTCCTGT
4141 TCCCCCCCAA GCCCAAGGAC ACCCTGATGA TCAGCAGAGC CCCCGAGGTG ACCTGCGTGG
4201 TGGTGGACGT GAGCCACGAG GACCCCGAGG TGAAGTTCAA CTGGTACGTG GACGGCGTGG
4261 AGGTGCACAA CGCCAAGACCC AAGCCCAGAG AGGAGCAGTA CAACAGCACC TACAGAGTGG
4321 TGAGCGTGCT GACCGTGCTG CACCAGGACT GGCTGAACGG CAAGGAGTAC AAGTGCAAGG
4381 TGAGCAACAA GGCCCTGCCC GCCCCCATCG AGAAGACCAT CAGCAAGGCC AAGGGCCAGC
4441 CCAGAGAGCC CCAGGTGTAC ACCCTGCCCC CCAGCAGAGA CGAGCTGACC AAGAACCAGG
4501 TGAGCCTGAC CTGCCTGGTG AAGGGCTTCT ACCCCAGCGA CATCGCCGTG GAGTGGGAGA
4561 GCAACGGCCA GCCCGAGAAC AACTACAAGA CCACCCCCCC CGTGCTGGAC AGCGACGGCA
4621 GCTTCTTCCT GTACAGCAAG CTGACCGTGG ACAAGAGCAG ATGGCAGCAG GGCAACGTGT
4681 TCAGCTGCAG CGTGATGCAC GAGGCCCTGC ACAACCACTA CACCCAGAAG AGCCTGAGCC
4741 TGAGCCCCGA GCTGCAGCTG GAGGAGAGCT GCGCCGAGGC CCAGGACGGC GAGCTGGACG
4801 GCCTGTGGAC CACCATCACC ATCTTCATCA CCCTGTTCCT GCTGAGCGTG TGCTACAGCG
4861 CCACCGTGAC CTTCTTCAAG GTGAAGTGGA TCTTCAGCAG CGTGGTGGAC CTGAAGCAGA
4921 CCATCATCCC CGACTACAGA AACATGATCG GCCAGGGCGC CTAAACCCAG CTTTCTTGTA
4981 CAAAGTGGTG ATAATCGAAT CTAAACCCA GCTTTCTTGT ACAAAGTGGT GATAATCGAA
5041 TTCCGATAAT CAACCTCTGG ATTACAAAAT TTGTGAAAGA TTGACTGGTA TTCTTAACTA
5101 TGTTGCTCCT TTTACGCTAT GTGGATACGC TGCTTTAATG CCTTTGTATC ATGCTATTGC
5161 TTCCCGTATG GCTTTCATTT TCTCCTCCTT GTATAAATCC TGGTTGCTGT CTCTTTATGA
5221 GGAGTTGTGG CCCGTTGTCA GGCAACGTGG CGTGGTGTGC ACTGTGTTTG CTGACGCAAC
5281 CCCCACTGGT TGGGGCATTG CCACCACCTG TCAGCTCCTT TCCGGGACTT TCGCTTTCCC
5341 CCTCCCTATT GCCACGGCGG AACTCATCGC CGCCTGCCTT GCCCGCTGCT GGACAGGGGC
5401 TCGGCTGTTG GGCACTGACA ATTCCGTGGT GTTGTCGGGG AAGCTGACGT CCTTTCCATG
5461 GCTGCTCGCC TGTGTTGCCA CCTGGATTCT GCGCGGGACG TCCTTCTGCT ACGTCCCTTC
5521 GGCCCTCAAT CCAGCGGACC TTCCTTCCCG CGGCCTGCTG CCGGCTCTGC GGCCTCTTCC
5581 GCGTCTTCGC CTTCGCCCTC AGACGAGTCG GATCTCCCTT TGGGCCGCCT CCCCGCATCG
5641 GGAATTCCCG CGGTTCGCTT TAAGACCAAT GACTTACAAG GCAGCTGTAG ATCTTAGCCA
5701 CTTTTTAAAA GAAAAGGGGG GACTGGAAGG GCTAATTCAC TCCCAACGAA GACAAGATCT
5761 GCTTTTTGCT TGTACTGGGT CTCTCTGGTT AGACCAGATC TGAGCCTGGG AGCTCTCTGG
5821 CTAACTAGGG AACCCACTGC TTAAGCCTCA ATAAAGCTTG CCTTGAGTGC TTCAAGTAGT
5881 GTGTGCCCGT CTGTTGTGTG ACTCTGGTAA CTAGAGATCC CTCAGACCCT TTTAGTCAGT
5941 GTGGAAAATC TCTAGCAGTA GTAGTTCATG TCATCTTATT ATTCAGTATT TATAACTTGC
6001 AAAGAAATGA ATATCAGAGA GTGAGAGGAA CTTGTTTATT GCAGCTTATA ATGGTTACAA
6061 ATAAAGCAAT AGCATCACAA ATTTCACAAA TAAAGCATTT TTTTCACTGC ATTCTAGTTG
6121 TGGTTTGTCC AAACTCATCA ATGTATCTTA TCATGTCTGG CTCTAGCTAT CCCGCCCCTA
6181 ACTCCGCCCA TCCCGCCCCT AACTCCGCCC AGTTCCGCCC ATTCTCCGCC CCATGGCTGA
6241 CTAATTTTTT TTATTTATGC AGAGGCCGAG GCCGCCTCGG CCTCTGAGCT ATTCCAGAAG
6301 TAGTGAGGAG GCTTTTTTGG AGGCCTAGGG ACGTACCCAA TTCGCCCTAT AGTGAGTCGT
6361 ATTACGCGCG CTCACTGGCC           AAAGGGGGA CTGGGAAAAC TAATTCACTC
```

FIG. 3B-2

```
6421 CCCAACTTAA TCGCCTTGCA GCACATCCCC CTTTCGCCAG CTGGCGTAAT AGCGAAGAGG
6481 CCCGCACCGA TCGCCCTTCC CAACAGTTGC GCAGCCTGAA TGGCGAATGG GACGCGCCCT
6541 GTAGCGGCGC ATTAAGCGCG GCGGGTGTGG TGGTTACGCG CAGCGTGACC GCTACACTTG
6601 CCAGCGCCCT AGCGCCCGCT CCTTTCGCTT TCTTCCCTTC CTTTCTCGCC ACGTTCGCCG
6661 GCTTTCCCCG TCAAGCTCTA AATCGGGGGC TCCCTTTAGG GTTCCGATTT AGTGCTTTAC
6721 GGCACCTCGA CCCCAAAAAA CTTGATTAGG GTGATGGTTC ACGTAGTGGG CCATCGCCCT
6781 GATAGACGGT TTTTCGCCCT TTGACGTTGG AGTCCACGTT CTTTAATAGT GGACTCTTGT
6841 TCCAAACTGG AACAACACTC AACCCTATCT CGGTCTATTC TTTTGATTTA TAAGGGATTT
6901 TGCCGATTTC GGCCTATTGG TTAAAAAATG AGCTGATTTA ACAAAAATTT AACGCGAATT
6961 TTAACAAAAT ATTAACGCTT ACAATTTAGG TGGCACTTTT CGGGGAAATG TGCGCGGAAC
7021 CCCTATTTGT TTATTTTTCT AAATACATTC AAATATGTAT CCGCTCATGA GACAATAACC
7081 CTGATAAATG CTTCAATAAT ATTGAAAAAG GAAGAGTATG AGTATTCAAC ATTTCCGTGT
7141 CGCCCTTATT CCCTTTTTTG CGGCATTTTG CCTTCCTGTT TTTGCTCACC CAGAAACGCT
7201 GGTGAAAGTA AAAGATGCTG AAGATCAGTT GGGTGCACGA GTGGGTTACA TCGAACTGGA
7261 TCTCAACAGC GGTAAGATCC TTGAGAGTTT TCGCCCCGAA GAACGTTTTC CAATGATGAG
7321 CACTTTTAAA GTTCTGCTAT GTGGCGCGGT ATTATCCCGT ATTGACGCCG GGCAAGAGCA
7381 ACTCGGTCGC CGCATACACT ATTCTCAGAA TGACTTGGTT GAGTACTCAC CAGTCACAGA
7441 AAAGCATCTT ACGGATGGCA TGACAGTAAG AGAATTATGC AGTGCTGCCA TAACCATGAG
7501 TGATAACACT GCGGCCAACT TACTTCTGAC AACGATCGGA GGACCGAAGG AGCTAACCGC
7561 TTTTTTGCAC AACATGGGGG ATCATGTAAC TCGCCTTGAT CGTTGGGAAC CGGAGCTGAA
7621 TGAAGCCATA CCAAACGACG AACTACTTAC CACGATGCCT GTAGCAATGG CAACAACGTT
7681 GCGCAAACTA TTAACTGGCG AACTACTTAC TCTAGCTTCC CGGCAACAAT TAATAGACTG
7741 GATGGAGGCG GATAAAGTTG CAGGACCACT TCTGCGCTCG GCCCTTCCGG CTGGCTGGTT
7801 TATTGCTGAT AAATCTGGAG CCGGTGAGCG TGGGTCTCGC GGTATCATTG CAGCACTGGG
7861 GCCAGATGGT AAGCCCTCCC GTATCGTAGT TATCTACACG ACGGGGAGTC AGGCAACTAT
7921 GGATGAACGA AATAGACAGA TCGCTGAGAT AGGTGCCTCA CTGATTAAGC ATTGGTAACT
7981 GTCAGACCAA GTTTACTCAT ATATACTTTA GATTGATTTA AAACTTCATT TTTAATTTAA
8041 AAGGATCTAG GTGAAGATCC TTTTTGATAA TCTCATGACC AAAATCCCTT AACGTGAGTT
8101 TTCGTTCCAC TGAGCGTCAG ACCCCGTAGA AAAGATCAAA GGATCTTCTT GAGATCCTTT
8161 TTTTCTGCGC GTAATCTGCT GCTTGCAAAC AAAAAAACCA CCGCTACCAG CGGTGGTTTG
8221 TTTGCCGGAT CAAGAGCTAC CAACTCTTTT TCCGAAGGTA ACTGGCTTCA GCAGAGCGCA
8281 GATACCAAAT ACTGTTCTTC TAGTGTAGCC GTAGTTAGGC CACCACTTCA AGAACTCTGT
8341 AGCACCGCCT ACATACCTCG CTCTGCTAAT CCTGTTACCA GTGGCTGCTG CCAGTGGCGA
8401 TAAGTCGTGT CTTACCGGGT TGGACTCAAG ACGATAGTTA CCGGATAAGG CGCAGCGGTC
8461 GGGCTGAACG GGGGGTTCGT GCACACAGCC CAGCTTGGAG CGAACGACCT ACACCGAACT
8521 GAGATACCTA CAGCGTGAGC TATGAGAAAG CGCCACGCTT CCCGAAGAGA GAAAGGCGGA
8581 CAGGTATCCG GTAAGCGGCA GGGTCGGAAC AGGAGAGCGC ACGAGGGAGC TTCCAGGGGG
8641 AAACGCCTGG TATCTTTATA GTCCTGTCGG GTTTCGCCAC CTCTGACTTG AGCGTCGATT
8701 TTTGTGATGC TCGTCAGGGG GGCGGAGCCT ATGGAAAAAC GCCAGCAACG CGGCCTTTTT
8761 ACGGTTGGTG GCCTTTTGCT GGCCTTTTGC TCACATGTTC TTTCCTGCGT TATCCCCTGA
8821 TTCTGTGGAT AACCGTATTA CCGCCTTTGA GTGAGCTGAT ACCGCTCGCC GCAGCCGAAC
8881 GACCGAGCGC AGCGAGTCAG TGAGCGAGGA AGCGGAAGAG CGCCCAATAC GCAAACCGCC
8941 TCTCCCCGCG CGTTGGCCGA TTCATTAATG CAGCTGGCAC GACAGGTTTC CCGACTGGAA
9001 AGCGGGCAGT GAGCGCAACG CAATTAATGT GAGTTAGCTC ACTCATTAGG CACCCCAGGC
9061 TTTACACTTT ATGCTTCCGG CTCGTATGTT GTGTGGAATT GTGAGCGGAT AACAATTTCA
9121 CACAGGAAAC AGCTATGACC ATGATTACGC CAAGCGCGCA ATTAACCCTC ACTAAAGGGA
9181 ACAAAAGCTG GAGCTGCAAG CTT
```

FIG. 4B
SEQ ID NO. 48

```
   1  AATGTAGTCT TATGCAATAC TCTTGTAGTC TTGCAACATG GTAACGATGA GTTAGCAACA
  61  TGCCTTACAA GGAGAGAAAA AGCACCGTGC ATGCCGATTG GTGGAAGTAA GGTGGTACGA
 121  TCGTGCCTTA TTAGGAAGGC AACAGACGGG TCTGACATGG ATTGGACGAA CCACTGAATT
 181  GCCGCATTGC AGAGATATTG TATTTAAGTG CCTAGCTCGA TACATAAACG GGTCTCTCTG
 241  GTTAGACCAG ATCTGAGCCT GGGAGCTCTC TGGCTAACTA GGGAACCCAC TGCTTAAGCC
 301  TCAATAAAGC TTGCCTTGAG TGCTTCAAGT AGTGTGTGCC CGTCTGTTGT GTGACTCTGG
 361  TAACTAGAGA TCCCTCAGAC CTTTTAGTC  AGTGTGGAAA ATCTCTAGCA ATATAAATTA
 421  AACAGGGACT TGAAAGCGAA AGGGAAACCA GAGGAGCTCT CTCGACGCAG GACTCGGCTT
 481  GCTGAAGCGC GCACGGCAAG AGGCGAGGGG CGGCGACTGG TGAGTACGCC AAAAATTTTG
 541  ACTAGCGGAG GCTAGAAGGA GAGAGATGGG TGCGAGAGCG TCAGTATTAA GCGGGGGAGA
 601  ATTAGATCGC GATGGGAAAA AATTCGGTTA AGGCCAGGGG GAAAGAAAAA ATATAAATTA
 661  AAACATATAG TATGGGCAAG CAGGGAGCTA GAACGATTCG CAGTTAATCC TGGCCTGTTA
 721  GAAACATCAG AAGGCTGTAG ACAAATACTG GGACAGCTAC AACCATCCCT TCAGACAGGA
 781  TCAGAAGAAC TTAGATCATT ATATAATACA GTAGCAACCC TCTATTGTGT GCATCAAAGG
 841  ATAGAGATAA AAGACACCAA GGAAGCTTTA GACAAGATAG AGGAAGAGCA AAACAAAAGT
 901  AAGACCACCG CACAGCAAGC GGCCGCTGAT CTTCAGACCT GGAGGAGGAG ATATGAGGGA
 961  CAATTGGAGA AGTGAATTAT ATAAATATAA AGTAGTAAAA ATTGAACCAT TAGGAGTAGC
1021  ACCCACCAAG GCAAAGAGAA GAGTGGTGCA GAGAGAAAAA AGAGCAGTGG ATATGAGGGA
1081  TTTGTTCCTT GGGTTCTTGG GAGCAGCAGG AAGCACTATG GGCGCAGCGT CAATGACGCT
1141  GACGGTACAG GCCAGACAAT TATTGTCTGG TATAGTGCAG CAGCAGAACA ATTTGCTGAG
1201  GGCTATTGAG GCGCAACAGC ATCTGTTGCA ACTCACAGTC TGGGGCATCA AGCAGCTCCA
1261  GGCAAGAATC CTGGCTGTGG AAAGATACCT AAAGGATCAA CAGCTCCTGG GGATTTGGGG
1321  TTGCTCTGGA AAACTCATTT GCACCACTGC TGTGCCTTGG AATGCTAGTT GGAGTAATAA
1381  ATCTCTGGAA CAGATTTGGA ATCACACGAC CTGGATGGAG TGGGACAGAG AAATTAACAA
1441  TTACACAAGC TTAATACACT CCTTAATTGA AGAATCGCAA AACCAGCAAG AAAAGAATGA
1501  ACAAGAATTA TTGGAATTAG ATAAATGGGC AAGTTTGTGG AATTGGTTTA ACATAACAAA
1561  TTGGCTGTGG TATATAAAAT TATTCATAAT GATAGTAGGA GGCTTGGTAG GTTTAAGAAT
1621  AGTTTTTGCT GTACTTTCTA TAGTGAATAG AGTTAGGCAG GGATATTCAC CATTATCGTT
1681  TCAGACCCAC CTCCCAACCC CGAGGGGACC CGACAGGCCC GAAGGAATAG AAGAAGAAGG
1741  TGGAGAGAGA GACAGAGACA GATCCATTCG ATTAGTGAAC GGATCTCGAC GGTATCGCTA
1801  GCTTTTAAAA GAAAAGGGGG GATTGGGGGG TACAGTGCAG GGGAAAGAAT AGTAGACATA
1861  ATAGCAACAG ACATACAAAC TAAAGAATTA CAAAAACAAA TTACAAAAAT TCAAAATTTT
1921  ACTAGTATCA ACTTTGTATA GAAAAGTTGG GCTCCGGTGC CCGTCAGTGG GCAGAGCGCA
1981  CATCGCCCAC CATCGCCCAC AAGTTGGGGG GAGGGGTCGG CAATTGAACC GGTGCCTAGA
2041  GAAGGTGGCG CGGGGTAAAC TGGGAAAGTG ATGTCGTGTA CTGGCTCCGC CTTTTTCCCG
2101  AGGGTGGGGG AGAACCGTAT ATAAGTGCAG TAGTCGCCGT GAACGTTCTT TTTCGCAACG
2161  GGTTTGCCGC CAGAACACAG GTAAGTGCCG TGTGTGGTTC CCGCGGGCCT GGCCTCTTTA
2221  CGGGTTATGG CCCTTCGCTG CCTTGAATTA CTTCCACCTG GCTGCAGTAC GTGATTCTTG
2281  ATCCCGAGCT TCGGGTTGGA AGTGGGTGGG AGAGTTCGAG GCCTTGCGCT TAAGGAGCCC
2341  CTTCGCCTCG TGCTTGAGTT GAGGCCTGGC CTGGGCGCTG GGGCCGCCGC CTGCGAATCT
2401  GGTGGCACCT TCGCGCCTGT CTCGCTGCTT TCGATAAGTC TCTAGCCATT TAAAATTTTT
2461  GATGACCTGC TGCGACGCTT TTTTTCTGGC AAGATAGTCT TGTAAATGCG GGCCAAGATC
2521  TGCACACTGG TATTTCGGTT TTTGGGGCCG CGGGCGGCGA CGGGGCCCGT GCGTCCCAGC
2581  GCACATGTTC GGCGAGGCGG GGCCTGCGAG CGCGGCCACC GAGAATCGGA CGGGGGTAGT
2641  CTCAAGCTGG CCGGCCTGCT CTGGTGCCTG GTCTCGCGCC GCCGTGTATC GCCCCGCCCT
2701  GGGCGGCAAG GCTGGCCCGG TCGGCACCAG TTGCGTGAGC GGAAAGATGG CCGCTTCCCG
2761  GCCCTGCTGC AGGGAGCTCA AAATGGAGGA CGCGGCGCTC GGGAGAGCGG GCGGGTGAGT
```

FIG. 4B-1

```
2821 CACCCACACA AAGGAAAAGG GCCTTTCCGT CCTCAGCCGT CGCTTCATGT GACTCCACGG
2881 AGTACCGGGC GCCGTCCAGG CACCTCGATT AGTTCTCGAG CTTTTGGAGT ACGTCGTCTT
2941 TAGGTTGGGG GGAGGGGTTT TATGCGATGG AGTTTCCCCA CACTGAGTGG GTGGAGACTG
3001 AAGTTAGGCC AGCTTGGCAC TTGATGTAAT TCTCCTTGGA ATTTGCCCTT TTTGAGTTTG
3061 GATCTTGGTT CATTCTCAAG CCTCAGACAC TGGTTCAAAG TTTTTTTCTT CCATTTCAGG
3121 TGTCGTGACA AGTTTGTACA AAAAAGCAGG CTGCCACCAT GGAGTTCGGC CTGAGCTGGG
3181 TGTTCCTGGT GGCCCTGTTC AGAGGCGTGC AGTGCCAGGT GAAGCTGCAG GAGAGCGGCC
3241 CCGGCCTGGT GGCCCCCAGC CAGAGCCTGA GCATCACCTG CACCGTGAGC GGCTTCAGCC
3301 TGACCGCCTA CGGCGTGGAC TGGGTGAGAC AGCCCCCGG CAAGGGCCTG GAGTGGCTGG
3361 GCGTGATCTG GGGCGGCGGC AGAACCAACT ACAACAGCGG CCTGATGAGC AGACTGAGCA
3421 TCAGAAAGGA CAACAGCAAG AGCCAGGTGT TCCTGACCAT GAACAGCCTG CAGACCGACG
3481 ACACCGCCAA GTACTACTGC GTGAAGCACA CCAACTGGGA CGGCGGCTTC GCCTACTGGC
3541 GCCAGGGCAC CACCGTGACC GTGAGCAGCC CAGCGTGTT CCCCCTGGCC CCCAGCAGCA
3601 AGAGCACCAG CGGCGGCACC GCCGCCCTGG GCTGCCTGGT GAAGGACTAC TTCCCCGAGC
3661 CCGTGACCGT GAGCTGGAAC AGCGGCGCCC TGACCAGCGG CGTGCACACC TTCCCCGCCG
3721 TGCTGCAGAG CAGCGCCCTG TACAGCCTGA GCAGGGTGGT GACCGTGCCC AGGAGCAGCC
3781 TGGGCACCCA GACCTACATC TGCAACGTGA ACCACAAGCC CAGCAACACC AAGGTGGACA
3841 AGAAGGTGGA GCTGAAGACC CCCCTGGGCG ACACCACCCA CACCTGCCCC AGATGCCCCG
3901 AGCCCAAGAG CTGCGACACC CCCCCCCCCT GCCCCAGATG CCCCGAGCCC AAGAGCTGCG
3961 ACACCCCCCC CCCCTGCCCC AGATGCCCCG AGCCCAAGAG CTGCGACACC CCCCCCCCCT
4021 GCCCCAGATG CCCCGCCCCC GAGCTGCTGG GCGGCCCCAG CGTGTTCCTG TTCCCCCCCA
4081 AGCCCAAGGA CACCCTGATG ATCAGCAGAG CCCCCGAGGT GACCTGCGTG GTGGTGGACG
4141 TGAGCCACGA GGACCCCGAG GTGAAGTTCA ACTGGTACGT GGACGGCGTG GAGGTGCACA
4201 ACGCCAAGAC CAAGCCCAGA GAGGAGCAGT ACAACAGCAC CTACAGAGTG GTGAGCGTGC
4261 TGACCGTGCT GCACCAGGAC TGGCTGAACG GCAAGGACTA CAAGTGCAAG GTGAGCAACA
4321 AGGCCCTGCC CGCCCCCATC GAGAAGACCA TCAGCAAGGC CAAGGGCCAG CCCAGAGAGC
4381 CCCAGGTGTA CACCCTGCCC CCAGCAGAG ACGAGCTGAC CAAGAACCAG GTGAGCCTGA
4441 CCTGCCTGGT GAAGGGCTTC TACCCCAGCG ACATCGCCGT GGAGTGGGAG AGCAACGGCC
4501 AGCCCGAGAA CAACTACAAG GACAAGAGCA GATGGCAGCA GGGCAACGTG TTCAGCTGCA
4621 GCGTGATGCA CGAGGCCCTG CACAACCACT ACACCCAGAA GAGCCTGAGC CTGAGCCCCG
4681 AGCTGCAGCT GGAGGAGAGC TGCGCCGAGG CCCAGGACGG CGAGCTGGAC GGCCTGTGGA
4741 CCACCATCAC CATCTTCATC ACCCTGTTCC TGCTGAGCGT GTGCTACAGC GCCACCGTGA
4801 CCTTCTTCAA GGTGAAGTGG ATCTTCAGCA GCGTGGTGGA CCTGAAGCAG ACCATCATCC
4861 CCGACTACAG AAAACATGATC GGCCAGGGCG CCTAAAACAA CAACAATTGC ATTCATTTTA
4921 TGTTTCAGGT TCAGGGGGAG GTGTGGGAGG TTTTTTAAAG CAAGTAAAAC CTCTACAAAT
4981 GTGGTACGCG TTAACAACAA CAATTGCATT CATTTATGT TTCAGGTTCA GGGGGAGGTG
5041 TGGGAGGTTT TTTAAACGAA GTAAAACCTC TACAAATGTG GTACGCGTTA CCCAGCTTTC
5101 TTGTACAAAG TGGTAAATAG ATAGAACAAC AACAATTGCA TTCATTTTTG ATTTCAGGTT
5161 CAGGGGGAGG TGTGGGAGGT TTTTTAAAGC AAGTAAAACC TCTACACTGA CGGTACGCGT
5221 TAACAACAAC AATTGCATTC ATTTGTAGTT TCAGGTTCAG GGGGAGGTGT GGGAGGTTTT
5281 TTAAAGCAAG TTAAACCTCT AAAATAGTGG TACGCGTTAC CCAGCTTTCT TGTACAAAGT
5341 GGACCCAGCT TTCTTGTACA AAGTGGGCCC CTCTCCCTCC CCCCCCCTA ACGTTACTGG
5401 CCGAAGCCGC TTGGAATAAG GCCGGTGTGC GTTTGTCTAT ATGTTATTTT CCACCATATT
5461 GCCGTCTTTT GGCAATGTGA GGGCCCGGAA ACCTGGCCCT GTCTTCTTGA ACGTTACTGG
5521 TAGGGGTCTT TCCCCTCTCG CCAAAGGAAT GCAAGGTCTG TTGAATGTCG TGAAGGAAGC
5581 AGTTCCTCTG GAAGCTTCTT GAAGACAAAC AACGTCTGTA GCGACCCTTT GCAGGCAGCG
5641 GAACCCCCCA CCTGGCGACA GGTGCCTCTG CGGCCAAAAG CCACGTGTAT AAGATACACC
5701 TGCAAAGGCG GCACAACCCC AGTGCCACGT TGTGAGTTGG ATAGTTGTGG AAAGAGTCAA
5761 ATGGCTCTCC TCAAGCGTAT TCAACAAGGG GCTGAAGGAT GCCCAGAAGG TACCCCATTG
5821 TATGGGATCT GATCTGGGGC CTCGGTGCAC ATGCTTTACA TGTGTTTAGT CGAGGTTAAA
```

FIG. 4B-2

```
5881  AAAACGTCTA  GGCCCCCCGA  ACCACGGGGA  CGTGGTTTTC  CTTTGAAAAA  CACGATGATA
5941  ATATGGCCAC  AACCATGGCC  ACGACATGA   GAGTGCCCGC  CCAGCTGCTG  GGCCTGCTGC
6001  TGCTGTGGCT  GAGCGGCGCC  AGATGCGGCA  GCCCCGGCCA  GAGCGTGAGC  ATCAGCTGCA
6061  GCGGCAGCAG  CAGCAACATC  GGCAACAACT  ACGTGTACTG  GTACCAGCAC  CTGCCCGGCA
6121  CCGGGCCCAA  GCTGCTGATC  TACAGCGACA  CCAAGAGACC  CAGCGGCGTG  CCCGACAGAA
6181  TCAGCGGCAG  CAAGAGCGGC  ACCAGCGCCA  GCCTGGCCAT  CAGCGGCCTG  CAGAGCGAGG
6241  ACGAGGCCGA  CTACTACTGC  GCCAGCTGGG  ACGACAGGCT  GGACGGCCCC  GTGTTCGGGG
6301  GCGGCACCAA  GCTGACCGTG  CTGGGCCAGC  CCAAGGCCAA  CCCCACCGTG  ACCCTGTTCC
6361  CCCCCAGCAG  CGAGGAGCTG  CAGGCCAACA  AGGCCACCCT  GGTGTGCCTG  ATCAGCGACT
6421  TCTACCCCGG  CGCCGTGACC  GTGGCCTGGA  AGGCCGACGG  CAGCCCCGTG  AAGGCCGGCG
6481  TGGAGACCAC  CAAGCCCAGC  AAGCAGAGCA  ACAACAAGTA  CGCCGCCAGC  AGCTACCTGA
6541  GCCTGACCCC  CGAGCAGTGG  AAGAGCCACA  GAAGCTACAG  CTGCCAGGTG  ACCCACGAGG
6601  GCAGCACCGT  GGAGAAGACC  GTGGCCCCCA  CCGAGTGCAG  CTAACAACTT  TATTATACAT
6661  AGTTGATCAA  TTCCAACTTT  ATTATACATA  GTTGATCAAT  TCCGATAATC  AACCTCTGGA
6721  TTACAAAATT  TGTGAAAGAT  TGACTGGTAT  TCTTAACTAT  GTTGCTCCTT  TTACGCTATG
6781  TGGATACGCT  GCTTTAATGC  CTTTGTATCA  TGCTATTGCT  TCCCGTATGG  CTTTCATTTT
6841  CTCCTCCTTG  TATAAATCCT  GGTTGCTGTC  TCTTTATGAG  GAGTTGTGGC  CCGTTGTCAG
6901  GCAACGTGGC  GTGGTGTGCA  CTGTGTTTGC  TGACGCAACC  CCCACTGGTT  CGGGCATTGC
6961  CACCACCTGT  CAGCTCCTTT  CCGGGACTTT  CGCTTTCCCC  CTCCCTATTG  CCACGGCGGA
7021  ACTCATCGCG  GCCTGCGTTG  CCCGCTGCTG  GACAGGGCCT  CGGCTGTTGG  GCACTGACAA
7081  TTCCGTGGTG  TTGTCGGGGA  AGCTGACGTC  CTTTCCATGG  CTGCTCGCCT  GTGTTGCCAC
7141  CTGGATTCTG  CGCGGGACGT  CCTTCTGCTA  CCTCCCTTCG  GCCCTCAATC  GCCCTCAATC
7201  TCCTTCCCGC  CGGCTCTGCG  GCCTCTTCCG  GCCTCTTCCG  CGTCTTCGCC  TTCGCCCTCA
7261  GACGACTCGG  ATCTCCCTTT  GGGCCGCCTC  CCCGCATCGG  GAATTCCCGC  GGTTCGCTTT
7321  AAGACCAATG  ACTTACAAGG  CAGCTGTAGA  TCTTAGCCAC  TTTTTAAAAG  AAAAGGGGGG
7381  ACTGGAAGGG  CTAATTCACT  CCCAACGAAG  ACAAGATCTG  CTTTTTGCTT  GTACTGGGTC
7441  TCTCTGGTTA  GACCAGATCT  GAGCCTGGGA  GCTCTCTGGC  TAACTAGGGA  ACCCACTGCT
7501  TAAGCCTCAA  TAAAGCTTGC  CTTGAGTGCT  TCAAGTAGTG  TGTGCCCGTC  TGTTGTGTGA
7561  CTCTGGTAAC  TAGAGATCCC  TCAGACCCTT  TTAGTCACTG  TGGAAAATCT  CTAGCAGTAG
7621  TAGTTCATGT  CATCTTATTA  TTCAGTATTT  ATAACTTGCA  AAGAAATGAA  TATCAGAGAG
7681  TGAGAGGAAC  TTGTTTATTG  CAGCTTATAA  TGGTTACAAA  TAAAGCAATA  GCATCACAAA
7741  TTTCACAAAT  AAAGCATTTT  TTTCACTGCA  TTCTAGTTGT  GGTTTGTCCA  AACTCATCAA
7801  TGTATCTTAT  CATGTGTGGC  TCTAGCTATC  CCGCCCCTAA  CTCCGCCCAT  CCCGCCCCTA
7861  ACTCCGCCCA  GTTCCGCCCA  TTCTCCGCCC  CATGGCTGAC  TATTTTTTTT  TATTTATGCA
7921  GAGGCCGAGG  CCGCCTCGGC  CTCTGAGCTA  TTCCAGAAGT  ACTGAGGAGG  CTTTTTTGCA
7981  GGCCTAGGGA  CGTACCCAAT  TCGCCCTATA  GTGAGTCGTA  TTACGCGCGC  TCACTGGCCG
8041  TCGTTTTACA  ACGTCGTGAC  TGGGAAAACC  CTGGCGTTAC  CCAACTTAAT  CGCCTTGCAG
8101  CACATCCCCC  TTTCGCCAGC  TGGCGTAATA  GCGAAGAGGC  CCGCACCGAT  CGCCCTTCCC
8161  AACAGTTGCG  CAGCCTGAAT  GGCGAATGGG  ACGCGCCCTG  TAGCGGCGCA  TTAAGCGCGG
8221  CGGGTGTGGT  GGTTACGCGC  AGCGTGACCG  CTACACTTGC  CAGCGCCCTA  GCGCCCGCTC
8281  CTTTCGCTTT  CTTCCCTTCC  TTTCTCGCCA  CGTTCGCCGG  CTTTCCCCGT  CAAGCTCTAA
8341  ATCGGGGGCT  CCCTTTAGGG  TTCCGATTTA  GTGCTTTACG  GCACCTCGAC  CCCAAAAAAC
8401  TTGATTAGGG  TGATGGTTCA  CGTAGTGGGC  CATCGCCCTG  ATAGACGGTT  TTTCGCCCTT
8461  TGACGTTGGA  GTCCACGTTC  TTTAATAGTG  GACTCTTGTT  CCAAACTGGA  ACAACACTCA
8521  ACCCTATCTC  GGTCTATTCT  TTTGATTTAT  AAGGGATTTT  GCCGATTTCG  GCCTATTGGT
8581  TAAAAAATGA  GCTGATTTAA  CAAAAATTTA  ACGCGAATTT  TAACAAAATA  TTAACGCTTA
8641  CAATTTAGGT  GGCACTTTTC  GGGGAAATGT  GCGCGGAACC  CCTATTTGTT  TATTTTTCTA
8701  AATACATTCA  AATATGTATC  CGCTCATGAG  ACAATAACCC  TGATAAATGC  TTCAATAATA
8761  TTGAAAAAGG  AAGAGTATGA  GTATTCAACA  TTTCCGTGTC  GCCCTTATTC  CCTTTTTTGC
8821  GGCATTTTGC  CTTCCTGTTT  TTGCTCACCC  AGAAACGCTG  GTGAAAGTAA  AAGATGCTGA
8881  AGATCAGTTG  GGTGCACGAG  TGGGTTACAT  CGAACTGGAT  CTCAACAGCG  GTAAGATCCT
```

FIG. 4B-3

```
 8941 TGAGAGTTTT CGCCCCGAAG AACGTTTTCC AATGATGAGC ACTTTTAAAG TTCTGCTATG
 9001 TGGCGCGGTA TTATCCCGTA TTGACGCCGG GCAAGAGCAA CTCGGTCGCC GCATACACTA
 9061 TTCTCAGAAT GACTTGGTTG AGTACTCACC AGTCACAGAA AAGCATCTTA CGGATGGCAT
 9121 GACAGTAAGA GAATTATGCA GTGCTGCCAT AACCATGAGT GATAACACTG CGGCCAACTT
 9181 ACTTCTGACA ACGATCGGAG GACCGAAGGA GCTAACCCCT TTTTTGCACA ACATGGGGGA
 9241 TCATGTAACT CGCCTTGATC GTTGGGAACC GGAGCTGAAT GAAGCCATAC CAAACGACGA
 9301 GCGTGACACC ACGATGCCTG TAGCAATGGC AACAACGTTG CGCAAACTAT TAACTGGCGA
 9361 ACTACTTACT CTAGCTTCCC GGCAACAATT AATAGACTGG ATGGAGGCGG ATAAAGTTGC
 9421 AGGACCACTT CTGCGCTCGG CCCTTCCGGC TGGCTGGTTT ATTCGTGATA AATCTGGAGC
 9481 CGGTGAGCGT GGGTCTCGCG GTATCATTGC AGCACTGGGG CCAGATGGTA AGCCCTCCCG
 9541 TATCGTAGTT ATCTACACGA CGGGGAGTCA GGCAACTATG GATGAACGAA ATAGACAGAT
 9601 CGCTGAGATA GGTGCCTCAC TGATTAAGCA TTGGTAACTG TCAGACCAAG TTTACTCATA
 9661 TATACTTTAG ATTGATTTAA AACTTCATTT TTAATTTAAA AGGATCTAGG TGAAGATCCT
 9721 TTTTGATAAT CTCATGACCA AAATCCCTTA ACGTGAGTTT TCGTTCCACT GAGCGTCAGA
 9781 CCCCGTAGAA AAGATCAAAG GATCTTCTTG AGATCCTTTT TTTCTGCGCG TAATCTGCTG
 9841 CTTCCAAACA AAAAAACCAC CGCTACCAGC GGTGGTTTGT TTGCCGGATC AAGAGCTACC
 9901 AACTCTTTTT CCGAAGGTAA CTGGCTTCAG CAGAGCGCAG ATACCAAATA CTGTTCTTCT
 9961 AGTGTAGCCG TAGTTAGGCC ACCACTTCAA GAACTCTGTA GCACCGCCTA CATACCTCGC
10021 TCTGCTAATC CTGTTACCAG TGGCTGCTGC CAGTGGCGAT AAGTCGTGTC TTACCGGGTT
10081 GGACTCAAGA CGATAGTTAC CGGATAAGGC GCAGCGGTCG GGCTGAACGG GGGGTTCGTG
10141 CACACAGCCC AGCTTGGAGC GAACGACCTA CACCGAACTG AGATACCTAC AGCGTGAGCT
10201 ATGAGAAAGC GCCACGCTTC CCGAAGAGAG AAAGGCGGAC AGGTATCCGG TAAGCGGCAG
10261 GGTCGGAACA GGAGAGCGCA CGAGGGAGCT TCCAGGGGGA AACGCCTGGT ATCTTTATAG
10321 TCCTGTCGGG TTTCGCCACC TCTGACTTGA GCGTCGATTT TTGTGATGCT CGTCAGGGGG
10381 GCGGAGCCTA TGGAAAAACG CCAGCAACGC GGCCTTTTTA CGGTTCCTGG CCTTTTGCTG
10441 GCCTTTTGCT CACATGTTCT TTCCTGCGTT ATCCCCTGAT TCTGTGGATA ACCGTATTAC
10501 CGCCTTTGAG TGAGCTGATA CCGCTCGCCG CAGCCGAACG ACCGAGCGCA GCGAGTCAGT
10561 GAGCGAGGAA GCGGAAGAGC GCCCAATACG CAAACCGCCT CTCCCCGCGC GTTGGCCGAT
10621 TCATTAATGC AGCTGGCACG ACAGGTTTCC CGACTGGAAA GCGGGCAGTG AGCGCAACGC
10681 AATTAATGTG AGTTAGCTCA CTCATTAGGC ACCCCAGGCT TTACACTTTA TGCTTCCGGC
10741 TCGTATGTTG TGTGGAATTG TGAGCGGATA ACAATTTCAC ACAGGAAACA GCTATGACCA
10801 TGATTACGCC AAGCGCGCAA TTAACCCTCA CTAAAGGGAA CAAAAGCTGG AGCTGCAAGC
10861 TT
```

FIG. 5B
SEQ ID NO. 49

```
   1 AATGTAGTCT TATGCAATAC TCTTGTAGTC TTGCAACATG GTAACGATGA GTTAGCAACA
  61 TGCCTTACAA GGAGAGAAAA AGCACCGTGC ATGCCGATTG GTGGAAGTAA GGTGGTACGA
 121 TCGTGCCTTA TTAGGAAGGC AACAGACGGG TCTGACATGG ATTGGACGAA CCACTGAATT
 181 GCCGCATTGC AGAGATATTG TATTTAAGTG CCTAGCTCGA TACATAAACG GGTCTCTCTG
 241 GTTAGACCAG ATCTGAGCCT GGGAGCTCTC TGGCTAACTA GGGAACCCAC TGCTTAAGCC
 301 TCAATAAAGC TTGCCTTGAG TGCTTCAAGT AGTGTGTGCC CGTCTGTTGT GTGACTCTGG
 361 TAACTAGAGA TCCCTCAGAC CCTTTTAGTC AGTGTGGAAA ATCTCTAGCA GTGGCGCCCG
 421 AACAGGGACT TGAAAGCGAA AGGGAAACCA GAGGAGCTCT CTCGACGCAG GACTCGGCTT
 481 GCTGAAGCGC GCACGGCAAG AGGCGAGGGG CGGCGACTGG TGAGTACGCC AAAAATTTTG
 541 ACTAGCGGAG GCTAGAAGGA GAGAGATGGG TGCGAGAGCG TCAGTATTAA GCGGGGGAGA
 601 ATTAGATCGC GATGGGAAAA AATTCGGTTA AGGCCAGGGG GAAAGAAAAA ATATAAATTA
 661 AAACATATAG TATGGGCAAG CAGGGAGCTA GAACGATTCG CAGTTAATCC TGGCCTGTTA
 721 GAAACATCAG AAGGCTGTAG ACAAATACTG GGACAGCTAC AACCATCCCT TCAGACAGGA
 781 TCAGAAGAAC TTAGATCATT ATATAATACA GTAGCAACCC TCTATTGTGT GCATCAAAGG
 841 ATAGAGATAA AAGACACCAA GGAAGCTTTA GACAAGATAG AGGAAGAGCA AAACAAAAGT
 901 AAGACCACCG CACAGCAAGC GGCCGCTGAT CTTCAGACCT GGAGGAGGAG ATATGAGGGA
 961 CAATTGGAGA AGTGAATTAT ATAAATATAA AGTAGTAAAA ATTGAACCAT TAGGAGTAGC
1021 ACCCACCAAG GCAAAGAGAA GAGTGGTGCA GAGAGAAAAA AGAGCAGTGG GAATAGGAGC
1081 TTTGTTCCTT GGGTTCTTGG GAGCAGCAGG AAGCACTATG GGCGCAGCGT CAATGACGCT
1141 GACGGTACAG GCCAGACAAT TATTGTCTGG TATAGTGCAG CAGCAGAACA ATTTGCTGAG
1201 GGCTATTGAG GCGCAACAGC ATCTGTTGCA ACTCACAGTC TGGGGCATCA AGCAGCTCCA
1261 GGCAAGAATC CTGGCTGTGG AAAGATACCT AAAGGATCAA CAGCTCCTGG GGATTTGGGG
1321 TTGCTCTGGA AAACTCATTT GCACCACTGC TGTGCCTTGG AATGCTAGTT GGAGTAATAA
1381 ATCTCTGGAA CAGATTTGGA ATCACACGAC CTGGATGGAG TGGGACAGAG AAATTAACAA
1441 TTACACAAGC TTAATACACT CCTTAATTGA AGAATCGCAA AACCAGCAAG AAAAGAATGA
1501 ACAAGAATTA TTGGAATTAG ATAAATGGGC AAGTTTGTGG AATTGGTTTA ACATAACAAA
1561 TTGGCTGTGG TATATAAAAT TATTCATAAT GATAGTAGGA GGCTTGGTAG GTTTAAGAAT
1621 AGTTTTTGCT GTACTTTCTA TAGTGAATAG AGTTAGGCAG GGATATTCAC CATTATCGTT
1681 TCAGACCCAC CTCCCAACCC CGAGGGGACC CGACAGGCCC GAAGGAATAG AAGAAGAAGG
1741 TGGAGAGAGA GACAGAGACA GATCCATTCG ATTAGTGAAC GGATCTCGAC GGTATCGCTA
1801 GCTTTTAAAA GAAAAGGGGG GATTGGGGGG TACAGTGCAG GGGAAAGAAT AGTAGACATA
1861 ATAGCAACAG ACATACAAAC TAAAGAATTA CAAAAACAAA TTACAAAAAT TCAAAATTTT
1921 ACTAGTATCA ACTTTGTATA GAAAAGTTGG GCTCCGGTGC CCGTCAGTGG GCAGAGCGCA
1981 CATCGCCCAC AGTCCCCGAG AAGTTGGGGG GAGGGGTCGG CAATTGAACC GGTGCCTAGA
2041 GAAGGTGGCG CGGGGTAAAC TGGGAAAGTG ATGTCGTGTA CTGGCTCCGC CTTTTTCCCG
2101 AGGGTGGGGG AGAACCGTAT ATAAGTGCAG TAGTCGCCGT GAACGTTCTT TTTCGCAACG
2161 GGTTTGCCGC CAGAACACAG GTAAGTGCCG TGTGTGGTTC CCGCGGGCCT GGCCTCTTTA
2221 CGGGTTATGG CCCTTGCGTG CCTTGAATTA CTTCCACCTG GCTGCAGTAC GTGATTCTTG
2281 ATCCCGAGCT TCGGGTTGGA AGTGGGTGGG AGAGTTCGAG GCCTTGCGCT TAAGGAGCCC
2341 CTTCGCCTCG TGCTTGAGTT GAGGCCTGGC CTGGGCGCTG GGGCCGCCGC GTGCGAATCT
2401 GGTGGCACCT TCGCGCCTGT CTCGCTGCTT TCGATAAGTC TCTAGCCATT TAAAATTTTT
2461 GATGACCTGC TGCGACGCTT TTTTTCTGGC AAGATAGTCT TGTAAATGCG GGCCAAGATC
2521 TGCACACTGG TATTTCGGTT TTTGGGGCCG CGGGCGGCGA CGGGGCCCGT GCGTCCCAGC
2581 GCACATGTTC GGCGAGGCGG GGCCTGCGAG CGCGGCCACC GAGAATCGGA CGGGGGTAGT
2641 CTCAAGCTGG CCGGCCTGCT CTGGTGCCTG GTCTCGCGCC GCCGTGTATC GCCCCGCCCT
2701 GGGCGGCAAG GCTGGCCCGG TCGGCACCAG TTGCGTGAGC GGAAAGATGG CCGCTTCCCG
2761 GCCCTGCTGC AGGGAGCTCA AAATGGAGGA CGCGGCGCTC GGGAGAGCGG GCGGGTGAGT
2821 CACCCACACA AAGGAAAAGG GCCTTTCCGT CCTCAGCCGT CGCTTCATGT GACTCCACGG
2881 AGTACCGGGC GCCGTCCAGG CACCTCGATT AGTTCTCGAG CTTTTGGAGT ACGTCGTCTT
```

FIG. 5B-1

```
2941 TAGGTTGGGG GGAGGGGTTT TATGCGATGG AGTTTCCCCA CACTGAGTGG GTGGAGACTG
3001 AAGTTAGGCC AGCTTGGCAC TTGATGTAAT TCTCCTTGGA ATTTGCCCTT TTTGAGTTTG
3061 GATCTTGGTT CATTCTCAAG CCTCAGACAG TGGTTCAAAG TTTTTTTCTT CCATTTCAGG
3121 TGTCGTGACA AGTTTGTACA AAAAAGCAGG CTGCCACCAT GTGGCTGCAG AGCCTGCTGC
3181 TGCTGGGCAC CGTGGCCTGC AGCATCAGCG CCCCCGCCAG AAGCCCCAGC CCCAGCACCC
3241 AGCCCTGGGA GCACGTGAAC GCCATCCAGG AGGCCAGAAG ACTGCTGAAC CTGAGCAGAG
3301 ACACCGCCGC CGAGATGAAC GAGACCGTGG AGGTGATCAG CGAGATGTTC GACCTGCAGG
3361 AGCCCACCTG CCTGCAGACC AGACTGGAGC TGTACAAGCA GGGCCTGAGA GGCAGCCTGA
3421 CCAAGCTGAA GGGCCCCCTG ACCATGATGG CCAGCCACTA CAAGCAGCAC TGCCCCCCCA
3481 CCCCCGAGAC CAGCTGCGCC ACCCAGATCA TCACCTTCGA GAGCTTCAAG GAGAACCTGA
3541 AGGACTTCCT GCTGGTGATC CCCTTCGACT GCTGGGAGCC CGTGCAGGAG TAAAACAACA
3601 ACAATTGCAT TCATTTTATG TTTCAGGTTC AGGGGGAGGT GTGGGAGGTT TTTAAAGCA
3661 AGTAAAACCT CTACAAATGT GGTACGCGTT AACAACAACA ATTGCATTCA TTTTATGTTT
3721 CAGGTTCAGG GGGAGGTGTG GGAGGTTTTT TAAAGCAAGT AAAACCTCTA CAAATGTGGT
3781 ACGCGTTACC CAGCTTTCTT GTACAAAGTG GTAAATAGAT AGAACAACAA CAATTGCATT
3841 CATTTTTGAT TTCAGGTTCA GGGGGAGGTG TGGGAGGTTT TTTAAAGCAA GTAAAACCTC
3901 TACACTGACG GTACGCGTTA ACAACAACAA TTGCATTCAT TTGTAGTTTC AGGTTCAGGG
3961 GGAGGTGTGG GAGGTTTTTT AAAGCAAGTT AAACCTCTAA AATAGTGGTA CGCGTTACCC
4021 AGCTTTCTTG TACAAAGTGG ACCCAGCTTT CTTGTACAAA GTGGGCCCCT CTCCCTCCCC
4081 CCCCCCTAAC GTTACTGGCC GAAGCCGCTT GGAATAAGGC CGGTGTGCGT TTGTCTATAT
4141 GTTATTTTCC ACCATATTGC CGTCTTTTGG CAATGTGAGG GCCCGGAAAC CTGGCCCTGT
4201 CTTCTTGACG AGCATTCCTA GGGGTCTTTC CCCTCTCGCC AAAGGAATGC AAGGTCTGTT
4261 GAATGTCGTG AAGGAAGCAG TTCCTCTGGA AGCTTCTTGA AGACAAACAA CGTCTGTAGC
4321 GACCCTTTGC AGGCAGCGGA ACCCCCACC TGGCGACAGG TGCCTCTGCG GCCAAAAGCC
4381 ACGTGTATAA GATACACCTG CAAAGGCGGC ACAACCCCAG TGCCACGTTG TGAGTTGGAT
4441 AGTTGTGGAA AGAGTCAAAT GGCTCTCCTC AAGCGTATTC AACAAGGGGC TGAAGGATGC
4501 CCAGAAGGTA CCCCATTGTA TGGGATCTGA TCTGGGGCCT CGGTGCACAT GCTTTACATG
4561 TGTTTAGTCG AGGTTAAAAA AACGTCTAGG CCCCCCGAAC CACGGGGACG TGGTTTTCCT
4621 TTGAAAAACA CGATGATAAT ATGGCCACAA CCATGGCCAC CGTGCTGGCC CCCGCCTGGA
4681 GCCCCACCAC CTACCTGCTG CTGCTGCTGC TGCTGAGCAG CGGCCTGAGC GGCACCCAGG
4741 ACTGCAGCTT CCAGCACAGC CCCATCAGCA GCGACTTCGC CGTGAAGATC AGAGAGCTGA
4801 GCGACTACCT GCTGCAGGAC TACCCCGTGA CCGTGGCCAG CAACCTGCAG GACGAGGAGC
4861 TGTGCGGCGG CCTGTGGAGA CTGGTGCTGG CCCAGAGATG GATGGAGAGA CTGAAGACCG
4921 TGGCCGGCAG CAAGATGCAG GGCCTGCTGG AGAGAGTGAA CACCGAGATC CACTTCGTGA
4981 CCAAGTGCGC CTTCCAGCCC CCCCCCAGCT GCCTGAGATT CGTGCAGACC AACATCAGCA
5041 GACTGCTGCA GGAGACCAGC GAGCAGCTGG TGGCCCTGAA GCCCTGGATC ACCAGACAGA
5101 ACTTCAGCAG ATGCCTGGAG CTGCAGTGCC AGCCCGACAG CAGCACCCTG CCCCCCCCCT
5161 GGAGCCCCAG ACCCTGGAG GCCACCGCCC CCACCGCCCC CCAGCCCCCC CTGCTGCTGC
5221 TGCTGCTGCT GCCCGTGGGC CTGCTGCTGC TGGCCGCCGC CTGGTGCCTG CACTGGCAGA
5281 GAACCAGAAG AAGAACCCCC AGACCCGGCG AGCAGGTGCC CCCCGTGCCC AGCCCCCAGG
5341 ACCTGCTGCT GGTGGAGCAC TAACAACTTT ATTATACATA GTTGATCAAT TCCAACTTTA
5401 TTATACATAG TTGATCAATT CCGATAATCA ACCTCTGGAT TACAAAATTT GTGAAAGATT
5461 GACTGGTATT CTTAACTATG TTGCTCCTTT TACGCTATGT GGATACGCTG CTTTAATGCC
5521 TTTGTATCAT GCTATTGCTT CCCGTATGGC TTTCATTTTC TCCTCCTTGT ATAAATCCTG
5581 GTTGCTGTCT CTTTATGAGG AGTTGTGGCC CGTTGTCAGG CAACGTGGCG TGGTGTGCAC
5641 TGTGTTTGCT GACGCAACCC CCACTGGTTG GGGCATTGCC ACCACCTGTC AGCTCCTTTC
5701 CGGGACTTTC GCTTTCCCCC TCCCTATTGC CACGGCGGAA CTCATCGCCG CCTGCCTTGC
5761 CCGCTGCTGG ACAGGGGCTC GGCTGTTGGG CACTGACAAT TCCGTGGTGT TGTCGGGGAA
5821 GCTGACGTCC TTTCCATGGC TGCTCGCCTG TGTTGCCACC TGGATTCTGC GCGGGACGTC
5881 CTTCTGCTAC GTCCCTTCGG CCCTCAATCC AGCGGACCTT CCTTCCCGCG GCCTGCTGCC
5941 GGCTCTGCGG CCTCTTCCGC GTCTTCGCCT TCGCCCTCAG ACGAGTCGGA TCTCCCTTTG
6001 GGCCGCCTCC CCGCATCGGG AATTCCCGCG GTTCGCTTTA AGACCAATGA CTTACAAGGC
6061 AGCTGTAGAT CTTAGCCACT TTTTAAAAGA AAAGGGGGGA CTGGAAGGGC TAATTCACTC
```

FIG. 5B-2

```
6121 CCAACGAAGA CAAGATCTGC TTTTTGCTTG TACTGGGTCT CTCTGGTTAG ACCAGATCTG
6181 AGCCTGGGAG CTCTCTGGCT AACTAGGGAA CCCACTGCTT AAGCCTCAAT AAAGCTTGCC
6241 TTGAGTGCTT CAAGTAGTGT GTGCCCGTCT GTTGTGTGAC TCTGGTAACT AGAGATCCCT
6301 CAGACCCTTT TAGTCAGTGT GGAAAATCTC TAGCAGTAGT AGTTCATGTC ATCTTATTAT
6361 TCAGTATTTA TAACTTGCAA AGAAATGAAT ATCAGAGAGT GAGAGGAACT TGTTTATTGC
6421 AGCTTATAAT GGTTACAAAT AAAGCAATAG CATCACAAAT TTCACAAATA AAGCATTTTT
6481 TTCACTGCAT TCTAGTTGTG GTTTGTCCAA ACTCATCAAT GTATCTTATC ATGTCTGGCT
6541 CTAGCTATCC CGCCCCTAAC TCCGCCCATC CCGCCCCTAA CTCCGCCCAG TTCCGCCCAT
6601 TCTCCGCCCC ATGGCTGACT AATTTTTTTT ATTTATGCAG AGGCCGAGGC CGCCTCGGCC
6661 TCTGAGCTAT TCCAGAAGTA GTGAGGAGGC TTTTTTGGAG GCCTAGGGAC GTACCCAATT
6721 CGCCCTATAG TGAGTCGTAT TACGCGCGCT CACTGGCCGT CGTTTTACAA CGTCGTGACT
6781 GGGAAAACCC TGGCGTTACC CAACTTAATC GCCTTGCAGC ACATCCCCCT TTCGCCAGCT
6841 GGCGTAATAG CGAAGAGGCC CGCACCGATC GCCCTTCCCA ACAGTTGCGC AGCCTGAATG
6901 GCGAATGGGA CGCGCCCTGT AGCGGCGCAT TAAGCGCGGC GGGTGTGGTG GTTACGCGCA
6961 GCGTGACCGC TACACTTGCC AGCGCCCTAG CGCCCGCTCC TTTCGCTTTC TTCCCTTCCT
7021 TTCTCGCCAC GTTCGCCGGC TTTCCCCGTC AAGCTCTAAA TCGGGGCTC CCTTTAGGGT
7081 TCCGATTTAG TGCTTTACGG CACCTCGACC CCAAAAAACT TGATTAGGGT GATGGTTCAC
7141 GTAGTGGGCC ATCGCCCTGA TAGACGGTTT TTCGCCCTTT GACGTTGGAG TCCACGTTCT
7201 TTAATAGTGG ACTCTTGTTC CAAACTGGAA CAACACTCAA CCCTATCTCG GTCTATTCTT
7261 TTGATTTATA AGGGATTTTG CCGATTTCGG CCTATTGGTT AAAAAATGAG CTGATTTAAC
7321 AAAAATTTAA CGCGAATTTT AACAAAATAT TAACGCTTAC AATTTAGGTG GCACTTTTCG
7381 GGGAAATGTG CGCGGAACCC CTATTTGTTT ATTTTTCTAA ATACATTCAA ATATGTATCC
7441 GCTCATGAGA CAATAACCCT GATAAATGCT TCAATAATAT TGAAAAAGGA AGAGTATGAG
7501 TATTCAACAT TTCCGTGTCG CCCTTATTCC CTTTTTTGCG GCATTTGCC TTCCTGTTTT
7561 TGCTCACCCA GAAACGCTGG TGAAAGTAAA AGATGCTGAA GATCAGTTGG GTGCACGAGT
7621 GGGTTACATC GAACTGGATC TCAACAGCGG TAAGATCCTT GAGAGTTTTC GCCCCGAAGA
7681 ACGTTTTCCA ATGATGAGCA CTTTTAAAGT TCTGCTATGT GGCGCGGTAT TATCCCGTAT
7741 TGACGCCGGG CAAGAGCAAC TCGGTCGCCG CATACACTAT TCTCAGAATG ACTTGGTTGA
7801 GTACTCACCA GTCACAGAAA AGCATCTTAC GGATGGCATG ACAGTAAGAG AATTATGCAG
7861 TGCTGCCATA ACCATGAGTG ATAACACTGC GGCCAACTTA CTTCTGACAA CGATCGGAGG
7921 ACCGAAGGAG CTAACCGCTT TTTTGCACAA CATGGGGGAT CATGTAACTC GCCTTGATCG
7981 TTGGGAACCG GAGCTGAATG AAGCCATACC AAACGACGAG CGTGACACCA CGATGCCTGT
8041 AGCAATGGCA ACAACGTTGC GCAAACTATT AACTGGCGAA CTACTTACTC TAGCTTCCCG
8101 GCAACAATTA ATAGACTGGA TGGAGGCGGA TAAAGTTGCA GGACCACTTC TGCGCTCGGC
8161 CCTTCCGGCT GGCTGGTTTA TTGCTGATAA ATCTGGAGCC GGTGAGCGTG GGTCTCGCGG
8221 TATCATTGCA GCACTGGGGC CAGATGGTAA GCCCTCCGT ATCGTAGTTA TCTACACGAC
8281 GGGGAGTCAG GCAACTATGG ATGAACGAAA TAGACAGATC GCTGAGATAG GTGCCTCACT
8341 GATTAAGCAT TGGTAACTGT CAGACCAAGT TTACTCATAT ATACTTTAGA TTGATTTAAA
8401 ACTTCATTTT TAATTTAAAA GGATCTAGGT GAAGATCCTT TTTGATAATC TCATGACCAA
8461 AATCCCTTAA CGTGAGTTTT CGTTCCACTG AGCGTCAGAC CCCGTAGAAA AGATCAAAGG
8521 ATCTTCTTGA GATCCTTTTT TTCTGCGCGT AATCTGCTGC TTGCAAACAA AAAAACCACC
8581 GCTACCAGCG GTGGTTTGTT TGCCGGATCA AGAGCTACCA ACTCTTTTTC CGAAGGTAAC
8641 TGGCTTCAGC AGAGCGCAGA TACCAAATAC TGTCTTCTA GTGTAGCCGT AGTTAGGCCA
8701 CCACTTCAAG AACTCTGTAG CACCGCCTAC ATACCTCGCT CTGCTAATCC TGTTACCAGT
8761 GGCTGCTGCC AGTGGCGATA AGTCGTGTCT TACCGGGTTG GACTCAAGAC GATAGTTACC
8821 GGATAAGGCG CAGCGGTCGG GCTGAACGGG GGGTTCGTGC ACACAGCCCA GCTTGGAGCG
8881 AACGACCTAC ACCGAACTGA GATACCTACA GCGTGAGCTA TGAGAAAGCG CCACGCTTCC
8941 CGAAGAGAGA AAGGCGGACA GGTATCCGGT AAGCGGCAGG GTCGGAACAG GAGAGCGCAC
9001 GAGGGAGCTT CCAGGGGGAA ACGCCTGGTA TCTTTATAGT CCTGTCGGGT TTCGCCACCT
9061 CTGACTTGAG CGTCGATTTT TGTGATGCTC GTCAGGGGGG CGGAGCCTAT GGAAAAACGC
9121 CAGCAACGCG GCCTTTTTAC GGTTCCTGGC CTTTTGCTGG CCTTTTGCTC ACATGTTCTT
9181 TCCTGCGTTA TCCCCTGATT CTGTGGATAA CCGTATTACC GCCTTTGAGT GAGCTGATAC
9241 CGCTCGCCGC AGCCGAACGA CCGAGCGCAG CGAGTCAGTG AGCGAGGAAG CGGAAGAGCG
```

FIG. 5B-3

```
9301 CCCAATACGC AAACCGCCTC TCCCCGCGCG TTGGCCGATT CATTAATGCA GCTGGCACGA
9361 CAGGTTTCCC GACTGGAAAG CGGGCAGTGA GCGCAACGCA ATTAATGTGA GTTAGCTCAC
9421 TCATTAGGCA CCCCAGGCTT TACACTTTAT GCTTCCGGCT CGTATGTTGT GTGGAATTGT
9481 GAGCGGATAA CAATTTCACA CAGGAAACAG CTATGACCAT GATTACGCCA AGCGCGCAAT
9541 TAACCCTCAC TAAAGGGAAC AAAAGCTGGA GCTGCAAGCT T
```

FIG. 6B
SEQ ID NO. 50

```
   1  AATGTAGTCT TATGCAATAC TCTTGTAGTC TTGCAACATG GTAACGATGA GTTAGCAACA
  61  TGCCTTACAA GGAGAGAAAA AGCACCGTGC ATGCCGATTG GTGGAAGTAA GGTGGTACGA
 121  TCGTGCCTTA TTAGGAAGGC AACAGACGGG TCTGACATGG ATTGGACGAA CCACTGAATT
 181  GCCGCATTGC AGAGATATTG TATTTAAGTG CCTAGCTCGA TACATAAACG GGTCTCTCTG
 241  GTTAGACCAG ATCTGAGCCT GGGAGCTCTC TGGCTAACTA GGGAACCCAC TGCTTAAGCC
 301  TCAATAAAGC TTGCCTTGAG TGCTTCAAGT AGTGTGTGCC CGTCTGTTGT GTGACTCTGG
 361  TAACTAGAGA TCCCTCAGAC CTTTTAGTC AGTGTGGAAA ATCTCTAGCA GTGGCGCCCG
 421  AACAGGGACT TGAAAGCGAA AGGGAAACCA GAGGAGCTCT CTCGACGCAG GACTCGGCTT
 481  GCTGAAGCGC GCACGGCAAG AGGCGAGGGG CGGCGACTGG TGAGTACGCC AAAAATTTTG
 541  ACTAGCGGAG GCTAGAAGGA GAGAGATGGG TGCGAGAGCG TCAGTATTAA GCGGGGGAGA
 601  ATTAGATCGC GATGGGAAAA AATTCGGTTA AGGCCAGGGG GAAAGAAAAA ATATAAATTA
 661  AAACATATAG TATGGGCAAG CAGGGAGCTA GAACGATTCG CAGTTAATCC TGGCCTGTTA
 721  GAAACATCAG AAGGCTGTAG ACAAATACTG GGACAGCTAC AACCATCCCT TCAGACAGGA
 781  TCAGAAGAAC TTAGATCATT ATATAATACA GTAGCAACCC TCTATTGTGT GCATCAAAGG
 841  ATAGAGATAA AAGACACCAA GGAAGCTTTA GACAAGATAG AGGAAGAGCA AAACAAAAGT
 901  AAGACCACCG CACAGCAAGC GGCCGCTGAT CTTCAGACCT GGAGGAGGAG ATATGAGGGA
 961  CAATTGGAGA AGTGAATTAT ATAAATATAA AGTAGTAAAA AGAGCAGTGG GAATAGGAGC
1021  ACCCACCAAG GCAAAGAGAA GAGTGGTGCA GAGAGAAAAA AGAGCAGTGG GAATAGGAGC
1081  TTTGTTCCTT GGGTTCTTGG GAGCAGCAGG AAGCACTATG GGCGCAGCGT CAATGACGCT
1141  GACGGTACAG GCCAGACAAT TATTGTCTGG TATAGTGCAG CAGCAGAACA ATTTGCTGAG
1201  GGCTATTGAG GCGCAACAGC ATCTGTTGCA ACTCACAGTC TGGGGCATCA AGCAGCTCCA
1261  GGCAAGAATC CTGGCTGTGG AAAGATACCT AAAGGATCAA CAGCTCCTGG GGATTTGGGG
1321  TTGCTCTGGA AAACTCATTT GCACCACTGC TGTGCCTTGG AATGCTAGTT GGAGTAATAA
1381  ATCTCTGGAA CAGATTTGGA ATCACACGAC CTGGATGGAG TGGGACAGAG AAATTAACAA
1441  TTACACAAGC TTAATACACT CCTTAATTGA AGAATCGCAA AACCAGCAAG AAAAGAATGA
1501  ACAAGAATTA TTGGAATTAG ATAAATGGGC AAGTTTGTGG AATTGGTTTA ACATAACAAA
1561  TTGGCTGTGG TATATAAAT TATTCATAAT GATAGTAGGA GGCTTGGTAG GTTTAAGAAT
1621  AGTTTTGCT GTACTTTCTA TAGTGAATAG AGTTAGGCAG GGATATTCAC CATTATCGTT
1681  TCAGACCCAC CTCCCAACCC CGAGGGGACC CGACAGGCCC GAAGGAATAG AAGAAGAAGG
1741  TGGAGAGAGA GACAGAGACA GATCCATTCG ATTAGTGAAC GGATCTCGAC GGTATCGCTA
1801  GCTTTTAAAA GAAAAGGGGG GATTGGGGGG TACAGTGCAG GGGAAAGAAT AGTAGACATA
1861  ATAGCAACAG ACATACAAAC TAAAGAATTA CAAAAACAAA TTACAAAAAT TCAAAATTTT
1921  ACTAGTATCA ACTTTGTATA GAAAAGTTGG GCTCCGGTGC CCGTCAGTGG GCAGAGCGCA
1981  CATCGCCCAC AGTCCCCGAG AAGTTGGGGG GAGGGGTCGG CAATTGAACC GGTGCCTAGA
2041  GAAGGTGGCG CGGGGTAAAC TGGGAAAGTG ATGTCGTGTA CTGGCTCCGC CTTTTTCCCG
2101  AGGGTGGGGG AGAACCGTAT ATAAGTGCAG TAGTCGCCGT GAACGTTCTT TTTCGCAACG
2161  GGTTTGCCGC CAGAACACAG GTAAGTGCCG TGTGTGGTTC CCGCGGGCCT GGCCTCTTTA
2221  CGGGTTATGG CCCTTGCGTG CCTTGAATTA CTTCCACCTG GCTGCAGTAC GTGATTCTTG
2281  ATCCCGAGCT TCGGGTTGGA AGTGGGTGGG AGAGTTCGAG GCCTTGCGCT TAAGGAGCCC
2341  CTTCGCCTCG TGCTTGAGTT GAGGCCTGGC CTGGGCGCTG GGGCCGCCGC GTGCGAATCT
2401  GGTGGCACCT TCGCGCCTGT CTCGCTGCTT TCGATAAGTC TCTAGCCATT TAAAATTTTT
2461  GATGACCTGC TGCGACGCTT TTTTTCTGGC AAGATAGTCT TGTAAATGCG GGCCAAGATC
2521  TGCACACTGG TATTTCGGTT TTTGGGGCCG CGGGCGGCGA CGGGGCCCGT GCGTCCCAGC
2581  GCACATGTTC GGCGAGGCGG GGCCTGCGAG CGCGGCCACC GAGAATCGGA CGGGGGTAGT
2641  CTCAAGCTGG CCGGCCTGCT CTGGTGCCTG GTCTCGCGCC GCCGTGTATC GCCCCGCCCT
2701  GGGCGGCAAG GCTGGCCCGG TCGGCACCAG TTGCGTGAGC GGAAAGATGG CCGCTTCCCG
2761  GCCCTGCTGC AGGGAGCTCA AAATGGAGGA CGCGGCGCTC GGGAGAGCGG GCGGGTGAGT
2821  CACCCACACA AAGGAAAAGG GCCTTTCCGT CCTCAGCCGT CGCTTCATGT GACTCCACGG
2881  AGTACCGGGC GCCGTCCAGG CACCTCGATT AGTTCTCGAG CTTTTGGAGT ACGTCGTCTT
```

FIG. 6B-1

```
2941 TAGGTTGGGG GGAGGGGTTT TATGCGATGG AGTTTCCCCA CACTGAGTGG GTGGAGACTG
3001 AAGTTAGGCC AGCTTGGCAC TTGATGTAAT TCTCCTTGGA ATTTGCCCTT TTTGAGTTTG
3061 GATCTTGGTT CATTCTCAAG CCTCAGACAG TGGTTCAAAG TTTTTTTCTT CCATTTCAGG
2121 TGTCGTGACA AGTTTGTACA AAAAAGCAGG CTGCCACCAT GACCGTGCTG GCCCCCGCCT
3181 GGAGCCCCAC CACCTACCTG CTGCTGCTGC TGCTGCTGAG CAGCGGCCTG AGCGGCACCC
3241 AGGACTGCAG CTTCCAGCAC AGCCCCATCA GCAGCGACTT CGCCGTGAAG ATCAGAGAGC
3301 TGAGCGACTA CCTGCTGCAG GACTACCCCG TGACCGTGGC CAGCAACCTG CAGGACGAGG
3361 AGCTGTGCGG CGGCCTGTGG AGACTGGTGC TGGCCCAGAG ATGGATGGAG AGACTGAAGA
3421 CCGTGGCCGG CAGCAAGATG CAGGGCCTGC TGGAGAGAGT GAACACCGAG ATCCACTTCG
3481 TGACCAAGTG CGCCTTCCAG CCCCCCCCCA GCTGCCTGAG ATTCGTGCAG ACCAACATCA
3541 GCAGACTGCT GCAGGAGACC AGCGAGCAGC TGGTGGCCCT GAAGCCCTGG ATCACCAGAC
3601 AGAACTTCAG CAGATGCCTG GAGCTGCAGT GCCAGCCCGA CAGCAGCACC CTGCCCCCCC
3661 CCTGGAGCCC CAGACCCCTG GAGCTGCAGT CCCCCACCGC CCCCCAGTAA AACAACAACA
3721 ATTGCATTCA TTTTATGTTT CAGGTTCAGG GGGAGGTGTG GGAGGTTTTT TAAAGCAAGT
3781 AAAACCTCTA CAAATGTGGT ACGCGTTAAC AACAACAATT GCATTCATTT TAAAGCAAGT
3841 GTTCAGGGGG AGGTGTGGGA GGTTTTTTAA AGCAAGTAAA ACCTCTACAA ATGTGGTACG
3901 CGTTACCCAG CTTTCTTGTA CAAAGTGGTA AATAGATAGA ACAACAACAA TTGCATTCAT
3961 TTTTGATTTC AGGTTCAGGG GGAGGTGTGG GAGGTTTTTT AAAGCAAGTA AAACCTCTAC
4021 ACTGACGGTA CGCCGTTAACA ACAACAATTG CATTCATTTG TAGTTTCAGG TTCAGGGGGA
4081 GGTGTGGGAG GTTTTTTAAA GCAAGTTAAA CCTCTAAAAT AGTGGTACGC GTTACCCAGC
4141 TTTCTTGTAC AAAGTGGACC CAGCTTTCTT GTACAAAGTG GCCCCTCTC CCTCCCCCCC
4201 CCCTAACGTT ACTGGCCGAA GCCGCTTGGA ATAAGGCCGG TGTGCGTTTG TCTATATGTT
4261 ATTTTCCACC ATATTGCCGT CTTTTGGCAA TGTGAGGGCC CGGAAACCTG GCCCTGTCTT
4321 CTTGACGAGC ATTCCTAGGG GTCTTTCCCC TCTCGCCAAA GGAATGCAAG GTCTGTTGAA
4381 TGTCGTGAAG GAAGCAGTTC CTCTGGAAGC TTCTTGAAGA CAAACAACGT CTGTAGCGAC
4441 CCTTTGCAGG CAGCGGAACC CCCCACCTGG CGACAGGTGC CTCTGCGGCC CCCGCCAGAA
4501 TGTATAAGAT ACACCTGCAA AGGCGGCACA TGGCCACCGT GCTGGCCCCC GCCTGGAGCC
4561 TGTGGAAAGA GTCAAATGGC TCTCCTCAAG CGTATTCAAC AAGGGGCTGA AGGATGCCCA
4621 GAAGGTACCC CATTGTATGG GATCTGATCT GGGGCCTCGG TGCACATGCT TTACATGTGT
4681 TTAGTCGAGG TTAAAAAAAC GTCTAGGCCC CCCGAACCAC GGGGACGTGG TTTTCCTTTG
4741 AAAAACACGA TGATAATATG GCCACAACCA TGGCCACCGT GCTGGCCCCC GCCTGGAGCC
4801 CCACCACCTA CCTGCTGCTG CTGCTGCTGC TGAGCAGCGG CCTGAGCGCC CCCGCCAGAA
4861 GCCCCAGCCC CAGCACCCAG CCCTGGGAGC ACGTGAACGC CATCCAGGAG GCCAGAAGAC
4921 TGCTGAACCT GAGCAGAGAC ACCGCCGCCG AGATGAACGA GACCGTGGAG GCCAGAAGAC
4981 AGATGTTCGA CCTGCAGGAG CCCACCTGCC TGCAGACCAG ACTGGAGCTG TACAAGCAGG
5041 GCCTGAGAGG CAGCCTGACC AAGCTGAAGG GCCCCCTGAC CATGATGGCC AGCCACTACA
5101 AGCAGCACTG CCCCCCCACC CCCGAGACCA GCTGCGCCAC CCAGATCATC ACCTTCGAGA
5161 GCTTCAAGGA GAACCTGAAG GACTTCCTGC TGGTGATCCC CTTCGACTGC TGGGAGCCCG
5221 TGCAGGAGCC CACCACCACC CCCGCCCCCA GACCCCCAC CCCCGCCCCC ACCATCGCCA
5281 GCCAGCCCCT GAGCCTGAGA CCCGAGGCCT GCAGACCCGC CGCCGGCGGC GCCGTGCACA
5341 CCAGAGGCCT GGACTTCGCC TGCGACATCT ACATCTGGGC CCCCCTGGCC GGCACCTGCG
5401 GCGTGCTGCT GCTGAGCCTG GTGATCACCC TGTACTGCAA CCACAGAAAC AGAAGAAGAG
5461 TGTGCAAGTG CCCCAGACCC GTGGTGAAGA GCGGCGACAA GCCCAGCCTG AGCGCCAGAT
5521 ACGTGTAACA ACTTTATTAT ACATAGTTGA TCAATTCCAA CTTTATTATA CATAGTTGAT
5581 CAATTCCGAT AATCAACCTC TGGATTACAA AATTTGTGAA AGATTGACTG GTATTCTTAA
5641 CTATGTTGCT CCTTTTACGC TATGTGGATA CGCTGCTTTA ATGCCTTTGT ATCATGCTAT
5701 TGCTTCCCGT ATGGCTTTCA TTTTCTCCTC CTTGTATAAA TCCTGGTTGC TGTCTCTTTA
5761 TGAGGAGTTG TGGCCCGTTG TCAGGCAACG TGGCGTGGTG TGCACTGTGT TTGCTGACGC
5821 AACCCCCACT GGTTGGGGCA TTGCCACCAC CTGTCAGCTC CTTTCCGGGA CTTTCGCTTT
5881 CCCCCTCCCT ATTGCCACGG CGGAACTCAT CGCCGCCTGC CTTGCCCGCT GCTGGACAGG
5941 GGCTCGGCTG TTGGGCACTG ACAATTCCGT GGTGTTGTCG CTTGCCCGCT GCTGGACAGG
6001 ATGGCTGCTC GCCTGTGTTG CCACCTGGAT TCTGCGCGGG ACGTCCTTCT GCTACGTCCC
6061 TTCGGCCCTC AATCCAGCGG ACCTTCCTTC CGCGGCCCTG CTGCCGGCTC TGCGGCCTCT
```

FIG. 6B-2

```
6121 TCCGCGTCTT CGCCTTCGCC CTCAGACGAG TCGGATCTCC CTTTGGGCCG CCTCCCCGCA
6181 TCGGGAATTC CCGCGGTTCG CTTTAAGACC AATGACTTAC AAGGCAGCTG TAGATCTTAG
6241 CCACTTTTTA AAAGAAAAGG GGGGACTGGA AGGGCTAATT CACTCCCAAC GAAGACAAGA
6301 TCTGCTTTTT GCTTGTACTG GGTCTCTCTG GTTAGACCAG ATCTGAGCCT GGGAGCTCTC
6361 TGGCTAACTA GGGAACCCAC TGCTTAAGCC TCAATAAAGC TTGCCTTGAG TGCTTCAAGT
6421 AGTGTGTGCC CGTCTGTTGT GTGACTCTGG TAACTAGAGA TCCCTCAGAC CCTTTTAGTC
6481 AGTGTGGAAA ATCTCTAGCA GTAGTAGTTC ATGTCATCTT ATTATTCAGT ATTTATAACT
6541 TGCAAAGAAA TGAATATCAG AGAGTGAGAG GAACTTGTTT ATTGCAGCTT ATAATGGTTA
6601 CAAATAAAGC AATAGCATCA CAAATTTCAC AAATAAAGCA TTTTTTTCAC TGCATTCTAG
6661 TTGTGGTTTG TCCAAACTCA TCAATGTATC TTATCATGTC TGGCTCTAGC TATCCCGCCC
6721 CTAACTCCGC CCATCCCGCC CCTAACTCCG CCCAGTTCCG CCCATTCTCC GCCCCATGGC
6781 TGACTAATTT TTTTTATTTA TGCAGAGGCC GAGGCCGCCT CGGCCTCTGA GCTATTCCAG
6841 AAGTAGTGAG GAGGCTTTTT TGGAGGCCTA GGGACGTACC CAATTCGCCC TATAGTGAGT
6901 CGTATTACGC GCGCTCACTG GCCGTCGTTT TACAACGTCG TGACTGGGAA AACCCTGGCG
6961 TTACCCAACT TAATCGCCTT GCAGCACATC CCCCTTTCGC CAGCTGGCGT AATAGCGAAC
7021 AGGCCCGCAC CGATCGCCCT TCCCAACAGT TGCGCAGCCT GAATGGCGAA TGGGACGCGC
7081 CCTGTAGCGG CGCATTAAGC GCGGCGGGTG TGGTGGTTAC GCGCAGCGTG ACCGCTACAC
7141 TTGCCAGCGC CCTAGCGCCC GCTCCTTTCG CTTTCTTCCC TTCCTTTCTC GCCACGTTCG
7201 CCGGCTTTCC CCGTCAAGCT CTAAATCGGG GGCTCCCTTT AGGGTTCCGA TTTAGTGCTT
7261 TACGGCACCT CGACCCCAAA AAACTTGATT AGGGTGATGG TTCACGTAGT GGGCCATCGC
7321 CCTGATAGAC GGTTTTTCGC CCTTTGACGT TGGAGTCCAC GTTCTTTAAT AGTGGACTCT
7381 TGTTCCAAAC TGGAACAACA CTCAACCCTA TCTCGGTCTA TTCTTTTGAT TTATAAGGGA
7441 TTTTGCCGAT TTCGGCCTAT TGGTTAAAAA ATGAGCTGAT TTAACAAAAA TTTAACGCGA
7501 ATTTTAACAA AATATTAACG CTTACAATTT AGGTGGCACT TTTCGGGGAA ATGTGCGCGG
7561 AACCCCTATT TGTTTATTTT TCTAAATACA TTCAAATATG TATCCGCTCA TGAGACAATA
7621 ACCCTGATAA ATGCTTCAAT AATATTGAAA AAGGAAGAGT ATGAGTATTC AACATTTCCG
7681 TGTCGCCCTT ATTCCCTTTT TTGCGGCATT TTGCCTTCCT GTTTTTGCTC ACCCAGAAAC
7741 GCTGGTGAAA GTAAAAGATG CTGAAGATCA GTTGGGTGCA CGAGTGGGTT ACATCGAACT
7801 GGATCTCAAC AGCGGTAAGA TCCTTGAGAG TTTTCGCCCC GAAGAACGTT TTCCAATGAT
7861 GAGCACTTTT AAAGTTCTGC TATGTGGCGC GGTATTATCC CGTATTGACG CCGGGCAAGA
7921 GCAACTCGGT CGCCGCATAC ACTATTCTCA GAATGACTTG GTTGAGTACT CACCAGTCAC
7981 AGAAAAGCAT CTTACGGATG GCATGACAGT AAGAGAATTA TGCAGTGCTG CCATAACCAT
8041 GAGTGATAAC ACTGCGGCCA ACTTACTTCT GACAACGATC GGAGGACCGA AGGAGCTAAC
8101 CGCTTTTTTG CACAACATGG GGGATCATGT AACTCGCCTT GATCGTTGGG AACCGGAGCT
8161 GAATGAAGCC ATACCAAACG ACGAGCGTGA CACCACGATG CCTGTAGCAA TGGCAACAAC
8221 GTTGCGCAAA CTATTAACTG GAGCCGGTGA GCGTGGGTCT CGCGGTATCA TTGCAGCACT
8281 CTGGATGGAG GCGGATAAAG TTGCAGGACC ACTTCTGCGC TCGGCCCTTC CGGCTGGCTG
8341 GTTTATTGCT GATAAATCTG GAGCCGGTGA GCGTGGGTCT CGCGGTATCA TTGCAGCACT
8401 GGGGCCAGAT GGTAAGCCCT CCCGTATCGT AGTTATCTAC ACGACGGGGA GTCAGGCAAC
8461 TATGGATGAA CGAAATAGAC AGATCGCTGA GATAGGTGCC TCACTGATTA AGCATTGGTA
8521 ACTGTCAGAC CAAGTTTACT CATATATACT TTAGATTGAT TTAAAACTTC ATTTTTAATT
8581 TAAAAGGATC TAGGTGAAGA TCCTTTTTGA TAATCTCATG ACCAAAATCC CTTAACGTGA
8641 GTTTTCGTTC CACTGAGCGT CAGACCCCGT AGAAAAGATC AAAGGATCTT CTTGAGATCC
8701 TTTTTTTCTG CGCGTAATCT GCTGCTTGCA AACAAAAAAA CCACCGCTAC CAGCGGTGGT
8761 TTGTTTGCCG GATCAAGAGC TACCAACTCT TTTTCCGAAG GTAACTGGCT TCAGCAGAGC
8821 GCAGATACCA AATACTGTTC TTCTAGTGTA GCCGTAGTTA GGCCACCACT TCAAGAACTC
8881 TGTAGCACCG CCTACATACC TCGCTCTGCT AATCCTGTTA CCAGTGGCTG CTGCCAGTGG
8941 CGATAAGTCG TGTCTTACCG GGTTGGACTC AAGACGATAG TTACCGGATA AGGCGCAGCG
9001 GTCGGGCTGA ACGGGGGGTT CGTGCACACA GCCCAGCTTG GAGCGAACGA CCTACACCGA
9061 ACTGAGATAC CTACAGCGTG AGCTATGAGA AAGCGCCACG CTTCCCGAAG AGAGAAAGGC
9121 GGACAGGTAT CCGGTAAGCG GCAGGGTCGG AACAGGAGAG CGCACGAGGG AGCTTCCAGG
9181 GGGAAACGCC TGGTATCTTT ATAGTCCTGT CGGGTTTCGC CACCTCTGAC TTGAGCGTCG
9241 ATTTTTGTGA TGCTCGTCAG GGGGGCGGAG CCTATGGAAA AACGCCAGCA ACGCGGCCTT
```

FIG. 6B-3

```
9301  TTTACGGTTC CTGGCCTTTT GCTGGCCTTT TGCTCACATG TTCTTTCCTG CGTTATCCCC
9361  TGATTCTGTG GATAACCGTA TTACCGCCTT TGAGTGAGCT GATACCGCTC GCCGCAGCCG
9421  AACGACCGAG CGCAGCGAGT CAGTGAGCGA GGAAGCGGAA GAGCGCCCAA TACGCAAACC
9481  GCCTCTCCCC GCGCGTTGGC CGATTCATTA ATGCAGCTGG CACGACAGGT TTCCCGACTG
9541  GAAAGCGGGC AGTGAGCGCA ACGCAATTAA TGTGAGTTAG CTCACTCATT AGGCACCCCA
9601  GGCTTTACAC TTTATGCTTC CGGCTCGTAT GTTGTGTGGA ATTGTGAGCG GATAAGAATT
9661  TCACACAGGA AACAGCTATG ACCATGATTA CGCCAAGCGC GCAATTAACC CTCACTAAAG
9721  GGAACAAAAG CTGGAGCTGC AAGCTT
```

FIG. 7B
SEQ ID NO. 51

```
   1  AATGTAGTCT TATGCAATAC TCTTGTAGTC TTGCAACATG GTAACGATGA GTTAGCAACA
  61  TGCCTTACAA GGAGAGAAAA AGCACCGTGC ATGCCGATTG GTGGAAGTAA GGTGGTACGA
 121  TCGTGCCTTA TTAGGAAGGC AACAGACGGG TCTGACATGG ATTGGACGAA CCACTGAATT
 181  GCCGCATTGC AGAGATATTG TATTTAAGTG CCTAGCTCGA TACATAAACG GGTCTCTCTG
 241  GTTAGACCAG ATCTGAGCCT GGGAGCTCTC TGGCTAACTA GGGAACCCAC TGCTTAAGCC
 301  TCAATAAAGC TTGCCTTGAG TGCTTCAAGT AGTGTGTGCC CGTCTGTTGT GTGACTCTGG
 361  TAACTAGAGA TCCCTCAGAC CCTTTTAGTC AGTGTGGAAA ATCTCTAGCA GTGGCGCCCG
 421  AACAGGGACT TGAAAGCGAA AGGGAAACCA GAGGAGCTCT CTCGACGCAG GACTCGGCTT
 481  GCTGAAGCGC GCACGGCAAG AGGCGAGGGG CGGCGACTGG TGAGTACGCC AAAAATTTTG
 541  ACTAGCGGAG GCTAGAAGGA GAGAGATGGG TGCGAGAGCG TCAGTATTAA GCGGGGGAGA
 601  ATTAGATCGC GATGGGAAAA ATTCGGTTA AGGCCAGGGG GAAAGAAAAA ATATAAATTA
 661  AAACATATAG TATGGGCAAG CAGGGAGCTA GAACGATTCG CAGTTAATCC TGGCCTGTTA
 721  GAAACATCAG AAGGCTGTAG ACAAATACTG GGACAGCTAC AACCATCCCT TCAGACAGGA
 781  TCAGAAGAAC TTAGATCATT ATATAATACA GTAGCAACCC TCTATTGTGT GCATCAAAGG
 841  ATAGAGATAA AAGACACCAA GGAAGCTTTA GACAAGATAG AGGAAGAGCA AAACAAAAGT
 901  AAGACCACCG CACAGCAAGC GGCCGCTGAT CTTCAGACCT GGAGGAGGAG ATATGAGGGA
 961  CAATTGGAGA AGTGAATTAT ATAAATATAA AGTAGTAAAA ATTGAACCAT TAGGAGTAGC
1021  ACCCACCAAG GCAAAGAGAA GAGTGGTGCA GAGAGAAAAA AGAGCAGTGG GAATAGGAGC
1081  TTTGTTCCTT GGGTTCTTGG GAGCAGCAGG AAGCACTATG GGCGCAGCGT CAATGACGCT
1141  GACGGTACAG GCCAGACAAT TATTGTCTGG TATAGTGCAG CAGCAGAACA ATTTGCTGAG
1201  GGCTATTGAG GCGCAACAGC ATCTGTTGCA ACTCACAGTC TGGGGCATCA AGCAGCTCCA
1261  CGCAAGAATC CTGGCTGTGG AAAGATACCT AAAGGATCAA CAGCTCCTGG GGATTTGGGG
1321  TTGCTCTGGA AAACTCATTT GCACCACTGC TGTGCCTTGG AATGCTAGTT GGAGTAATAA
1381  ATCTCTGGAA CAGATTTGGA ATCACACGAC CTGGATGGAG TGGGACAGAG AAAATTAACAA
1441  TTACACAAGC TTAATACACT CCTTAATTGA AGAATCGCAA AACCAGCAAG AAAAGAATGA
1501  ACAAGAATTA TTGGAATTAG ATAAATGGGC AAGTTTGTGG AATTGGTTTA ACATAACAAA
1561  TTGGCTGTGG TATATAAAT TATTCATAAT GATAGTAGGA GGCTTGGTAG GTTTAAGAAT
1621  AGTTTTTGCT GTACTTTCTA TAGTGAATAG AGTTAGGCAG GGATATTCAC CATTATCGTT
1681  TCAGACCCAC CTCCCAACCC CGAGGGGACC CGACAGGCCC GAAGGAATAG AAGAAGAAGG
1741  TGGAGAGAGA GACAGAGACA GATCCATTCG ATTAGTGAAC GGATCTCGAC GGTATCGCTA
1801  GCTTTTAAAA GAAAAGGGGG GATTGGGGGG TACAGTGCAG GGGAAAGAAT AGTAGACATA
1861  ATAGCAACAG ACATACAAAC TAAAGAATTA CAAAAACAAA TTACAAAAAT TCAAAATTTT
1921  ACTAGTGATT ATCGGATCAA CTTTGTATAG AAAAGTTGGG CTCCGGTGCC CGTCAGTGGG
1981  CAGAGCGCAC ATCGCCCACA GTCCCCGAGA AGTTGGGGGG AGGGTCGGC AATTGAACCG
2041  GTGCCTAGAG AAGGTGGCGC GGGGTAAACT GGGAAAGTGA GTGCGTGTAC TGGCTCCGCC
2101  TTTTTCCCGA GGGTGGGGGA GAACCGTATA TAAGTGCAGT AGTCGCCGTG AACGTTCTTT
2161  TTCGCAACGG GTTTGCCGCC AGAACACAGG TAAGTGCCGT GTGTGGTTCC CGCGGGCCTG
2221  GCCTCTTTAC GGGTTATGGC CCTTGCGTGC CTTGAATTAC TTCCACCTGG CTGCAGTACG
2281  TGATTCTTGA TCCCGAGCTT CGGGTTGGAA GTGGGTGGGA GAGTTCGAGG CCTTGCGCTT
2341  AAGGAGCCCC TTCGCCTCGT GCTTGAGTTG AGGCCTGGCC TGGGCGCTGG GGCCGCCGCG
2401  TGCGAATCTG GTGGCACCTT CGCGCCTGTC TCGCTGCTTT CGATAAGTCT CTAGCCATTT
2461  AAAATTTTTG ATGACCTGCT GCGACGCTTT TTTTCTGGCA AGATAGTCTT GTAAATGCGG
2521  GCCAAGATCT GCACACTGGT ATTTCGGTTT TTGGGGCCGC GGGCGGCGAC GGGGCCCGTG
2581  CGTCCCAGCG CACATGTTCG GCGAGGCGGG GCCTGCGAGC GCGGCCACCG AGAATCGGAC
2641  GGGGGTAGTC TCAAGCTGGC CGGCCTGCTC TGGTGCCTGG TCTCGCGCCG CCGTGTATCG
2701  CCCCGCCCTG GGCGGCAAGG CTGGCCCGGT CGGCACCAGT TGCGTGAGCG GAAAGATGGC
2761  CGCTTCCCGG CCCTGCTGCA GGGAGCTCAA AATGGAGGAC GCGGCGCTCG GGAGAGCGGG
2821  CGGGTGAGTC ACCCACACAA AGGAAAAGGG CCTTTCCGTC CTCAGCCGTC GCTTCATGTG
2881  ACTCCACGGA GTACCGGGCG CCGTCCAGGC ACCTCGATTA GTTCTCGAGC TTTTGGAGTA
```

FIG. 7B-1

```
2941 CGTCGTCTTT AGGTTGGGGG GAGGGGTTTT ATGCGATGGA GTTTCCCCAC ACTGAGTGGG
3001 TGGAGACTGA AGTTAGGCCA GCTTGGCACT TGATGTAATT CTCCTTGGAA TTTGCCCTTT
3061 TTGAGTTTGG ATCTTGGTTC ATTCTCAAGC CTCAGACAGT GGTTCAAAGT TTTTTTCTTC
3121 CATTTCAGGT GTCGTGACAA GTTTGTACAA AAAAGCAGGC TGCCACCATG AAGATCTTCA
3181 ACAACCAGCA CAGCCCCAGA AGCGCCGCCA CCGGCCTGCC CATCAGCATG AAGATCTTCA
3241 TGTACCTGCT GACCGTGTTC CTGATCACCC AGATGATCGG CAGCGCCCTG TTCGCCGTGT
3301 ACCTGCACAG AAGACTGGAC AAGATCGAGG ACGAGAGAAA CCTGCACGAG GACTTCGTGT
3361 TCATGAAGAC CATCCAGAGA TGCAACACCG GCCAGAGAAG CCTGAGCCTG CTGAACTGCG
3421 AGGAGATCAA GAGCCAGTTC GAGGGCTTCG TGAAGGACAT CATGCTGAAC AAGGAGGAGA
3481 CCAAGAAGGA GAACAGCTTC GAGATGCCCA GAGGCGAGGA GGACAGCCAG ATCGCCGCCC
3541 ACGTGATCAG CGAGGCCAGC AGCAAGACCA CCAGCGTGCT GCAGTGGGCC GAGAAGGGCT
3601 ACTACACCAT GAGCAACAAC CTGGTGACCC TGGAGAACGG CAAGCAGCTG ACCGTGAAGA
3661 GACAGGGCCT GTACTACATC TACGCCCAGG TGACCTTCTG CAGCAACAGA GAGGCCAGCA
3721 GCCAGGCCCC CTTCATCGCC CACAGCAGCG CCAAGCCCTG CGGCCAGCAG AGCATCCACC
3781 TGCTGAGAGC CGCCAACACC CACAGCAGCG CCAAGCCCTG CGGCCAGCAG AGCATCCACC
3841 TGGGCGGCGT GTTCGAGCTG CAGCCCGGCG CCAGCGTGTT CGTGAACGTG ACCGACCCCA
3901 GCCAGGTGAG CCACGGCACC GGCTTCACCA GCTTCGGCCT GCTGAAGCTG TAAACCCAGC
3961 TTTCTTGTAC AAAGTGGTGA TAATCGAATT CACCCAGCTT TCTTGTACAA AGTGGTGATA
4021 ATCGAATTCC GATAATCAAC CTCTGGATTA CAAAATTTGT GAAAGATTGA CTGGTATTCT
4081 TAACTATGTT GCTCCTTTTA CGCTATGTGG ATACGCTGCT TTAATGCCTT TGTATCATGC
4141 TATTCGTTCC CGTATGGCTT TCATTTTCTC CTCCTTGTAT AAATCCTGGT TGCTGTCTCT
4201 TTATGAGGAG TTGTGGCCCG TTGTCAGGCA ACGTGGCGTG GTGTGCACTG TGTTTGCTGA
4261 CGCAACCCCC ACTGGTTGGG GCATTGCCAC CACCTGTCAG CTCCTTTCCG GGACTTTCGC
4321 TTTCCCCCTC CCTATTGCCA CGGCGGAACT CATCGCCGCC TGCCTTGCCC GCTGCTGGAC
4381 AGGGGCTCGG CTGTTGGGCA CTGACAATTC CGTGGTGTTG TCGGGAAGC TGACGTCCTT
4441 TCCATGGCTG CTCGCCTGTG TTGCCACCTG GATTCTGCGC GGGACGTCCT TCTGCTACGT
4501 CCCTTCGGCC CTCAATCCAG CGGACCTTCC TTCCCGCGGC CTGCTGCCGG CTCTGCGGCC
4561 TCTTCCGCGT CTTCGCCTTC GCCCTCAGAC GAGTCGGATC TCCCTTTGGG CCGCCTCCCC
4621 GCATCGGGAA TTCCCGCGGT TCGCTTTAAG ACCAATGACT TACAAGGCAG CTGTAGATCT
4681 TAGCCACTTT TTAAAAGAAA AGGGGGGACT GGAAGGGCTA ATTCACTCCC AACGAAGACA
4741 AGATCTGCTT TTTGCTTGTA CTGGGTCTCT CTGGTTAGAC CAGATCTGAG CCTGGGAGCT
4801 CTCTGGCTAA CTAGGGAACC CACTGCTTAA GCCTCAATAA AGCTTGCCTT GAGTGCTTCA
4861 AGTAGTGTGT GCCCGTCTGT TGTGTGACTC TGGTAACTAG AGATCCCTCA GACCCTTTTA
4921 GTCAGTGTGG AAAATCTCTA GCAGTAGTAG TTCATGTCAT CTTATTATTC AGTATTTATA
4981 ACTTGCAAAG AAATGAATAT CAGAGAGTGA GAGGAACTTG TTTATTGCAG CTTATAATGG
5041 TTACAAATAA AGCAATAGCA TCACAAATTT CACAAATAAA GCATTTTTTT CACTGCATTC
5101 TAGTTGTGGT TTGTCCAAAC TCATCAATGT ATCTTATCAT GTCTGGCTCT AGCTATCCCG
5161 CCCCTAACTC CGCCCATCCC GCCCCTAACT CCGCCCAGTT CCGCCCATTC TCCGCCCCAT
5221 GGCTGACTAA TTTTTTTTAT TTATGCAGAG GCCGAGGCCG CCTCGGCCTC TGAGCTATTC
5281 CAGAAGTAGT GAGGAGGCTT TTTTGGAGGC CTAGGGACGT ACCCAATTCG CCCTATAGTG
5341 AGTCGTATTA CGCGCGCTCA CTGGCCGTCG TTTTACAACG TCGTGACTGG GAAAACCCTG
5401 GCGTTACCCA ACTTAATCGC CTTGCAGCAC ATCCCCCTTT CGCCAGCTGG CGTAATAGCG
5461 AAGAGGCCCG CACCGATCGC CCTTCCCAAC AGTTGCGCAG CCTGAATGGC GAATGGGACG
5521 CGCCCTGTAG CGGCGCATTA AGCGCGGCGG GTGTGGTGGT TACGCGCAGC GTGACCGCTA
5581 CACTTGCCAG CGCCCTAGCG CCCGCTCCTT TCGCTTTCTT CCCTTCCTTT CTCGCCACGT
5641 TCGCCGGCTT TCCCCGTCAA GCTCTAAATC GGGGGCTCCC TTTAGGGTTC CGATTTAGTG
5701 CTTTACGGCA CCTCGACCCC AAAAAACTTG ATTAGGGTGA TGGTTCACGT AGTGGGCCAT
5761 CGCCCTGATA GACGGTTTTT CGCCCTTTGA CGTTGGAGTC CACGTTCTTT AATAGTGGAC
5821 TCTTGTTCCA AACTGGAACA ACACTCAACC CTATCTCGGT CTATTCTTTT GATTTATAAG
5881 GGATTTTGCC GATTTCGGCC TATTGGTTAA AAAATGAGCT GATTTAACAA AAATTTAACG
5941 CGAATTTTAA CAAAATATTA ACGCTTACAA TTAGGTGGC ACTTTTCGGG GAAATGTGCG
6001 CGGAACCCCT ATTTGTTTAT TTTTCTAAAT ACATTCAAAT ATGTATCCGC TCATGAGACA
6061 ATAACCCTGA TAAATGCTTC AATAATATTG AAAAAGGAAG AGTATGAGTA TTCAACATTT
```

FIG. 7B-2

```
6121 CCGTGTCGCC CTTATTCCCT TTTTTGCGGC ATTTTGCCTT CCTGTTTTTG CTCACCCAGA
6181 AACGCTGGTG AAAGTAAAAG ATGCTGAAGA TCAGTTGGGT GCACGAGTGG GTTACATCGA
6241 ACTGGATCTC AACAGCGGTA AGATCCTTGA GAGTTTTCGC CCCGAAGAAC GTTTTCCAAT
6301 GATGAGCACT TTTAAAGTTC TGCTATGTGG CGCGGTATTA TCCCGTATTG ACGCCGGGCA
6361 AGAGCAACTC GGTCGCCGCA TACACTATTC TCAGAATGAC TTGGTTGAGT ACTCACCAGT
6421 CACAGAAAAG CATCTTACGG ATGGCATGAC AGTAAGAGAA TTATGCAGTG CTGCCATAAC
6481 CATGAGTGAT AACACTGCGG CCAACTTACT TCTGACAACG ATCGGAGGAC CGAAGGAGCT
6541 AACCGCTTTT TTGCACAACA TGGGGGATCA TGTAACTCGC CTTGATCGTT GGGAACCGGA
6601 GCTGAATGAA GCCATACCAA ACGACGAGCG TGACACCACG ATGCCTGTAG CAATGGCAAC
6661 AACGTTGCGC AAACTATTAA CTGGCGAACT ACTTACTCTA GCTTCCCGGC AACAATTAAT
6721 AGACTGGATG GAGGCGGATA AAGTTGCAGG ACCACTTCTG CGCTCGGCCC TTCCGGCTGG
6781 CTGGTTTATT GCTGATAAAT CTGGAGCCGG TGAGCGTGGG TCTCGCGGTA TCATTGCAGC
6841 ACTGGGGCCA GATGGTAAGC CCTCCCGTAT CGTAGTTATC TACACGACGG GGAGTCAGGC
6901 AACTATGGAT GAACGAAATA GACGATCGC TGAGATAGGT GCCTCACTGA TTAAGCATTG
6961 GTAACTGTCA GACCAAGTTT ACTCATATAT ACTTTAGATT GATTTAAAAC TTCATTTTTA
7021 ATTTAAAAGG ATCTAGGTGA AGATCCTTTT TGATAATCTC ATGACCAAAA TCCCTTAACG
7081 TGAGTTTTCG TTCCACTGAG CGTCAGACCC CGTAGAAAAG ATCAAAGGAT CTTCTTGAGA
7141 TCCTTTTTTT CTGCGCGTAA TCTGCTGCTT GCAAACAAAA AAACCACCGC TACCAGCGGT
7201 GGTTTGTTTG CCGGATCAAG AGCTACCAAC TCTTTTTCCG AAGGTAACTG GCTTCAGCAG
7261 AGCGCAGATA CCAAATACTG TTCTTCTAGT GTAGCCGTAG TTAGGCCACC ACTTCAAGAA
7321 CTCTGTAGCA CCGCCTACAT ACCTCGCTCT GCTAATCCTG TTACCAGTGG CTGCTGCCAG
7381 TGGCGATAAG TCGTGTCTTA CCGGGTTGGA CTCAAGACGA TAGTTACCGG ATAAGGCGCA
7441 GCGGTCGGGC TGAACGGGGG GTTCGTGCAC ACAGCCCAGC TTGGAGCGAA CGACCTACAC
7501 CGAACTGAGA TACCTACAGC GTGAGCTATG AGAAAGCGCC ACGCTTCCCG AAGAGAGAAA
7561 GGCGGACAGG TATCCGGTAA GCGGCAGGGT CGGAACAGGA GAGCGCACGA GGGAGCTTCC
7621 AGGGGGAAAC GCCTGGTATC TTTATAGTCC TGTCGGGTTT CGCCACCTCT GACTTGAGCG
7681 TCGATTTTTG TGATGCTCGT CAGGGGGGCG GAGCCTATGG AAAAACGCCA GCAACGCGGC
7741 CTTTTTACGG TTCCTGGCCT TTTGCTGGCC TTTTGCTCAC ATGTTCTTTC CTGCGTTATC
7801 CCCTGATTCT GTGGATAACC GTATTACCGC CTTTGAGTGA GCTGATACCG CTCGCCGCAG
7861 CCGAACGACC GAGCGCAGCG AGTCAGTGAG CGAGGAAGCG GAAGAGCGCC CAATACGCAA
7921 ACCGCCTCTC CCCGCGCGTT GGCCGATTCA TTAATGCAGC TGGCACGACA GGTTTCCCGA
7981 ACCGCCTCTC GGCAGTGAGC GCAACGCAAT TAATGTGAGT TAGCTCACTC ATTAGGCACC
8041 CCAGGCTTTA CACTTTATGC TTCCGGCTCG TATGTTGTGT GGAATTGTGA GCGGATAACA
8101 ATTTCACACA GGAAACAGCT ATGACCATGA TTACGCCAAG AGAGCAATTA ACCCTCACTA
8161 AAGGGAACAA AAGCTGGAGC TGCAAGCTT
```

FIG. 8B
SEQ ID NO. 52

```
   1   AATGTAGTCT TATGCAATAC TCTTGTAGTC TTGCAACATG GTAACGATGA GTTAGCAACA
  61   TGCCTTACAA GGAGAGAAAA AGCACCGTGC ATGCCGATTG GTGGAAGTAA GGTGGTACGA
 121   TCGTGCCTTA TTAGGAAGGC AACAGACGGG TCTGACATGG ATTGGACGAA CCACTGAATT
 181   GCCGCATTGC AGAGATATTG TATTTAAGTG CCTAGCTCGA TACATAAACG GGTCTCTCTG
 241   GTTAGACCAG ATCTGAGCCT GGGAGCTCTC TGGCTAACTA GGGAACCCAC TGCTTAAGCC
 301   TCAATAAAGC TTGCCTTGAG TGCTTCAAGT AGTGTGTGCC CGTCTGTTGT GTGACTCTGG
 361   TAACTAGAGA TCCCTCAGAC CCTTTTAGTC AGTGTGGAAA ATCTCTAGCA GTGGCGCCCG
 421   AACAGGGACT TGAAAGCGAA AGGGAAACCA GAGGAGCTCT CTCGACGCAG GACTCGGCTT
 481   GCTGAAGCGC GCACGGCAAG AGGCGAGGGG CGGCGACTGG TGAGTACGCC AAAAATTTTG
 541   ACTAGCGGAG GCTAGAAGGA GAGAGATGGG TGCGAGAGCG TCAGTATTAA GCGGGGGAGA
 601   ATTAGATCGC GATGGGAAAA AATTCGGTTA AGGCCAGGGG GAAAGAAAAA ATATAAATTA
 661   AAACATATAG TATGGGCAAG CAGGGAGCTA GAACGATTCG CAGTTAATCC TGGCCTGTTA
 721   GAAACATCAG AAGGCTGTAG ACAAATACTG GGACAGCTAC AACCATCCCT TCAGACAGGA
 781   TCAGAAGAAC TTAGATCATT ATATAATACA GTAGCAACCC TCTATTGTGT GCATCAAAGG
 841   ATAGAGATAA AAGACACCAA GGAAGCTTTA GACAAGATAG AGGAAGAGCA AAACAAAAGT
 901   AAGACCACCG CACAGCAAGC GGCCGCTGAT CTTCAGACCT GGAGGAGGAG ATATGAGGGA
 961   CAATTGGAGA AGTGAATTAT ATAAATATAA AGTAGTAAAA ATTGAACCAT TAGGAGTAGC
1021   ACCCACCAAG GCAAAGAGAA GAGTGGTGCA GAGAGAAAAA AGAGCAGTGG GAATAGGAGC
1081   TTTGTTCCTT GGGTTCTTGG GAGCAGCAGG AAGCACTATG GGCGCAGCGT CAATGACGCT
1141   GACGGTACAG GCCAGACAAT TATTGTCTGG TATAGTGCAG CAGCAGAACA ATTTGCTGAG
1201   GGCTATTGAG GCGCAACAGC ATCTGTTGCA ACTCACAGTC TGGGGCATCA AGCAGCTCCA
1261   GGCAAGAATC CTGGCTGTGG AAAGATACCT AAAGGATCAA CAGCTCCTGG GGATTTGGGG
1321   TTGCTCTGGA AAACTCATTT GCACCACTGC TGTGCCTTGG AATGCTAGTT GGAGTAATAA
1381   ATCTCTGGAA CAGATTTGGA ATCACACGAC CTGGATGGAG TGGGACAGAG AAATTAACAA
1441   TTACACAAGC TTAATACACT CCTTAATTGA AGAATCGCAA AACCAGCAAG AAAAGAATGA
1501   ACAAGAATTA TTGGAATTAG ATAAATGGGC AAGTTTGTGG AATTGGTTTA ACATAACAAA
1561   TTGGCTGTGG TATATAAAAT TATTCATAAT GATAGTAGGA GGCTTGGTAG GTTTAAGAAT
1621   AGTTTTTGCT GTACTTTCTA TAGTGAATAG AGTTAGGCAG GGATATTCAC CATTATCGTT
1681   TCAGACCCAC CTCCCAACCC CGAGGGGACC CGACAGGCCC GAAGGAATAG AAGAAGAAGG
1741   TGGAGAGAGA GACAGAGACA GATCCATTCG ATTAGTGAAC GGATCTCGAC GGTATCGCTA
1801   GCTTTTAAAA GAAAAGGGGG GATTGGGGGG TACAGTGCAG GGGAAAGAAT AGTAGACATA
1861   ATAGCAACAG ACATACAAAC TAAAGAATTA CAAAAACAAA TTACAAAAAT TCAAAATTTT
1921   ACTAGTGATT ATCGGATCAA CTTTGTATAG AAAAGTTGGG CTCCGGTGCC CGTCAGTGGG
1981   CAGAGCGCAC ATCGCCCACA GTCCCCGAGA AGTTGGGGGG AGGGGTCGGC AATTGAACCG
2041   GTGCCTAGAG AAGGTGGCGC GGGGTAAACT GGGAAAGTGA TGTCGTGTAC TGGCTCCGCC
2101   TTTTTCCCGA GGGTGGGGGA GAACCGTATA TAAGTGCAGT AGTCGCCGTG AACGTTCTTT
2161   TTCGCAACGG GTTTGCCGCC AGAACACAGG TAAGTGCCGT GTGTGGTTCC CGCGGGCCTG
2221   GCCTCTTTAC GGGTTATGGC CCTTGCGTGC CTTGAATTAC TTCCACCTGG CTGCAGTACG
2281   TGATTCTTGA TCCCGAGCTT CGGGTTGGAA GTGGGTGGGA GAGTTCGAGG CCTTGCGCTT
2341   AAGGAGCCCC TTCGCCTCGT GCTTGAGTTG AGGCCTGGCC TGGGCGCTGG GGCCGCCGCG
2401   TGCGAATCTG GTGGCACCTT CGCGCCTGTC TCGCTGCTTT CGATAAGTCT CTAGCCATTT
2461   AAAATTTTTG ATGACCTGCT GCGACGCTTT TTTTCTGGCA AGATAGTCTT GTAAATGCGG
2521   GCCAAGATCT GCACACTGGT ATTTCGGTTT TTGGGGCCGC GGGCGGCGAC GGGGCCCGTG
2581   CGTCCCAGCG CACATGTTCG GCGAGGCGGG GCCTGCGAGC GCGGCCACCG AGAATCGGAC
2641   GGGGGTAGTC TCAAGCTGGC CGGCCTGCTC TGGTGCCTGG TCTCGCGCCG CCGTGTATCG
2701   CCCCGCCCTG GGCGGCAAGG CTGGCCCGGT CGGCACCAGT TGCGTGAGCG GAAAGATGGC
2761   CGCTTCCCGG CCTGCTGCA  GGGAGCTCAA AATGGAGGAC GCGGCGCTCG GGAGAGCGGG
2821   CGGGTGAGTC ACCCACACAA AGGAAAAGGG CCTTTCCGTC CTCAGCCGTC GCTTCATGTG
```

FIG. 8B-1

```
2881 ACTCCACGGA GTACCGGGCG CCGTCCAGGC ACCTCGATTA GTTCTCGAGC TTTTGGAGTA
2941 CGTCGTCTTT AGGTTGGGGG GAGGGGTTTT ATGCGATGGA GTTTCCCCAC ACTGAGTGGG
3001 TGGAGACTGA AGTTAGGCCA GCTTGGCACT TGATGTAATT CTCCTTGGAA TTTGCCCTTT
3061 TTGAGTTTGG ATCTTGGTTC ATTCTCAAGC CTCAGACAGT GGTTCAAAGT TTTTTTCTTC
3121 CATTTCAGGT GTCGTGACAA GTTTGTACAA AAAAGCAGGC TGCCACCATG AGCACCGAGA
3181 GCATGATCAG AGACGTGGAG CTGGCCGAGG AGGCCCTGCC CAAGAAGACC GGCGGCCCCC
3241 AGGGCAGCAG AAGATGCCTG TTCCTGAGCC TGTTCAGCTT CCTGATCGTG GCCGGCGCCA
3301 CCACCCTGTT CTGCCTGCTG CACTTCGGCG TGATCGGCCC CCAGAGAGAG GAGTTCCCCA
3361 GAGACCTGAG CCTGATCAGC CCCCTGGCCC AGGCCGTGGC CCACGTGGTG GCCAACCCCC
3421 AGGCCGAGGG CCAGCTGCAG TGGCTGAACA GAAGAGCCAA CGCCCTGCTG GCCAACGGCG
3481 TGGAGCTGAG AGACAACCAG CTGGTGGTGC CCAGCGAGGG CCTGTACCTG ATCTACAGCC
3541 AGGTGCTGTT CAAGGGCCAG GGCTGCCCCA GCACCCACGT GCTGCTGACC CACACCATCA
3601 GCAGAATCGC CGTGAGCTAC CAGACCAAGG TGAACCTGCT GAGCGCCATC AAGAGCCCCT
3661 GCCAGAGAGA GACCCCCGAG GGCGCCGAGG CCAAGCCCTG GTACGAGCCC ATCTACCTGG
3721 GCGGCGTGTT CCAGCTGGAG AAGGGCGACA GACTGAGCGC CGAGATCAAG AGACCCGACT
3781 ACCTGGACTT CGCCGAGAGC GGCCAGGTGT ACTTCGGCAT CATCGCCCTG TAAACCCAGC
3841 TTTCTTGTAC AAAGTGGTGA TAATCGAATT CACCCAGCTT TCTTGTACAA AGTGGTGATA
3901 ATCGAATTCC GATAATCAAC CTCTGGATTA CAAAATTTGT GAAAGATTGA CTGGTATTCT
3961 TAACTATGTT GCTCCTTTTA CGCTATGTGG ATACGCTGCT TTAATGCCTT TGTATCATGC
4021 TATTGCTTCC CGTATGGCTT TCATTTTCTC CTCCTTGTAT AAATCCTGGT TGCTGTCTCT
4081 TTATGAGGAG TTGTGGCCCG TTGTCAGGCA ACGTGGCGTG GTGTGCACTG TGTTTGCTGA
4141 CGCAACCCCC ACTGGTTGGG GCATTGCCAC CACCTGTCAG CTCCTTTCCG GGACTTTCGC
4201 TTTCCCCCTC CCTATTGCCA CGGCGGAACT CATCGCCGCC TGCCTTGCCC GCTGCTGGAC
4261 AGGGGCTCGG CTGTTGGGCA CTGACAATTC CGTGGTGTTG TCGGGGAAGC TGACGTCCTT
4321 TCCATGGCTG CTCGCCTGTG TTGCCACCTG GATTCTGCGC GGGACGTCCT TCTGCTACGT
4381 CCCTTCGGCC CTCAATCCAG CGGACCTTCC TTCCCGCGGC CTGCTGCCGG CTCTGCGGCC
4441 TCTTCCGCGT CTTCGCCTTC GCCCTCAGAC GAGTCGGATC TCCCTTTGGG CCGCCTCCCC
4501 GCATCGGGAA TTCCCGCGGT TCGCTTTAAG ACCAATGACT TACAAGGCAG CTGTAGATCT
4561 TAGCCACTTT TTAAAAGAAA AGGGGGGACT GGAAGGGCTA ATTCACTCCC AACGAAGACA
4621 AGATCTGCTT TTTGCTTGTA CTGGGTCTCT CTGGTTAGAC CAGATCTGAG CCTGGGAGCT
4681 CTCTGGCTAA CTAGGGAACC CACTGCTTAA GCCTCAATAA AGCTTGCCTT GAGTGCTTCA
4741 AGTAGTGTGT GCCCGTCTGT TGTGTGACTC TGGTAACTAG AGATCCCTCA GACCCTTTTA
4801 GTCAGTGTGG AAAATCTCTA GCAGTAGTAG TTCATGTCAT CTTATTATTC AGTATTTATA
4861 ACTTGCAAAG AAATGAATAT CAGAGAGTGA GAGGAACTTG TTTATTGCAG CTTATAATGG
4921 TTACAAATAA AGCAATAGCA TCACAAATT CACAAATAAA GCATTTTTT CACTGCATTC
4981 TAGTTGTGGT TTGTCCAAAC TCATCAATGT ATCTTATCAT GTCTGGCTCT AGCTATCCCG
5041 CCCCTAACTC CGCCCATCCC GCCCCTAACT CCGCCCAGTT CCGCCCATTC TCCGCCCCAT
5101 GGCTGACTAA TTTTTTTTAT TTATGCAGAG GCCGAGGCCG CCTCGGCCTC TGAGCTATTC
5161 CAGAAGTAGT GAGGAGGCTT TTTTGGAGGC CTAGGGACGT ACCCAATTCG CCCTATAGTG
5221 AGTCGTATTA CGCGCGCTCA CTGGCCGTCG TTTTACAACG TCGTGACTGG GAAAACCCTG
5281 GCGTTACCCA ACTTAATCGC CTTGCAGCAC ATCCCCCTTT CGCCAGCTGG CGTAATAGCG
5341 AAGAGGCCCG CACCGATCGC CCTTCCCAAC AGTTGCGCAG CCTGAATGGC GAATGGGACG
5401 CGCCCTGTAG CGGCGCATTA AGCGCGGCGG GTGTGGTGGT TACGCGCAGC GTGACCGCTA
5461 CACTTGCCAG CGCCCTAGCG CCCGCTCCTT TCGCTTTCTT CCCTTCCTTT CTCGCCACGT
5521 TCGCCGGCTT TCCCCGTCAA GCTCTAAATC GGGGGCTCCC TTTAGGGTTC CGATTTAGTG
5581 CTTTACGGCA CCTCGACCCC AAAAAACTTG ATTAGGGTGA TGGTTCACGT AGTGGGCCAT
5641 CGCCCTGATA GACGGTTTTT CGCCCTTTGA CGTTGGAGTC CACGTTCTTT AATAGTGGAC
5701 TCTTGTTCCA AACTGGAACA ACACTCAACC CTATCTCGGT CTATTCTTTT GATTTATAAG
5761 GGATTTTGCC GATTTCGGCC ATTTGGTTAA AAAATGAGCT GATTTAACAA AAATTTAACG
5821 CGAATTTTAA CAAAATATTA ACGCTTACAA TTTAGGTGGC ACTTTCGGG GAAATGTGCG
5881 CGGAACCCCT ATTTGTTTAT TTTTCTAAAT ACATTCAAT ATGTATCCGC TCATGAGACA
5941 ATAACCCTGA TAAATGCTTC AATAATATTG AAAAAGGAAG AGTATGAGTA TTCAACATTT
```

FIG. 8B-2

```
6001 CCGTGTCGCC CTTATTCCCT TTTTTGCGGC ATTTTGCCTT CCTGTTTTTG CTCACCCAGA
6061 AACGCTGGTG AAAGTAAAAG ATGCTGAAGA TCAGTTGGGT GCACGAGTGG GTTACATCGA
6121 ACTGGATCTC AACAGCGGTA AGATCCTTGA GAGTTTTCGC CCCGAAGAAC GTTTTCCAAT
6181 GATGAGCACT TTTAAAGTTC TGCTATGTGG CGCGGTATTA TCCCGTATTG ACGCCGGGCA
6241 AGAGCAACTC GGTCGCCGCA TACACTATTC TCAGAATGAC TTGGTTGAGT ACTCACCAGT
6301 CACAGAAAAG CATCTTACGG ATGGCATGAC AGTAAGAGAA TTATGCAGTG CTGCCATAAC
6361 CATGAGTGAT AACACTGCGG CCAACTTACT TCTGACAACG ATCGGAGGAC CGAAGGAGCT
6421 AACCGCTTTT TTGCACAACA TGGGGGATCA TGTAACTCGC CTTGATCGTT GGGAACCGGA
6481 GCTGAATGAA GCCATACCAA ACGACGAGCG TGACACCACG ATGCCTGTAG CAATGGCAAC
6541 AACGTTGCGC AAACTATTAA CTGGCGAACT ACTTACTCTA GCTTCCCGGC AACAATTAAT
6601 AGACTGGATG GAGGCGGATA AAGTTGCAGG ACCACTTCTG CGCTCGGCCC TTCCGGCTGG
6661 CTGGTTTATT GCTGATAAAT CTGGAGCCGG TAGCGTGGG TCTCGCGGTA TCATTGCAGC
6721 ACTGGGGCCA GATGGTAAGC CCTCCCGTAT CGTAGTTATC TACACGACGG GGAGTCAGGC
6781 AACTATGGAT GAACGAAATA GACAGATCGC TGAGATAGGT GCCTCACTGA TTAAGCATTG
6841 GTAACTGTCA GACCAAGTTT ACTCATATAT ACTTTAGATT GATTTAAAAC TTCATTTTTA
6901 TGAGTTTTCG TTCCACTGAG CGTCAGACCC CGTAGAAAAG ATCAAAGGAT CTTCTTGAGA
6961 TGAGTTTTCG TTCCACTGAG CGTCAGACCC CGTAGAAAAG ATCAAAGGAT CTTCTTGAGA
7021 TCCTTTTTTT CTGCGCGTAA TCTGCTGCTT GCAAACAAAA AAACCACCGC TACCAGCGGT
7081 GGTTTGTTTG CCGGATCAAG AGCTACCAAC TCTTTTTCCG AAGGTAACTG GCTTCAGCAG
7141 AGCGCAGATA CCAAATACTG TTCTTCTAGT GTAGCCGTAG TTAGGCCACC ACTTCAAGAA
7201 CTCTGTAGCA CCGCCTACAT ACCTCGCTCT GCTAATCCTG TTACCAGTGG CTGCTGCCAG
7261 TGGCGATAAG TCGTGTCTTA CCGGGTTGGA CTCAAGACGA TAGTTACCGG ATAAGGCGCA
7321 GCGGTCGGGC TGAACGGGGG GTTCGTGCAC ACAGCCCAGC TTGGAGCGAA CGACCTACAC
7381 CGAACTGAGA TACCTACAGC GTGAGCTATG AGAAAGCGCC ACGCTTCCCG AAGAGAGAAA
7441 GGCGGACAGG TATCCGGTAA GCGGCAGGGT CGGAACAGGA GAGCGCACGA GGGAGCTTCC
7501 AGGGGGAAAC GCCTGGTATC TTTATAGTCC TGTCGGGTTT CGCCACCTCT GACTTGAGCG
7561 TCGATTTTTG TGATGCTCGT CAGGGGGGCG GAGCCTATGG AAAAACGCCA GCAACGCGGC
7621 CTTTTTACGG TTCCTGGCCT TTTCGTGGCC TTTTGCTCAC ATGTTCTTTC CTGCGTTATC
7681 CCCTGATTCT GTGGATAACC GTATTACCGC CTTTGAGTGA GCTGATACCG CTCGCCGCAG
7741 CCGAACGACC GAGCGCAGCG AGTCAGTGAG CGAGGAAGCG GAAGAGCGCC CAATACGCAA
7801 ACCGCCTCTC CCCGCGCGTT GGCCGATTCA TTAATGCAGC TGGCACGACA GGTTTCCCGA
7861 CTGGAAAGCG GGCAGTGAGC GCAACGCAAT TAATGTGAGT TAGCTCACTC ATTAGGCACC
7921 CCAGGCTTTA CACTTTATGC TTCCGGCTCG TATGTTGTGT GGAATTGTGA GCGGATAACA
7981 ATTTCACACA GGAAACAGCT ATGACCATGA TTACGCCAAG CGCGCAATTA ACCCTCACTA
8041 AAGGGAACAA AAGCTGGAGC TGCAAGCTT
```

FIG. 9B
SEQ ID NO. 53

```
   1 AATGTAGTCT TATGCAATAC TCTTGTAGTC TTGCAACATG GTAACGATGA GTTAGCAACA
  61 TGCCTTACAA GGAGAGAAAA AGCACCGTGC ATGCCGATTG GTGGAAGTAA GGTGGTACGA
 121 TCGTGCCTTA TTAGGAAGGC AACAGACGGG TCTGACATGG ATTGGACGAA CCACTGAATT
 181 GCCGCATTGC AGAGATATTG TATTTAAGTG CCTAGCTCGA TACATAAACG GGTCTCTCTG
 241 GTTAGACCAG ATCTGAGCCT GGGAGCTCTC TGGCTAACTA GGGAACCCAC TGCTTAAGCC
 301 TCAATAAAGC TTGCCTTGAG TGCTTCAAGT AGTGTGTGCC CGTCTGTTGT GTGACTCTGG
 361 TAACTAGAGA TCCCTCAGAC CCTTTTAGTC AGTGTGGAAA ATCTCTAGCA GTGGCGCCCG
 421 AACAGGGACT TGAAAGCGAA AGGGAAACCA GAGGAGCTCT CTCGACGCAG GACTCGGCTT
 481 GCTGAAGCGC GCACGGCAAG AGGCGAGGGG CGGCGACTGG TGAGTACGCC AAAAATTTTG
 541 ACTAGCGGAG GCTAGAAGGA GAGAGATGGG TGCGAGAGCG TCAGTATTAA GCGGGGGAGA
 601 ATTAGATCGC GATGGGAAAA AATTCGGTTA AGGCCAGGGG GAAAGAAAAA ATATAAATTA
 661 AAACATATAG TATGGGCAAG CAGGGAGCTA GAACGATTCG CAGTTAATCC TGGCCTGTTA
 721 GAAACATCAG AAGGCTGTAG ACAAATACTG GGACAGCTAC AACCATCCCT TCAGACAGGA
 781 TCAGAAGAAC TTAGATCATT ATATAATACA GTAGCAACCC TCTATTGTGT GCATCAAAGG
 841 ATAGAGATAA AAGACACCAA GGAAGCTTTA GACAAGATAG AGGAAGAGCA AAACAAAAGT
 901 AAGACCACCG CACAGCAAGC GGCCGCTGAT CTTCAGACCT GGAGGAGGAG ATATGAGGGA
 961 CAATTGGAGA AGTGAATTAT ATAAATATAA AGTAGTAAAA ATTGAACCAT TAGGAGTAGC
1021 ACCCACCAAG GCAAAGAGAA GAGTGGTGCA GAGAGAAAAA AGAGCAGTGG GAATAGGAGC
1081 TTTGTTCCTT GGGTTCTTGG GAGCAGCAGG AAGCACTATG GGCGCAGCGT CAATGACGCT
1141 GACGGTACAG GCCAGACAAT TATTGTCTGG TATAGTGCAG CAGCAGAACA ATTTGCTGAG
1201 GGCTATTGAG GCGCAACAGC ATCTGTTGCA ACTCACAGTC TGGGGCATCA AGCAGCTCCA
1261 GGCAAGAATC CTGGCTGTGG AAAAGATACCT AAAGGATCAA CAGCTCCTGG GGATTTGGGG
1321 TTGCTCTGGA AAACTCATTT GCACCACTGC TGTGCCTTGG AATGCTAGTT GGAGTAATAA
1381 ATCTCTGGAA CAGATTTGGA ATCACACGAC CTGGATGGAG TGGGACAGAG AAAATTAACAA
1441 TTACACAAGC TTAATACACT CCTTAATTGA AGAATCGCAA AACCAGCAAG AAAAGAATGA
1501 ACAAGAATTA TTGGAATTAG ATAAATGGGC AAGTTTGTGG AATTGGTTTA ACATAACAAA
1561 TTGGCTGTGG TATATAAAAT TATTCATAAT GATAGTAGGA GGCTTGGTAG GTTTAAGAAT
1621 AGTTTTTGCT GTACTTTCTA TAGTGAATAG AGTTAGGCAG GGATATTCAC CATTATCGTT
1681 TCAGACCCAC CTCCCAACCC CGAGGGGACC CGACAGGCCC GAAGGAATAG AAGAAGAAGG
1741 TGGAGAGAGA GACAGAGACA GATCCATTCG ATTAGTGAAC GGATCTCGAC GGTATCGCTA
1801 GCTTTTAAAA GAAAAGGGGG GATTGGGGGG TACAGTGCAG GGGAAAGAAT AGTAGACATA
1861 ATAGCAACAG ACATACAAAC TAAAGAATTA CAAAAACAAA TTACAAAAAT TCAAAATTTT
1921 ACTAGTATCA ACTTTGTATA GAAAAGTTGG GCTCCGGTGC CCGTCAGTGG GCAGAGCGCA
1981 CATCGCCCAC AGTCCCCGAG AAGTTGGGGG GAGGGGTCGG CAATTGAACC GGTGCCTAGA
2041 GAAGGTGGCG CGGGGTAAAC TGGGAAAGTG ATGTCGTGTA CTGGCTCCGC CTTTTTCCCG
2101 AGGGTGGGGG AGAACCGTAT ATAAGTGCAG TAGTCGCCGT GAACGTTCTT TTTCGCAACG
2161 GGTTTGCCGC CAGAACACAG GTAAGTGCCG TGTGTGGTTC CCGCGGGCCT GGCCTCTTTA
2221 CGGGTTATGG CCCTTGCGTG CCTTGAATTA CTTCCACCTG GCTGCAGTAC GTGATTCTTG
2281 ATCCCGAGCT TCGGGTTGGA AGTGGGTGGG AGAGTTCGAG GCCTTGCGCT TAAGGAGCCC
2341 CTTCGCCTCG TGCTTGAGTT GAGGCCTGGC CTGGGCGCTG GGGCCGCCGC GTGCGAATCT
2401 GGTGGCACCT TCGCGCCTGT CTCGCTGCTT TCGATAAGTC TCTAGCCATT TAAAATTTTT
2461 GATGACCTGC TGCGACGCTT TTTTTCTGGC AAGATAGTCT TGTAAATGCG GGCCAAGATC
2521 TGCACACTGG TATTTCGGTT TTTGGGGCCG CGGGCGGCGA CGGGGCCCGT GCGTCCAGC
2581 GCACATGTTC GGCGAGGCGG GGCCTGCGAG CGCGGCCACC GAGAATCGGA CGGGGGTAGT
2641 CTCAAGCTGG CCGGCCTGCT CTGGTGCCTG GTCTCGCGCC GCCGTGTATC GCCCCGCCCT
2701 GGGCGGCAAG GCTGGCCCGG TCGGCACCAG TTGCGTGAGC GGAAAGATGG CCGCTTCCCG
```

FIG. 9B-1

```
2761 GCCCTGCTGC AGGGAGCTCA AAATGGAGGA CGCGGCGCTC GGGAGAGCGG GCGGGTGAGT
2821 CACCCACACA AAGGAAAAGG GCCTTTCCGT CCTCAGCCGT CGCTTCATGT GACTCCACGG
2881 AGTACCGGGC GCCGTCCAGG CACCTCGATT AGTTCTCGAG CTTTTGGAGT ACGTCGTCTT
2941 TAGGTTGGGG GGAGGGGTTT TATGCGATGG AGTTTCCCCA CACTGAGTGG GTGGAGACTG
3001 AAGTTAGGCC AGCTTGGCAC TTGATGTAAT TCTCCTTGGA ATTTGCCCTT TTTGAGTTTG
3061 GATCTTGGTT CATTCTCAAG CCTCAGACAG TGGTTCAAAG TTTTTTTCTT CCATTTCAGG
3121 TGTCGTGACA AGTTTGTACA AAAAAGCAGG CTGCCACCAT GAGCACGAG AGCATGATCA
3181 GAGACGTGGA GCTGGCCGAG GAGGCCCTGC CCAAGAAGAC CGGCGGCCCC CAGGGCAGCA
3241 GAAGATGCCT GTTCCTGAGC CTGTTCAGCT TCCTGATCGT GGCCGGCGCC ACCACCCTGT
3301 TCTGCCTGCT GCACTTCGGC GTGATCGGCC CCAGAGAGA GGAGTTCCCC AGAGACCTGA
3361 GCCTGATCAG CCCCCTGGCC CAGGCCGTGG CCCACGTGGT GGCCAACCCC CAGGCCGAGG
3421 GCCAGCTGCA GTGGCTGAAC AGAAGAGCCA ACGCCCTGCT GGCCAACGGC GTGGAGCTGA
3481 GAGACAACCA GCTGGTGGTG CCCAGCGAGG GCCTGTACCT GATCTACAGC CAGGTGCTGT
3541 TCAAGGGCCA GGGCTGCCCC AGCACCCACG TGCTGCTGAC CCACACCATC AGCAGAATCG
3601 CCGTGAGCTA CCAGACCAAG GTGAACCTGC TGAGCGCCAT CAAGAGCCCC TGCCAGAGAG
3661 AGACCCCCGA GGGCGCCGAG GCCAAGCCCT GGTACGAGCC CATCTACCTG GGCGGCGTGT
3721 TCCAGCTGGA GAAGGGCGAC AGACTGAGCG CCGAGATCAA CAGACCCGAC TACCTGGACT
3781 TCGCCGAGAG CGGCCAGGTG TACTTCGGCA TCATCGCCCT GTAAACCCAG CTTTCTTGTA
3841 CAAAGTGGTG ATAATCGAAT TCTAAATAGA TAGAACAACA ACAATTGCAT TCATTTTTGA
3901 TTTCAGGTTC AGGGGGAGGT GTGGGAGGTT TTTTAAAGCA AGTAAAACCT CTACACTGAC
3961 GGTACGCGTT AACAACAACA ATTGCATTCA TTTGTAGTTT CAGGTTCAGG GGGAGGTGTG
4021 GGAGGTTTTT TAAAGCAAGT TAAACCTCTA AAATAGTGGT ACGCGTTACC CAGCTTTCTT
4081 GTACAAAGTG GACCCAGCTT TCTTGTACAA AGTGGGCCCC TCTCCCTCCC CCCCCCCTAA
4141 CGTTACTGGC CGAAGCCGCT TGGAATAAGG CCGGTGTGCG TTTGTCTATA TGTTATTTTC
4201 CACCATATTG CCGTCTTTTG GCAATGTGAG GGCCCGGAAA CCTGGCCCTG TCTTCTTGAC
4261 GAGCATTCCT AGGGGTCTTT CCCCTCTCGC CAAAGGAATG CAAGGTCTGT TGAATGTCGT
4321 GAAGGAAGCA GTTCCTCTGG AAGCTTCTTG AAGACAAACA ACGTCTGTAG CGACCCTTTG
4381 CAGGCAGCGG AACCCCCCAC CTGGCGACAG GTGCCTCTGC GGCCAAAAGC CACGTGTATA
4441 AGATACACCT GCAAAGGCGG CACAACCCCA GTGCCACGTT GTGAGTTGGA TAGTTGTGGA
4501 AAGAGTCAAA TGGCTCTCCT CAAGCGTATT CAACAAGGGG CTGAAGGATG CCCAGAAGGT
4561 ACCCCATTGT ATGGGATCTG ATCTGGGGCC TCGGTGCACA TGCTTTACAT GTGTTTAGTC
4621 GAGGTTAAAA AAACGTCTAG GCCCCCCGAA CCACGGGGAC GTGGTTTTCC TTTGAAAAAC
4681 ACGATGATAA TATGGCCACA ACCATGGCCA CCGTGCTGGC CCCCGCCTGG AGCCCCACCA
4741 CCTACCTGCT GCTGCTGCTG CTGCTGAGCA GCGGCCTGAG CGGCGGCGGC GGCAGCGGCA
4801 AGCCCATCCC CAACCCCCTG CTGGGCCTGG ACAGCACCGG CGGCGGCGGC AGCCAGGTGA
4861 AGCTGCAGGA GAGCGGCCCC GGCCTGGTGG CCCCCAGCCA GAGCCTGAGC ATCACCTGCA
4921 CCGTGAGCGG CTTCAGCCTG ACCGCCTACG GCGTGGACTG GGTGAGACAG CCCCCCGGCA
4981 AGTGCCTGGA GTGGCTGGGC GTGATCTGGG GCGGCGGCAG AACCAACTAC AACAGCGGCC
5041 TGATGAGCAG ACTGAGCATC AGAAAGGACA ACAGCAAGAG CCAGGTGTTC CTGACCATGA
5101 ACAGCCTGCA GACCGACGAC ACCGCCAAGT ACTACTGCGT GAAGCACACC AACTGGGACG
5161 GCGGCTTCGC CTACTGGGGC CAGGGCACCA CCGTGACCGT GAGCAGCGGC GGCGGCGGCA
5221 GCGGCGGCGG CGGCAGCGGC GGCGGCGGCA GGCAGCCC CGGCCAGAGC GTGAGCATCA
5281 GCTGCAGCGG CAGCAGCAGC AACATCGGCA ACAACTACGT GTACTGGTAC CAGCACCTGC
5341 CCGGCACCGC CCCCAAGCTG CTGATCTACA GCGACACCAA GAGACCCAGC GGCGTGCCCG
5401 ACAGAATCAG CGGCAGCAAG AGCGGCACCA GCGCCAGCCT GGCCATCAGC GGCCTGCAGA
5461 GCGAGGACGA GGCCGACTAC TACTGCGCCA GCTGGGACGA CAGCCTGGAC GGCCCCGTGT
5521 TCGGCTGCGG CACCAAGCTG ACCGTGCTGC CCACCACCAC CCCCGCCCCC AGACCCCCA
5581 CCCCCGCCCC CACCATCGCC AGCCAGCCCC TGAGCCTGAG ACCCGAGGCC TGCAGACCCG
5641 CCGCCGGCGG CGCCGTGCAC ACCAGAGGCC TGGACTTCGC CTGCGACATC TACATCTGGG
5701 CCCCCCTGGC CGGCACCTGC GGCGTGCTGC TGCTGAGCCT GGTGATCACC CGTGGTGAAG
5761 ACCACAGAAA CAGAAGAAGA GTGTGCAAGT GCCCCAGACC CGTGGTGAAG AGCGGCGACA
```

FIG. 9B-2

```
5821  AGCCCAGCCT GAGCGCCAGA TACGTGTAAC AACTTTATTA TACATAGTTG ATCAATTCCA
5881  ACTTTATTAT ACATAGTTGA TCAATTCCGA TAATCAACCT CTGGATTACA AAATTTGTGA
5941  AAGATTGACT GGTATTCTTA ACTATGTTGC TCCTTTTACG CTATGTGGAT ACGCTGCTTT
6001  AATGCCTTTG TATCATGCTA TTGCTTCCCG TATGGCTTTC ATTTTCTCCT CCTTGTATAA
6061  ATCCTGGTTG CTGTCTCTTT ATGAGGAGTT GTGGCCCGTT GTCAGGCAAC GTGGCGTGGT
6121  GTGCACTGTG TTTGCTGACG CAACCCCCAC TGGTTGGGGC ATTGCCACCA CCTGTCAGCT
6181  CCTTTCCGGG ACTTTCGCTT TCCCCCTCCC TATTGCCACG GCGGAACTCA TCGCCGCCTG
6241  CCTTGCCCGC TGCTGGACAG GGGCTCGGCT GTTGGGCACT GACAATTCCG TGGTGTTGTC
6301  GGGGAAGCTG ACGTCCTTTC CATGGCTGCT CGCCTGTGTT GCCACCTGGA TTCTGCGCGG
6361  GACGTCCTTC TGCTACGTCC CTTCGGCCCT CAATCCAGCG GACCTTCCTT CCCGCGGCCT
6421  GCTGCCGGCT CTGCGGCCTC TTCCGCGTCT TCGCCTTCGC CCTCAGACGA GTCGGATCTC
6481  CCTTTGGGCC GCCTCCCCGC ATCGGGAATT CCCGCGGTTC GCTTTAAGAC CAATGACTTA
6541  CAAGGCAGCT GTAGATCTTA GCCACTTTTT AAAAGAAAAG GGGGGACTGG AAGGGCTAAT
6601  TCACTCCCAA CGAAGACAAG ATCTGCTTTT TGCTTGTACT GGGTCTCTCT GGTTAGACCA
6661  GATCTGAGCC TGGGAGCTCT CTGGCTAACT AGGGAACCCA CTGCTTAAGC CTCAATAAAG
6721  CTTGCCTTGA GTGCTTCAAG TAGTGTGTGC CCGTCTGTTG TGTGACTCTG GTAACTAGAG
6781  ATCCCTCAGA CCCTTTTAGT CAGTGTGGAA AATCTCTAGC AGTAGTAGTT CATGTCATCT
6841  TATTATTCAG TATTTATAAC TTGCAAAGAA ATGAATATCA GAGAGTGAGA GGAACTTGTT
6901  TATTGCAGCT TATAATGGTT ACAAATAAAG CAATAGCATC ACAAATTTCA CAAATAAAGC
6961  ATTTTTTTCA CTGCATTCTA GTTGTGGTTT GTCCAAACTC ATCAATGTAT CTTATCATGT
7021  CTGGCTCTAG CTATCCCGCC CCTAACTCCG CCCATCCCGC CCTAACTCC GCCCAGTTCC
7081  GCCCATTCTC CGCCCCATGG CTGACTAATT TTTTTTATTT ATGCAGAGGC CGAGGCCGCC
7141  TCGGCCTCTG AGCTATTCCA GAAGTAGTGA GGAGGCTTTT TTGGAGGCCT AGGGACGTAC
7201  CCAATTCGCC CTATAGTGAG TCGTATTACG CGCGCTCACT GGCCGTCGTT TTACAACGTC
7261  GTGACTGGGA AAACCCTGGC GTTACCCAAC TTAATCGCCT TGCAGCACAT CCCCCTTTCG
7321  CCAGCTGGCG TAATAGCGAA GAGGCCCGCA CCGATCGCCC TTCCCAACAG TTGCGCAGCC
7381  TGAATGGCGA ATGGGACGCG CCCTGTAGCG GCGCATTAAG CGCGGCGGGT GTGGTGGTTA
7441  CGCGCAGCGT GACCGCTACA CTTGCCAGCG CCCTAGCGCC CGCTCCTTTC GCTTTCTTCC
7501  CTTCCTTTCT CGCCACGTTC GCCGGCTTTC CCCGTCAAGC TCTAAATCGG GGGCTCCCTT
7561  TAGGGTTCCG ATTTAGTGCT TTACGGCACC TCGACCCCAA AAAACTTGAT TAGGGTGATG
7621  GTTCACGTAG TGGGCCATCG CCCTGATAGA CGGTTTTTCG CCCTTTGACG TTGGAGTCCA
7681  CGTTCTTTAA TAGTGGACTC TTGTTCCAAA CTGGAACAAC ACTCAACCCT ATCTCGGTCT
7741  ATTCTTTTGA TTTATAAGGG ATTTTGCCGA TTTCGGCCTA TTGGTTAAAA AATGAGCTGA
7801  TTTAACAAAA ATTTAACGCG AATTTTAACA AAATATTAAC GCTTACAATT TAGGTGGCAC
7861  TTTTCGGGGA AATGTGCGCG GAACCCCTAT TTGTTTATTT TTCTAAATAC ATTCAAATAT
7921  GTATCCGCTC ATGAGACAAT AACCCTGATA AATGCTTCAA TAATATTGAA AAAGGAAGAG
7981  TATGAGTATT CAACATTTCC GTGTCGCCCT TATTCCCTTT TTTGCGGCAT TTTGCCTTCC
8041  TGTTTTTGCT CACCCAGAAA CGCTGGTGAA AGTAAAAGAT GCTGAAGATC AGTTGGGTGC
8101  ACGAGTGGGT TACATCGAAC TGGATCTCAA CAGCGGTAAG ATCCTTGAGA GTTTTCGCCC
8161  CGAAGAACGT TTTCCAATGA TGAGCACTTT TAAAGTTCTG CTATGTGGCG CGGTATTATC
8221  CCGTATTGAC GCCGGGCAAG AGCAACTCGG TCGCCGCATA CACTATTCTC AGAATGACTT
8281  GGTTGAGTAC TCACCAGTCA CAGAAAAGCA TCTTACGGAT GGCATGACAG TAAGAGAATT
8341  ATGCAGTGCT GCCATAACCA TGAGTGATAA CACTGCGGCC AACTTACTTC TGACAACGAT
8401  CGGAGGACCG AAGGAGCTAA CCGCTTTTTT GCACAACATG GGGGATCATG TAACTCGCCT
8461  TGATCGTTGG GAACCGGAGC TGAATGAAGC CATACCAAAC GACGAGCGTG ACACCACGAT
8521  GCCTGTAGCA ATGGCAACAA CGTTGCGCAA ACTATTAACT GGCGAACTAC TTACTCTAGC
8581  TTCCCGGCAA CAATTAATAG ACTGGATGGA GGCGGATAAA GTTGCAGGAC CACTTCTGCG
8641  CTCGGCCCTT CCGGCTGGCT GGTTTATTGC TGATAAATCT GGAGCCGGTG AGCGTGGGTC
8701  TCGCGGTATC ATTGCAGCAC TGGGGCCAGA TGGTAAGCCC TCCCGTATCG TAGTTATCTA
8761  CACGACGGGG AGTCAGGCAA CTATGGATGA ACGAAATAGA CAGATCGCTG AGATAGGTGC
8821  CTCACTGATT AAGCATTGGT AACTGTCAGA CCAAGTTTAC TCATATATAC TTTAGATTGA
```

FIG. 9B-3

```
8881 TTTAAAACTT CATTTTTAAT TTAAAAGGAT CTAGGTGAAG ATCCTTTTTG ATAATCTCAT
8941 GACCAAAATC CCTTAACGTG AGTTTTCGTT CCACTGAGCG TCAGACCCCG TAGAAAAGAT
9001 CAAAGGATCT TCTTGAGATC CTTTTTTTCT GCGCGTAATC TGCTGCTTGC AAACAAAAAA
9061 ACCACCGCTA CCAGCGGTGG TTTGTTTGCC GGATCAAGAG CTACCAACTC TTTTTCCGAA
9121 GGTAACTGGC TTCAGCAGAG CGCAGATACC AAATACTGTT CTTCTAGTGT AGCCGTAGTT
9181 AGGCCACCAC TTCAAGAACT CTGTAGCACC GCCTACATAC CTGGCTCTGC TAATCCTGTT
9241 ACCAGTGGCT GCTGCCAGTG GCGATAAGTC GTGTCTTACC GGGTTGGACT CAAGACGATA
9301 GTTACCGGAT AAGGCGCAGC GGTCGGGCTG AACGGGGGGT TCGTGCACAC AGCCCAGCTT
9361 GGAGCGAACG ACCTACACCG AACTGAGATA CCTACAGCGT GAGCTATGAG AAAGCGCCAC
9421 GCTTCCCGAA GAGAGAAAGG CGGACAGGTA TCCGGTAAGC GGCAGGGTCG GAACAGGAGA
9481 GCGCACGAGG GAGCTTCCAG GGGGAAACGC CTGGTATCTT TATAGTCCTG TCGGGTTTCG
9541 CCACCTCTGA CTTGAGCGTC GATTTTTGTG ATGCTCGTCA GGGGGGCGGA GCCTATGGAA
9601 AAACGCCAGC AACGCGGCCT TTTTACGGTT CCTGGCCTTT TGCTGGCCTT TTGCTCACAT
9661 GTTCTTTCCT GCGTTATCCC CTGATTCTGT GGATAACCGT ATTACCGCCT TTGAGTGAGC
9721 TGATACCGCT CGCCGCAGCC GAACGACCGA GCGCAGCGAG TCAGTGAGCG AGGAAGCGGA
9781 AGAGCGCCCA ATACGCAAAC CGCCTCTCCC CGCGCGTTGG CCGATTCATT AATGCAGCTG
9841 GCACGACAGC TTTCCCGACT GGAAAGCGGG CAGTGAGCGC AACGCAATTA ATGTGAGTTA
9901 GCTCACTCAT TAGGCACCCC AGGCTTTACA CTTTATGCTT CCGGCTCGTA TGTTGTGTGG
9961 AATTGTGAGC GGATAACAAT TTCACACAGG AAACAGCTAT GACCATGATT ACGCCAAGCG
10021CGCAATTAAC CCTCACTAAA GGGAACAAAA GCTGGAGCTG CAAGCTT
```

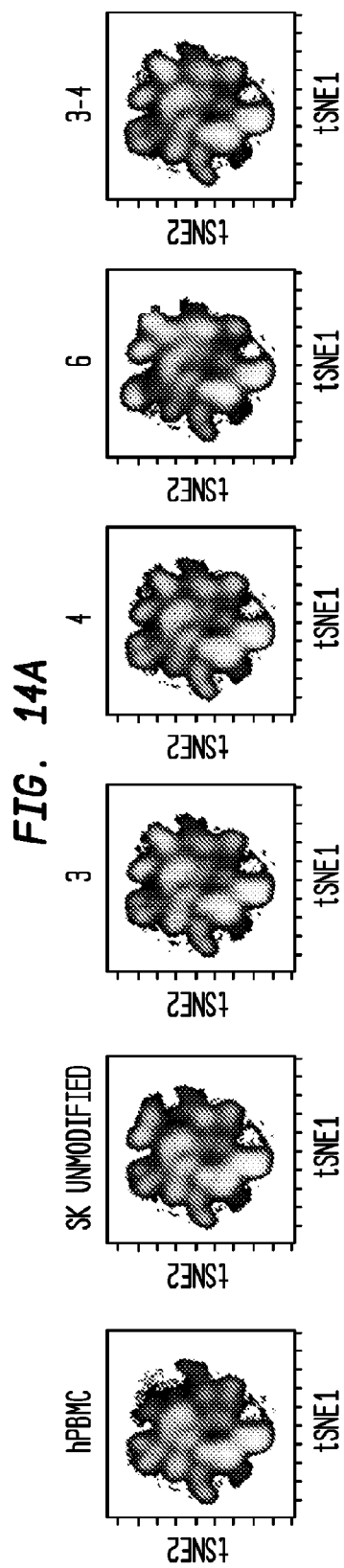
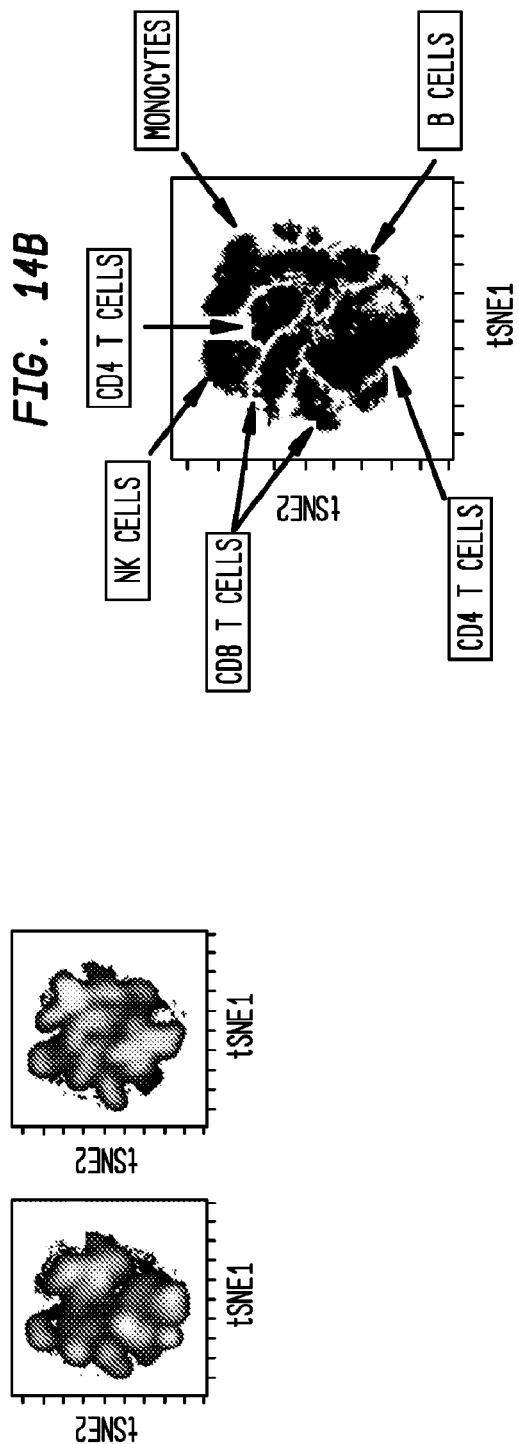
FIG. 14A
FIG. 14B

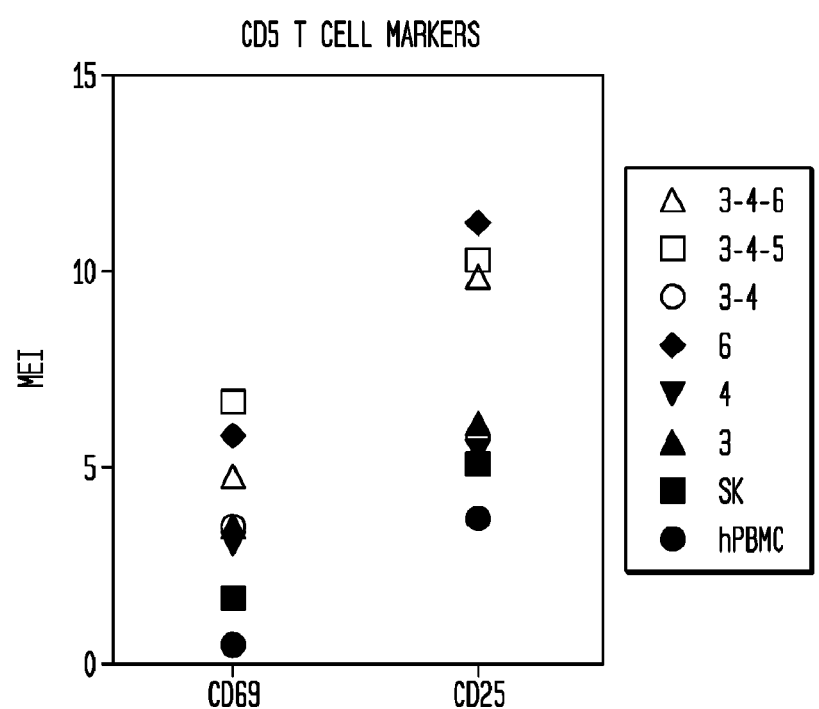

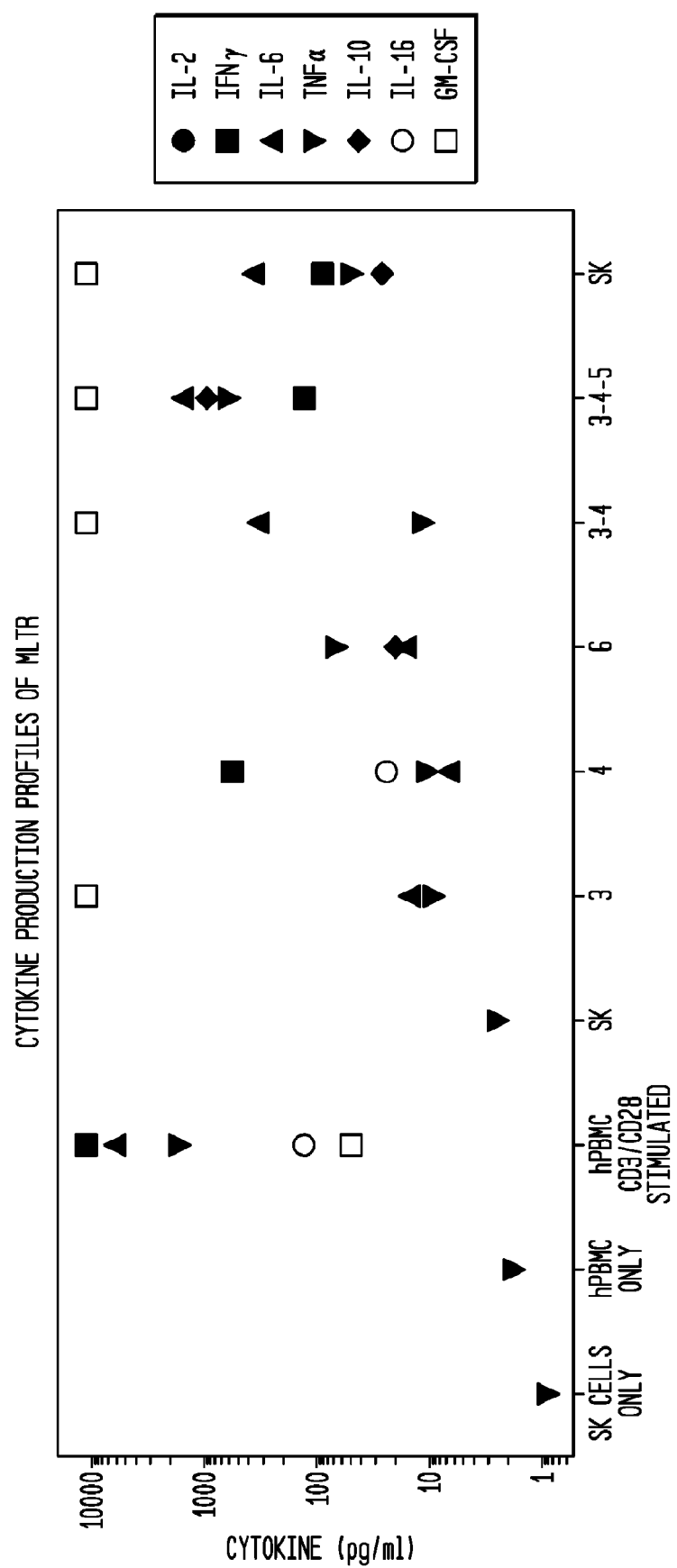

ALLOGENEIC TUMOR CELL VACCINE

RELATED APPLICATIONS

This Application is a continuation of U.S. application Ser. No. 15/821,105, filed on Nov. 22, 2017, which claims priority to U.S. Provisional Application No. 62/425,424, filed on Nov. 22, 2016. The contents of each of these applications are incorporated herein by reference in their entirety.

SEQUENCE LISTING

The instant application contains a Sequence Listing which has been submitted electronically in ASCII format via EFS-Web in accordance with 37 C.F.R. §§ 1.821-1.825. Said ASCII copy, created on Apr. 15, 2021, is named "128663-00104SL" and is 247 KB in size.

FIELD OF THE INVENTION

The described invention relates generally to immunological approaches to the treatment of cancer, and more particularly to cancer vaccines comprising modified tumor cells.

BACKGROUND OF THE INVENTION

Immune Response

Generally speaking, immune responses are initiated by an encounter between an individual and a foreign antigenic substance, e.g., an infectious microorganism. The infected individual rapidly responds with both a humoral immune response with the production of antibody molecules specific for the antigenic determinants/epitopes of the immunogen and a cell mediated immune response with the expansion and differentiation of antigen-specific regulatory and effector T-lymphocytes, including both cells that produce cytokines and killer T cells, capable of lysing infected cells. Primary immunization with a given microorganism evokes antibodies and T cells that are specific for the antigenic determinants/epitopes found on that microorganism, but that usually fail to recognize or recognize only poorly antigenic determinants expressed by unrelated microbes (Paul, W. E., "Chapter 1: The immune system: an introduction," Fundamental Immunology, 4th Edition, Ed. Paul, W. E., Lippicott-Raven Publishers, Philadelphia, (1999), at p. 102).

As a consequence of this initial response, the immunized individual develops a state of immunologic memory. If the same or a closely related microorganism is encountered again, a secondary response ensues. This secondary response generally consists of an antibody response that is more rapid, greater in magnitude and composed of antibodies that bind to the antigen with greater affinity and are more effective in clearing the microbe from the body, and a similarly enhanced and often more effective T-cell response. However, immune responses against infectious agents do not always lead to elimination of the pathogen. (Paul, W. E., "Chapter 1: The immune system: an introduction," Fundamental Immunology, 4th Edition, Ed. Paul, W. E., Lippicott-Raven Publishers, Philadelphia, (1999), at p. 102).

Immune Tolerance of Cancer

Cancer is characterized by genetic instability of particular cells but has also been described as a disorder of the immune system, based on the fact that the immune system fails, at least in certain segments of the afflicted human population, to respond optimally to cancerous cells that have taken on a distinctly non-self phenotype that should be recognized as foreign. Several reasons have been advanced to explain the basis of this observation. For example, first, cancer cells consist mainly of self-antigens, in striking contrast to the situation with infectious organisms. Some antigens that are classified as cancer antigens are actually normal antigens that are overexpressed, or normal antigens that have a mutation in only one or two amino acids in the polypeptide chain. Second, cancer cells down-regulate Major Histocompatibility Complex (MHC), and thus do not much present tumor cell-derived peptides by way of MHC. Third, cancer cells, and associated tumor-associated macrophages, express cytokines that dampen the immune response (see, e.g., Yu et al (2007) Nature Rev. Immunol. 7:41-51). This dampening is caused, for example, by the secretion of interleukin-10 (IL-10) by the cancer cells or by the associated macrophages. Fourth, unlike the situation with infections, cancer cells do not provide any immune adjuvant. Pathogens express a variety of naturally-occurring immune adjuvants, which take the form of toll-like receptor (TLR) agonists and NOD agonists (see, e.g., Kleinnijenhuis et al (2011) Clin. Dev. Immunol. 405310 (12 pages)). Generally, optimal activation of dendritic cells requires contact of an immune adjuvant with one or more toll-like receptors (TLRs) expressed by the dendritic cell. Without activation of the dendritic cell, contact between the dendritic cell and T cells (immune synapse) fails to result in optimal activation of the T cell.

Immune Surveillance and Immune Editing

Tumor immune editing is divided into three phases: an elimination phase, an equilibrium phase, and an escape phase. The elimination phase, also known as immune surveillance, is the process by which the immune system identifies cancerous or pre-cancerous cells and eliminates them before they grow out of control. This phase can be complete when all cancerous or precancerous cells are eliminated. If some tumor cells are not eliminated, a temporary state of equilibrium may be achieved between the immune system and tumor cell growth. In this equilibrium phase, tumors cells can either remain dormant or continue to evolve by accumulating further changes to genomic DNA that can modulate the antigens they present. During this process, the immune system exerts a selective pressure on evolving cells, whereby the tumor cells that are less able to be recognized have a survival advantage. Eventually the immune response is unable to recognize cells of the tumor, resulting in the transition to the escape phase wherein tumor cells progressively grow out of control.

Tumor Microenvironment

The tumor microenvironment provides a consistently effective barrier to immune cell function because tumors actively downregulate all phases of anti-tumor immune responses using a spectrum of different strategies and mechanisms. Many molecular mechanisms that cause dysfunction of immune cells in the tumor microenvironment have been identified, including those directly mediated by factors produced by tumors, and others resulting from alterations of normal tissue homeostasis in the presence of cancer. Most human tumors appear to be able to interfere with one or more stages of immune cell development, differentiation, migration, cytotoxicity and other effector functions (T L Whiteside, The tumor microenvironment and its role in promoting tumor growth, Oncogene (2008) 27, 5904-5912).

One such mechanism involves accumulation in tumors of $T_{reg}$ (CD4$^+$CD25$^{bright}$ Foxp3$^+$ T cells) and myeloid-derived cells (CD34$^+$CD33$^+$CD13$^+$CD11b$^+$CD15$^-$), which are common features of human tumors, and have been linked to poor prognosis in patients with cancer (T L Whiteside, The tumor microenvironment and its role in promoting tumor growth, Oncogene (2008) 27, 5904-5912). Under normal conditions, $T_{reg}$ cells are involved in the important role of preventing autoimmunity, but in cancer, they expand, migrate to tumors, downregulate autologous effector T-cell proliferation and suppress anti-tumor responses of both $CD4^+CD25^-$ and $CD8^+CD25^-$ T cells using distinct molecular pathways. The $T_{reg}$ cells in the tumor are a heterogeneous population of regulatory $CD3^+CD4^+$ T cells, comprising natural $T_{reg}$, antigen-specific Tr1 cells, and other less well defined subsets of suppressor cells. Tr1 cells are induced in the tumor microenvironment, which is rich in IL-10, TGF-β, and prostaglandin $E_2$ ($PGE_2$), all of which have been shown to promote Tr1 generation (T L Whiteside, The tumor microenvironment and its role in promoting tumor growth, Oncogene (2008) 27, 5904-5912).

Myeloid suppressor cells (MSCs) also suppress T-cell responses in the tumor microenvironment, where they secrete TGF-β or induce TGF-β secretion. Immunosuppressive $CD34^+$ cell-derived myeloid cells have been identified in the peripheral blood of cancer patients. In tumor-bearing mice, MSCs accumulate in the spleen and peripheral circulation in very high amounts, exerting potent immunosuppression and favoring tumor growth. MSCs also control the availability of essential amino acids such as L-arginine and produce high levels of reactive oxygen species. The MSCs found in tumors also constitutively express iNOS and arginase 1, an enzyme involved in metabolism of L-arginine, which also synergizes with iNOS to increase superoxide and NO production, which have been found to interfere with lymphocyte responses. GM-CSF, which is also often secreted by tumor cells, recruits MSCs and induces dose-dependent in vivo immune suppression and tumor promotion, while at the same time, GM-CSF has been used as immune adjuvant in antitumor vaccines. GM-CSF was observed to increase a subset of TGF-β-producing MSCs in the circulation of patients with metastatic melanoma. The concurrent stimulatory and suppressive roles suggest that GM-CSF and MSCs are involved in maintaining immune homeostasis in normal tissue, but in the tumor microenvironment promote tumor cell escape (T L Whiteside, The tumor microenvironment and its role in promoting tumor growth, Oncogene (2008) 27, 5904-5912).

Tumor Immunotherapy

Cancer therapy is evolving rapidly as new molecular targets are being discovered. Despite the advent of biologics targeting specific pathways (e.g., HERCEPTIN® (Trastuzumab), ERBITUX[[rbitux]]® (Cetuximab)) and small molecules designed against specific targets (NOLVADEX® (Tamoxifen), GLEEVEC™ (Imatinib)), nonspecific modalities such as chemotherapy and radiation remain a standard of care.

Anti-cancer immunotherapy has been a goal for many years with a variety of approaches being tested. One difficulty of developing this immunotherapy is that target antigens are often tissue specific molecules found on both cancer cells and normal cells, and either do not elicit immunity or show non-specificity regarding cell killing (Kaufman and Wolchok eds., General Principles of Tumor Immunotherapy, Chpt 5, 67-121 (2007)). Furthermore, tumor cells have features that make immune recognition difficult, such as loss of expression of antigens that elicit immune response, lack of major histocompatibility (MHC) class II, and downregulation of MHC class I expression. These features can lead to non-recognition of tumor cells by both CD4+ and CD8+ T cells (Kaufman and Wolchok eds., General Principles of Tumor Immunotherapy, Chpt 5, 67-121 (2007)). Tumors may also evade detection through active mechanisms, such as the production of immunosuppressive cytokines (Kaufman and Wolchok eds., General Principles of Tumor Immunotherapy, Chpt 5, 67-121 (2007)).

DCs generated ex vivo by culturing hematopoietic progenitor cells or monocytes with cytokine combinations have been tested as therapeutic vaccines in cancer patients for more than a decade (Ueno H, et al., Immunol. Rev. (2010) 234: 199-212). For example, treatment of metastatic prostate cancer with sipuleucel-T (also known as APC 8015), which is a cellular product based on enriched blood APCs that are briefly cultured with a fusion protein of prostatic acid phosphatase (PAP) and granulocyte macrophage colony-stimulating factor (GM-CSF), resulted in an approximately 4-month-prolonged median survival in Phase III trials (Higano C S, et al., Cancer (2009) 115: 3670-3679; Kantoff P W, et al., N. Engl. J. Med. (2010) 363: 411-422). This study concluded that DC-based vaccines are safe and can induce the expansion of circulating CD4+ T-cells and CD8+ T-cells specific for tumor antigens. As a result of this and similar studies, sipuleucel-T has been approved by the US Food and Drug Administration (FDA) for the treatment of metastatic prostate cancer, thereby paving the clinical development and regulatory path for the next generation of cellular immunotherapy products (Palucka K and Banchereau J, Nature Reviews Cancer (April 2012) 12: 265-276).

Vaccination strategies involving DCs to induce tumor-specific effector T cells that can reduce the tumor mass specifically and that can induce immunological memory to control tumor relapse have been developed. For example, DCs can be provided with tumor-specific antigens by culturing DCs ex vivo with an adjuvant and a tumor-specific antigen, and then injecting these cells back into the patient. Tumor cells obtained from an excised tumor, needle biopsy, core biopsy, vacuum-assisted biopsy or peritoneal lavage have been used to generate immunogenic compositions comprising tumor-specific-antigen presenting dendritic cells.

Cancer Treatment Strategies

Antibody therapies such as HERCEPTIN™ (Trastuzumab) and ERBITUX™ (Cetuximab) are passive immunotherapies, but have yielded considerable improvement in clinical outcome, as measured by, e.g. the recurrence rate, progression free survival and overall survival. More recently, PD-1 and CTLA4 inhibitors have been reported to block discrete checkpoints in an active host immune response allowing an endogenous anti-cancer immune response to be sustained. The term "immune checkpoints" refers to the array of inhibitory pathways that are necessary for maintaining self-tolerance and modulating the duration and extent of immune responses to minimize damage to normal tissue. Immune checkpoint molecules such as PD-1, PD-L1, CTLA-4 are cell surface signaling receptors that play an important role in modulating the T-cell response in the tumor microenvironment. Tumor cells have been shown to utilize these checkpoints to their benefit by up regulating their expression and activity. With the tumor cell's ability to commandeer some immune checkpoint pathways as a mechanism of immune resistance, it has been hypothesized that checkpoint inhibitors that bind to molecules of immune cells to activate or inactivate them may relieve the inhibition of an immune response. Recent discoveries have identified immune checkpoints or targets, like PD-1, PD-L1, PD-L2, CTLA4, TIM3, LAG3, CCR4, OX40, OX40L, IDO, and A2AR, as proteins responsible for immune evasion. Specific immune checkpoint inhibitors, including antibodies against CTLA-4, PD-1 receptor or its ligand PD-L1 have produced impressive results in the clinic in a range of cancers, leading to FDA approvals for YERVOY™ (Ipilimumab; CTLA-4 antagonist), OPDIVO™ (Nivolumab; PD-1 antagonist) and KEYTRUDA™ (Pembrolizumab; PD-1 antagonist) in multiple tumor indications and with ongoing registration trials in many more. This method of therapy, however, can only be successful if a pre-existing antitumor immune response is present within a patient (Pardoll, D., The blockade of immune checkpoints in cancer immunotherapy, Nature Reviews: Cancer, Vol. 12, April 2012, 253). Recent cellular therapies, such as chimeric antigen receptor T-cell therapy (CAR-T), attempt to use synthetic biology to redirect T-cells to specific cell surface tumor antigens. Genetic modification of T-cells is used to confer tumor antigen recognition by transgenic expression of chimeric antigen receptor (CAR). CARs are engineered molecules that can be introduced into T cells to enable them to target tumor antigens (Frey, N. V., Porter, D. L., The Promise of Chimeric Antigen Receptor T-Cell Therapy, Oncology (2016); 30(1)) pii 219281). CAR T cells have been shown to have some efficacy against hematologic malignancies and to a lesser extent solid tumors. CAR T therapy, however, has been shown to cause several types of toxicities, including cytokine release syndrome, neurological toxicity, non-tumor recognition, and anaphylaxis (Bonifant C L, et al., Toxicity and management in CAR T-cell therapy, Molecular Therapy—Oncolytics (2016) 3, 16011).

Cellular vaccines have also been used as a cancer treatment. GVAX™ (Ipilimumab), a prototypical example, is a GM-CSF gene transduced tumor vaccine within either an autologous or allogeneic population of tumor cells. It is believed that GM-CSF secretion of genetically modified tumor cells stimulates cytokine release at the vaccine site to activate antigen presenting cells to induce a tumor specific cellular immune response (Eager, R. & Nemunaitis, J., GM-CSF Gene-Transduced Tumor Vaccines, Molecular Therapy, Vol. 12, No. 1, 18 (July 2005)). However, GVAX™ yielded only limited clinical responses.

Dendritic cell (DC)-tumor cell fusions have been developed to generate hybrid cells that express the relevant tumor associated antigens derived from the parent tumor cells, and also have the ability to process and present such antigens to appropriate cells of the immune system. The DC-tumor cell fusions provide a greater variety of tumor antigens, but have been met with limited success in human trials, likely due to the autologous components required, the heterogeneity of the product caused by maturation of DC cells, and variations in antigen loading (Browning, M., Antigen presenting cell/tumor cell fusion vaccines for cancer, Human Vaccines & Immunotherapeutics 9:7, 1545-1548; July 2013; Butterfield, L., Dendritic Cells in Cancer Immunotherapy Clinical Trials: Are We Making Progress?, Frontiers of Immunology, 2013 4: 454).

Cells of the Immune System

There are a large number of cellular interactions that comprise the immune system. These interactions occur through specific receptor-ligand pairs that signal in both directions so that each cell receives instructions based on the temporal and spatial distribution of those signals.

Murine models have been highly useful in discovering immunomodulatory pathways, but clinical utility of these pathways does not always translate from an inbred mouse strain to an outbred human population, since an outbred human population may have individuals that rely to varying extents on individual immunomodulatory pathways.

Cells of the immune system include lymphocytes, monocytes/macrophages, dendritic cells, the closely related Langerhans cells, natural killer (NK) cells, mast cells, basophils, and other members of the myeloid lineage of cells. In addition, a series of specialized epithelial and stromal cells provide the anatomic environment in which immunity occurs, often by secreting critical factors that regulate growth and/or gene activation in cells of the immune system, which also play direct roles in the induction and effector phases of the response. (Paul, W. E., "Chapter 1: The immune system: an introduction," Fundamental Immunology, 4th Edition, Ed. Paul, W. E., Lippicott-Raven Publishers, Philadelphia, (1999), at p. 102).

The cells of the immune system are found in peripheral organized tissues, such as the spleen, lymph nodes, Peyer's patches of the intestine and tonsils. Lymphocytes also are found in the central lymphoid organs, the thymus, and bone marrow where they undergo developmental steps that equip them to mediate the myriad responses of the mature immune system. A substantial portion of lymphocytes and macrophages comprise a recirculating pool of cells found in the blood and lymph, providing the means to deliver immunocompetent cells to sites where they are needed and to allow immunity that is generated locally to become generalized. (Paul, W. E., "Chapter 1: The immune system: an introduction," Fundamental Immunology, 4th Edition, Ed. Paul, W. E., Lippicott-Raven Publishers, Philadelphia, (1999), at p. 102).

The term "lymphocyte" refers to a small white blood cell formed in lymphatic tissue throughout the body and in normal adults making up about 22-28% of the total number of leukocytes in the circulating blood that plays a large role in defending the body against disease. Individual lymphocytes are specialized in that they are committed to respond to a limited set of structurally related antigens through recombination of their genetic material (e.g. to create a T cell receptor and a B cell receptor). This commitment, which exists before the first contact of the immune system with a given antigen, is expressed by the presence of receptors specific for determinants (epitopes) on the antigen on the lymphocyte's surface membrane. Each lymphocyte possesses a unique population of receptors, all of which have identical combining sites. One set, or clone, of lymphocytes differs from another clone in the structure of the combining region of its receptors and thus differs in the epitopes that it can recognize. Lymphocytes differ from each other not only in the specificity of their receptors, but also in their functions. (Paul, W. E., "Chapter 1: The immune system: an introduction," Fundamental Immunology, 4th Edition, Ed. Paul, W. E., Lippicott-Raven Publishers, Philadelphia, (1999), at p. 102).

Two broad classes of lymphocytes are recognized: the B-lymphocytes (B-cells), which are precursors of antibody-secreting cells, and T-lymphocytes (T-cells).

B-Lymphocytes

B-lymphocytes are derived from hematopoietic cells of the bone marrow. A mature B-cell can be activated with an antigen that expresses epitopes that are recognized by its cell surface. The activation process may be direct, dependent on cross-linkage of membrane Ig molecules by the antigen (cross-linkage-dependent B-cell activation), or indirect, via interaction with a helper T-cell, in a process referred to as cognate help. In many physiological situations, receptor cross-linkage stimuli and cognate help synergize to yield more vigorous B-cell responses (Paul, W. E., "Chapter 1: The immune system: an introduction," Fundamental Immunology, 4th Edition, Ed. Paul, W. E., Lippicott-Raven Publishers, Philadelphia, (1999)).

Cross-linkage dependent B-cell activation requires that the antigen express multiple copies of the epitope complementary to the binding site of the cell surface receptors, because each B-cell expresses Ig molecules with identical variable regions. Such a requirement is fulfilled by other antigens with repetitive epitopes, such as capsular polysaccharides of microorganisms or viral envelope proteins. Cross-linkage-dependent B-cell activation is a major protective immune response mounted against these microbes (Paul, W. E., "Chapter 1: The immune system: an introduction", Fundamental Immunology, 4th Edition, Ed. Paul, W. E., Lippicott-Raven Publishers, Philadelphia, (1999)).

Cognate help allows B-cells to mount responses against antigens that cannot cross-link receptors and, at the same time, provides costimulatory signals that rescue B cells from inactivation when they are stimulated by weak cross-linkage events. Cognate help is dependent on the binding of antigen by the B-cell's membrane immunoglobulin (Ig), the endocytosis of the antigen, and its fragmentation into peptides within the endosomal/lysosomal compartment of the cell. Some of the resultant peptides are loaded into a groove in a specialized set of cell surface proteins known as class II major histocompatibility complex (MHC) molecules. The resultant class II/peptide complexes are expressed on the cell surface and act as ligands for the antigen-specific receptors of a set of T-cells designated as $CD4^+$ T-cells. The $CD4^+$ T-cells bear receptors on their surface specific for the B-cell's class II/peptide complex. B-cell activation depends not only on the binding of the T cell through its T cell receptor (TCR), but this interaction also allows an activation ligand on the T-cell (CD40 ligand) to bind to its receptor on the B-cell (CD40) signaling B-cell activation. In addition, T helper cells secrete several cytokines that regulate the growth and differentiation of the stimulated B-cell by binding to cytokine receptors on the B cell (Paul, W. E., "Chapter 1: The immune system: an introduction," Fundamental Immunology, 4th Edition, Ed. Paul, W. E., Lippicott-Raven Publishers, Philadelphia, (1999)).

During cognate help for antibody production, the CD40 ligand is transiently expressed on activated $CD4^+$ T helper cells, and it binds to CD40 on the antigen-specific B cells, thereby transducing a second costimulatory signal. The latter signal is essential for B cell growth and differentiation and for the generation of memory B cells by preventing apoptosis of germinal center B cells that have encountered antigen. Hyperexpression of the CD40 ligand in both B and T cells is implicated in pathogenic autoantibody production in human SLE patients (Desai-Mehta, A. et al., "Hyperexpression of CD40 ligand by B and T cells in human lupus and its role in pathogenic autoantibody production," J. Clin. Invest. Vol. 97(9), 2063-2073, (1996)).

T-Lymphocytes

T-lymphocytes derived from precursors in hematopoietic tissue, undergo differentiation in the thymus, and are then seeded to peripheral lymphoid tissue and to the recirculating pool of lymphocytes. T-lymphocytes or T cells mediate a wide range of immunologic functions. These include the capacity to help B cells develop into antibody-producing cells, the capacity to increase the microbicidal action of monocytes/macrophages, the inhibition of certain types of immune responses, direct killing of target cells, and mobilization of the inflammatory response. These effects depend on T cell expression of specific cell surface molecules and the secretion of cytokines (Paul, W. E., "Chapter 1: The immune system: an introduction", Fundamental Immunology, 4th Edition, Ed. Paul, W. E., Lippicott-Raven Publishers, Philadelphia, (1999)).

T cells differ from B cells in their mechanism of antigen recognition. Immunoglobulin, the B cell's receptor, binds to individual epitopes on soluble molecules or on particulate surfaces. B-cell receptors see epitopes expressed on the surface of native molecules. While antibody and B-cell receptors evolved to bind to and to protect against microorganisms in extracellular fluids, T cells recognize antigens on the surface of other cells and mediate their functions by interacting with, and altering, the behavior of these antigen-presenting cells (APCs). There are three main types of APCs in peripheral lymphoid organs that can activate T cells: dendritic cells, macrophages and B cells. The most potent of these are the dendritic cells, whose only function is to present foreign antigens to T cells. Immature dendritic cells are located in tissues throughout the body, including the skin, gut, and respiratory tract. When they encounter invading microbes at these sites, they endocytose the pathogens and their products, and carry them via the lymph to local lymph nodes or gut associated lymphoid organs. The encounter with a pathogen induces the dendritic cell to mature from an antigen-capturing cell to an APC that can activate T cells. APCs display three types of protein molecules on their surface that have a role in activating a T cell to become an effector cell: (1) MHC proteins, which present foreign antigen to the T cell receptor; (2) costimulatory proteins which bind to complementary receptors on the T cell surface; and (3) cell-cell adhesion molecules, which enable a T cell to bind to the APC for long enough to become activated ("Chapter 24: The adaptive immune system," Molecular Biology of the Cell, Alberts, B. et al., Garland Science, NY, (2002)).

T-cells are subdivided into two distinct classes based on the cell surface receptors they express. The majority of T cells express T cell receptors (TCR) consisting of $\alpha$ and $\beta$-chains. A small group of T cells express receptors made of $\gamma$ and $\delta$ chains. Among the $\alpha/\beta$ T cells are two sub-lineages: those that express the coreceptor molecule CD4 ($CD4^+$ T cells); and those that express CD8 ($CD8^+$ T cells). These cells differ in how they recognize antigen and in their effector and regulatory functions.

$CD4^+$ T cells are the major regulatory cells of the immune system. Their regulatory function depends both on the expression of their cell-surface molecules, such as CD40 ligand whose expression is induced when the T cells are activated, and the wide array of cytokines they secrete when activated.

T cells also mediate important effector functions, some of which are determined by the patterns of cytokines they secrete. The cytokines can be directly toxic to target cells and can mobilize potent inflammatory mechanisms.

In addition, T cells, particularly $CD8^+$ T cells, can develop into cytotoxic T-lymphocytes (CTLs) capable of efficiently lysing target cells that express antigens recognized by the CTLs (Paul, W. E., "Chapter 1: The immune system: an introduction," Fundamental Immunology, 4th Edition, Ed. Paul, W. E., Lippicott-Raven Publishers, Philadelphia, (1999)).

T cell receptors (TCRs) recognize a complex consisting of a peptide derived by proteolysis of the antigen bound to a specialized groove of a class II or class I MHC protein. $CD4^+$ T cells recognize only peptide/class II complexes while $CD8^+$ T cells recognize peptide/class I complexes (Paul, W. E., "Chapter 1: The immune system: an introduction," Fundamental Immunology, 4th Edition, Ed. Paul, W. E., Lippicott-Raven Publishers, Philadelphia, (1999)).

The TCR's ligand (i.e., the peptide/MHC protein complex) is created within APCs. In general, class II MHC molecules bind peptides derived from proteins that have been taken up by the APC through an endocytic process. These peptide-loaded class II molecules are then expressed on the surface of the cell, where they are available to be bound by CD4+ T cells with TCRs capable of recognizing the expressed cell surface complex. Thus, CD4+ T cells are specialized to react with antigens derived from extracellular sources (Paul, W. E., "Chapter 1: The immune system: an introduction," Fundamental Immunology, 4th Edition, Ed. Paul, W. E., Lippicott-Raven Publishers, Philadelphia, (1999)).

In contrast, class I MHC molecules are mainly loaded with peptides derived from internally synthesized proteins, such as viral proteins. These peptides are produced from cytosolic proteins by proteolysis by the proteosome and are translocated into the rough endoplasmic reticulum. Such peptides, generally composed of nine amino acids in length, are bound into the class I MHC molecules and are brought to the cell surface, where they can be recognized by CD8+ T cells expressing appropriate receptors. This gives the T cell system, particularly CD8+ T cells, the ability to detect cells expressing proteins that are different from, or produced in much larger amounts than, those of cells of the remainder of the organism (e.g., viral antigens) or mutant antigens (such as active oncogene products), even if these proteins in their intact form are neither expressed on the cell surface nor secreted (Paul, W. E., "Chapter 1: The immune system: an introduction," Fundamental Immunology, 4th Edition, Ed. Paul, W. E., Lippicott-Raven Publishers, Philadelphia, (1999)).

T cells can also be classified based on their function as helper T cells; T cells involved in inducing cellular immunity; suppressor T cells; and cytotoxic T cells.

Helper T Cells

Helper T cells are T cells that stimulate B cells to make antibody responses to proteins and other T cell-dependent antigens. T cell-dependent antigens are immunogens in which individual epitopes appear only once or a limited number of times such that they are unable to cross-link the membrane immunoglobulin (Ig) of B cells or do so inefficiently. B cells bind the antigen through their membrane Ig, and the complex undergoes endocytosis. Within the endosomal and lysosomal compartments, the antigen is fragmented into peptides by proteolytic enzymes, and one or more of the generated peptides are loaded into class II MHC molecules, which traffic through this vesicular compartment. The resulting peptide/class II MHC complex is then exported to the B-cell surface membrane. T cells with receptors specific for the peptide/class II molecular complex recognize this complex on the B-cell surface. (Paul, W. E., "Chapter 1: The immune system: an introduction," Fundamental Immunology, 4th Edition, Ed. Paul, W. E., Lippicott-Raven Publishers, Philadelphia (1999)).

B-cell activation depends both on the binding of the T cell through its TCR and on the interaction of the T-cell CD40 ligand (CD40L) with CD40 on the B cell. T cells do not constitutively express CD40L. Rather, CD40L expression is induced as a result of an interaction with an APC that expresses both a cognate antigen recognized by the TCR of the T cell and CD80 or CD86. CD80/CD86 is generally expressed by activated, but not resting, B cells so that the helper interaction involving an activated B cell and a T cell can lead to efficient antibody production. In many cases, however, the initial induction of CD40L on T cells is dependent on their recognition of antigen on the surface of APCs that constitutively express CD80/86, such as dendritic cells. Such activated helper T cells can then efficiently interact with and help B cells. Cross-linkage of membrane Ig on the B cell, even if inefficient, may synergize with the CD40L/CD40 interaction to yield vigorous B-cell activation. The subsequent events in the B-cell response, including proliferation, Ig secretion, and class switching of the Ig class being expressed, either depend or are enhanced by the actions of T cell-derived cytokines (Paul, W. E., "Chapter 1: The immune system: an introduction," Fundamental Immunology, 4th Edition, Ed. Paul, W. E., Lippicott-Raven Publishers, Philadelphia, (1999)).

CD4+ T cells tend to differentiate into cells that principally secrete the cytokines IL-4, IL-5, IL-6, and IL-10 ($T_H2$ cells) or into cells that mainly produce IL-2, IFN-γ, and lymphotoxin ($T_H1$ cells). The $T_H2$ cells are very effective in helping B-cells develop into antibody-producing cells, whereas the $T_H1$ cells are effective inducers of cellular immune responses, involving enhancement of microbicidal activity of monocytes and macrophages, and consequent increased efficiency in lysing microorganisms in intracellular vesicular compartments. Although CD4+ T cells with the phenotype of $T_H2$ cells (i.e., IL-4, IL-5, IL-6 and IL-10) are efficient helper cells, $T_H1$ cells also have the capacity to be helpers (Paul, W. E., "Chapter 1: The immune system: an introduction," Fundamental Immunology, 4th Edition, Ed. Paul, W. E., Lippicott-Raven Publishers, Philadelphia, (1999)).

T Cell Involvement in Cellular Immunity Induction

T cells also may act to enhance the capacity of monocytes and macrophages to destroy intracellular microorganisms. In particular, interferon-gamma (IFN-γ) produced by helper T cells enhances several mechanisms through which mononuclear phagocytes destroy intracellular bacteria and parasitism including the generation of nitric oxide and induction of tumor necrosis factor (TNF) production. $T_{H1}$ cells are effective in enhancing the microbicidal action, because they produce IFN-γ. In contrast, two of the major cytokines produced by $T_{H2}$ cells, IL-4 and IL-10, block these activities (Paul, W. E., "Chapter 1: The immune system: an introduction," Fundamental Immunology, 4th Edition, Ed. Paul, W. E., Lippicott-Raven Publishers, Philadelphia, (1999)).

Regulatory T (Treg) Cells

Immune homeostasis is maintained by a controlled balance between initiation and downregulation of the immune response. The mechanisms of both apoptosis and T cell anergy (a tolerance mechanism in which the T cells are intrinsically functionally inactivated following an antigen encounter (Scwartz, R. H., "T cell anergy", Annu. Rev. Immunol., Vol. 21: 305-334 (2003)) contribute to the downregulation of the immune response. A third mechanism is provided by active suppression of activated T cells by suppressor or regulatory CD4+ T (Treg) cells (Reviewed in Kronenberg, M. et al., "Regulation of immunity by self-reactive T cells", Nature, Vol. 435: 598-604 (2005)). CD4+ Tregs that constitutively express the IL-2 receptor alpha (IL-2Rα) chain (CD4+ CD25+) are a naturally occurring T cell subset that are anergic and suppressive (Taams, L. S. et al., "Human anergic/suppressive CD4+CD25+ T cells: a highly differentiated and apoptosis-prone population", Eur. J. Immunol. Vol. 31: 1122-1131 (2001)). Depletion of CD4+ CD25+ Tregs results in systemic autoimmune disease in mice. Furthermore, transfer of these Tregs prevents development of autoimmune disease. Human CD4+CD25+ Tregs, similar to their murine counterpart, are generated in the thymus and are characterized by the ability to suppress proliferation of responder T cells through a cell-cell contact-dependent mechanism, the inability to produce IL-2, and the anergic phenotype in vitro. Human CD4⁺CD25⁺ T cells can be split into suppressive (CD25$^{high}$) and nonsuppressive (CD25$^{low}$) cells, according to the level of CD25 expression. A member of the forkhead family of transcription factors, FOXP3, has been shown to be expressed in murine and human CD4⁺CD25⁺ Tregs and appears to be a master gene controlling CD4⁺CD25⁺ Treg development (Battaglia, M. et al., "Rapamycin promotes expansion of functional CD4⁺ CD25⁺Foxp3⁺ regulator T cells of both healthy subjects and type 1 diabetic patients", J. Immunol., Vol. 177: 8338-8347, (2006)).

Cytotoxic T Lymphocytes

CD8⁺ T cells that recognize peptides from proteins produced within the target cell have cytotoxic properties in that they lead to lysis of the target cells. The mechanism of CTL-induced lysis involves the production by the CTL of perforin, a molecule that can insert into the membrane of target cells and promote the lysis of that cell. Perforin-mediated lysis is enhanced by granzymes, a series of enzymes produced by activated CTLs. Many active CTLs also express large amounts of fas ligand on their surface. The interaction of fas ligand on the surface of CTL with fas on the surface of the target cell initiates apoptosis in the target cell, leading to the death of these cells. CTL-mediated lysis appears to be a major mechanism for the destruction of virally infected cells.

Priming

The term "unprimed cells" (also referred to as virgin, naïve, or inexperienced cells) as used herein refers to T cells and B cells that have generated an antigen receptor (TCR for T cells, BCR for B cells) of a particular specificity, but have never encountered the antigen. The term "priming" as used herein refers to the process whereby T cells and B cell precursors encounter the antigen for which they are specific.

For example, before helper T cells and B cells can interact to produce specific antibody, the antigen-specific T cell precursors must be primed. Priming involves several steps: antigen uptake, processing, and cell surface expression bound to class II MHC molecules by an antigen presenting cell, recirculation and antigen-specific trapping of helper T cell precursors in lymphoid tissue, and T cell proliferation and differentiation (Janeway, C A, Jr., "The priming of helper T cells", Semin. Immunol., Vol. 1(1): 13-20 (1989)). Helper T cells express CD4, but not all CD4 T cells are helper cells. Id. The signals required for clonal expansion of helper T cells differ from those required by other CD4 T cells. The critical antigen-presenting cell for helper T cell priming appears to be a macrophage; and the critical second signal for helper T cell growth is the macrophage product interleukin 1 (IL-1). Id. If the primed T cells and/or B cells receive a second, co-stimulatory signal, they become activated T cells or B cells.

Lymphocyte Activation

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immuno-globulin Ig. The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the APC. The soluble product of an activated B lymphocyte is immmunoglobulins (antibodies). The soluble product of an activated T lymphocyte is lymphokines.

Chemokines are chemotactic cytokines, which constitute a family of low molecular mass (8-11 kDa) structurally-related proteins with diverse immune and neural functions (Mackay C. R., "Chemokines: immunology's high impact factors", Nat Immunol., Vol. 2: 95-101, (2001)); (Youn B. et al., "Chemokines, chemokine receptors and hematopoiesis", Immunol Rev, Vol. 177: 150-174, (2000)) that can be categorized into four subfamilies (C, CC, CXC and CX3C) based on the relative positions of conserved cysteine residues (Rossi D. et al., "The biology of chemokines and their receptors", Annu Rev Immunol,, Vol. 18: 217-242, (2000)). Chemokines are essential molecules in directing leucocyte migration between blood, lymph nodes and tissues. They constitute a complex signaling network because they are not always restricted to one type of receptor (Loetscher P. et al., "The ligands of CXC chemokine receptor 3, I-TAC, Mig, and IP10, are natural antagonists for CCR3", J. Biol. Chem., Vol. 276: 2986-2991, (2001)). Chemokines affect cells by activating surface receptors that are seven-transmembrane-domain G-protein-coupled receptors. Leukocyte responses to particular chemokines are determined by their expression of chemokine receptors. The binding of the chemokine to the receptor activates various signaling cascades, similar to the action of cytokines that culminate in the activation of a biological response. Secretion of the ligands for the CCR5 receptor, regulated upon activation normal T cell expressed and secreted (RANTES), macrophage inflammatory protein (MIP)-1α/and MIP-1β (Schrum S. et al., "Synthesis of the CC-chemokines MIP-1alpha, MIP-1beta, and RANTES is associated with a type 1 immune response", J Immunol, Vol. 157: 3598-3604, (1996)) and the ligand for CXC chemokine receptor 3 (CXCR3), induced protein (IP)-10 (Taub D. D. et al., "Recombinant human interferon-inducible protein 10 is a chemoattractant for human monocytes and T lymphocytes and promotes T cell adhesion to endothelial cells", J Exp Med., Vol. 177:1809-1814, (1993)) have been associated with unwanted heightened $T_{H1}$ responses. Additionally, elevated damaging pro-inflammatory cytokine levels of IL-2 and IFN-γ correlate with type 1 diabetes (T1D) (Rabinovitch A. et al., "Roles of cytokines in the pathogenesis and therapy of type 1 diabetes", Cell Biochem Biophys, Vol. 48(2-3): 159-63, (2007)). Chemokines have been observed in $T_{H1}$ pancreatic infiltrates and other inflammatory lesions characterized by T cell infiltration (Bradley L. M. et al., "Islet-specific Th1, but not Th2, cells secrete multiple chemokines and promote rapid induction of autoimmune diabetes", J Immunol, Vol. 162:2511-2520, (1999)).

Pro-inflammatory cytokines like IL-1β, IL-6, and TNF-α in the plasma have been primarily detected and involved in the insulin resistance and development of T2D which are kept in check and modulated by the anti-inflammatory and immune suppressive cytokines TGF-β1 and IL-10 (Alexandraki K. et al., "Inflammatory process in type 2 diabetes: The role of cytokines", Annals of the New York Academy of Sciences, 1084: 89-117, (2006); Kumar N. P. et al. 2015. Eur J Immunol. doi: 10.1002/eji.201545973 ahead of print). IL-17A is a well-known pro-inflammatory cytokine involved in several autoimmune diseases.

Immune Tolerance

The immune system is tolerant of self-antigens, i.e., it can discriminate between antigenic determinants expressed on foreign substances, and antigenic determinants expressed by tissues of the host. The capacity of the system to ignore host antigens, referred to as immune tolerance or immunological tolerance, is an active process involving the elimination or inactivation of cells that could recognize self-antigens through immunologic tolerance (Fundamental immunology, 4th Edn, William E. Paul, Ed. Lippincott-Raven Publishers, Philadelphia, (1999), at p. 2).

Immune tolerance is classified into 1) central tolerance or 2) peripheral tolerance depending on where the state is originally induced, i.e., whether it is in the thymus and bone marrow (central) or in other tissues and lymph nodes (peripheral). The biological mechanisms whereby these forms of tolerance are established are distinct, but the resulting effect is similar (Raker V. K. et al., "Tolerogenic Dendritic Cells for Regulatory T Cell Induction in Man", Front Immunol, Vol., 6(569): 1-11, (2015)).

Central tolerance, the principal way in which the immune system is educated to discriminate self-molecules from non-self-molecules, is established by deleting autoreactive lymphocyte clones at a point before they mature into fully immunocompetent cells. It occurs during lymphocyte development in the thymus and bone marrow for T and B lymphocytes, respectively (Sprent J. et al., "The thymus and central tolerance", Philos Trans R Soc Lond B Biol Sci, Vol. 356(1409): 609-616, (2001)). In these tissues, maturing lymphocytes are exposed to self-antigens presented by thymic epithelial cells and thymic dendritic cells, or bone marrow cells. Self-antigens are present due to endogenous expression, importation of antigen from peripheral sites via circulating blood, and in the case of thymic stromal cells, expression of proteins of other non-thymic tissues by the action of the transcription factor AIRE (Murphy, Kenneth. Janeway's Immunobiology: 8th ed. Chapter 15: Garland Science. (2012), pp. 611-668; Klein L., "Aire gets company for immune tolerance", Cell, Vol. 163(4):794-795, (2015)). Those lymphocytes that have receptors that bind strongly to self-antigens are removed by means of apoptosis of the autoreactive cells, or by induction of anergy (Id. at pp. 275-334). Weakly autoreactive B cells may also remain in a state of immunological inactivity where they do not respond to stimulation of their B cell receptor. Some weakly self-recognizing T cells are alternatively differentiated into natural regulatory T cells (nTreg cells), which act as sentinels in the periphery to lower potential instances of T cell autoreactivity (Id. at pp. 611-668).

The deletion threshold is more stringent for T cells than for B cells since T cells are the main populations of cells that can cause direct tissue damage. Furthermore, it is more advantageous for the organism to let its B cells recognize a wider variety of antigens, so that they can elicit antibodies against a greater diversity of pathogens. Since B cells can only be fully activated after confirmation by more self-restricted T cells that recognize the same antigen, autoreactivity is held in great check (Murphy, Kenneth. Janeway's Immunobiology: 8th ed. Chapter 8: Garland Sciences. pp. 275-334).

This process of negative selection ensures that T and B cells that potentially may initiate a potent immune response to the individual's own tissues are destroyed while preserving the ability to recognize foreign antigens. This step in lymphocyte education is detrimental to preventing autoimmunity. Lymphocyte development and education is most active in fetal development, but continues throughout life as immature lymphocytes are generated, slowing as the thymus degenerates and the bone marrow shrinks in the adult life (Murphy, Kenneth. Janeway's Immunobiology: 8th ed. Chapter 8: Garland Sciences. (2012), pp. 275-334; Jiang T. T., "Regulatory T cells: new keys for further unlocking the enigma of fetal tolerance and pregnancy complications", J Immunol., Vol. 192(11): 4949-4956, (2014)).

Peripheral tolerance develops after T and B cells mature and enter the peripheral tissues and lymph nodes (Murphy, Kenneth. Janeway's Immunobiology: 8th ed. Chapter 8: Garland Sciences. pp. 275-334). It is set forth by a number of overlapping mechanisms that predominantly involve control at the level of T cells, especially CD4$^+$ helper T cells, which orchestrate immune responses and give B cells the confirmatory signals that the B cells need in order to progress to produce antibodies. Inappropriate reactivity toward a normal self-antigen that was not eliminated in the thymus can occur, since the T cells that leave the thymus are relatively, but not completely, safe. Some will have receptors (TCRs) that can respond to self-antigens that the T cell did not encounter in the thymus (Murphy, Kenneth. Janeway's Immunobiology: 8th ed. Chapter 8: Garland Sciences. (2012), pp. 275-334). Those self-reactive T cells that escape intra-thymic negative selection in the thymus can inflict cell injury unless they are deleted in the peripheral tissue chiefly by nTreg cells.

Autoimmune regulator (Aire), usually expressed in thymic medullary epithelial cells, plays a role in immune tolerance by mediating ectopic expression of peripheral self-antigens and mediating the deletion of auto-reactive T cells. (Metzger T. C. et al., "Control of central and peripheral tolerance by Aire", Immunol. Rev. 2011, Vol. 241: 89-103, (2011)).

Appropriate reactivity towards certain antigens can also be suppressed by induction of tolerance after repeated exposure. Naïve CD4$^+$ helper T cells differentiate into induced Treg cells (iTreg cells) in the peripheral tissue, or accordingly, in nearby lymphoid tissue (lymph nodes, mucosal-associated lymphoid tissue, etc.). This differentiation is mediated by IL-2 produced upon T cell-activation, and TGF-β from any of a variety of sources, including tolerizing dendritic cells (DCs) or other antigen presenting cells (Curotto de Lafaille et al., "Effective recruitment and retention of older adults in physical activity research: PALS study", Immunity, Vol. 30(6): 626-635, (2009)).

T-Memory Cells

Following the recognition and eradication of pathogens through adaptive immune responses, the vast majority (90-95%) of T cells undergo apoptosis with the remaining cells forming a pool of memory T cells, designated central memory T cells (TCM), effector memory T cells (TEM), and resident memory T cells (TRM) (Clark, R. A., "Resident memory T cells in human health and disease", Sci. Transl. Med., 7, 269rv1, (2015)).

Compared to standard T cells, these memory T cells are long-lived with distinct phenotypes such as expression of specific surface markers, rapid production of different cytokine profiles, capability of direct effector cell function, and unique homing distribution patterns. Memory T cells exhibit quick reactions upon re-exposure to their respective antigens in order to eliminate the reinfection of the offender and thereby restore balance of the immune system rapidly. Increasing evidence substantiates that autoimmune memory T cells hinder most attempts to treat or cure autoimmune diseases (Clark, R. A., "Resident memory T cells in human health and disease", Sci. Transl. Med., Vol. 7, 269rv1, (2015)).

The Complement System

The complement system comprises over 30 different proteins that circulate in blood plasma. In the absence of an infection, the complement proteins circulate in an inactive form. In the presence of a pathogen, the complement proteins become activated to kill the pathogen either directly or by facilitating phagocytosis. There are three ways in which the complement system is activated.

Antibody-dependent cell mediated cytotoxicity (ADCC) is a mechanism by which effector cells of the immune system (e.g. natural killer cells) actively lyse target cells that have been bound by antibodies. The ADCC killing mechanism of an antibody-coated target cell by a cytotoxic effector cell is through a nonphagocytic process. This process involves the release of the content of cytotoxic granules or by the expression of cell death-inducing molecules. ADCC is triggered through interaction of target-bound antibodies (belonging to IgG or IgA or IgE classes) with certain Fc receptor glycoproteins present on the effector cell surface that bind the Fc region of immunoglobulins (Ig). Effector cells that mediate ADCC include natural killer (NK) cells, monocytes, macrophages, neutrophils, eosinophils and dendritic cells. ADCC is dependent on a number of parameters such as density and stability of the antigen on the surface of the target cell, antibody affinity, and FcR-binding affinity.

In contrast with ADCC, complement dependent cell cytotoxicity (CDCC) is a process of the immune system that kills pathogens by damaging target cell membrane without the involvement of antibodies. This alternative pathway is initiated by spontaneous hydrolysis and activation of the complement component C3, which binds directly to microbial surfaces. Alternatively the lectin pathway is initiated by soluble carbohydrate binding proteins that bind to specific carbohydrate molecules on microbial surfaces.

Each of the ADCC and CDCC mechanisms generates a C3 convertase that cleaves C3, leaving behind C3b bound to the pathogen's surface and releasing C3a. This results in recruitment of phagocytic cells to the site of an infection, phagocytosis of pathogens by immune cells, and/or formation of a membrane attack complex (MAC) that disrupts pathogen cell membrane and causes cell lysis.

Co-Stimulatory Molecules

Co-stimulatory molecules are the highly active immunomodulatory proteins that play a critical role in the development and maintenance of an immune response (Kaufman and Wolchok eds., General Principles of Tumor Immunotherapy, Chpt 5, 67-121 (2007)). The two signal hypothesis of T cell response involves the interaction between an antigen bound to an MHC molecule and the T cell receptor (TCR), and an interaction of a co-stimulatory molecule and its ligand. Specialized APCs, which are carriers of a co-stimulatory second signal, are able to activate T cell responses following binding of the MHC molecule with TCR. By contrast, somatic tissues do not express the second signal and thereby induce T cell unresponsiveness (Kaufman and Wolchok eds., General Principles of Tumor Immunotherapy, Chpt 5, 67-121 (2007)). The two signal model explains the peripheral tolerance to self-antigens and why cancer cells can evade immune detection: tumor cells rarely express co-stimulatory molecules, and thereby lack the second signal critical to activating T cells.

Furthermore, many of the co-stimulatory molecules involved in the two-signal model can be blocked by co-inhibitory molecules that are expresses by normal tissue and by cancer cells (Kaufman and Wolchok eds., General Principles of Tumor Immunotherapy, Chpt 5, 67-121 (2007)). In fact, many types of interacting immunomodulatory molecules expressed on a wide variety of tissues may exert both stimulatory and inhibitory functions depending on the immunologic context (Kaufman and Wolchok eds., General Principles of Tumor Immunotherapy, Chpt 5, 67-121 (2007)).

DNA motifs consisting of an unmethylated CpG dinucleotide flanked by two 5' purines (e.g. GpA) and two 3' pyrimidines (e.g. TpC or TpT) are capable of stimulating an innate immune response by mimicking bacterial DNA. CpG oligodeoxynucleotides can be used as immune adjuvants to improve the function of professional antigen-presenting cells and increase generation of humoral and cellular vaccine-specific immune responses. CpG DNA is able to directly activate dendritic cells and B cells, resulting in the induction of both innate and adaptive immune responses (Bode, C., CpG DNA as a vaccine adjuvant, Expert Rev Vaccines. 2011 April; 10(4): 499-511).

Cell-surface immunomodulatory molecules can be grouped according to structure into two large families of receptors/ligands: the B7/CD28 immunoglobulin family and the Tumor Necrosis Factor (TNF)-related family (Kaufman and Wolchok eds., General Principles of Tumor Immunotherapy, Chpt 5, 67-121 (2007)). Many members of these families have been characterized and evaluated for cancer immunotherapy.

CD28/CTLA-4/B7-1/B7-2 Family

B7-1(CD80) and B7-2 (CD86) are expressed on activated APCs and bind to CD28 on T cells, providing the necessary co-stimulation for naïve T-cell activation, inducing IL-2 production, cell division, and the inhibition of activation induced cell death (AICD) (Kaufman and Wolchok eds., General Principles of Tumor Immunotherapy, Chpt 5, 67-121 (2007)). A homologue to CD28, Cytotoxic T lymphocyte-associated antigen 4 (CTLA-4, CD152), binds both B7-1 and B7-2 molecules and, in contrast to CD28, inhibits T-cell proliferation. B7 molecules therefore have two ligands, CD28 and CTLA-4, with opposing effects on T cells (Kaufman and Wolchok eds., General Principles of Tumor Immunotherapy, Chpt 5, 67-121 (2007)).

Ligation of CTLA-4 in isolation may cause apoptosis of T cells, whereas CTLA-4 ligation in conjunction with signaling via the TCR and CD28 inhibits T-cell activation. Accordingly, CTLA-4 −/− mice develop a fatal lymphoproliferative disorder (Kaufman and Wolchok eds., General Principles of Tumor Immunotherapy, Chpt 5, 67-121 (2007)).

The differential expression of CD28 and CTLA-4 in time and location at the cell surface has implications for their respective roles in the generation of immune responses. While CD28 is uniformly distributed throughout the membrane and aggregates rapidly to the immunologic synapse with T-cell activation, CTLA-4 is present in intracellular vesicles and is mobilized to the cell surface later (Kaufman and Wolchok eds., General Principles of Tumor Immunotherapy, Chpt 5, 67-121 (2007)). Mobilization of CTLA-4 is tightly regulated by B7.1 expression on the APC, and by the strength of TCR stimulation. As a result, CTLA-4 may act to attenuate the T cell response, limiting the activity of high affinity T-cell clones (Kaufman and Wolchok eds., General Principles of Tumor Immunotherapy, Chpt 5, 67-121 (2007)).

CTLA-4 has been implicated in many aspects of immune regulation. For example, it may be involved in causing T cell anergy, modulating memory T cell responses, shaping diversity of a polyclonal T cell response, and raising levels of inhibitory cytokines TGF-beta and IL10 (Kaufman and Wolchok eds., General Principles of Tumor Immunotherapy, Chpt 5, 67-121 (2007)). CTLA-4 may also "back-signal" via B7 to down-regulate dendritic cell activation markers (Kaufman and Wolchok eds., General Principles of Tumor Immunotherapy, Chpt 5, 67-121 (2007)). CTLA-4 may also play a role in regulatory T-cell (Treg) function, as it is expressed on Tregs and on cutaneous T cell lymphoma, which may arise from Tregs (Kaufman and Wolchok eds., General Principles of Tumor Immunotherapy, Chpt 5, 67-121 (2007)).

The CD28/B7/CTLA-4 co-stimulatory mechanism has been investigated for cancer immunotherapy, such as by transfecting tumors with B7 molecules and use of anti-CTLA-4 antibodies.

In initial experiments involving transfection of B7.1 into poorly immunogenic melanoma cell lines, tumors grew but then regressed in a CD8+ T-cell-dependent process. Furthermore, animals treated with B7.1 melanoma cells became immune to further tumor challenge, demonstrating induction of immunologic memory, and inoculation with B7-expressing tumor cells caused regression of small pre-existing B7-negative tumors. Generally, larger tumors (greater than 2-3 mm) were not affected, and similar results were seen with B7.2-expressing tumors. Similar results have been shown in other tumor models including lymphoma and prostate cancer. The B7 surface molecule appears to be directly contacting and activating T cells, and B7-transfected tumor cells appear to function as APCs. Despite these promising results, human clinical trials of B7-containing vaccines have demonstrated increased immune response, but with only limited clinical benefit. (Kaufman and Wolchok eds., General Principles of Tumor Immunotherapy, Chpt 5, 67-121 (2007)).

Anti-CTLA antibodies have been shown to be effective in murine colon carcinoma and fibrosarcoma, as well as in murine models of prostate cancer, breast cancer, and melanoma, but not in some models of poorly immunogenic tumors. Anti-CTLA-4 antibodies have also been combined with other modes of immunotherapy and conventional therapies (e.g. surgery, chemotherapy) in mouse models. The results of mouse models and human studies suggest that mechanisms by which CTLA-4 blockade enhances anti-tumor immunity are not due to regulatory T cell-mediated suppression but instead to enhanced proliferation of effector T cells through down-regulation of CTLA-4-mediated inhibition (Kaufman and Wolchok eds., General Principles of Tumor Immunotherapy, Chpt 5, 67-121 (2007)). Human clinical trials of anti-CTLA-4 antibodies have demonstrated potential as an immune therapy, but because CTLA-4 plays a role in controlling T-cell responses, blocking its activity has the potential to lead to autoimmunity.

PD-1/PD-L1 (B7-H1), PD-L2 (B7-DC)

Programmed Death-1 (PD-1) is expressed by activated T cells, and is thought to be primarily an inhibitory modulator. Evidence from murine models suggests that expression of PD-L1 may protect tumors from the immune system. PD-L1 on tumors causes apoptosis in tumor-reactive T cells, and a myeloma cell line expressing PD-L1 fails to grow in PD-1 knock-out mice. In one model, PD-L1 blocking antibodies cured mice of squamous cell carcinoma. In another model, PD-L1 blocking antibodies restored responsiveness to immunologic therapy with a 4-1BB (CD137) agonist. Furthermore, PD-1 -/- T cells have been shown to have enhanced anti-tumor characteristics. PD-L1 may also play an important role in the function of "suppressor" myeloid cells. It was reported that culturing dendritic cells in the presence of blocking antibody enhanced the development of T-cell responses against ovarian cancer. The mechanism through which PD-L1 may mediate immune suppression is through Interleukin-10 (IL-10) production. In contrast, the other PD-1 ligand, PD-L2, stimulated immunity in mice to the poorly immunogenic B16 melanoma (Kaufman and Wolchok eds., General Principles of Tumor Immunotherapy, Chpt 5, 67-121 (2007)).

Many human cancers have been found to express PD-L1 including tumors of the breast, cervix, lung, ovary, colon, as well as melanoma, glioblastoma and primary T cell lymphomas, which is consistent with the role of the PD-L1 pathway in tumor immune evasion. Furthermore, a poor prognosis in esophageal cancer and renal cell cancer may be associated with expression of PD-L1. Similarly, PD-L2 is highly expressed in Hodgkin lymphoma cell lines and may also serve as a prognostic marker (Kaufman and Wolchok eds., General Principles of Tumor Immunotherapy, Chpt 5, 67-121 (2007)).

CD27/CD70

Upon T cell activation, CD27 is transiently up-regulated and is also expressed on B cells and NK cells. The ligand of CD27, CD70, is expressed on activated lymphocytes and mature dendritic cells. A transition from central-memory to effector-memory phenotype is associated with loss of CD27 expression on CD8+ T cells, and CD27 -/- mice show impaired memory T cell function along with decreased accumulation in peripheral tissues during viral infection. In contrast, mice with constitutive CD27 expression display accumulating increased T cell populations, and ultimately develop a paucity of B cells and eventually succumb to a lethal T-cell immunodeficiency, possibly due to an excessive shift in the T-cell population towards a terminally differentiated, non-reproducing memory phenotype (Kaufman and Wolchok eds., General Principles of Tumor Immunotherapy, Chpt 5, 67-121 (2007)).

OX40/OX40L

OX40 (CD134) is expressed only on activated T-cells, and predominately CD4+ T cells. Its ligand, OX40L, is found on a wide variety of immune cells including activated B cells, T cells, dendritic cells, and vascular epithelial cells. Ligation of OX40 on T-cells promotes survival, expansion, and cytokine production, and studies in knock-out animals show that OX40 is critical for CD4, but not CD8 responses. OX40 is also important for the homeostasis and development of Tregs. In the context of immunotherapy, OX40 ligation may reverse T-cell anergy and render silent epitopes immunogenic (Kaufman and Wolchok eds., General Principles of Tumor Immunotherapy, Chpt 5, 67-121 (2007)).

Various strategies of augmenting OX40 signaling in anti-tumor T cells have shown promise in developing tumor immunotherapy in mouse models. OX40 ligation has been found to increase tumor-free survival and cure some mice in animal models of cancers such as melanoma, sarcoma, colon cancer, breast cancer, and glioma. Furthermore, treatment was effective in animal models of metastatic disease, where mice developed strong anti-tumor T-cell responses, in particular memory CD4+ T-cells, which protected them from further challenge with the same tumor. Furthermore, vaccines comprising cells transfected with OX40L and GMCSF cure colon cancer in murine colon cancer models. OX40 ligation has also shown synergy with a combination of 4-1BB ligation and Interleukin 12 (IL-12). In total, evidence from murine studies suggests that ligation of OX40, combined with other immunotherapies, shows promise in the treatment of human cancers (Kaufman and Wolchok eds., General Principles of Tumor Immunotherapy, Chpt 5, 67-121 (2007)).

4-IBB/4-IBBL 4-1BB (CD137) is expressed on activated T cells, NK cells, and dendritic cells, while 4-1BBL is expressed on activated antigen presenting cells (APCs). Studies have found that 4-1BB ligation particularly stimulates CD8+ T cells, and promotes their differentiation into effectors. It has been reported that 4-1BB signaling is able to reverse the anergy induced by soluble antigens and rescue CD28-/-CD8+ T cells. Accumulation of such T cells occurs in the elderly, during chronic inflammation, and cancer. In contrast, 4-1BB ligation has been shown to suppress CD4+ T cells and B cells. Agonist anti-4-1BB antibody has been identified as being able to reverse autoimmunity in mice (Kaufman and Wolchok eds., General Principles of Tumor Immunotherapy, Chpt 5, 67-121 (2007)).

Anti-4-1BB antibodies have been able to achieve eradication of established tumors in mouse models, and ligation of 4-1BB by systemically administered antibodies, as well as vaccination with 4-1-BBL expressing tumor cells, have been shown to cause rejection of tumors. Furthermore, tumor cells transfected with single-chain Fv fragments specific for 4-1BB have also been found to be effective anti-tumor agents. CD8+ T cells are believed to primarily be effectors in 4-1BB mouse models, but tumor rejection has also been identified as being dependent on CD4+ T cells, NK cells, and on myeloid cells. Ligation of 4-1BB is ineffective, however, when CD28 is present and an immune response is already present. Thus, 4-1BB ligation has been used in combination with CD28 stimulation to target both pathways together (Kaufman and Wolchok eds., General Principles of Tumor Immunotherapy, Chpt 5, 67-121 (2007)).

HVEM-LIGHT

Herpes Virus Entry Mediator (HVEM) is a biochemical switch regulating T cell activation in a costimulatory or co-inhibitory fashion. The stimulatory or inhibitory outcome depends on the specific ligand engaged (Cai, G., The CD160, BTLA, LIGHT/HVEM pathway: a bidirectional switch regulating T-cell activation, Immunol. Rev., May; 229(1):244-58 (2009)). HVEM binds to at least three ligands: lymphotoxin-like, exhibits inducible expression, and competes with herpes simplex virus glycoprotein D for HVEM, a receptor expressed by T lymphocytes (LIGHT), lymphotoxin alpha 3 (Ltα3), and B- and T-lymphocyte attenuator (BTLA). LIGHT, Ltα3, and BTLA are HVEM ligands. The binding of LIGHT or Ltα3 to HVEM delivers a costimulatory signal, while binding of BTLA to HVEM delivers a co-inhibitory signal. The LIGHT receptor binds two receptors in addition to HVEM: LTβR and CdR3/TR6. HVEM is found on resting T cells, monocytes, and immature dendritic cells. LIGHT can be found on activated T cells, monocytes, and NK cells, and also on immature dendritic cells. LIGHT signaling causes proliferation of T cells stimulated with CD3 or CD3/CD28, and can induce DC maturation, while over-expression of LIGHT can cause autoimmunity with increased T cell populations and inflammation of mucosal tissues. LIGHT deficiency causes CD8+ T-cell dysfunction. BTLA is expressed on activated T cells, B cells and dendritic cells, and its signals can suppress T-cell responses (Kaufman and Wolchok eds., General Principles of Tumor Immunotherapy, Chpt 5, 67-121 (2007)).

LIGHT is believed to have an anti-tumor effect through apoptosis induction and immune activation, and it can kill tumors expressing HVEM via a death-domain pathway. Furthermore, transfection of tumor cells with LIGHT are capable of causing T-cell dependent tumor rejection, in some cases by inducing changes to tumor stromal cells facilitating entry of T cells into the tumor (Kaufman and Wolchok eds., General Principles of Tumor Immunotherapy, Chpt 5, 67-121 (2007)).

CpG

DNA motifs consisting of an unmethylated CpG dinucleotide flanked by two 5' purines (e.g. GpA) and two 3' pyrimidines (e.g. TpC or TpT) are capable of stimulating an innate immune response by mimicking bacterial DNA. CpG oligodeoxynucleotides can be used as immune adjuvants to improve the function of professional antigen-presenting cells and increase generation of humoral and cellular vaccine-specific immune responses. CpG DNA is able to directly activate dendritic cells and B cells, resulting in the induction of both innate and adaptive immune responses (Bode, C., CpG DNA as a vaccine adjuvant, Expert Rev Vaccines. 2011 April; 10(4): 499-511). The efficacy of oligodeoxynucleotides containing unmethylated CpG motifs as an immune therapy adjuvant is dependent on the spatial and temporal proximity between the CpG and an antigen. Studies have shown that physically attaching a CpG oligonucleotide to an antigen can increase immunity to that antigen by more than 100-fold relative to a CpG oligonucleotide diffusely mixed with an antigen. Furthermore, CpG conjugated increases dendritic cell uptake of cell based vaccines, increases co-stimulatory molecule expression, increases production of immunostimulatory cytokines, and causes expansion of cytotoxic T cells (Shirota, H., CpG-conjugated apoptotic tumor cells elicit potent tumor-specific immunity, Cancer Immunol Immunother (2011) 60:659-669 incorporated by reference herein in its entirety).

Immunogenic Potential of Vaccines

Vaccines against infectious agents are prime examples of specific receptor-ligand interactions being used to shape an immune response for the therapeutic goal of preventing or reducing infection (e.g. flu vaccine). Generally, an antigen is presented to the immune system in the context of an adjuvant (e.g., a synthetic small molecule immunomodulator).

The allogeneic tumor vaccines of the described invention are distinct from such vaccines in several key features. First, they are designed to be capable of treating existing tumors, although prevention of tumor formation is theoretically also possible. Second, their efficacy tends to be limited by the fact that while tumors express neoantigens (i.e. new, non-self elements) that are foreign and new to the individual, they are also undoubtedly human tumor cells and thus not always recognized as foreign (i.e. non-self) by the individual.

The aforementioned difficulties notwithstanding, evidence has now emerged that 1) endogenous antitumor responses exist, 2) that these immune responses can be modulated and 3) that this modulation can be measured in terms of overall survival in standard clinical trials.

According to aspects of the described invention, a series of immunomodulators that can be co-expressed either on a tumor cell line derived from a cancer patient, or on a multiply genetically modified allogeneic tumor cell line has been identified that, when used as a tumor vaccine, may serve 1) to efficiently load the broad array of tumor antigens into the endogenous antigen presenting cells, 2) to efficiently stimulate several cell types by enhancing the normal signals received during an immune response, 3) to impede the mechanisms by which T regulatory cells suppress the immune response, 4) to impede the signals by which immune responses are generally resolved, and 5) to result in enhanced overall survival of cancer patients vaccinated with such a formulation. Although in certain embodiments, the modified tumor cell line can be derived from the patient who receives the vaccine, the allogeneic tumor cell line vaccine approach is distinct from a personalized therapy approach, because the modified tumor cells are not necessarily derived from the individual who ultimately receives the vaccine. Instead, an allogeneic tumor cell vaccine aims to focus an immune response on the many elements that individual tumors of the same tumor type have in common.

One strategy for exploiting the large number of potential tumor antigens for each individual type of cancer is to vaccinate with whole tumor cells to avoid accidentally excluding potentially relevant antigens. The invention described herein provides, among other things, a vaccine with whole tumor cells possessing an array of antigens and modified to express two or more immune modulators.

BRIEF SUMMARY OF THE INVENTION

According to some aspects, a method of treating a cancer in a patient comprises the steps of (a) preparing an allogeneic tumor cell line variant transfected to express two or more immunomodulator peptides by: (1) providing an allogeneic parental tumor cell line; (2) transfecting or transducing recombinant DNA sequences coding for two or more of immunomodulator peptides selected from IgG1, CD40L, TNF-alpha, GM-CSF, and Flt-3L; (3) generating the tumor cell line variants by selecting for tumor cell clones that stably express an immunogenic amount of the two or more immune modulator peptides selected from IgG1, CD40L, TNF-alpha, GM-CSF, and Flt-3L; (4) selecting in a mixed lymphocyte tumor cell reaction clonally derived cell line variants by one or more of the following parameters selected from cellular proliferation, cellular subset differentiation, cytokine release profile, and tumor cell lysis; wherein the selected clonally derived cell line variant is effective to stimulate activation of one or more of T cells, B cells, and dendritic cells, and (b) administering to the patient that has cancer an immunostimulatory amount of the tumor cell line variant vaccine, wherein the immunostimulatory amount is effective to improve clinical outcome.

According to some embodiments, the immunomodulator peptides are selected from membrane expressed IgG1, CD40L, TNF-alpha, as well as membrane and soluble forms of GM-CSF, and Flt-3L.

According to some embodiments, the tumor cell line variant vaccine is effective to improve overall survival of cancer patients relative to placebo controls. According to some embodiments the parental tumor cell line is derived from a melanoma. According to some embodiments the parental tumor cell line is derived from a prostate cancer. According to some embodiments the parental tumor cell line is derived from a breast cancer.

According to some embodiments, the IgG1 immunomodulator peptide sequence is of at least 60% identity to SEQ ID NO: 45. According to some embodiments, the CD40L immune modulator peptides sequence is of at least 60% identity to SEQ ID NO: 7. According to some embodiments, the TNF-alpha immune modulator peptide sequence is of at least 60% identity to SEQ ID NO: 11. According to some embodiments, the GM-CSF immune modulator peptide sequence is of at least 60% identity to SEQ ID NO: 13 or SEQ ID NO: 5. According to some embodiments, the Flt-3L immune modulator peptide sequence is of at least 60% identity to SEQ ID NO: 14 or SEQ ID NO: 44.

According to some aspects, an allogeneic tumor cell vaccine comprises (1) a tumor cell line variant comprising (a) two or more stably expressed recombinant membrane bound immunomodulatory molecules selected from IgG1, CD40L, TNF-alpha, and Flt-3L peptides; and (b) stably expressed recombinant soluble GM-CSF peptides; and (2) a pharmaceutically acceptable carrier; wherein an immune stimulatory amount of the tumor cell line variant is effective to elicit an immune response that improves progression free survival, overall survival, or both relative to placebo controls.

According to some embodiments, the tumor cell line variant expresses two or more of (a) a membrane bound IgG1 peptide with at least 60% identity to SEQ ID NO: 45; (b) a membrane bound CD40L peptide with at least 60% identity to SEQ ID NO: 7; (c) a membrane bound form of TNF-alpha peptide with at least 60% identity to SEQ ID NO: 11; (d) a membrane bound form of Flt-3L peptide with at least 60% identity to SEQ ID NO: 14; and (e) a soluble GM-CSF peptide with at least 60% identity to SEQ ID NO: 13.

According to some embodiments, the tumor cell line variant comprises a membrane bound fusion protein of CD40L peptide and TNF-alpha peptide. According to some embodiments, the CD40L peptide is of at least 60% identity to SEQ ID NO: 9, and the TNF-alpha peptide is of at least 60% identity to SEQ ID NO: 10. According to some embodiments, the TNF-alpha peptide is of at least 60% identity to SEQ ID NO: 11,. According to some embodiments, the tumor cell line variants comprise soluble GM-CSF and membrane bound IgG1, CD40L, TNF-alpha, and Flt-3L. According to some embodiments, the tumor cell line variant comprises a fusion of CD40L and TNFa peptides. According to some embodiments, the tumor cell line variant comprises an immune modulator peptide sequence of at least 60% identity to SEQ ID NO: 31. According to some embodiments, the tumor cell line variant comprises membrane and soluble forms of GM-CSF and membrane and soluble forms of Flt-3L. According to some embodiments, the tumor cell line variant comprises membrane bound forms of IgG, CD40L, and TNF-alpha.

These and other advantages of the invention will be apparent to those of ordinary skill in the art by reference to the following detailed description.

BRIEF DESCRIPTION OF THE DRAWINGS

FIG. 3B shows the nucleotide sequence of vector 1 (SEQ ID NO. 47).

FIG. 4B shows the nucleotide sequence of vector 2 (SEQ ID NO. 48).

FIG. 5B shows the nucleotide sequence of vector 3 (SEQ ID NO. 49).

FIG. 6B shows the nucleotide sequence of vector 4 (SEQ ID NO. 50).

FIG. 7B shows the nucleotide sequence of vector 5 (SEQ ID NO. 51).

FIG. 8B shows the nucleotide sequence of vector 6 (SEQ ID NO. 52).

FIG. 9B shows the nucleotide sequence of vector 7 (SEQ ID NO. 53).

FIG. 14A and FIG. 14B show the results of CyTOF mass cytometry single-cell phenotype analysis of hPBMC response to SK melanoma cells with modification by expression of immunomodulatory factors. FIG. 14A shows viSNE density contour plots of CyTOF staining data showing relative changes in immune cell subset abundance and phenotype. FIG. 14B shows single-cell phenotype analysis. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.

FIG. 15F shows CyTOF monocyte cluster analysis of hPBMC indicating relative median expression levels of CD4 T cell markers CD69 and CD25.

FIG. 16 is a graph that shows the results of LUMINEX® multiplex cytokine profiling of human PBMC responses to SK parent line and genetically modified SK lines. Control cultures included SK cells alone, hPBMCs alone, and hPBMCs stimulated with a mixture of anti-CD3 and anti-CD28 antibodies (1 µg/ml final concentration). Symbols indicate cytokine levels in pg/ml as estimated from a standard curve using recombinant cytokines. Absence of symbols indicates the cytokine was not detected. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.

DETAILED DESCRIPTION

Definitions

Figure 1:
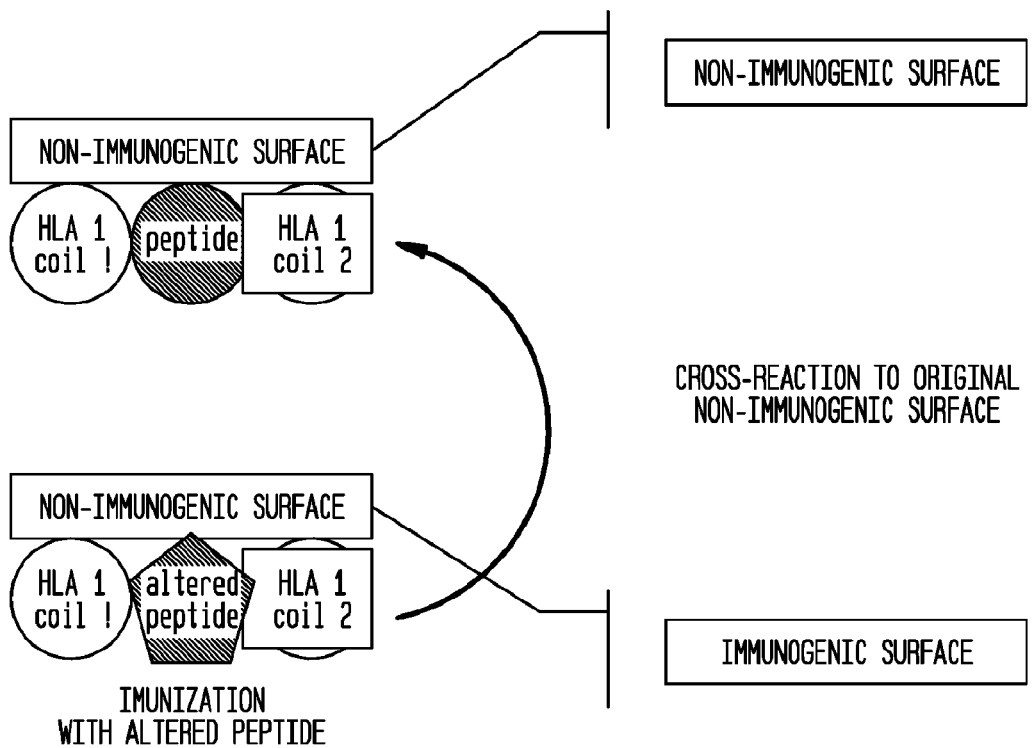
FIG. 1 shows one embodiment of a heteroclitic cross reaction between a peptide native to a tumor cell line and a peptide native to a tumor cell of a patient receiving immunotherapy.
Figure 1:
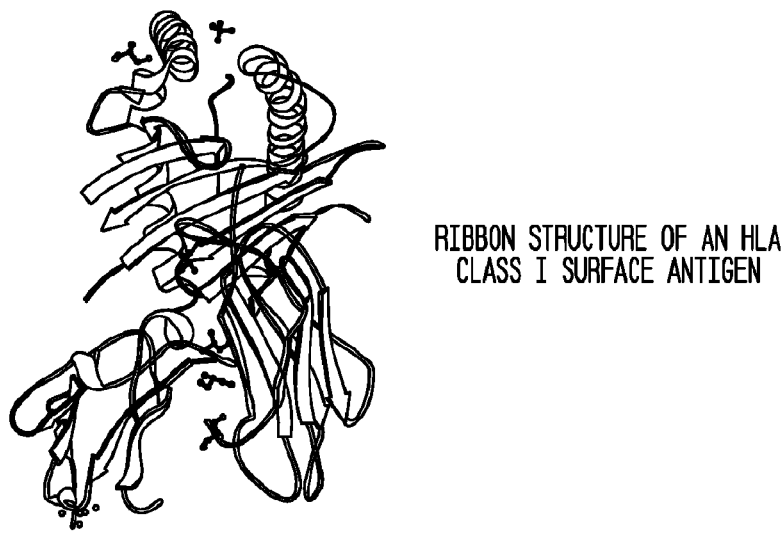

The term "activation" or "lymphocyte activation" refers to stimulation of lymphocytes by specific antigens, nonspecific mitogens, or allogeneic cells resulting in synthesis of RNA, protein and DNA and production of lymphokines; it is followed by proliferation and differentiation of various effector and memory cells. For example, a mature B cell can be activated by an encounter with an antigen that expresses epitopes that are recognized by its cell surface immunoglobulin Ig). The activation process may be a direct one, dependent on cross-linkage of membrane Ig molecules by the antigen (cross-linkage-dependent B cell activation) or an indirect one, occurring most efficiently in the context of an intimate interaction with a helper T cell ("cognate help process"). T-cell activation is dependent on the interaction of the TCR/CD3 complex with its cognate ligand, a peptide bound in the groove of a class I or class II MHC molecule. The molecular events set in motion by receptor engagement are complex. Among the earliest steps appears to be the activation of tyrosine kinases leading to the tyrosine phosphorylation of a set of substrates that control several signaling pathways. These include a set of adapter proteins that link the TCR to the ras pathway, phospholipase Cγ1, the tyrosine phosphorylation of which increases its catalytic activity and engages the inositol phospholipid metabolic pathway, leading to elevation of intracellular free calcium concentration and activation of protein kinase C, and a series of other enzymes that control cellular growth and differentiation. Full responsiveness of a T cell requires, in addition to receptor engagement, an accessory cell-delivered costimulatory activity, e.g., engagement of CD28 on the T cell by CD80 and/or CD86 on the antigen presenting cell (APC). The soluble product of an activated B lymphocyte is immmunoglobulins (antibodies). The soluble product of an activated T lymphocyte is lymphokines.

As used herein, the term "administration" and its various grammatical forms as it applies to a mammal, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. "Administration" also encompasses in vitro and ex vivo treatments, e.g., of a cell, by a reagent, diagnostic, binding composition, or by another cell.

The term "allogeneic" as used herein means that the donor and the recipient (host) are of different genetic makeup, but of the same species. As used herein, an "allogeneic cell" refers to a cell that is not derived from the individual to which the cell is to be administered, that is, it has a different genetic constitution than the individual. An allogeneic cell is generally obtained from the same species as the individual to which the cell is to be administered. For example, the allogeneic cell can be a human cell, as disclosed herein, for administering to a human patient such as a cancer patient. As used herein, an "allogeneic tumor cell" refers to a tumor cell that is not derived from the individual to which the allogeneic cell is to be administered. Generally, the allogeneic tumor cell expresses one or more tumor antigens that can stimulate an immune response against a tumor in an individual to which the cell is to be administered. As used herein, an "allogeneic cancer cell," for example, a lung cancer cell, refers to a cancer cell that is not derived from the individual to which the allogeneic cell is to be administered.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids. The amino acids may be L- or D-amino acids. An amino acid may be replaced by a synthetic amino acid, which is altered so as to increase the half-life of the peptide, increase the potency of the peptide, or increase the bioavailability of the peptide. The single letter designation for amino acids is used predominately herein. Such single letter designations are as follows: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine. The following represents groups of amino acids that are conservative substitutions for one another: 1) Alanine (A), Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The term "autologous" as used herein means derived from the same individual.

The term "cancer" as used herein refers to diseases in which abnormal cells divide without control and are able to invade other tissues. There are more than 100 different types of cancer. Most cancers are named for the organ or type of cell in which they start—for example, cancer that begins in the colon is called colon cancer; cancer that begins in melanocytes of the skin is called melanoma. Cancer types can be grouped into broader categories. The main categories of cancer include: carcinoma (meaning a cancer that begins in the skin or in tissues that line or cover internal organs, and its subtypes, including adenocarcinoma, basal cell carcinoma, squamous cell carcinoma, and transitional cell carcinoma); sarcoma (meaning a cancer that begins in bone, cartilage, fat, muscle, blood vessels, or other connective or supportive tissue); leukemia (meaning a cancer that starts in blood-forming tissue (e.g., bone marrow) and causes large numbers of abnormal blood cells to be produced and enter the blood; lymphoma and myeloma (meaning cancers that begin in the cells of the immune system); and Central nervous system cancers (meaning cancers that begin in the tissues of the brain and spinal cord). The term "myelodysplastic syndrome" refers to a type of cancer in which the bone marrow does not make enough healthy blood cells (white blood cells, red blood cells, and platelets) and there are abnormal cells in the blood and/or bone marrow. Myelodysplastic syndrome may become acute myeloid leukemia (AML).

The term "contact" and its various grammatical forms as used herein refers to a state or condition of touching or of immediate or local proximity. Contacting a composition to a target destination may occur by any means of administration known to the skilled artisan.

The term "costimulatory molecule" as used herein refers to one of two or more molecules that are displayed on the cell surface that have a role in activating a T cell to become an effector cell. For example MHC proteins, which present foreign antigen to the T cell receptor, also require costimulatory proteins which bind to complementary receptors on the T cell's surface to result in activation of the T cell.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Cytokines can act both locally and distantly from a site of release. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of other cytokines. Nonlimiting examples of cytokines include e.g., IL-1α., IL-β., IL-2, IL-3, IL-4, IL-5, IL-6, IL-7, IL-8, IL-9, IL-10, IL-11, IL-12/IL-23 P40, IL13, IL-15, IL-17, IL-18, IL-21, IL-23, TGF-β, IFN-γ, GM-CSF, Gro.alpha., MCP-1 and TNF-α.

The term "derived from" as used herein encompasses any method for receiving, obtaining, or modifying something from a source of origin.

The term "derivative" or "variant" with respect to a peptide or DNA sequence (e.g. immune modulator peptide sequence) as used herein refers to a non-identical peptide or DNA sequence that is modified from its original sequence. The terms "derivative" or "variant" with respect to cells as used herein refers to a cell line that has been modified from its cell line of origin (e.g. modified to express recombinant DNA sequences).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition. A "detection reagent" is any molecule that generates a detectable response indicative of the presence or absence of a substance of interest. Detection reagents include any of a variety of molecules, such as antibodies, nucleic acid sequences and enzymes. To facilitate detection, a detection reagent may comprise a marker.

The term "dose" as used herein refers to the quantity of a therapeutic substance prescribed to be taken at one time.

The term "enrich" as used herein refers to increasing the proportion of a desired substance, for example, to increase the relative frequency of a subtype of cell compared to its natural frequency in a cell population. Positive selection, negative selection, or both are generally considered necessary to any enrichment scheme. Selection methods include, without limitation, magnetic separation and FACS. Regardless of the specific technology used for enrichment, the specific markers used in the selection process are critical, since developmental stages and activation-specific responses can change a cell's antigenic profile.

As used herein, the term "expression" encompasses the biosynthesis of mRNA, polypeptide biosynthesis, polypeptide activation, e.g., by post-translational modification, or an activation of expression by changing the subcellular location or by recruitment to chromatin.

The term "expression vector" refers a DNA molecule comprising a gene that is expressed in a host cell. Typically, gene expression is placed under the control of certain regulatory elements including, but not limited to, promoters, tissue specific regulatory elements, and enhancers. Such a gene is said to be "operably linked to" the regulatory elements.

The term "flow cytometry" as used herein refers to a tool for interrogating the phenotype and characteristics of cells. It senses cells or particles as they move in a liquid stream through a laser (light amplification by stimulated emission of radiation)/light beam past a sensing area. The relative light-scattering and color-discriminated fluorescence of the microscopic particles is measured. Flow Analysis and differentiation of the cells is based on size, granularity, and whether the cells is carrying fluorescent molecules in the form of either antibodies or dyes. As the cell passes through the laser beam, light is scattered in all directions, and the light scattered in the forward direction at low angles (0.5-10°) from the axis is proportional to the square of the radius of a sphere and so to the size of the cell or particle. Light may enter the cell; thus, the 90° light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population (Marion G. Macey, Flow cytometry: principles and applications, Humana Press, 2007). Fluorescence-activated cell sorting (FACS), which allows isolation of distinct cell populations too similar in physical characteristics to be separated by size or density, uses fluorescent tags to detect surface proteins that are differentially expressed, allowing fine distinctions to be made among physically homogeneous populations of cells.

The term "functional equivalent" or "functionally equivalent" are used interchangeably herein to refer to substances, molecules, polynucleotides, proteins, peptides, or polypeptides having similar or identical effects or use.

The term "heteroclitic" is used herein to refer to peptides of higher biological potency than the original peptide. A "heteroclitic immunogen" is an immunogen that elicits an immune response that cross-reacts to an original poorly immunogenic antigen.

The terms "immune response" and "immune-mediated" are used interchangeably herein to refer to any functional expression of a subject's immune system, against either foreign or self-antigens, whether the consequences of these reactions are beneficial or harmful to the subject.

The terms "immunomodulatory", "immune modulator" and "immune modulatory" are used interchangeably herein to refer to a substance, agent, or cell that is capable of augmenting or diminishing immune responses directly or indirectly by expressing chemokines, cytokines and other mediators of immune responses.

As used herein the term "immunostimulatory amount" of the disclosed compositions refers to an amount of an immunogenic composition that is effective to stimulate an immune response, for example, as measured by ELISPOT assay (cellular immune response), ICS (intracellular cytokine staining assay) and major histocompatibility complex (MHC) tetramer assay to detect and quantify antigen-specific T cells, quantifying the blood population of antigen-specific CD4+ T cells, or quantifying the blood population of antigen specific CD8+ T cells by a measurable amount, or where the increase is by at least 10%, at least 20%, at least 30%, at least 40%, at least 50%, at least 60%, at least 70%, at least 80%, at least 90%, at least 95%, at least 96%, at least 97%, at least 98%, at least 99%, at least 100%, when compared to a suitable control (e.g., a control composition where dendritic cells are not loaded with tumor-specific cells, or not loaded with peptide derived from tumor-specific cells).

The term "integrate into the genome" as used herein refers to a recombinant DNA sequence being concomitantly joined to the genomic DNA comprising a host cell's genome.

The term "Kaplan Meier plot" or "Kaplan Meier survival curve" as used herein refers to the plot of probability of clinical study subjects surviving in a given length of time while considering time in many small intervals. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of events are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "labeling" as used herein refers to a process of distinguishing a compound, structure, protein, peptide, antibody, cell or cell component by introducing a traceable constituent. Common traceable constituents include, but are not limited to, a fluorescent antibody, a fluorophore, a dye or a fluorescent dye, a stain or a fluorescent stain, a marker, a fluorescent marker, a chemical stain, a differential stain, a differential label, and a radioisotope.

The terms "marker" or "cell surface marker" are used interchangeably herein to refer to an antigenic determinant or epitope found on the surface of a specific type of cell. Cell surface markers can facilitate the characterization of a cell type, its identification, and eventually its isolation. Cell sorting techniques are based on cellular biomarkers where a cell surface marker(s) may be used for either positive selection or negative selection, i.e., for inclusion or exclusion, from a cell population.

The terms "mixed lymphocyte tumor reaction" or "MLTR" are used interchangeably herein to refer to a reaction similar to a mixed lymphocyte reaction but rather than using allogeneic lymphocytes to stimulate a response, allogeneic tumor cells are used instead. The MLTR method comprises contacting tumor cells being tested for immunogenic potential with mixed lymphocytes from peripheral blood mononuclear cells, followed by measuring one or more of cellular proliferation of the lymphocytes, cellular subset differentiation of the lymphocytes, cytokine release profile of the lymphocytes, and tumor cell death.

The term "modified" or "modulated" as used herein with respect to immune response to tumor cells refers to changing the form or character of the immune response to the tumor cells via one or more recombinant DNA techniques such that the immune cells are able to recognize and kill tumor cells.

The term "myeloid suppressor cells" or "myeloid-derived suppressor cells" as used herein refers to the heterogeneous population of cells characterized by myeloid origin, immature state, and ability to potently suppress T cell responses. These cells regulate immune responses and tissue repair in healthy individuals and the population rapidly expands during inflammation.

The term "open reading frame" as used herein refers to a sequence of nucleotides in a DNA molecule that has the potential to encode a peptide or protein: it starts with a start triplet (ATG), is followed by a string of triplets each of which encodes an amino acid, and ends with a stop triplet (TAA, TAG or TGA).

The phrase "operably linked" refers (1) to a first sequence(s) or domain being positioned sufficiently proximal to a second sequence(s) or domain so that the first sequence(s) or domain can exert influence over the second sequence(s) or domain or a region under control of that second sequence or domain; and (2) to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, are in the same reading frame. According to some embodiments, the phrase "operatively linked" refers to a linkage in which two or more protein domains or polypeptides are ligated or combined via recombinant DNA technology or chemical reaction such that each protein domain or polypeptide of the resulting fusion protein retains its original function.

The term "overall survival" (OS) as used herein refers to the length of time from either the date of diagnosis or the start of treatment for a disease, such as cancer, that patients diagnosed with the disease are still alive.

The term "parenteral" and its other grammatical forms as used herein refers to administration of a substance occurring in the body other than by the mouth or alimentary canal. For example, the term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques.

The terms "peripheral blood mononuclear cells" or "PBMCs" are used interchangeably herein to refer to blood cells having a single round nucleus such as, for example, a lymphocyte or a monocyte.

The term "pharmaceutical composition" as used herein refers to a composition that is employed to prevent, reduce in intensity, cure or otherwise treat a target condition, syndrome, disorder or disease.

The term "pharmaceutically acceptable carrier" as used herein refers to any substantially non-toxic carrier conventionally useable for administration of pharmaceuticals in which the isolated polypeptide of the present invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids.

The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well. According to some embodiments, the peptide is of any length or size.

The terms "protein domain" and "domain" are used interchangably to refer to a portion of a protein that has its own tertiary structure. Large proteins are generally composed of several domains connected to one another via flexible regions of polypeptide chain.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity." (a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence. (b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches. Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, *CABIOS* 5:151-153 (1989); Corpet, et al., Nucleic Acids Research 16:10881-90 (1988); Huang, et al., Computer Applications in the *Biosciences,* 8:155-65 (1992), and Pearson, et al., *Methods in Molecular Biology,* 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology,* Chapter 19, Ausubel, et al., Eds., Greene Publishing and Wiley-Interscience, New York (1995). Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=-4, and a comparison of both strands. For amino acid sequences, the BLASTP program uses as defaults a word length (W) of 3, an expectation (E) of 10, and the BLOSUM62 scoring matrix (see Henikoff & Henikoff (1989) *Proc. Natl. Acad. Sci. USA* 89:10915). In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, *Comput. Chem.,* 17:149-163 (1993)) and XNU (Claverie and States, *Comput. Chem.,* 17:191-201 (1993)) low-complexity filters may be employed alone or in combination. (c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4:11-17 (1988) e.g., as implemented in the program PC/GENE (Intelligenetics, Mountain View, Calif, USA). (d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. (e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid. Mutations may also be made to the nucleotide sequences of the present proteins by reference to the genetic code, including taking into account codon degeneracy.

The term "prime" (or "priming") as used herein refers to the process of increasing sensitivity to. When used in an immunological sense it refers to a process whereby a specific antigen is presented to naïve lymphocytes causing them to differentiate.

The term "progression free survival" or "PFS" as used herein refers to length of time during and after the treatment of a disease, such as cancer, that a patient lives with the disease but it does not get worse. In a clinical trial, measuring the progression free survival is one way to determine how well a new treatment works.

The term "recurrence" as used herein with respect to cancer refers to a cancer that has recurred (come back), usually after a period of time during which the cancer could not be detected. The cancer may come back to the same place as the original (primary) tumor or to another place in the body.

The term "relapse-free survival (RFS)" as used herein refers to the length of time after primary treatment for a cancer during which the patient survives without any signs or symptoms of that cancer. Also called disease-free survival (DFS) and progression free survival (PFS).

The term "response rate" as used herein refers to the percentage of patients whose cancer shrinks or disappears after treatment.

The term "resistant cancer" as used herein refers to a cancer that does not respond to a treatment at the beginning of such treatment or sometime during such treatment.

The term "reporter gene" ("reporter") or "assay marker" refers to a gene and/or peptide that can be detected, or easily identified and measured. The expression of the reporter may be measured at either the RNA level, or at the protein level. The gene product, which may be detected in an experimental assay protocol, includes, but is not limited to, marker enzymes, antigens, amino acid sequence markers, cellular phenotypic markers, nucleic acid sequence markers, and the like. Researchers may attach a reporter gene to another gene of interest in cell culture, bacteria, animals, or plants. For example, some reporters are selectable markers, or confer characteristics upon on organisms expressing them allowing the organism to be easily identified and assayed. To introduce a reporter gene into an organism, researchers may place the reporter gene and the gene of interest in the same DNA construct to be inserted into the cell or organism. For bacteria or eukaryotic cells in culture, this may be in the form of a plasmid. Commonly used reporter genes may include, but are not limited to, fluorescent proteins, luciferase, beta-galactosidase, and selectable markers, such as chloramphenicol and kanomycin.

The term "stimulate" in any of its grammatical forms as used herein refers to inducing activation or increasing activity.

As used herein, the terms "subject" or "individual" or "patient" are used interchangeably to refer to a member of an animal species of mammalian origin, including humans.

The phrase "subject in need thereof" as used herein refers to a patient that (i) will be administered an immunogenic composition according to the described invention, (ii) is receiving an immunogenic composition according to the described invention; or (iii) has received an immunogenic composition according to the described invention, unless the context and usage of the phrase indicates otherwise.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein. The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The terms "therapeutic amount", "therapeutically effective amount", an "amount effective", or "pharmaceutically effective amount" of an active agent is used interchangeably to refer to an amount that is sufficient to provide the intended benefit of treatment. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutic amount", "therapeutically effective amounts" and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein.

The term "therapeutic effect" as used herein refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered compound. Adjusting the dose to achieve maximal efficacy based on the methods described above and other well-known methods is within the capabilities of the ordinarily skilled artisan.

General principles for determining therapeutic effectiveness, which may be found in Chapter 1 of Goodman and Gilman's The Pharmacological Basis of Therapeutics, 10th Edition, McGraw-Hill (New York) (2001), incorporated herein by reference, are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

Drug products are considered to be pharmaceutical equivalents if they contain the same active ingredients and are identical in strength or concentration, dosage form, and route of administration. Two pharmaceutically equivalent drug products are considered to be bioequivalent when the rates and extents of bioavailability of the active ingredient in the two products are not significantly different under suitable test conditions.

The term "therapeutic window" refers to a concentration range that provides therapeutic efficacy without unacceptable toxicity. Following administration of a dose of a drug, its effects usually show a characteristic temporal pattern. A lag period is present before the drug concentration exceeds the minimum effective concentration ("MEC") for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. Accordingly, the duration of a drug's action is determined by the time period over which concentrations exceed the MEC. The therapeutic goal is to obtain and maintain concentrations within the therapeutic window for the desired response with a minimum of toxicity. Drug response below the MEC for the desired effect will be subtherapeutic, whereas for an adverse effect, the probability of toxicity will increase above the MEC. Increasing or decreasing drug dosage shifts the response curve up or down the intensity scale and is used to modulate the drug's effect. Increasing the dose also prolongs a drug's duration of action but at the risk of increasing the likelihood of adverse effects. Accordingly, unless the drug is nontoxic, increasing the dose is not a useful strategy for extending a drug's duration of action.

Instead, another dose of drug should be given to maintain concentrations within the therapeutic window. In general, the lower limit of the therapeutic range of a drug appears to be approximately equal to the drug concentration that produces about half of the greatest possible therapeutic effect, and the upper limit of the therapeutic range is such that no more than about 5% to about 10% of patients will experience a toxic effect. These figures can be highly variable, and some patients may benefit greatly from drug concentrations that exceed the therapeutic range, while others may suffer significant toxicity at much lower values. The therapeutic goal is to maintain steady-state drug levels within the therapeutic window. For most drugs, the actual concentrations associated with this desired range are not and need not be known, and it is sufficient to understand that efficacy and toxicity are generally concentration-dependent, and how drug dosage and frequency of administration affect the drug level. For a small number of drugs where there is a small (two- to three-fold) difference between concentrations resulting in efficacy and toxicity, a plasma-concentration range associated with effective therapy has been defined.

In this case, a target level strategy is reasonable, wherein a desired target steady-state concentration of the drug (usually in plasma) associated with efficacy and minimal toxicity is chosen, and a dosage is computed that is expected to achieve this value. Drug concentrations subsequently are measured and dosage is adjusted if necessary to approximate the target more closely.

In most clinical situations, drugs are administered in a series of repetitive doses or as a continuous infusion to maintain a steady-state concentration of drug associated with the therapeutic window. To maintain the chosen steady-state or target concentration ("maintenance dose"), the rate of drug administration is adjusted such that the rate of input equals the rate of loss. If the clinician chooses the desired concentration of drug in plasma and knows the clearance and bioavailability for that drug in a particular patient, the appropriate dose and dosing interval can be calculated.

As used herein the term "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vaccinated" as used herein refers to being treated with a vaccine.

The term "vaccination" as used herein refers to treatment with a vaccine.

The term "vaccine" as used herein refers a substance or group of substances meant to cause the immune system to respond to a tumor or to microorganisms, or help the body recognize and destroy cancer cells or microorganisms. The term vaccine also refers to an artificial stimulus used to stimulate a robust immune response against that exposure (e.g. infectious agent, cancer cell).

The term "vaccine therapy" as used herein refers to a type of treatment that uses a substance or group of substances to stimulate the immune system to destroy a tumor or infectious microorganisms.

Allogeneic Vaccine

Vaccine proteins can induce immune responses that find use in the described invention. According to one aspect, the described invention comprises a tumor-type specific allogeneic tumor vaccine for the treatment of cancer. According to some embodiments, the cancer is prostate cancer. According to some embodiments, the vaccine comprises an allogeneic cancer cell line that is genetically modified by two or more immunomodulatory molecules. According to some embodiments, the tumor cell provides a broad array of tumor specific antigens, most of which are of unknown nature. According to some embodiments, the immunomodulatory molecules genetically engineered or added to the cells are selected from a group for their ability to either initiate or sustain an anti-tumor immune response, or alternatively for their ability to abrogate pre-existing immunosuppression characteristically present in cancer patients, or a combination of all three. According to some embodiments, combinations of immunomodulatory molecules are evaluated and selected by a human mixed lymphocyte tumor cell reaction.

According to some embodiments, the allogeneic vaccine composition is administered to a subject diagnosed with cancer in combination with an agent that inhibits immunosuppressive molecules produced by tumor cells.

According to some embodiments, the allogeneic vaccine further comprises one or more checkpoint inhibitors that are sufficient to prevent premature termination of an effective immune response once such an immune response is initiated.

According to some embodiments, a subject (i.e. a subject diagnosed with cancer) is treated by checkpoint inhibitor therapy prior to or concurrently with administration of the allogeneic vaccine composition. In certain embodiments, the cancer is a melanoma.

Checkpoint Blockade/Blockage of Tumor Immunosuppression

Some human tumors can be eliminated by a patient's immune system. For example, administration of a monoclonal antibody targeted to an immune "checkpoint" molecule can lead to complete response and tumor remission. A mode of action of such antibodies is through inhibition of an immune regulatory molecule that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

For example, administration of a monoclonal antibody targeted to by way of example, without limitation, CTLA-4 or PD-1 can lead to a complete response and tumor remission. The mode of action of such antibodies is through inhibition of CTLA-4 or PD-1 that the tumors have co-opted as protection from an anti-tumor immune response. By inhibiting these "checkpoint" molecules (e.g., with an antagonistic antibody), a patient's CD8+ T cells may be allowed to proliferate and destroy tumor cells.

Thus, the allogeneic vaccine compositions provided herein can be used in combination with one or more blocking antibodies targeted to an immune "checkpoint" molecule. For instance, in some embodiments, the allogeneic vaccine compositions provided herein can be used in combination with one or more blocking antibodies targeted to a molecule such as CTLA-4 or PD-1. For example, the allogeneic vaccine compositions provided herein may be used in combination with an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), pidilizumab (CT-011, CURE TECH), MK-3475 (MERCK), BMS 936559 (BRISTOL MYERS SQUIBB), MPDL3280A (ROCHE)). In an embodiment, the allogeneic vaccine compositions provided herein may be used in combination with an agent that blocks, reduces and/or inhibits the activity of CTLA-4 and/or the binding of CTLA-4 with one or more receptors (e.g. CD80, CD86, AP2M1, SHP-2, and PPP2R5A). For instance, in some embodiments, the immune-modulating agent is an antibody such as, by way of non-limitation, ipilimumab (MDX-010, MDX-101, Yervoy, BMS) and/or tremelimumab (Pfizer). Blocking antibodies against these molecules can be obtained from, for example, Bristol Myers Squibb (New York, N.Y.), Merck (Kenilworth, N.J.), MedImmune (Gaithersburg, Md.), and Pfizer (New York, N.Y.).

Further, the allogeneic immune compositions provided herein can be used in combination with one or more blocking antibodies targeted to an immune "checkpoint" molecule such as for example, BTLA, HVEM, TIM3, GALS, LAG3, VISTA, KIR, 2B4, CD160 (also referred to as BY55), CGEN-15049, CHK 1 and CHK2 kinases, A2aR, CEACAM (e.g., CEACAM-1, CEACAM-3 and/or CEACAM-5), GITR, GITRL, galectin-9, CD244, CD160, TIGIT, SIRPα, ICOS, CD172a, and TMIGD2 and various B-7 family ligands (including, but are not limited to, B7-1, B7-2, B7-DC, B7-H1, B7-H2, B7-H3, B7-H4, B7-H5, B7-H6 and B7-H7).

According to some embodiments, the allogeneic vaccine is adapted for rapid in vitro evaluation using human peripheral blood mononuclear cells from healthy subjects and cancer patients to examine inter-individual variability as well as normal to patient differences, thus avoiding animal experimentation.

According to some embodiments, the described invention comprises an allogeneic tumor cell vaccine for an active immunotherapy that can be universally administered to all patients with a particular type of cancer. According to some embodiments, the allogeneic vaccine comprises a genetically modified allogeneic tumor-type specific cell, or a membrane lysate derived from modified allogeneic tumor-type specific cells, formulated in a pharmaceutically acceptable carrier. According to some embodiments, the modified allogeneic tumor-type specific cells are derived from previously established cell lines.

According to some embodiments, the allogeneic vaccine is adapted to treat patients with minimal residual disease and a functional immune system. For example, according to some embodiments, the allogeneic vaccine is adapted to treat a patient with minimal residual disease obtained shortly after a primary lesion is surgically removed. According to some embodiments, the allogeneic vaccine is adapted for subcutaneous administration of the vaccine. According to some embodiments, the dose and schedule for administering the allogeneic vaccine are determined by using immunologic responses to the vaccine as a guide for eventual enhancement of overall survival.

According to some embodiments, the allogeneic vaccine is adapted to provide clinical benefit in the short term by the induction of strong anti-allogeneic vaccine responses, and, in the long term, to provide a long lived and cross reactive response to the endogenous unmodified host tumor. According to some embodiments, the immune response against the allogeneic tumor cell vaccine comprises a heteroclitic cross reaction between a peptide native to the tumor cell line and a peptide native to the tumor cells of a patient receiving the vaccine (See, e.g., FIG. 1). According to some embodiments, the heteroclitic cross reaction enhances immunogenicity via enhanced binding of a T cell receptor with a tumor cell peptide-MHC complex that normally provides a non-immunogenic surface. According to some embodiments, the allogeneic tumor cell vaccine comprises peptides altered relative to tumor cells of a subject with cancer, where the altered peptides provide an immunogenic surface that results in a heteroclitic cross-reaction to the non-immunogenic peptide of tumor cells from the subject with cancer. According to some embodiments, the heteroclitic recognition and alloreactive antigen recognition of the tumor cell vaccine provides a broad array of antigens useful to elicit an immune response against the tumor cells of a patient receiving the vaccine. According to some embodiments, the allogeneic vaccine is adapted to provide a clinical benefit, e.g., in the form of progression free survival, relapse-free survival, or overall survival. According to some embodiments, the allogeneic vaccine is effective to provide heteroclitic immunization induced tumor immunity (Dyall R., et al., Heteroclitic Immunization Induces Tumor Immunity, J. Exp. Med., Vol. 188, No. 9, Nov. 2, 1998, incorporated by reference herein in its entirety).

According to some embodiments, the allogeneic vaccine is derived from tumor cell lines genetically modified to comprise recombinant immunomodulatory signals that are expressed in therapeutic amounts. According to some embodiments, the allogeneic vaccine is derived from a uniform starting material, such as a tumor cell line, wherein multiple discrete biologics are expressed in the starting material in either soluble or membrane bound form. According to some embodiments, expression and activity of the soluble and membrane bound forms are confirmed, in vitro, by flow cytometry and mixed lymphocyte tumor assays using peripheral blood mononuclear cells, respectively. According to some embodiments, expression and activity of the soluble and membrane bound forms are confirmed, in vitro, by flow cytometry and mixed lymphocyte tumor assays using peripheral blood mononuclear cells of the vaccinated cancer patient against the allogeneic tumor cells used to immunize.

According to some embodiments, the allogeneic vaccine comprises genetically modified immunomodulatory molecules each encoding a membrane bound or secreted signaling molecule. According to some embodiments, each membrane bound immunomodulatory molecule is adapted to deliver a therapeutic amount in sub-pharmacologic doses that is active in a spatially and temporally restricted manner to provide signaling predominantly at the time and place of antigen presentation. According to some embodiments, the membrane bound immunomodulatory molecules are adapted to decrease the probability of systemic side effects. According to some embodiments, the secreted immunomodulatory molecules are adapted to deliver local, not systemic, signals.

According to some aspects, the allogeneic vaccine comprises genetic material that is effective to genetically introduce one or more immunomodulatory molecules into a tumor cell line. According to some embodiments, the genetic material can be introduced by viral transduction techniques and isolated by positive selection for the genetically introduced immune modulator. For example, according to some embodiments, the positive selection of the genetically introduced immune modulator molecule comprises selection using antibodies. According to some embodiments, the immunomodulatory molecules are diverse and complementary with respect to impact on key immune cell subsets such as dendritic cell, lymphocyte sub-populations (e.g. T cells, Natural Killer cells, and T-regulatory cells). According to some embodiments, the allogeneic vaccine comprises a variety of immunomodulatory molecules directed to a variety of immunomodulatory pathways on various immune cell subsets, wherein not all pathways will equally contribute to immunogenic response in individual cancer patients. According to some embodiments, the immunomodulatory molecules genetically introduced into a tumor cell line are stably expressed.

Tumor Antigen Specificity

Immunologic antigenic specificity may arise from one or more of the amino acid sequence of the antigen, from the degree of expression of that antigen by the tumor cell, from post-translational modification of the antigen, and the like.

Immunologic antigen specificity to a certain type of cancer cell may also arise from one or more of a particular fingerprint of a plurality of tumor antigens, from the fact that a particular antigen, while expressed by a wide variety of tumor cells, has particular use in immunotherapy against a smaller number of tumor types, from the fact that a particular collection of MHC class I presentable and MHC class II presentable epitopes exist on a particular polypeptide or polypeptide fragment, and by omitting one or more peptides that may provoke immunotolerance. The skilled artisan can locate the relevant nucleic acid and polypeptide sequences, e.g., on the U.S. government's web site, at ncbi.nlm.nih.

According to some embodiments, tumor antigen specificity of the present invention may be determined by the parental tumor cell line that is selected for modification with immune modulators.

Parent Cell Lines

According to some embodiments, tumor cell line variants may be derived from established cell lines from either public sources (e.g. NIH, DCTD Tumor Repository operated by Charles River Laboratories Inc.) or commercial sources (e.g. ATCC® (American Type Culture Collection), Sigma Alrich, Thermo Fischer Scientific, Genescript, DSM2). According to some embodiments, new cell lines can be established de novo from tumor cells taken from the tumor of a cancer patient.

According to some embodiments, cancer tissues, cancer cells, cells infected with a cancer-causing agent, other preneoplastic cells, and cell lines of human origin can be used. In some embodiments, a cancer cell can be from an established tumor cell line such as, without limitation, an established non-small cell lung carcinoma (NSCLC), bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line.

According to some embodiments, the established cell lines comprise the LNCaP clone FGC (ATCC® CRL-1740), which itself is derived from a metastatic prostate cancer that had migrated to a lymph node. According to some embodiments, the established cell lines comprise the PC-3 (ATCC® CRL-1435) cell line, which itself is derived from metastatic prostate cancer that migrated to bone. According to some embodiments, the tumor cell line variants are derived from one or more of the following ATCC® cell lines: VCaP (ATCC® CRL-2876); MDA PCa 2b (ATCC® CRL-2422); or DU 145 (ATCC® HTB-81).

According to some embodiments, the established cell lines comprise the SK-MEL-2 clone (ATCC® HTB-68), which itself is derived from metastasis on skin of thigh.

According to some embodiments, the established cell lines comprise one or more of mammary carcinoma cell lines designated COO-G, DU4475, ELL-G, HIG-G, MCF/7, MDA-MB-436, MX-1, SW-613, and VAN-G. According to some embodiments, the established cell lines comprise one or more of alveolar soft part sarcoma cell lines designated ASPS, and ASPS-1. According to some embodiments, the established cell lines comprise one or more lung cell lines designated LX-1, COS-G, H-MESO-1, H-MESO-1A, NCI-H23, and NCI-H460. According to some embodiments, the established cell lines comprise one or more colon cancer cell lines designated CX-5, GOB-G, HCC-2998, HCT-15, KLO-G, KM20L2, MRI-H-194, LOVO I, LOVO II, and MRI-H-250. According to some embodiments, the established cell lines comprise one or more melanoma cell lines designated NIS-G, TRI-G, WIL-G, MRI-H-121B, MRI-H-187, MRI-H-221, and MRI-H-255. According to some embodiments, the established cell lines comprise one or more cervical cancer cell lines designated MRI-H-177, MRI-H-186, MRI-H-196, and MRI-H-215. According to some embodiments, the established cell lines comprise one or more kidney cancer cell lines designated MRI-H-121 and MRI-H-166. According to some embodiments, the established cell lines comprise one or more endometrium cancer cell lines designated MRI-H-147 and MRI-H-220. According to some embodiments, the established cell lines comprise one or more ovarian cancer cell lines designated MRI-H-258, MRI-H-273, MRI-H-1834, and SWA-G. According to some embodiments, the established cell lines comprise one or more sarcoma cell lines designated HS-1, OGL-G, and DEL-G. According to some embodiments, the established cell lines comprise the epidermoid cell line designated DEAC-1. According to some embodiments, the established cell line comprises the glioblastoma cell line designated SF 295. According to some embodiments, the established cell line comprises the prostate cancer cell line designated CWR-22. According to some embodiments, the established cell line comprises the Burkitt's lymphoma cell line designated DAU.

According to some embodiments, exemplary established cell lines comprise one or more of the following cell lines:

| Designation | Tissue of Origin | Histologic Type |
|---|---|---|
| 786-0 | Kidney | Renal Cell Carcinoma |
| A2780 | Ovary | Adenocarcinoma |
| A498 | Kidney | Renal Cell Carcinoma |
| A549 | Lung | Non-small Cell |
| A704 | Kidney | Renal Cell Carcinoma |
| ACHN | Kidney | Renal Cell Carcinoma |
| ASPS-1 | Lymph Node | Alveolar Soft Part Sarcoma |
| BT-549 | Breast | Adenocarcinoma |
| CAKI-1 | Kidney | Renal Cell Carcinoma |
| CCRF-CEM | Lymph | Leukemia |
| CCRF-SB | Lymph | Leukemia |
| CHA-59 | Bone | Osteosarcoma |
| COLO 205 | Colon | Adenocarcinoma |
| DMS-114 | Lung | Small Cell |
| DU-145 | Prostate | Carcinoma |
| EKVX | Lung | Adenocarcinoma |
| HCC-2998 | Colon | Adenocarcinoma |
| HCT-15 | Colon | Carcinoma |
| HCT-116 | Colon | Adenocarcinoma |
| HOP-18 | Lung | Large Cell Carcinoma |
| HOP-62 | Lung | Adenocarcinoma |
| HL-60 | Ascites | Pro-myelocytic Leukemia |
| H-MESO-1 | | Mesothelioma |
| HS 578T | Breast | Adenocarcinoma |
| HS 913T | Lung | Mixed Cell |
| HT-29 | Colon | Adenocarcinoma |
| IGR-OV1 | Ovary | Adenocarcinoma |
| KM-12 | Colon | Adenocarcinoma |
| KM 20L2 | Colon | Adenocarcinoma |
| K-562 | Lymph | Leukemia |
| LOVO | Colon | Adenocarcinoma |
| LOX IMVI | Lymph Node Metastisis | Amelanotic Melanoma |
| LXFL 529 | Lung | Large Cell Carcinoma |
| NCI-H1299 | Lung | Adenocarcinoma |
| NCI-H2887 | Lung | Adenocarcinoma |
| NCI-H3122 | Lung | Adenocarcinoma |
| NCI-H322M | Lung | Adenocarcinoma |
| NCI-H3255 | Lung | Adenocarcinoma |
| NCI-H358M | Lung | Bronchioalveolar Carcinoma |
| NCI-H460 | Lung | Large Cell |
| NCI-H522 | Lung | Adenocarcinoma |
| NCI-H69 | Lung | Small Cell Carcinoma |
| NCI-H82 | Lung | Small Cell Carcinoma |
| NCI-H838 | Lung | Adenocarcinoma |
| NCI/ADR-RES | Ovary | Adenocarcinoma |
| OVCAR-3 | Ovary | Adenocarcinoma |
| OVCAR-4 | Ovary | Adenocarcinoma |
| OVCAR-5 | Ovary | Adenocarcinoma |
| OVCAR-8 | Ovary | Adenocarcinoma |
| PC-3 | Prostate | Carcinoma |
| PC-3/M | Prostate | Carcinoma |
| RPMI-7951 | Skin | Melanoma |

-continued

| Designation | Tissue of Origin | Histologic Type |
|---|---|---|
| RPMI-8226 | Lymph | Leukemia |
| RXF 393 | Kidney | Renal Cell Carcinoma |
| RXF 631 | Kidney | Renal Cell Carcinoma |
| TK-10 | Kidney | Renal Cell Carcinoma |
| UACC-62 | Skin | Melanoma |
| UACC-257 | Skin | Melanoma |
| UCSD 242L | Skin | Melanoma |
| UCSD 354K | Skin | Melanoma |
| UO-31 | Kidney | Renal Cell Carcinoma |
| U-251 | CNS | Glioblastoma |
| WIDR | Colon | Adenocarcinoma |
| XF 498 | CNS | Glioblastoma |

According to some embodiments, the choice of the parental cell line from which the tumor cell line variant may be derived affects the specificity of the allogeneic vaccine. For example, the use of a tumor cell line variant derived from metastatic prostate cancer that migrated to the bone of a patient may result in an allogeneic vaccine that elicits an immune response specific for metastatic prostate cancer in the bone of a patient.

According to some embodiments, the tumor cell line variants may be derived from a parental cell that comprises a universal cancer specific antigen. For example, the use of a parental tumor cell line variant derived from metastatic prostate cancer that migrated to the bone of a patient may result in an allogeneic vaccine that elicits an immune response against all prostate cancer cells.

According to some embodiments, the tumor cell line variants are derived from patient derived cells derived from various cancers. According to some embodiments, fresh tissue surgically removed from a tumor is enzymatically digested by type IV collagenase, followed by collection of disaggregated cells. According to some embodiments, disaggregated cells may then be grown in vitro in growth media with 10% fetal bovine serum on an extracellular matrix substrate, such as collagen or fibronectin, to promote attachment. According to some embodiments, adherent cells may then be passaged until the immortal cancer cells outgrow the non-cancerous fibroblast cells.

For example, according to some embodiments, the tumor cell line variants may be derived from a solid tumor comprising tumor cells, including cancer stem cells, a metastatic cancer comprising metastatic tumor cells, comprising cancer stem cells, or a non-metastatic cancer. According to some embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. According to some embodiments, the cancer may be of a histological type, e.g., a cancer that begins in the skin or tissues that line or cover internal organs (carcinoma); a cancer that begins in bone or in the soft tissue of the body including cartilage, fat, muscle, blood vessels, and fibrous tissue (sarcoma); a cancer that starts in blood-forming tissue (leukemia); a cancer that begins in cells of the immune system (lymphoma); a cancer that arises in plasma cells (myeloma), or a brain/spinal cord cancer.

Examples of carcinomas include, without limitation, giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; an adenocarcinoma; a gastrinoma, a cholangiocarcinoma; a hepatocellular carcinoma; a combined hepatocellular carcinoma and cholangiocarcinoma; a trabecular adenocarcinoma; an adenoid cystic carcinoma; an adenocarcinoma in adenomatous polyp; an adenocarcinoma, familial polyposis coli; a solid carcinoma; a carcinoid tumor; a branchiolo-alveolar adenocarcinoma; a papillary adenocarcinoma; a chromophobe carcinoma; an acidophil carcinoma; an oxyphilic adenocarcinoma; a basophil carcinoma; a clear cell adenocarcinoma; a granular cell carcinoma; a follicular adenocarcinoma; a non-encapsulating sclerosing carcinoma; adrenal cortical carcinoma; an endometroid carcinoma; a skin appendage carcinoma; an apocrine adenocarcinoma; a sebaceous adenocarcinoma; a ceruminous adenocarcinoma; a mucoepidermoid carcinoma; a cystadenocarcinoma; a papillary cystadenocarcinoma; a papillary serous cystadenocarcinoma; a mucinous cystadenocarcinoma; a mucinous adenocarcinoma; a signet ring cell carcinoma; an infiltrating duct carcinoma; a medullary carcinoma; a lobular carcinoma; an inflammatory carcinoma; paget's disease, a mammary acinar cell carcinoma; an adenosquamous carcinoma; an adenocarcinoma w/squamous metaplasia; a sertoli cell carcinoma; embryonal carcinoma; choriocarcinoma.

Examples of sarcomas include, without limitation, glomangiosarcoma; sarcoma; fibrosarcoma; myxosarcoma; liposarcoma; leiomyosarcoma; rhabdomyosarcoma; embryonal rhabdomyosarcoma; alveolar rhabdomyosarcoma; stromal sarcoma; carcinosarcoma; synovial sarcoma; hemangiosarcoma; kaposi's sarcoma; lymphangiosarcoma; osteosarcoma; juxtacortical osteosarcoma; chondrosarcoma; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; myeloid sarcoma; mast cell sarcoma.

Examples of leukemias include, without limitation, leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; and hairy cell leukemia.

Examples of lymphomas and myelomas include, without limitation, malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant melanoma; amelanotic melanoma; superficial spreading melanoma; malignant melanoma in giant pigmented nevus; epithelioid cell melanoma; multiple myeloma.

Examples of brain/spinal cord cancers include, without limitation, pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant.

Examples of other cancers include, without limitation, a thymoma; an ovarian stromal tumor; a thecoma; a granulosa cell tumor; an androblastoma; a leydig cell tumor; a lipid cell tumor; a paraganglioma; an extra-mammary paraganglioma; a pheochromocytoma; blue nevus, malignant; fibrous histiocytoma, malignant; mixed tumor, malignant; mullerian mixed tumor; nephroblastoma; hepatoblastoma; mesenchymoma, malignant; brenner tumor, malignant; phyllodes tumor, malignant; mesothelioma, malignant; dysgerminoma; teratoma, malignant; struma ovarii, malignant; mesonephroma, malignant; hemangioendothelioma, malignant; hemangiopericytoma, malignant; chondroblastoma, malignant; granular cell tumor, malignant; malignant histiocytosis; immunoproliferative small intestinal disease.

For any given tumor type, several tumor cell lines may be commercially available. According to some embodiments, pooling of several of these cells lines, either as a mixture of whole cells or by making a membrane preparation out of the mixture of whole cells, may provide an array of cell surface tumor antigens for that tumor type.

Selection of Immune Modulators

According to some embodiments, the tumor cell line variants may be engineered to express two or more recombinant sequences of DNA and protein that are then presented on the tumor cell and are functional.

IgG Heavy Chain Constant and Variable Region

Immunoglobulins (Ig) are glycoproteins produced by immune cells. Antibodies are serum proteins, the molecules of which possess small areas of their surface that are complementary to small chemical groupings on their targets. These complementary regions (referred to as complementary determining regions (CDRs), or antibody combining sites, or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice. Immunoglobulins play a critical role in an immune response by binding to particular antigens, such as those exhibited by bacteria or viruses. According to some embodiments, the binding of immunoglobulins to antigens may target them for destruction by the subject's immune cells.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

In mammals, there are five classes of antibodies, IgA, IgD, IgE, IgG, and IgM, each with its own class of heavy chain—α (for IgA), δ (for IgD), ε (for IgE), γ (for IgG) and μ(for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer can be made by randomly combining heavy and light chain V-genes using PCR.

According to some embodiments, the tumor cell line variants may be engineered to express an IgG1 heavy chain constant region. In nature, the Ig gamma-1 (IgG-1) chain C region is a protein encoded by the IGHG1 gene in humans.

According to some embodiments, a tumor cell line variant may express a membrane bound form IgG-1 chain C protein of SEQ ID NO: 1. According to some embodiments, a tumor cell line variant may express a secreted form of IgG-1 chain C of SEQ ID NO: 2. According to some embodiments, a tumor cell line variant may express a secreted form of IgG-1 chain C of SEQ ID NO: 3. According to some embodiments, a tumor cell line variant may comprise one or more proteins with a sequence identity of at least 60% to one or more of proteins with an amino acid sequence SEQ ID NO: 1, SEQ ID NO: 2, and SEQ ID NO: 3. According to some embodiments, a tumor cell line variant may comprise one or more proteins with a sequence identity of at least 70% to one or more of proteins with an amino acid sequence SEQ ID NO: 1, SEQ ID NO: 2, and SEQ ID NO: 3. According to some embodiments, a tumor cell line variant may comprise one or more proteins with a sequence identity of at least 80% to one or more of proteins with an amino acid sequence SEQ ID NO: 1, SEQ ID NO: 2, and SEQ ID NO: 3. According to some embodiments, a tumor cell line variant may comprise one or more proteins with a sequence identity of at least 90% to one or more of proteins with an amino acid sequence SEQ ID NO: 1, SEQ ID NO: 2, and SEQ ID NO: 3. According to some embodiments, a tumor cell line variant may comprise one or more proteins with a sequence identity of at least 95% to one or more of proteins with an amino acid sequence SEQ ID NO: 1, SEQ ID NO: 2, and SEQ ID NO: 3. According to some embodiments, a tumor cell line variant may comprise one or more proteins with a sequence identity of at least 96% to one or more of proteins with an amino acid sequence SEQ ID NO: 1, SEQ ID NO: 2, and SEQ ID NO: 3. According to some embodiments, a tumor cell line variant may comprise one or more proteins with a sequence identity of at least 97% to one or more of proteins with an amino acid sequence SEQ ID NO: 1, SEQ ID NO: 2, and SEQ ID NO: 3. According to some embodiments, a tumor cell line variant may comprise one or more proteins with a sequence identity of at least 98% to one or more of proteins with an amino acid sequence SEQ ID NO: 1, SEQ ID NO: 2, and SEQ ID NO: 3. According to some embodiments, a tumor cell line variant may comprise one or more proteins with a sequence identity of at least 99% to one or more of proteins with an amino acid sequence SEQ ID NO: 1, SEQ ID NO: 2, and SEQ ID NO: 3.

According to some embodiments, a tumor cell line variant may comprise one or more proteins with a sequence identity of at least 60% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line variant may comprise one or more proteins with a sequence identity of at least 70% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line variant may comprise one or more proteins with a sequence identity of at least 80% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line variant may comprise one or more proteins with a sequence identity of at least 90% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line variant may comprise one or more proteins with a sequence identity of at least 95% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line variant may comprise one or more proteins with a sequence identity of at least 96% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line variant may comprise one or more proteins with a sequence identity of at least 97% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line variant may comprise one or more proteins with a sequence identity of at least 98% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46. According to some embodiments, a tumor cell line variant may comprise one or more proteins with a sequence identity of at least 99% to one or more proteins with amino acid sequence SEQ ID NO: 12, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 45, and SEQ ID NO: 46.

According to some embodiments, the tumor cell line variant may be engineered to express an IgG protein that is capable of binding to tumor cell specific antigens. For example, the tumor cell line variant may be engineered to express an IgG protein capable of binding to a prostate cancer specific antigen; e.g., the extracellular region of prostate-specific membrane antigen (PSMA) (See Chang, S., Overview of Prostate-Specific Membrane Antigen, Reviews in Urology, Vol. 6 Suppl. 10, S13 (2004)). According to some embodiments, the tumor cell line variant may be engineered to express an IgG protein that is capable of binding to immune cell specific antigens. For example, the tumor cell line variant may be engineered to express an IgG protein capable of binding to T cell markers, e.g., CD3, CD4, or CD8. According to another example, the tumor cell line variant may be engineered to express an IgG protein capable of binding to dendritic cell markers, e.g. CD11c or CD123.

According to some embodiments, the tumor cell line variants may be engineered to express an IgG3 heavy chain constant region. In nature, the IgG3 heavy chain constant region comprises CH1-hinge-CH2-CH3 domains, and is encoded by the IGHG3 gene in humans; the IGHG3 gene comprises structural polymorphisms comprising different hinge lengths. According to some embodiments, a tumor cell line variant may express an IgG-3 heavy chain constant region of SEQ ID NO: 4. According to some embodiments, a tumor cell line variant may express a derivative of SEQ ID NO: 4 with amino acids 1-76 missing. According to some embodiments, a tumor cell line variant may express the derivative of SEQ ID NO: 4 with amino acids 1-76 missing.

According to some embodiments, a tumor cell line variant may express the derivative of SEQ ID NO: 4 with amino acids 77-98 replaced with amino acids QMQGVNCTVSS. According to some embodiments, a tumor cell line variant may express the derivative of SEQ ID NO: 4 comprising an E213Q variant (SEQ ID NO: 16). According to some embodiments, a tumor cell line variant may express the derivative of SEQ ID NO: 4 comprising a P221L variant (SEQ ID NO: 17). According to some embodiments, a tumor cell line variant may express the derivative of SEQ ID NO: 4 comprising an E224Q variant (SEQ ID NO: 18). According to some embodiments, a tumor cell line variant may express the derivative of SEQ ID NO: 4 comprising a Y226F variant (SEQ ID NO: 19). According to some embodiments, a tumor cell line variant may express the derivative of SEQ ID NO: 4 comprising a D242N variant (SEQ ID NO: 20). According to some embodiments, a tumor cell line variant may express the derivative of SEQ ID NO: 4 comprising a N245D variant (SEQ ID NO: 21). According to some embodiments, a tumor cell line variant may express the derivative of SEQ ID NO: 4 comprising a T269A variant (SEQ ID NO: 22). According to some embodiments, a tumor cell line variant may express the derivative of SEQ ID NO: 4 comprising a S314N variant (SEQ ID NO: 23). According to some embodiments, a tumor cell line variant may express the derivative of SEQ ID NO: 4 comprising a deleted S314 (SEQ ID NO: 24). According to some embodiments, a tumor cell line variant may express the derivative of SEQ ID NO: 4 comprising F366Y variant (SEQ ID NO: 25).

According to some embodiments, a tumor cell line variant may comprise one or more proteins with a sequence identity of at least 60% to the protein of SEQ ID NO: 4. According to some embodiments, a tumor cell line variant may comprise one or more proteins with a sequence identity of at least 70% to the protein of SEQ ID NO: 4. According to some embodiments, a tumor cell line variant may comprise one or more proteins with a sequence identity of at least 80% to the protein of SEQ ID NO: 4. According to some embodiments, a tumor cell line variant may comprise one or more proteins with a sequence identity of at least 90% to the protein of SEQ ID NO: 4. According to some embodiments, a tumor cell line variant may comprise one or more proteins with a sequence identity of at least 95% to the protein of SEQ ID NO: 4. According to some embodiments, a tumor cell line variant may comprise one or more proteins with a sequence identity of at least 96% to the protein of SEQ ID NO: 4. According to some embodiments, a tumor cell line variant may comprise one or more proteins with a sequence identity of at least 97% to the protein of SEQ ID NO: 4. According to some embodiments, a tumor cell line variant may comprise one or more proteins with a sequence identity of at least 98% to the protein of SEQ ID NO: 4. According to some embodiments, a tumor cell line variant may comprise one or more proteins with a sequence identity of at least 99% to the protein of SEQ ID NO: 4.

According to some embodiments, a tumor cell line variant may be engineered to express one or more IgG heavy chain variable regions. According to some embodiments, a tumor cell line variant may be engineered to express a lambda/kappa light chain constant and/or light chain variable region. According to some embodiments, the hinge region of IgG binds to the FcγR receptors on immune cells. According to some embodiments, the IgG is effective to activate the FcγR and enhance presentation of antigens (e.g. PSA associated with prostate cancer cells).

According to some embodiments, a tumor cell line variant may be engineered to express an intact monoclonal or polyclonal antibody on the cell surface of the tumor cell. According to some embodiments, the intact monoclonal or polyclonal antibody may be designed to deliver a molecule that elicits an immunogenic response. For example, according to some embodiments, the intact monoclonal antibody may be designed to bind to DNA to deliver CpG motifs to immune cells.

According to some embodiments, the immunostimulatory activity of bacterial DNA may be mimicked by engineering an immunomodulator to deliver unmethylated CpG motifs to immune cells. For example, according to some embodiments, the IgG may be engineered to bind to biotin, which is then capable of delivering biotinylated CpG to cells of the immune system. According to some embodiments, CpG motifs may be bound directly or indirectly to the surface of the tumor cells of the tumor cell vaccine to prevent systemic effects. According to some embodiments, CpG motifs may be conjugated to one or more antigens presented on the surface of tumor cells from the tumor cell line variant. According to some embodiments, the CpG is a class A CpG. According to some embodiments, the CpG is a class B CpG. According to some embodiments, the CpG is a class C CpG. According to some embodiments, the CpG is a CpG 30-mer of the sequence 5' EEAACCGTATCGGCGATATCGGT-TEEEEEG 3'. As used herein with respect to CpG motifs, "E" is a G-phosphorothioate and this linkage refers to the 3' end of the nucleotide (i.e. the phosphorothioate bond substitutes a sulfur atom for a non-bridging oxygen in the nucleotide backbone). According to some embodiments, the CpG is a biotinylated 30-mer of the sequence 5'-biotin-EEAACCGTATCGGCGATATCGGTTEEEEEG-3'.

According to some embodiments, the CpG is a CpG 30-mer of the sequence 5' EEAACCGTATGCGGCATATCGGT-TEEEEEG 3'. According to some embodiments, the CpG is a biotinylated CpG 30-mer of the sequence 5'-biotin-EE-AACCGTATGCGGCATATCGGTTEEEEEG-3'.

According to some embodiments, the IgG may be engineered as a hybrid of one or more IgG subclasses. For example, according to some embodiments, the IgG comprises sequences from IgG1 and IgG3. According to some embodiments, the IgG may be engineered to have an affinity for biotin. According to some embodiments, a tumor cell line variant may comprise one or more proteins with a sequence identity of at least 60% to the protein of SEQ ID NO: 45. According to some embodiments, a tumor cell line variant may comprise one or more proteins with a sequence identity of at least 70% to the protein of SEQ ID NO: 45. According to some embodiments, a tumor cell line variant may comprise one or more proteins with a sequence identity of at least 80% to the protein of SEQ ID NO: 45. According to some embodiments, a tumor cell line variant may comprise one or more proteins with a sequence identity of at least 90% to the protein of SEQ ID NO: 45. According to some embodiments, a tumor cell line variant may comprise one or more proteins with a sequence identity of at least 95% to the protein of SEQ ID NO: 45. According to some embodiments, a tumor cell line variant may comprise one or more proteins with a sequence identity of at least 96% to the protein of SEQ ID NO: 45. According to some embodiments, a tumor cell line variant may comprise one or more proteins with a sequence identity of at least 97% to the protein of SEQ ID NO: 45. According to some embodiments, a tumor cell line variant may comprise one or more proteins with a sequence identity of at least 98% to the protein of SEQ ID NO: 45. According to some embodiments, a tumor cell line variant may comprise one or more proteins with a sequence identity of at least 99% to the protein of SEQ ID NO: 45.

According to some embodiments, the IgG comprises one or more mutations relative to wild type IgG that enhance affinity for FcγR. According to some embodiments, a tumor cell line variant may comprise one or more proteins of SEQ ID NO: 45 with one or more of mutations T323A and E325A. According to some embodiments, a tumor cell line variant may comprise one or more proteins with a sequence identity of at least 60% to the proteins of one or more of SEQ ID NO: 41, SEQ ID NO: 30, and SEQ ID NO: 43. According to some embodiments, a tumor cell line variant may comprise one or more proteins with a sequence identity of at least 70% to the proteins of one or more of SEQ ID NO: 41, SEQ ID NO: 30, and SEQ ID NO: 43. According to some embodiments, a tumor cell line variant may comprise one or more proteins with a sequence identity of at least 80% to the proteins of one or more of SEQ ID NO: 41, SEQ ID NO: 30, and SEQ ID NO: 43. According to some embodiments, a tumor cell line variant may comprise one or more proteins with a sequence identity of at least 90% to the proteins of one or more of SEQ ID NO: 41, SEQ ID NO: 30, and SEQ ID NO: 43. According to some embodiments, a tumor cell line variant may comprise one or more proteins with a sequence identity of at least 95% to the proteins of one or more of SEQ ID NO: 41, SEQ ID NO: 30, and SEQ ID NO: 43. According to some embodiments, a tumor cell line variant may comprise one or more proteins with a sequence identity of at least 96% to the proteins of one or more of SEQ ID NO: 41, SEQ ID NO: 30, and SEQ ID NO: 43. According to some embodiments, a tumor cell line variant may comprise one or more proteins with a sequence identity of at least 97% to the proteins of one or more of SEQ ID NO: 41, SEQ ID NO: 30, and SEQ ID NO: 43. According to some embodiments, a tumor cell line variant may comprise one or more proteins with a sequence identity of at least 98% to the proteins of one or more of SEQ ID NO: 41, SEQ ID NO: 30, and SEQ ID NO: 43. According to some embodiments, a tumor cell line variant may comprise one or more proteins with a sequence identity of at least 99% to the proteins of one or more of SEQ ID NO: 41, SEQ ID NO: 30, and SEQ ID NO: 43.

CD40L

The ligand of CD40, known as CD154 or CD40L, is a type II transmembrane protein, with a variable molecular weight between 32 and 39 kDa because of post-translation modifications (Elgueta R et al., Molecular mechanism and function of CD40/CD40L engagement in the immune system. Immunological reviews. 2009; 229(1):10.1111/j.1600-065X.2009.00782.x. doi:10.1111/j.1600-065X.2009.00782.x, citing van Kooten C et al., J. Leukoc Biol. 2000 January; 67(1):2-17.). A soluble form of CD40L has been reported that has activities similar to the transmembrane form (Id. citing Graf D et al., Eur J Immunol. 1995 June; 25(6):1749-54; Mazzei G J et al., J Biol Chem. 1995 Mar. 31; 270(13):7025-8.).

In nature, CD40L is a member of the TNF superfamily and is characterized by a sandwich extracellular structure that is composed of a β-sheet, α-helix loop, and a β-sheet, which allows for the trimerization of CD40L (Id. citing Karpusas M et al., Structure. 1995 Oct. 15; 3(10):1031-9). CD40L is expressed primarily by activated T cells, as well as activated B cells and platelets; under inflammatory conditions it is also induced on monocytic cells, natural killer cells, mast cells, and basophils (Id. citing Carbone E et al., J Exp Med. 1997 Jun. 16; 185(12):2053-60). The wide spread expression of the costimulatory pair of CD40L and CD40 indicates the pivotal roles they play in different cellular immune processes.

CD40L has three binding partners: CD40, α5β1 integrin and αIIbβ3 integrin. CD40L acts as a costimulatory molecule and is particularly important on a subset of T cells called T follicular helper cells (TFH cells), where it promotes B cell maturation and function by engaging CD40 on the B cell surface facilitating cell-cell communication. A defect in the CD40L gene results in an inability to undergo immunoglobulin class switching and is associated with hyper-IgM syndrome. Absence of CD40L also stops the formation of germinal centers thereby prohibiting antibody affinity maturation, an important process in the adaptive immune system.

CD40 has been found to be expressed on APCs, while its ligand, CD40L, has been found on activated T cells. CD40 has been found to play a critical role in the humoral immune response, and has been identified as enabling APCs to activate T cells. Several pathologies have been associated with the CD40/CD40L pathway including lupus and atherosclerosis, but anti-CD40L antibodies have been limited to clinical applications of thrombic complications from CD40 expression on activated platelets (Kaufman and Wolchok eds., General Principles of Tumor Immunotherapy, Chpt 5, 67-121 (2007)).

CD40 has also been found on several types of cancer, including solid tumors and hematologic malignancies. Signaling through CD40 in hematological cancer may mediate growth or regression, while CD40 signaling in solid tumors is only tumoricidal. These characteristics are found even in SCID mouse models, and therefore are likely due to TNF death domain signaling. There is also evidence of immune modulation, for example blockade of the CD40/CD40L pathway mitigates the protective effect of GM-CSF secreting melanoma vaccines (Kaufman and Wolchok eds., General Principles of Tumor Immunotherapy, Chpt 5, 67-121 (2007)).

Tumor cell vaccines expressing CD40L have proved useful in cancer models. For example, ligation of CD40 with CD40L or anti-CD40 antibodies has shown synergy with GM-CSF, IFN-gamma, IL-2, and CTLA-4 blockade. Furthermore, anti-CD40 antibodies have been reported to have anti-tumor activity in a pre-clinical mouse model (Kaufman and Wolchok eds., General Principles of Tumor Immunotherapy, Chpt 5, 67-121 (2007)).

According to some embodiments of the disclosed invention, the tumor cell line variant may be engineered to express the cleavable CD40L peptide of SEQ ID NO: 6. According to some embodiments, a tumor cell line variant may comprise one or more proteins with a sequence identity of at least 60% to the protein of SEQ ID NO: 6. According to some embodiments, a tumor cell line variant may comprise one or more proteins with a sequence identity of at least 70% to the protein of SEQ ID NO: 6. According to some embodiments, a tumor cell line variant may comprise one or more proteins with a sequence identity of at least 80% to the protein of SEQ ID NO: 6. According to some embodiments, a tumor cell line variant may comprise one or more proteins with a sequence identity of at least 90% to the protein of SEQ ID NO: 6. According to some embodiments, a tumor cell line variant may comprise one or more proteins with a sequence identity of at least 95% to the protein of SEQ ID NO: 6. According to some embodiments, a tumor cell line variant may comprise one or more proteins with a sequence identity of at least 96% to the protein of SEQ ID NO: 6. According to some embodiments, a tumor cell line variant may comprise one or more proteins with a sequence identity of at least 97% to the protein of SEQ ID NO: 6. According to some embodiments, a tumor cell line variant may comprise one or more proteins with a sequence identity of at least 98% to the protein of SEQ ID NO: 6. According to some embodiments, a tumor cell line variant may comprise one or more proteins with a sequence identity of at least 99% to the protein of SEQ ID NO: 6.

According to some embodiments, the tumor cell line variant may be engineered to express the non-cleavable membrane bound CD40L peptide of SEQ ID NO: 7 on the membrane surface of the tumor cell. According to some embodiments, a tumor cell line variant may comprise one or more proteins with a sequence identity of at least 60% to the protein of SEQ ID NO: 7. According to some embodiments, a tumor cell line variant may comprise one or more proteins with a sequence identity of at least 70% to the protein of SEQ ID NO: 7. According to some embodiments, a tumor cell line variant may comprise one or more proteins with a sequence identity of at least 80% to the protein of SEQ ID NO: 7. According to some embodiments, a tumor cell line variant may comprise one or more proteins with a sequence identity of at least 90% to the protein of SEQ ID NO: 7. According to some embodiments, a tumor cell line variant may comprise one or more proteins with a sequence identity of at least 95% to the protein of SEQ ID NO: 7. According to some embodiments, a tumor cell line variant may comprise one or more proteins with a sequence identity of at least 96% to the protein of SEQ ID NO: 7. According to some embodiments, a tumor cell line variant may comprise one or more proteins with a sequence identity of at least 97% to the protein of SEQ ID NO: 7. According to some embodiments, a tumor cell line variant may comprise one or more proteins with a sequence identity of at least 98% to the protein of SEQ ID NO: 7. According to some embodiments, a tumor cell line variant may comprise one or more proteins with a sequence identity of at least 99% to the protein of SEQ ID NO: 7.

Tumor Necrosis Factor Alpha

Tumor necrosis factor (TNF; tumor necrosis factor alpha (TNFα); cachexin, cachectin) is a cytokine, primarily produced by activated macrophages and lymphocytes, which is involved in systemic inflammation. It is also one of the cytokines involved in the acute phase of an immunogenic response. TNF may be produced by other cell types such as, for example, CD4+ lymphocytes, NK cells, neutrophils, mast cells, eosinophils, and neurons.

In its primary role as a regulator of immune cells, TNF is capable of inducing fever, apoptotic cell death, cachexia, inflammation, and inhibition of tumorigenesis; of inhibiting viral replication; and of initiating a response to sepsis vial IL-1 and IL-6 producing cells. Dysregulated TNF production has been associated with a wide array of human diseases, including Alzheimer's disease, major depression, psoriasis, and inflammatory bowel disease (IBD). TNF can be produced ectopically in the setting of malignancy and parallels parathyroid hormone both in causing secondary hypercalcemia and in the cancers with which excessive production is associated.

TNF comprises a 26 kDa membrane bound form and 17 kDa soluble cytokine form. The soluble form of TNF is derived from proteolytic cleavage of the membrane bound form by TNF-alpha converting enzyme (TACE) (Grell M. et al., The Transmembrane Form of Tumor Necrosis Factor Is the Prime Activating Ligand of the 80 kDa Tumor Necrosis Factor Receptor, Cell, Vol. 83, 793-802). TACE is a matrix metalloprotease that recognizes a cleavage site in the extracellular domain of full-length TNF (Rieger, R., Chimeric form of tumor necrosis factor-alpha has enhanced surface expression and antitumor activity, Cancer Gene Therapy, 2009, 16, 53-64). Deletion of the cleavage site on TNF results in enhanced membrane stability of TNF (Id.).

TNF has antiproliferative and cytotoxic effects on cells, is known to reduce tumor blood flow and tumor vascular damage, and is able to modulate immune response by stimulating macrophage and NK cell activity. However, the use of TNF as a therapeutic itself has been limited by dose-dependent hypotension and capillary leak that can cause a sepsis-like syndrome. For that reason, it must be delivered in a manner that limits systemic effects. TNF has been added to standard chemotherapy agents to improve response rates. Other approaches to administering TNF include injection of adenovirus altered to express TNF in gastrointestinal malignancies. A tumor vascular-targeted TNF compound has also been developed (Kaufman and Wolchok eds., General Principles of Tumor Immunotherapy, Chpt 5, 67-121 (2007)). Recombinant TNF has been used as an immunostimulant under the name tasonermin, while HUMIRA® is an antibody to TNF, useful for the treatment of inflammatory diseases (e.g. psoriasis and rheumatoid arthritis). In recognition of this role, molecules such as antibodies have been designed to interfere with TNF activity. However, such therapies pose the risk of initiating a cytokine storm caused by the inappropriate systemic release of cytokines, resulting in a positive feedback loop of white blood cell activation/cytokine release that potentially can be fatal.

According to some embodiments, a tumor cell line variant may express the membrane bound form of TNF on the membrane of the tumor cell. For example, according to some embodiments, the cell line variants comprise the peptide of SEQ ID NO: 8. According to some embodiments, a tumor cell line variant may comprise one or more proteins with a sequence identity of at least 60% to the protein of SEQ ID NO: 8. According to some embodiments, a tumor cell line variant may comprise one or more proteins with a sequence identity of at least 70% to the protein of SEQ ID NO: 8. According to some embodiments, a tumor cell line variant may comprise one or more proteins with a sequence identity of at least 80% to the protein of SEQ ID NO: 8. According to some embodiments, a tumor cell line variant may comprise one or more proteins with a sequence identity of at least 90% to the protein of SEQ ID NO: 8. According to some embodiments, a tumor cell line variant may comprise one or more proteins with a sequence identity of at least 95% to the protein of SEQ ID NO: 8. According to some embodiments, a tumor cell line variant may comprise one or more proteins with a sequence identity of at least 96% to the protein of SEQ ID NO: 8. According to some embodiments, a tumor cell line variant may comprise one or more proteins with a sequence identity of at least 97% to the protein of SEQ ID NO: 8. According to some embodiments, a tumor cell line variant may comprise one or more proteins with a sequence identity of at least 98% to the protein of SEQ ID NO: 8. According to some embodiments, a tumor cell line variant may comprise one or more proteins with a sequence identity of at least 99% to the protein of SEQ ID NO: 8.

According to some embodiments, a tumor cell line variant may express a non-cleavable membrane bound form of TNF. For example, according to some embodiments, the tumor cell line variant may comprise the TNF protein of SEQ ID NO: 8 with one or more of amino acids VRSSSRTPSDKP deleted (see e.g. SEQ ID NO: 26).

According to some embodiments, a tumor cell line variant may express a soluble form of TNF. For example, according to some embodiments, the tumor cell line variant may express the TNF protein of SEQ ID NO: 8 with part or the entire transmembrane region removed. For example, according to some embodiments, the tumor cell line variant may comprise a derivative TNF protein of SEQ ID NO: 8 with one or more of amino acids F, S, F, L, I, V, A, G, A, T, T, L, F, C, L, L, H, F, G, V, I deleted (see e.g. SEQ ID NO: 27).

According to some embodiments, a tumor cell line variant may express a non-cleavable membrane bound chimeric form of CD40L and TNF. For example, according to some embodiments, the ligand binding portion of a TNF molecule may be fused with the transmembrane and proximal extracellular domains of CD40L, such that the TNF lacks a defined TNF alpha cleaving enzyme (TACE) site. According to some embodiments, the intracellular, transmembrane, and partial extracellular portions CD40L may be fused with the extracellular region of TNF distal to the TACE cleavage site. According to some embodiments, the chimeric form of CD40L/TNF may comprise the CD40L sequence of SEQ ID NO: 9 and the TNF sequence of SEQ ID NO: 10. According to some embodiments, the CD40L/TNF sequences are operably linked via a linking peptide between 1 and 30 amino acids in length. According to some embodiments, a tumor cell line variant may comprise a fusion protein with a sequence identity of at least 60% to the proteins of SEQ ID NO: 9 and SEQ ID NO: 10. According to some embodiments, a tumor cell line variant may comprise a fusion protein with a sequence identity of at least 70% to the proteins of SEQ ID NO: 9 and SEQ ID NO: 10. According to some embodiments, a tumor cell line variant may comprise a fusion protein with a sequence identity of at least 80% to the proteins of SEQ ID NO: 9 and SEQ ID NO: 10. According to some embodiments, a tumor cell line variant may comprise a fusion protein with a sequence identity of at least 90% to the proteins of SEQ ID NO: 9 and SEQ ID NO: 10. According to some embodiments, a tumor cell line variant may comprise a fusion protein with a sequence identity of at least 95% to the proteins of SEQ ID NO: 9 and SEQ ID NO: 10. According to some embodiments, a tumor cell line variant may comprise a fusion protein with a sequence identity of at least 96% to the proteins of SEQ ID NO: 9 and SEQ ID NO: 10. According to some embodiments, a tumor cell line variant may comprise a fusion protein with a sequence identity of at least 97% to the proteins of SEQ ID NO: 9 and SEQ ID NO: 10. According to some embodiments, a tumor cell line variant may comprise a fusion protein with a sequence identity of at least 98% to the proteins of SEQ ID NO: 9 and SEQ ID NO: 10. According to some embodiments, a tumor cell line variant may comprise a fusion protein with a sequence identity of at least 99% to the proteins of SEQ ID NO: 9 and SEQ ID NO: 10.

According to some embodiments, a tumor cell line variant may express a non-cleavable membrane bound form of TNF with a sequence identity of at least 60% to the protein of SEQ ID NO: 11. According to some embodiments, a tumor cell line variant may express a non-cleavable membrane bound form of TNF with a sequence identity of at least 70% to the protein of SEQ ID NO: 11. According to some embodiments, a tumor cell line variant may express a non-cleavable membrane bound form of TNF with a sequence identity of at least 80% to the protein of SEQ ID NO: 11. According to some embodiments, a tumor cell line variant may express a non-cleavable membrane bound form of TNF with a sequence identity of at least 90% to the protein of SEQ ID NO: 11. According to some embodiments, a tumor cell line variant may express a non-cleavable membrane bound form of TNF with a sequence identity of at least 95% to the protein of SEQ ID NO: 11. According to some embodiments, a tumor cell line variant may express a non-cleavable membrane bound form of TNF with a sequence identity of at least 96% to the protein of SEQ ID NO: 11. According to some embodiments, a tumor cell line variant may express a non-cleavable membrane bound form of TNF with a sequence identity of at least 97% to the protein of SEQ ID NO: 11. According to some embodiments, a tumor cell line variant may express a non-cleavable membrane bound form of TNF with a sequence identity of at least 98% to the protein of SEQ ID NO: 11. According to some embodiments, a tumor cell line variant may express a non-cleavable membrane bound form of TNF with a sequence identity of at least 99% to the protein of SEQ ID NO: 11.

According to some embodiments, a tumor cell line variant may express a non-cleavable membrane bound chimeric form of CD40L and TNF. For example, according to some embodiments, the ligand portion of a TNF molecule may be fused with extracellular portions of CD40L, wherein CD40L comprises an extracellular portion that is non-cleavable and the TNF lacks a defined TACE site (e.g. cleavage site between amino acids 76 and 77). According to some embodiments, some or all of a CD40L peptide sequence is fused with the extracellular region of a TNF peptide sequence distal to the TACE cleavage site. According to some embodiments, the chimeric form of CD40L/TNF may comprise the sequence of SEQ ID NO: 31. According to some embodiments, a tumor cell line variant may comprise a fusion protein with a sequence identity of at least 60% to the protein of SEQ ID NO: 31. According to some embodiments, a tumor cell line variant may comprise a fusion protein with a sequence identity of at least 70% to the protein of SEQ ID NO: 31. According to some embodiments, a tumor cell line variant may comprise a fusion protein with a sequence identity of at least 80% to the protein of SEQ ID NO: 31. According to some embodiments, a tumor cell line variant may comprise a fusion protein with a sequence identity of at least 90% to the protein of SEQ ID NO: 31. According to some embodiments, a tumor cell line variant may comprise a fusion protein with a sequence identity of at least 95% to the protein of SEQ ID NO: 31. According to some embodiments, a tumor cell line variant may comprise a fusion protein with a sequence identity of at least 96% to the protein of SEQ ID NO: 31. According to some embodiments, a tumor cell line variant may comprise a fusion protein with a sequence identity of at least 97% to the protein of SEQ ID NO: 31. According to some embodiments, a tumor cell line variant may comprise a fusion protein with a sequence identity of at least 98% to the protein of SEQ ID NO: 31. According to some embodiments, a tumor cell line variant may comprise a fusion protein with a sequence identity of at least 99% to the protein of SEQ ID NO: 31.

Granulocyte-Macrophage Colony Stimulating Factor (GM-CSF)

Granulocyte-macrophage colony-stimulating factor (GM-CSF; colony stimulating factor 2; CSF2) is found in monocytes/macrophages and activated T cells, and can act as a growth factor to stimulate and recruit dendritic cells. GM-CSF is a monomeric glycoprotein secreted by cells of the immune system, as well as endothelial cells and fibroblasts. Human GM-CSF is a 144 amino acid protein comprising a 17 amino acid signal peptide that can be cleaved to produce a mature 127 amino acid protein. Biological activity of GM-CSF occurs via binding to heteromeric cell surface receptors that are expressed on monocytes, macrophages, granulocytes, lymphocytes, endothelial cells and alveolar epithelial cells. The GM-CSF receptor (GM-CSFR) typically has a low expression (e.g. 20-200/cell), but has a high affinity (Shi Y et al., Granulocyte-macrophage colony-stimulating factor (GM-CSF) and T-cell responses: what we do and don't know, Cell Research (2006) 16: 126-133).

In some mouse models, vaccination with syngeneic mouse melanoma cells that secrete GM-CSF stimulates a more potent and long-lasting antitumor immunity than vaccines produced by other cytokines. Melanoma patients treated with soluble GM-CSF as an adjuvant therapy displayed an increase in disease free survival compared to controls. GM-CSF has been used as an immune adjuvant in various ways, including, without limitation, systemic and topical application of soluble GM-CSF, GM-CSF fusion proteins, transfection of tumor cells with GM-CSF and injection of GM-CSF DNA. Recombinant GM-CSF has been used an adjuvant for various peptide, protein, and viral vaccines, and has been shown to be an effective adjuvant in patients with melanoma, breast, and ovarian cancer. A fusion protein comprising GM-CSF has also been shown to enhance immunogenicity of an antigen. GM-CSF has been tested for use in a gene therapy approach where allogeneic or autologous GM-CSF expressing cells are used as a vaccine (Kaufman and Wolchok eds., General Principles of Tumor Immunotherapy, Chpt 5, 67-121 (2007)). Such vaccines have had varying degrees of effectiveness among several different cancer types.

According to some embodiments, a tumor cell line variant may express the GM-CSF peptide of SEQ ID NO: 13. According to some embodiments, a tumor cell line variant may comprise one or more proteins with a sequence identity of at least 60% to the protein of SEQ ID NO: 13. According to some embodiments, a tumor cell line variant may comprise one or more proteins with a sequence identity of at least 70% to the protein of SEQ ID NO: 13. According to some embodiments, a tumor cell line variant may comprise one or more proteins with a sequence identity of at least 80% to the protein of SEQ ID NO: 13. According to some embodiments, a tumor cell line variant may comprise one or more proteins with a sequence identity of at least 90% to the protein of SEQ ID NO: 13. According to some embodiments, a tumor cell line variant may comprise one or more proteins with a sequence identity of at least 95% to the protein of SEQ ID NO: 13. According to some embodiments, a tumor cell line variant may comprise one or more proteins with a sequence identity of at least 96% to the protein of SEQ ID NO: 13. According to some embodiments, a tumor cell line variant may comprise one or more proteins with a sequence identity of at least 97% to the protein of SEQ ID NO: 13. According to some embodiments, a tumor cell line variant may comprise one or more proteins with a sequence identity of at least 98% to the protein of SEQ ID NO: 13. According to some embodiments, a tumor cell line variant may comprise one or more proteins with a sequence identity of at least 99% to the protein of SEQ ID NO: 13.

According to some embodiments, a tumor cell line variant may comprise one or more proteins comprising a fusion between GM-CSF and HLA-I to enable membrane expression. According to some embodiments, a tumor cell line variant may comprise one or more proteins with a sequence identity of at least 60% to the protein of SEQ ID NO: 42 or SEQ ID NO: 5. According to some embodiments, a tumor cell line variant may comprise one or more proteins with a sequence identity of at least 70% to the protein of SEQ ID NO: 42 or SEQ ID NO: 5. According to some embodiments, a tumor cell line variant may comprise one or more proteins with a sequence identity of at least 80% to the protein of SEQ ID NO: 42 or SEQ ID NO: 5. According to some embodiments, a tumor cell line variant may comprise one or more proteins with a sequence identity of at least 90% to the protein of SEQ ID NO: 42 or SEQ ID NO: 5. According to some embodiments, a tumor cell line variant may comprise one or more proteins with a sequence identity of at least 95% to the protein of SEQ ID NO: 42 or SEQ ID NO: 5. According to some embodiments, a tumor cell line variant may comprise one or more proteins with a sequence identity of at least 96% to the protein of SEQ ID NO: 42 or SEQ ID NO: 5. According to some embodiments, a tumor cell line variant may comprise one or more proteins with a sequence identity of at least 97% to the protein of SEQ ID NO: 42 or SEQ ID NO: 5. According to some embodiments, a tumor cell line variant may comprise one or more proteins with a sequence identity of at least 98% to the protein of SEQ ID NO: 42 or SEQ ID NO: 5. According to some embodiments, a tumor cell line variant may comprise one or more proteins with a sequence identity of at least 99% to the protein of SEQ ID NO: 42 or SEQ ID NO: 5.

Fms-Like Tyrosine Kinase-3 Ligand (Flt-3L)

The human Flt3L protein is a membrane bound hematopoietic four helical bundle cytokine encoded by the FLT3LG gene. Flt3L acts as a growth factor that stimulates proliferation and differentiation of various blood cell progenitors, and is crucial for production and development of dendritic cells. Mice that lack Flt3L have low levels of dendritic cells, while Flt3L administered to mice or humans results in very high levels of dendritic cells (Shortman et al., Steady-state and inflammatory dendritic-cell development, Nature Reviews Immunology, Vol. 7. 19-30 (2007)).

According to some embodiments, a tumor cell line variant expresses the Flt3L peptide of SEQ ID NO: 14. According to some embodiments, a tumor cell line variant may comprise one or more proteins with a sequence identity of at least 60% to the protein of SEQ ID NO: 14. According to some embodiments, a tumor cell line variant may comprise one or more proteins with a sequence identity of at least 70% to the protein of SEQ ID NO: 14. According to some embodiments, a tumor cell line variant may comprise one or more proteins with a sequence identity of at least 80% to the protein of SEQ ID NO: 14. According to some embodiments, a tumor cell line variant may comprise one or more proteins with a sequence identity of at least 90% to the protein of SEQ ID NO: 14. According to some embodiments, a tumor cell line variant may comprise one or more proteins with a sequence identity of at least 95% to the protein of SEQ ID NO: 14. According to some embodiments, a tumor cell line variant may comprise one or more proteins with a sequence identity of at least 96% to the protein of SEQ ID NO: 14. According to some embodiments, a tumor cell line variant may comprise one or more proteins with a sequence identity of at least 97% to the protein of SEQ ID NO: 14. According to some embodiments, a tumor cell line variant may comprise one or more proteins with a sequence identity of at least 98% to the protein of SEQ ID NO: 14. According to some embodiments, a tumor cell line variant may comprise one or more proteins with a sequence identity of at least 99% to the protein of SEQ ID NO: 14.

According to some embodiments, a tumor cell line variant comprises a soluble form of Flt3L. According to some embodiments, a tumor cell line variant may comprise one or more proteins with a sequence identity of at least 60% to the protein of SEQ ID NO: 44. According to some embodiments, a tumor cell line variant may comprise one or more proteins with a sequence identity of at least 70% to the protein of SEQ ID NO: 44. According to some embodiments, a tumor cell line variant may comprise one or more proteins with a sequence identity of at least 80% to the protein of SEQ ID NO: 44. According to some embodiments, a tumor cell line variant may comprise one or more proteins with a sequence identity of at least 90% to the protein of SEQ ID NO: 44. According to some embodiments, a tumor cell line variant may comprise one or more proteins with a sequence identity of at least 95% to the protein of SEQ ID NO: 44. According to some embodiments, a tumor cell line variant may comprise one or more proteins with a sequence identity of at least 96% to the protein of SEQ ID NO: 44. According to some embodiments, a tumor cell line variant may comprise one or more proteins with a sequence identity of at least 97% to the protein of SEQ ID NO: 44. According to some embodiments, a tumor cell line variant may comprise one or more proteins with a sequence identity of at least 98% to the protein of SEQ ID NO: 44. According to some embodiments, a tumor cell line variant may comprise one or more proteins with a sequence identity of at least 99% to the protein of SEQ ID NO: 44.

Vectors and Host Cells

The described invention provides nucleic acid constructs that encode two or more immune modulators that can be expressed in prokaryotic and eukaryotic cells. For example, the described invention provides expression vectors (e.g., DNA- or RNA-based vectors) containing nucleotide sequences that encode two or more immune modulators. In addition, the described invention provides methods for making the vectors described herein, as well as methods for introducing the vectors into appropriate host cells for expression of the encoded polypeptides. In general, the methods provided herein include constructing nucleic acid sequences encoding two or more immune modulators, and cloning the sequences into an expression vector. The expression vector can be introduced into host cells or incorporated into virus particles, either of which can be administered to a subject to, for example, treat cancer.

cDNA or DNA sequences encoding two or more immune modulators can be obtained (and, if desired, modified) using conventional DNA cloning and mutagenesis methods, DNA amplification methods, and/or synthetic methods. In general, a sequence encoding two or more immune modulators can be inserted into a cloning vector for genetic modification and replication purposes prior to expression. Each coding sequence can be operably linked to a regulatory element, such as a promoter, for purposes of expressing the encoded protein in suitable host cells in vitro and in vivo.

Expression vectors can be introduced into host cells for producing secreted immune modulators. There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; and natural polymer-based delivery vehicles, such as chitosan and gelatin; viral vectors are also suitable for in vivo transduction. In some situations it is desirable to provide a targeting agent, such as an antibody or ligand specific for a cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003).

Cells may be cultured in vitro or genetically engineered, for example. Host cells can be obtained from normal or affected subjects, including healthy humans, cancer patients, private laboratory deposits, public culture collections such as the American Type Culture Collection, or from commercial suppliers.

Cells that can be used for production and secretion of two or more immune modulators in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, or granulocytes, various stem or progenitor cells, such as hematopoietic stem or progenitor cells (e.g., as obtained from bone marrow), umbilical cord blood, peripheral blood, fetal liver, etc., and tumor cells (e.g., human tumor cells). The choice of cell type depends on the type of tumor or infectious disease being treated or prevented, and can be determined by one of skill in the art.

Different host cells have characteristic and specific mechanisms for post-translational processing and modification of proteins. A host cell may be chosen which modifies and processes the expressed gene products in a specific fashion similar to the way the recipient processes its heat shock proteins (hsps).

In some embodiments, an expression construct as provided herein can be introduced into an antigenic cell. As used herein, antigenic cells can include preoplastic cells that are infected with a cancer-causing infectious agent, such as a virus, but that are not yet neoplastic, or antigenic cells that have been exposed to a mutagen or cancer-causing agent, such as a DNA-damaging agent or radiation, for example. Other cells that can be used are preoplastic cells that are in transition from a normal to a neoplastic form as characterized by morphology or physiological or biochemical function.

Typically, the cancer cells and preneoplastic cells used in the methods provided herein are of mammalian origin. In some embodiments, cancer cells (e.g., human tumor cells) can be used in the methods described herein. Cell lines derived from a preneoplastic lesion, cancer tissue, or cancer cells also can be used. Cancer tissues, cancer cells, cells infected with a cancer-causing agent, other preneoplastic cells, and cell lines of human origin can be used. In some embodiments, a cancer cell can be from an established tumor cell line such as, without limitation, an established non-small cell lung carcinoma (NSCLC), bladder cancer, melanoma, ovarian cancer, renal cell carcinoma, prostate carcinoma, sarcoma, breast carcinoma, squamous cell carcinoma, head and neck carcinoma, hepatocellular carcinoma, pancreatic carcinoma, or colon carcinoma cell line.

Parent cell lines are described supra.

Further, in some embodiments, the allogeneic tumor cell vaccines provide for an adjuvant effect that further allows the immune system of a patient, when used in the various methods described herein, to be activated against a disease of interest.

Both prokaryotic and eukaryotic vectors can be used for expression of the two or more immune modulators in the methods provided herein. Prokaryotic vectors include constructs based on E. coli sequences (see, e.g., Makrides, Microbiol Rev 1996, 60:512-538). Non-limiting examples of regulatory regions that can be used for expression in E. coli include lac, trp, 1pp, phoA, recA, tac, T3, T7 and lamda $P_L$. Non-limiting examples of prokaryotic expression vectors may include the Agt vector series such as .lamda.gt11 (Huynh et al., in "DNA Cloning Techniques, Vol. I: A Practical Approach," 1984, (D. Glover, ed.), pp. 49-78, IRL Press, Oxford), and the pET vector series (Studier et al., Methods Enzymol 1990, 185:60-89).

A variety of regulatory regions can be used for expression of the allogeneic tumor vaccines in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the n-interferon gene, and the hsp70 gene (see, Williams et al., Cancer Res 1989, 49:2735-42; and Taylor et al., Mol Cell Biol 1990, 10:165-75). Heat shock promoters or stress promoters also may be advantageous for driving expression of the fusion proteins in recombinant host cells.

Animal regulatory regions that exhibit tissue specificity and have been utilized in transgenic animals also can be used in tumor cells of a particular tissue type: the elastase I gene control region that is active in pancreatic acinar cells (Swift et al., Cell 1984, 38:639-646; Ornitz et al., Cold Spring Harbor Symp Quant Biol 1986, 50:399-409; and MacDonald, Hepatology 1987, 7:425-515); the insulin gene control region that is active in pancreatic beta cells (Hanahan, Nature 1985, 315:115-122), the immunoglobulin gene control region that is active in lymphoid cells (Grosschedl et al., Cell 1984, 38:647-658; Adames et al., Nature 1985, 318:533-538; and Alexander et al., Mol Cell Biol 1987, 7:1436-1444), the mouse mammary tumor virus control region that is active in testicular, breast, lymphoid and mast cells (Leder et al., Cell 1986, 45:485-495), the albumin gene control region that is active in liver (Pinkert et al., Genes Devel, 1987, 1:268-276), the alpha-fetoprotein gene control region that is active in liver (Krumlauf et al., Mol Cell Biol 1985, 5:1639-1648; and Hammer et al., Science 1987, 235:53-58); the alpha 1-antitrypsin gene control region that is active in liver (Kelsey et al., Genes Devel 1987, 1:161-171), the beta-globin gene control region that is active in myeloid cells (Mogram et al., Nature 1985, 315:338-340; and Kollias et al., Cell 1986, 46:89-94); the myelin basic protein gene control region that is active in oligodendrocyte cells in the brain (Readhead et al., Cell 1987, 48:703-712); the myosin light chain-2 gene control region that is active in skeletal muscle (Sani, Nature 1985, 314:283-286), and the gonadotropic releasing hormone gene control region that is active in the hypothalamus (Mason et al., Science 1986, 234:1372-1378).

An expression vector also can include transcription enhancer elements, such as those found in SV40 virus, Hepatitis B virus, cytomegalovirus, immunoglobulin genes, metallothionein, and .beta.-actin (see, Bittner et al., Meth Enzymol 1987, 153:516-544; and Gorman, Curr Op Biotechnol 1990, 1:36-47). In addition, an expression vector can contain sequences that permit maintenance and replication of the vector in more than one type of host cell, or integration of the vector into the host chromosome. Such sequences include, without limitation, to replication origins, autonomously replicating sequences (ARS), centromere DNA, and telomere DNA.

In addition, an expression vector can contain one or more selectable or screenable marker genes for initially isolating, identifying, or tracking host cells that contain DNA encoding the immunogenic proteins as described herein. For long term, high yield production of gp96-Ig and T cell costimulatory fusion proteins, stable expression in mammalian cells can be useful. A number of selection systems can be used for mammalian cells. For example, the Herpes simplex virus thymidine kinase (Wigler et al., Cell 1977, 11:223), hypoxanthine-guanine phosphoribosyltransferase (Szybalski and Szybalski, Proc Natl Acad Sci USA 1962, 48:2026), and adenine phosphoribosyltransferase (Lowy et al., Cell 1980, 22:817) genes can be employed in tk⁻, hgprf⁻, or aprf⁻ cells, respectively. In addition, antimetabolite resistance can be used as the basis of selection for dihydrofolate reductase (dhfr), which confers resistance to methotrexate (Wigler et al., Proc Natl Acad Sci USA 1980, 77:3567; O'Hare et al., Proc Natl Acad Sci USA 1981, 78:1527); gpt, which confers resistance to mycophenolic acid (Mulligan and Berg, Proc Natl Acad Sci USA 1981, 78:2072); neomycin phosphotransferase (neo), which confers resistance to the aminoglycoside G-418 (Colberre-Garapin et al., J Mol Biol 1981, 150:1); and hygromycin phosphotransferase (hyg), which confers resistance to hygromycin (Santerre et al., Gene 1984, 30:147). Other selectable markers such as histidinol and Zeocin™ also can be used.

A number of viral-based expression systems also can be used with mammalian cells to produce the allogeneic tumor cell vaccines. Vectors using DNA virus backbones have been derived from simian virus 40 (SV40) (Hamer et al., Cell 1979, 17:725), adenovirus (Van Doren et al., Mol Cell Biol 1984, 4:1653), adeno-associated virus (McLaughlin et al., J Virol 1988, 62:1963), and bovine papillomas virus (Zinn et al., Proc Natl Acad Sci USA 1982, 79:4897). When an adenovirus is used as an expression vector, the donor DNA sequence may be ligated to an adenovirus transcription/translation control complex, e.g., the late promoter and tripartite leader sequence. This fusion gene may then be inserted in the adenovirus genome by in vitro or in vivo recombination. Insertion in a non-essential region of the viral genome (e.g., region E1 or E3) can result in a recombinant virus that is viable and capable of expressing heterologous products in infected hosts. (See, e.g., Logan and Shenk, Proc Natl Acad Sci USA 1984, 81:3655-3659).

Bovine papillomavirus (BPV) can infect many higher vertebrates, including man, and its DNA replicates as an episome. A number of shuttle vectors have been developed for recombinant gene expression, which exist as stable, multicopy (20-300 copies/cell) extrachromosomal elements in mammalian cells. Typically, these vectors contain a segment of BPV DNA (the entire genome or a 69% transforming fragment), a promoter with a broad host range, a polyadenylation signal, splice signals, a selectable marker, and "poisonless" plasmid sequences that allow the vector to be propagated in E. coli. Following construction and amplification in bacteria, the expression gene constructs are transfected into cultured mammalian cells by, for example, calcium phosphate coprecipitation. For those host cells that do not manifest a transformed phenotype, selection of transformants is achieved by use of a dominant selectable marker, such as histidinol and G418 resistance.

Alternatively, the vaccinia 7.5K promoter can be used. (See, e.g., Mackett et al., Proc Natl Acad Sci USA 1982, 79:7415-7419; Mackett et al., J Virol 1984, 49:857-864; and Panicali et al., Proc Natl Acad Sci USA 1982, 79:4927-4931.) In cases where a human host cell is used, vectors based on the Epstein-Barr virus (EBV) origin (OriP) and EBV nuclear antigen 1 (EBNA-1; a trans-acting replication factor) can be used. Such vectors can be used with a broad range of human host cells, e.g., EBO-pCD (Spickofsky et al., DNA Prot Eng Tech 1990, 2:14-18); pDR2 and .lamda.DR2 (available from Clontech Laboratories).

Allogeneic tumor cell vaccines also can be made with retrovirus-based expression systems. Retroviruses, such as Moloney murine leukemia virus, can be used since most of the viral gene sequence can be removed and replaced with exogenous coding sequence while the missing viral functions can be supplied in trans. In contrast to transfection, retroviruses can efficiently infect and transfer genes to a wide range of cell types including, for example, primary hematopoietic cells. Moreover, the host range for infection by a retroviral vector can be manipulated by the choice of envelope used for vector packaging.

For example, a retroviral vector can comprise a 5' long terminal repeat (LTR), a 3' LTR, a packaging signal, a bacterial origin of replication, and a selectable marker. The gp96-Ig fusion protein coding sequence, for example, can be inserted into a position between the 5' LTR and 3' LTR, such that transcription from the 5' LTR promoter transcribes the cloned DNA. The 5' LTR contains a promoter (e.g., an LTR promoter), an R region, a U5 region, and a primer binding site, in that order. Nucleotide sequences of these LTR elements are well known in the art. A heterologous promoter as well as multiple drug selection markers also can be included in the expression vector to facilitate selection of infected cells. See, McLauchlin et al., Prog Nucleic Acid Res Mol Biol 1990, 38:91-135; Morgenstern et al., Nucleic Acid Res 1990, 18:3587-3596; Choulika et al., J Virol 1996, 70:1792-1798; Boesen et al., Biotherapy 1994, 6:291-302; Salmons and Gunzberg, Human Gene Ther 1993, 4:129-141; and Grossman and Wilson, Curr Opin Genet Devel 1993, 3:110-114.

Any of the cloning and expression vectors described herein may be synthesized and assembled from known DNA sequences using techniques that are known in the art. The regulatory regions and enhancer elements can be of a variety of origins, both natural and synthetic. Some vectors and host cells may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Recombinant Immunomodulators

According to some embodiments, two or more immune modulators may be cloned into plasmid constructs for transfection (via, e.g., lipids, calcium phosphate, cationic polymers, DEAE-dextran, activated dendrimers, magnetic beads, electroporation, biolistic technology, microinjection, laserfection/optoinjection) or transduction (via, e.g., retrovirus, lentivirus, adenovirus, adeno-associated virus) into cells of tumor cell lines. According to some embodiments, recombinant DNA encoding each immune modulator protein may be cloned into a lentiviral vector plasmid for integration into the genome of cells of tumor cell lines. According to some embodiments, recombinant DNA encoding the immune modulator protein may be cloned into a plasmid DNA construct encoding a selectable trait, such as an antibiotic resistance gene. According to some embodiments, recombinant DNA encoding the immune modulator protein may be cloned into a plasmid construct that is adapted to stably express each recombinant protein in the cells of the tumor cell line. According to some embodiments, the transfected or transduced tumor cells may be clonally expanded to achieve a cell line variant with a homogenous site of integration of the recombinant DNA encoding each immune modulator protein into the genome of the cells of the tumor cell line.

Lentiviral Constructs

According to some embodiments, the DNA sequences coding for immune modulator proteins may be cloned into a lentiviral vector for transduction into mammalian cells. According to some embodiments, the lentiviral system may comprise a lentiviral transfer plasmid encoding the two or more immune modulator sequences, packaging plasmids encoding the GAG, POL, TAT, and REV sequences, and an envelope plasmid encoding the ENV sequences. According to some embodiments, the lentiviral transfer plasmid uses a viral LTR promoter for gene expression. According to some embodiments, the lentiviral transfer plasmid uses a hybrid promoter, or other specialized promoter. According to some embodiments, the promoter of the lentiviral transfer plasmid is selected to express the two or more immune modulator sequences at a desired level relative to other immunomodulatory sequences. According to some embodiments, the relative level is measured on the level of transcription as mRNA transcripts. According to some embodiments, the relative level is measured on the level of translation as protein expression.

Multicistronic Plasmid Constructs

According to some embodiments, one or more immune modulator sequence may be cloned in a multicistronic vector for co-expression of one immune modulator with a second immune modulator or other recombinant sequence. According to some embodiments, an immune modulator sequence may be cloned into a plasmid comprising an IRES element to promote translation of two or more proteins from a single transcript. According to some embodiments, one or more immune modulator sequences is cloned into a multicistronic vector comprising sequences for a self cleaving 2A peptide to produce two or more immune modulator proteins from a single transcript.

Genetic Introduction of Immune Modulators

According to some embodiments, plasmid constructs comprising the recombinant immune modulator sequences may be transfected or transduced into tumor cell lines.

Lentiviral System

According to some embodiments, the lentiviral system may be employed where the transfer vector with immune modulator sequences, an envelope vector, and a packaging vector are each transfected into host cells for virus production. According to some embodiments, the lentiviral vectors may be transfected into 293T cells by any of calcium phosphate precipitation transfection, lipid based transfection, or electroporation, and incubated overnight. For embodiments where the immune modulator sequence may be accompanied by a fluorescence reporter, inspection of the 293T cells for florescence may be checked after overnight incubation. The culture medium of the 293T cells comprising virus particles may be harvested 2 or 3 times every 8-12 hours and centrifuged to sediment detached cells and debris. The culture medium may then be used directly, frozen or concentrated as needed.

Tumor cell lines may be grown to a confluency of about 70% under standard tissue culture conditions. The cells may then be treated with hexadimethrine bromide (to enhance transduction of cells) and lentiviral particles comprising recombinant constructs in fresh media, and incubated for 18-20 hours followed by a media change.

Lipid Based Transfection

According to some embodiments, cells of tumor cell lines may be transfected with immune modulator sequences using a lipid based transfection method. According to some embodiments, established lipid based transfection reagents, such as LIPOFECTAMINE™, may be used. Tumor cell lines may be grown to about 70-90% confluence in a tissue culture vessel. Appropriate amounts of LIPOFECTAMINE™ and plasmid construct comprising the immune modulator sequences may be separately diluted in tissue culture media and briefly incubated at room temperature. The diluted LIPOFECTAMINE™ and plasmid constructs in media may be mixed together and incubated briefly at room temperature. The plasmid LIPOFECTAMINE™ mixture may then be added to the cells of the tumor cell lines in the tissue culture vessel and incubated for 1-3 days under standard tissue culture conditions.

Selection of Expressing Clones

According to some embodiments, tumor cells of the tumor cell line that have been transfected with immune modulator sequences may be selected for various levels of expression.

According to some embodiments, the immune modulator sequences may be accompanied by antibiotic resistance genes, which may be used to select for clones with stable integration of the recombinant DNA encoding the immune modulator sequences. According to some embodiments, the immune modulator sequences may be cloned into a plasmid construct comprising antibiotic resistance, such as the Neomycin/Kanamycin resistance gene. Transfected cells are treated with antibiotics according to the manufacturer's protocol for 1-2 weeks or more with daily media changes. At some point during antibiotic treatment, there is massive tumor cell death of all cells that have not stably integrated the antibiotic resistance gene, leaving behind small colonies of stably expressing clones. Each of the stably expressing clones may be picked, cultured in a separate tissue culture container, and tested for levels of immune modulator expression by any established method, such as western blot, flow cytometry, and fluorescence microscopy.

According to some embodiments, transfected tumor cells may be selected for high expression of the immune modulators by fluorescence activated cell sorting (FACS). According to some embodiments, immune modulator sequences may be accompanied by one or more fluorescent proteins (e.g. GFP), which can be used to quantify expression of immune modulator. For example, a bicistronic plasmid comprising an immune modulator sequence connected to a GFP sequence via IRES sequence would result in both an immune modulator and GFP protein translated from the same transcript. Thus, the GFP expression level would act as a proxy for the expression level of immune modulator. Single cell suspensions of immune modulator/GFP transfected tumor cells could be selected for the desired level of expression by FACS based on the fluorescence intensity. Any fluorescent protein may be used in this regard. For example, any of the following recombinant fluorescent proteins may be used: EBFP, ECFP, EGFP, YFP, mHoneydew, mBanana, mOrange, tdTomato, mTangerine, mStrawberry, mCherry, mGrape, mRasberry, mGrape2, mPlum.

Alternatively, the expression of the recombinant immune modulator may be directly observed by fluorescent antibodies specific to each immune modulator or specific to a tag engineered onto each immune modulator. For example, according to some embodiments the extracellular region of an immune modulator sequence may be fused with a FLAG tag or HA tag. Anti-FLAG or anti-HA antibodies may be used, along with a fluorophore attached to the primary antibody or a secondary antibody) to detect the expression of the immune modulator on the surface of the transfected tumor cells. Tumor cells expressing the desired level of immune modulator may be selected by FACS sorting and cultured separately.

Testing of Clones for Immunogenic Potential

Mixed Lymphocyte Tumor Cell Reactivity

According to some embodiments, the genetically introduced immunomodulators may be assessed for their immunogenic potential by a mixed lymphocyte tumor cell reaction (MLTR). The MLTR assay comprises incubating mixed lymphocytes with tumor cell line variants (or controls) for several days to allow the tumor cells of the tumor cell line variant to elicit an immune response from the mixed lymphocytes in vitro. This method may provide a rapid in vitro method to assess mixed lymphocyte responses (such as cellular proliferation of lymphocytes, cellular subset differentiation of lymphocytes, cytokine release profile of lymphocytes, and tumor cell death) to tumor cells or lysates. This approach may enable comprehensive monitoring of cellular, humoral, or both, immunity responses to phenotypically modified transfected tumor cells using human peripheral blood mononuclear cells. The MLTR also may provide an alternative to murine tumor survival studies, and may result in selection of optimal tumor cell line variants for anti-tumor response. A similar assay has been described by Hunter T B et al., (2007) Scandanavian J. Immunology 65, 479-486, which is incorporated herein by reference in its entirety.

According to some embodiments, tumor cell line variants may be tested for immunogenic potential by contacting transfected tumor cells with mixed lymphocytes from peripheral blood mononuclear cells, followed by measuring cellular proliferation, cellular subset differentiation, cytokine release profile, and tumor cell lysate.

According to some embodiments, mixed lymphocytes may be obtained from peripheral blood mononuclear cells isolated by a FICOLL-PAQUE® gradient. Briefly, anticoagulant-treated blood may be diluted in the range of 1:2 to 1:4 with PBS/EDTA to reduce aggregation of erythrocytes. The diluted blood may then be layered above a FICOLL-PAQUE® solution in a centrifuge tube, without mixing. The layered blood/FICOLL-PAQUE® may be centrifuged for 40 minutes at 400×g between 18° and 20° C., without the use of the centrifuge brake, resulting in the formation of blood fractions comprising, from top to bottom, a first fraction comprising blood plasma; a second fraction comprising mononuclear cells; a third fraction comprising FICOLL-PAQUE® media; and a fourth fraction comprising granulocytes and erythrocytes.

The fractions may be further processed to isolate specific fraction components. For example, to further process mononuclear cells, the second fraction comprising mononuclear cells may be carefully removed from the FICOLL-PAQUE® gradient using a Pasteur pipet. Alternatively, the second fraction may be removed directly by puncturing the tube with a needle and directly withdrawing the second fraction. The second fraction may then be washed and centrifuged at 300×g, 18° and 20° C., three times with PBS/EDTA, discarding the supernatant after each round.

According to some embodiments, tumor cell line variants may be co-cultured with the PBMCs comprising lymphocytes for seven days to allow for direct evaluation of activation of anti-tumor response in the presence of immune modulators from the tumor cell line variants.

According to some embodiments, one parameter used for measuring activation of lymphocytes may be cellular proliferation. According to some embodiments, proliferation may be detected by $^3$H-thymidine incorporation. Briefly, approximately $5 \times 10^3$ tumor cell line variant cells may be co-cultured with approximately $1 \times 10^6$ mixed lymphocytes in round bottomed 96-well plates. After three days of culture, cells may be pulsed with 1 µCi of $^3$H-thymidine for 18 hours. The cells may then be harvested onto filter mats, and $^3$H-thymidine incorporation may be measured using a scintillation counter. Proliferation of tumor cell line variants compared to non-transfected tumor cell controls may be measured. An increase, a decrease, or no change in proliferation relative to controls, are possible outcomes.

According to some embodiments, another parameter for measuring activation of lymphocytes may be the cytokine release profile. For example, the number of responsive T cells in the mixed lymphocyte population may be quantified by enzyme linked immunospot (ELISpot) analysis of IFN-gamma and/or IL-2 production by PBMCs. Briefly, PBMCs comprising mixed lymphocytes and a tumor cell line variant may be co-cultured between 3 and 7 days. Co-cultured cells may then be harvested and incubated on ELISpot plates pre-coated with anti-IFN-gamma and/or anti-IL-2 antibodies. After 20 hours, cells may be removed by washing 2 times in distilled water and two times in washing buffer. ELISpot plates may then be contacted with biotinylated anti-IFN-gamma and/or anti-IL-2 antibodies and streptavidin alkaline phosphatase in blocking buffer for 1-2 hours. After washing, plates may be contacted with alkaline phosphatase substrate until dark spot emerge. Plates may then be washed in tap water and air dried. Spots are then quantified manually or by plate reader and compared to non-transfected tumor cell line control group.

According to some embodiments, another parameter for measuring activation of lymphocytes may be by quantifying cellular subset differentiation. For example, the differentiation of CD45+/CD3+ T-lymphocytes to CD45+/CD3+/CD4+ helper T-lymphocytes, CD45+/CD3+/CD8+ cytotoxic T-lymphocytes, and CD45+/CD3+/CD25+ activated T-lymphocytes may be quantified by flow cytometry analysis.

According to some embodiments, another parameter for measuring activation of lymphocytes may be by quantifying tumor cell cytotoxicity. Cytotoxicity of tumor cells may be measured by any number of established methods. For example, according to some embodiments, an LDH-Cytotoxicity colorimetric assay kit (BioVision Cat. #K311-400) may be used to measure cytotoxicity of tumor cells by testing for lactate dehydrogenase (LDH) released from damaged cells into the growth media. Briefly, 100 µl of media from each of the control group (comprising untransfected tumor cells), the experimental group (comprising immune modulator transfected tumor cells), and media alone may be pipetted into the wells of a 96 well plate. 100 µl of the LDH reaction mixture, comprising dye solution and catalyst solution, may then be added to the wells of the 96 well plate and incubated for 30 minutes at room temperature. Then the samples may be measured for light absorbance at 490-500 nm using a microtiter plate reader.

Sequentially Add New Plasmid Constructs to the Clones

According to some embodiments, tumor cell line variants that express one or more immune modulator sequences are transfected with additional immune modulators for stable expression in a sequential manner. By sequentially adding recombinant immune modulators in successive fashion, cells of a tumor cell line variant may be created that express several immune modulators simultaneously. According to some embodiments, a tumor cell line variant may be created that expresses two immune modulators simultaneously. According to some embodiments, a tumor cell line variant may be created that expresses three immune modulators simultaneously. According to some embodiments, a tumor cell line variant may be created that expresses four immune modulators simultaneously. According to some embodiments, a tumor cell line variant may be created that expresses five immune modulators simultaneously.

Variably Expressing Clones

According to one aspect of the disclosed invention, multiple recombinant immune modulator peptides may be expressed in a single clonally derived tumor cell line variant. According to some embodiments, the amount (or level) of each individual immune modulator expressed in each cell is the same as the level of expression of all other immune modulator peptides. According to some embodiments, however, the level of each individual immune modulator expressed in each cell is different from the level of expression of the other immune modulators expressed in the cell. According to some embodiments, clonally derived tumor cell line variants that express the same complement of immune modulators stably express those immune modulators in varying amounts relative to each other.

The relative amount of recombinant immune modulator expressed within each clonally derived tumor cell line variant, and between tumor cell line variants, can be measured on the level of transcription or translation. For example, the relative amount of recombinant immune modulator can be quantified by western blot, RT-PCR, flow cytometry, immunofluorescence, and northern blot, among others.

According to some embodiments, the differences in the amount of expressed immune modulators relative to one another may be a result of random integration into more or less transcriptionally active regions of the genome of the tumor cell line variant. According to some embodiments, the relative differences in the amount of expressed immune modulator may be achieved by elements engineered into the transfected or transduced DNA used to create the tumor cell line variant.

For example, according to some embodiments, the level of expression of the immune modulator proteins may be achieved on the transcriptional level by engineering stronger or weaker gene promoter sequences to control expression of the immune modulator gene. According to some embodiments, one or more of the following promoters may be used to control expression of immune modulators: simian virus 40 early promoter (SV40), cytomegalovirus immediate-early promoter (CMV), human Ubiquitin C promoter (UBC), human elongation factor 1α promoter (EF1A), mouse phosphoglycerate kinase 1 promoter (PGK), and chicken β-Actin promoter coupled with CMV early enhancer (CAGG).

According to some embodiments, the level of expression of the immune modulator proteins may be achieved on the translational level by engineering stronger or weaker Kozak consensus sequences around the start codon of the immune modulator transcript. According to some embodiments, the following nucleotide sequences may be provided to control immune modulator translation: GCCGCC(A/G)CCAUGG (SEQ ID NO: 15). According to some embodiments, a sequence that is at least 60% identical to SEQ ID NO: 15 may be provided to control immune modulator translation. According to some embodiments, a sequence that is at least 70% identical to SEQ ID NO: 15 may be provided to control immune modulator translation. According to some embodiments, a sequence that is at least 80% identical to SEQ ID NO: 15 may be provided to control immune modulator translation. According to some embodiments, a sequence that is at least 90% identical to SEQ ID NO: 15 may be provided to control immune modulator translation. According to some embodiments, a sequence that is at least 95% identical to SEQ ID NO: 15 may be provided to control immune modulator translation. According to some embodiments, a sequence that is at least 96% identical to SEQ ID NO: 15 may be provided to control immune modulator translation. According to some embodiments, a sequence that is at least 97% identical to SEQ ID NO: 15 may be provided to control immune modulator translation. According to some embodiments, a sequence that is at least 98% identical to SEQ ID NO: 15 may be provided to control immune modulator translation. According to some embodiments, a sequence that is at least 99% identical to SEQ ID NO: 15 may be provided to control immune modulator translation.

Therapeutic Compositions

According to another aspect of the disclosed invention, an immunogenic composition may comprise an amount of a tumor cell line variant comprising two or more genes encoding human immune modulators. According to some embodiments, clones of tumor cell line variants that maximally express the human immune modulators are identified and selected. According to some embodiments, expression of the human immune modulators by populations of the tumor cell line variants is determined by flow cytometry. According to some embodiments, flow cytometry is used to gate on the maximally expressing population(s) of tumor cell line variants.

According to some embodiments, the immunogenic amount may be effective to stimulate an anti-tumor immune response to one or more tumor specific antigens. According to some embodiments, the immunogenic amount may be titrated to provide both safety and efficacy.

According to some embodiments, the immunogenic composition comprises a pharmaceutically acceptable carrier.

According to some embodiments, the immunogenic composition further comprises an adjuvant.

According to some embodiments, the tumor cell line variant may comprise tumor cells derived from an established cell line. According to some embodiments, the tumor cell line variant comprises tumor cells derived from a patient with cancer, wherein the tumor cells are derived from a solid tumor.

According to some embodiments, the tumor cell line variant comprises an immunogenic amount of a disrupted tumor cell line variant. Examples of methods for physical disruption include, without limitation, sonication, cavitation, dehydration, ion depletion, or by toxicity from exposure to one or more salts.

According to some embodiments, the immunogenic amount of the immunogenic composition may comprise at least $1 \times 10^3$ whole or disrupted tumor cell line variant cells. According to some embodiments, the amount of the immunogenic composition may comprises at least $1 \times 10^4$ whole or disrupted tumor cell line variant cells. According to some embodiments, the amount of the immunogenic composition may comprise at least $1 \times 10^5$ whole or disrupted tumor cell line variant cells. According to some embodiments, the amount of the immunogenic composition may comprise at least $1 \times 10^6$ whole or disrupted tumor cell line variant cells. According to some embodiments, the amount of the immunogenic composition may comprise at least $1 \times 10^7$ whole or disrupted tumor cell line variant cells. According to some embodiments, the amount of the immunogenic composition may comprise at least $1 \times 10^8$ whole or disrupted tumor cell line variant cells. According to some embodiments, the amount of the immunogenic composition may comprise at least $1 \times 10^9$ whole or disrupted tumor cell line variant cells. According to some embodiments, the immunogenic amount may be a therapeutic amount.

According to some embodiments, the immunogenic amount may be effective (1) to stimulate an effective immune response comprising one or more of cytotoxic T cells, natural killer cells, antibodies, APCs, T cells, B cells, and dendritic cells; and (2) to improve a clinical outcome parameter selected from one or more of progression-free survival, disease-free survival, time to progression, time to distant metastasis, and overall survival of the subject, when compared to a suitable control.

According to some embodiments, the immunogenic composition may be administered once per week, twice per week, once every two weeks, once every three weeks, once every four weeks, once per month, once every two months, once every three months, once every four months, once every five months, once every six months, once every seven months, once every eight months, once every nine months, once every ten months, once every eleven months, or once a year. According to some embodiments, administration occurs in one day or over 2 days, 3 days, 4, days, 5 days, 6 days, 7 days, 8, days, 9 days, 10 days, 11 days, 12 days, 13 days, 14 days, 15 days, 16 days, 17 days, 18 days, 19 days, 20 days, or more. According to some embodiments, administration may involve two or more administrations on the same day.

Combination Therapies

According to some embodiments, the disclosure provides methods that further comprise administering an additional agent to a subject. In some embodiments, the invention pertains to co-administration and/or co-formulation.

In some embodiments, administration of the immunogenic composition acts synergistically when co-administered with another agent and is administered at doses that are lower than the doses commonly employed when such agents are used as monotherapy.

In some embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma11 and calicheamicin omega11; dynemicin, including dynemicin A; bisphosphonates, such as clodronate; an esperamicin; as well as neocarzinostatin chromophore and related chromoprotein enediyne antibiotic chromophores), aclacinomy sins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxete; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel, and TAXOTERE doxetaxel; chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYK-ERB); inhibitors of PKC-.alpha., Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation.

Other additional agents are described elsewhere herein, including the blocking antibodies targeted to an immune "checkpoint" molecule.

According to some embodiments, the treatment regimen may comprise a standard anti-tumor therapy (such as surgery, radiation therapy, a targeted therapy that precisely identifies and attacks cancer cells, a hormone therapy, or a combination thereof). According to some embodiments, the standard anti-tumor therapy is effective to treat the tumor while preserving any existing anti-tumor immune response. According to some embodiments, the immunogenic composition is not applied after chemotherapy. According to some embodiments, the immunogenic composition is applied after low-dose chemotherapy.

According to some embodiments, the immunogenic composition comprises two or more clonally derived tumor cell line variants. According to some embodiments, the two or more tumor cell line variants comprise the same complement of recombinant immune modulators. According to some embodiments, the two or more tumor cell line variants comprise different panels of recombinant immune modulators.

According to some embodiments, the tumor cell line variants are treated with an agent that prevents cell division prior to administration to a subject. According to some embodiments, the tumor cell line variants are irradiated. According to some embodiments, the tumor cell line variants are treated with a chemical agent that prevents proliferation.

According to some embodiments, the tumor cell line variants may be administered parenterally. According to some embodiments, the tumor cell line variants may be administered locally into a surgical excision cavity. According to some embodiments, the tumor cell variants may be administered by intradermal injection. According to some embodiments, the tumor cell line variants may be administered by subcutaneous injection. According to some embodiments, the tumor cell line variants may be administered by intramuscular injection.

Methods of Treatment

Tumor cell line variants as provided herein can be incorporated into a composition for administration to a subject (e.g., a research animal or a mammal, such as a human, having a clinical condition such as cancer or an infection).

For example, an allogeneic tumor cell vaccine comprising a tumor cell line variant comprising two or more stably expressed recombinant membrane bound immunomodulatory molecules selected from IgG1, CD40L, TNF-alpha, and Flt-3L peptides; and stably expressed recombinant soluble GM-CSF peptides; and a pharmaceutically acceptable carrier; can be administered to a subject for the treatment of cancer. In another example, an allogeneic tumor cell vaccine comprising a tumor-type specific cell line variant is used to deliver a broad array of tumor antigens in the context of immunomodulatory signals sufficient to elicit a potent anti-tumor response as reflected in improved progression free survival, overall survival, or both relative to placebo controls, wherein the immunomodulatory signals are comprised of two or more stably expressed recombinant membrane bound immunomodulatory molecules selected from membrane expressed IgG1, CD40L, TNF-alpha, as well as membrane and soluble forms of GM-CSF, and Flt-3L.

Thus, the described invention provides methods for treating clinical conditions such as cancer with the allogeneic tumor vaccines provided herein.

In various embodiments, the described invention pertains to cancers and/or tumors; for example, the treatment or prevention of cancers and/or tumors. The phrase "cancers or tumors" refers to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also included are cells having abnormal proliferation that is not impeded by the immune system (e.g. virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

Illustrative cancers that may be treated include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

In certain embodiments, cancers/tumors that may be treated are those where the standard of care is no longer chemotherapy, since chemotherapy is known to interfere with immune responses, which are expected to occur during a successful vaccination protocol. Exemplary tumor types include tumor types treated with hormonal therapies such as prostate and breast cancers (e.g. Abiraterone® for prostate cancer and Tamoxifen® for breast cancer), tumor types treated with targeted therapies like antibodies (e.g. Rituxan® for B cell malignancies, Herceptin® for breast cancer), tumor types treated with kinase inhibitors such as GLEEVEC™ for chronic myelogenous leukemia and tumor types treated with other immune system sparing or enhancing modalities, such as checkpoint inhibitors, oncolytic viruses and CAR-T cells Representative cancers and/or tumors of the present invention are described herein. The described invention also provides compositions containing an allogeneic tumor cell vaccine comprising a tumor cell line variant comprising two or more stably expressed recombinant membrane bound immunomodulatory molecules selected from IgG1, CD40L, TNF-alpha, and Flt-3L peptides; and stably expressed recombinant soluble GM-CSF peptides; and a pharmaceutically acceptable carrier, as described herein, in combination with a physiologically and pharmaceutically acceptable carrier. The physiologically and pharmaceutically acceptable carrier can include any of the well-known components useful for immunization. The carrier can facilitate or enhance an immune response to an antigen administered in a vaccine. The cell formulations can contain buffers to maintain a preferred pH range, salts or other components that present an antigen to an individual in a composition that stimulates an immune response to the antigen. The physiologically acceptable carrier also can contain one or more adjuvants that enhance the immune response to an antigen. Pharmaceutically acceptable carriers include, for example, pharmaceutically acceptable solvents, suspending agents, or any other pharmacologically inert vehicles for delivering compounds to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water, saline solution, binding agents (e.g., polyvinylpyrrolidone or hydroxypropyl methylcellulose); fillers (e.g., lactose or dextrose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Compositions can be formulated for subcutaneous, intramuscular, or intradermal administration, or in any manner acceptable for immunization.

An "adjuvant" refers to a substance which, when added to an immunogenic agent such as a tumor cell expressing secreted vaccine protein, nonspecifically enhances or potentiates an immune response to the agent in the recipient host upon exposure to the mixture. Adjuvants can include, for example, oil-in-water emulsions, water-in oil emulsions, alum (aluminum salts), liposomes and microparticles, such as, polysytrene, starch, polyphosphazene and polylactide/polyglycosides.

Adjuvants can also include, for example, squalene mixtures (SAF-I), muramyl peptide, saponin derivatives, mycobacterium cell wall preparations, monophosphoryl lipid A, mycolic acid derivatives, nonionic block copolymer surfactants, QUIL-A®, cholera toxin B subunit, polyphosphazene and derivatives, and immunostimulating complexes (ISCOMs) such as those described by Takahashi et al., Nature 1990, 344:873-875. For veterinary use and for production of antibodies in animals, mitogenic components of Freund's adjuvant (both complete and incomplete) can be used. In humans, Incomplete Freund's Adjuvant (IFA) is a useful adjuvant. Various appropriate adjuvants are well known in the art (see, for example, Warren and Chedid, CRC Critical Reviews in Immunology 1988, 8:83; and Allison and Byars, in Vaccines: New Approaches to Immunological Problems, 1992, Ellis, ed., Butterworth-Heinemann, Boston). Additional adjuvants include, for example, bacille Calmett-Guerin (BCG), DETOX (containing cell wall skeleton of *Mycobacterium phlei* (CWS) and monophosphoryl lipid A from *Salmonella minnesota* (MPL)), and the like (see, for example, Hoover et al., J Clin Oncol 1993, 11:390; and Woodlock et al., J Immunother 1999, 22:251-259).

In some embodiments, an allogeneic tumor cell vaccine can be administered to a subject one or more times (e.g., once, twice, two to four times, three to five times, five to eight times, six to ten times, eight to 12 times, or more than 12 times). An allogeneic tumor cell vaccine as provided herein can be administered one or more times per day, one or more times per week, every other week, one or more times per month, once every two to three months, once every three to six months, or once every six to 12 months. An allogeneic tumor cell vaccine can be administered over any suitable period of time, such as a period from about 1 day to about 12 months. In some embodiments, for example, the period of administration can be from about 1 day to 90 days; from about 1 day to 60 days; from about 1 day to 30 days; from about 1 day to 20 days; from about 1 day to 10 days; from about 1 day to 7 days. In some embodiments, the period of administration can be from about 1 week to 50 weeks; from about 1 week to 50 weeks; from about 1 week to 40 weeks; from about 1 week to 30 weeks; from about 1 week to 24 weeks; from about 1 week to 20 weeks; from about 1 week to 16 weeks; from about 1 week to 12 weeks; from about 1 week to 8 weeks; from about 1 week to 4 weeks; from about 1 week to 3 weeks; from about 1 week to 2 weeks; from about 2 weeks to 3 weeks; from about 2 weeks to 4 weeks; from about 2 weeks to 6 weeks; from about 2 weeks to 8 weeks; from about 3 weeks to 8 weeks; from about 3 weeks to 12 weeks; or from about 4 weeks to 20 weeks.

In some embodiments, after an initial dose (sometimes referred to as a "priming" dose) of an allogeneic tumor cell vaccine has been administered and a maximal antigen-specific immune response has been achieved, one or more boosting doses can be administered. For example, a boosting dose can be administered about 10 to 30 days, about 15 to 35 days, about 20 to 40 days, about 25 to 45 days, or about 30 to 50 days after a priming dose.

In some embodiments, the methods provided herein can be used for controlling solid tumor growth and/or metastasis. The methods can include administering an effective amount of an allogeneic tumor cell vaccine as described herein to a subject in need thereof.

The vectors and methods provided herein can be useful for stimulating an immune response against a tumor. Such immune response is useful in treating or alleviating a sign or symptom associated with the tumor. A practitioner will appreciate that the methods described herein are to be used in concomitance with continuous clinical evaluations by a skilled practitioner (physician or veterinarian) to determine subsequent therapy. Such evaluations will aid and inform in evaluating whether to increase, reduce, or continue a particular treatment dose, mode of administration, etc.

The methods provided herein can thus be used to treat a tumor, including, for example, a cancer. The methods can be used, for example, to inhibit the growth of a tumor by preventing further tumor growth, by slowing tumor growth, or by causing tumor regression. Thus, the methods can be used, for example, to treat a cancer. It will be understood that the subject to which a compound is administered need not suffer from a specific traumatic state. Indeed, the allogeneic tumor cell vaccine described herein may be administered prophylactically, prior to development of symptoms (e.g., a patient in remission from cancer).

Anti-tumor and anti-cancer effects include, without limitation, modulation of tumor growth (e.g., tumor growth delay), tumor size, or metastasis, the reduction of toxicity and side effects associated with a particular anti-cancer agent, the amelioration or minimization of the clinical impairment or symptoms of cancer, extending the survival of the subject beyond that which would otherwise be expected in the absence of such treatment, and the prevention of tumor growth in an animal lacking tumor formation prior to administration, i.e., prophylactic administration.

Therapeutically effective amounts can be determined by, for example, starting at relatively low amounts and using step-wise increments with concurrent evaluation of beneficial effects. The methods provided herein thus can be used alone or in combination with other well-known tumor therapies, to treat a patient having a tumor. One skilled in the art will readily understand advantageous uses of the allogeneic tumor cell vaccines and methods provided herein, for example, in prolonging the life expectancy of a cancer patient and/or improving the quality of life of a cancer patient (e.g., a lung cancer patient).

Subjects

The methods described herein are intended for use with any subject that may experience the benefits of these methods. Thus, "subjects," "patients," and "individuals" (used interchangeably) include humans as well as non-human subjects, particularly domesticated animals.

In some embodiments, the subject and/or animal is a mammal, e g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human In some embodiments, the human is a pediatric human In other embodiments, the human is an adult human. In other embodiments, the human is a geriatric human In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal In certain embodiments, the subject is a human cancer patient that cannot receive chemotherapy, e.g. the patient is unresponsive to chemotherapy or too ill to have a suitable therapeutic window for chemotherapy (e.g. experiencing too many dose- or regimen-limiting side effects). In certain embodiments, the subject is a human cancer patient having advanced and/or metastatic disease.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "an", and "the" include plural references unless the context clearly dictates otherwise. All technical and scientific terms used herein have the same meaning.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Examples 2-5 make use of, but are not limited to, the methods described hereinbelow.

Western Blotting

Briefly, cells are lysed with cold lysis buffer and centrifuged to pellet cellular debris. Protein concentration of the supernatant is determined by a protein quantification assay (e.g., Bradford Protein Assay, Bio-Rad Laboratories). The lysate supernatant is then combined with an equal volume of 2× SDS sample buffer and boiled at 100° C. for 5 minutes. Equal amounts of protein in sample buffer are loaded into the wells of an SDS-PAGE gel along with molecular weight marker and electrophoresed for 1-2 hours at 100 V. Proteins are then transferred to a nitrocellulose or PVDF membrane. The membrane is then blocked for 1 hour at room temperature using 5% non-fat dry milk in TBST blocking buffer. The membrane is then incubated with a 1:500 dilution of primary antibody in 5% non-fat dry milk in TBST blocking buffer, followed by three washes in 20 Mn Tris (tris(hydroxymethyl)aminomethane), Ph 7.5; 150 mM NaCl, 0.1% Tween 20® (Polysorbate 20) (TBST) for 5 minutes. The membrane is then incubated with conjugated secondary antibody at a 1:2000 dilution in 5% non-fat dry milk in TBST blocking buffer for 1 hour at room temperature, followed by three washes in TBST for 5 minutes each. Images of the blot are obtained using dark room development techniques for chemiluminesence detection, or using image scanning techniques for colorimetric or fluorescent detection.

Real Time PCR

Real-time PCR techniques may be performed as described to analyze expression level of mRNAs (Zhao Y. et al., Biochemical and Biophysical Research Communications 360 (2007) 205-211). Briefly, total RNA is extracted from cells using the Quiagen kit (Valencia CA), followed by first strand cDNA synthesis using random hexamer primers (Fermentas, Hanover MD). Real-time PCR is performed on each sample using the Mx3000p Quantitative PCR system (Stratagene, La Jolla, CA), for 40 cycles using validated gene specific RT-PCR primer sets for each gene of interest. Relative expression level of each transcript is corrected for that of the house keeping gene beta-actin as an internal control.

Immunofluorescence

Briefly, adherent tumor cell line variant cells are fixed with 4% formaldehyde diluted in warm PBS for 15 minutes at room temperature. The fixative is aspirated and the cells washed three times with PBS for 5 minutes each. Cells are blocked in a 5% BSA blocking buffer for 60 minutes at room temperature. Blocking buffer is then aspirated and a solution of primary antibody (e.g. 1:100 dilution) is incubated with the cells overnight at 4° C. Cells are then rinsed three times with PBS for 5 minutes each, and subsequently incubated with a solution of fluorochrome conjugated secondary antibody (e.g. 1:1000 dilution) for 1-2 hours at room temperature. Cells are then washed three times with PBS for 5 minutes each and visualized by fluorescence microscopy.

Flow Cytometry

Flow Cytometry analysis may be performed as described (Zhao Y. et al., Exp. Cell Res., 312, 2454 (2006)). Briefly, tumor cell line variant cells that are either treated with trypsin/EDTA or left untreated are collected by centrifugation and re-suspended in PBS. The cells are fixed in 4% formaldehyde for 10 minutes at 37° C. For extracellular staining with antibodies, cells are not permeabilized. For intracellular staining, cells are permeabilized by adding ice-cold 100% methanol to pre-chilled cells to a final concentration of 90% methanol and incubated on ice for 30 minutes. Cells are immunostained by first resuspending cells in incubation buffer and adding dilutions of primary antibody. Cells are incubated with primary antibody for 1 hour at room temperature, followed by three washes with incubation buffer. Cells are then resuspended in incubation buffer with dilutions of conjugated secondary antibody for 30 minutes at room temperature, followed by three washes in incubation buffer. Stained cells are then analyzed by flow cytometry.

Enzyme-Linked Immunosorbent Assay (ELISA)

Briefly, a capture antibody, specific for a protein of interest, is coated onto the wells of a microplate. Samples, including a standard containing protein of interest, control specimens, and unknowns, are pipetted into wells of the microplate, where the protein antigen binds to the capture antibody. After washing 4 times, a detection antibody is added to the wells for one hour, binding to the immobilized protein captured during the first incubation. After removal of excess detection antibody and washing 4 times, a horse radish peroxidase (HRP) conjugate (secondary antibody or streptavidin) is added for 30 minutes to bind to the detection antibody. After washing 4 more times to remove the excess HRP conjugate, a substrate solution is added for 30 minutes in the dark to be converted by the enzyme to a detectable form (color signal). A stop solution is added to each well of the microplate and evaluated within 30 minutes of stopping the reaction. Intensity of the colored product may be directly proportional to the concentration of antigen present in the original specimen.

Human Mixed Lymphocyte Tumor Reaction (MLTR) Testing

The mixed lymphocyte tumor reaction (MLTR) is an all human, in vitro assay, designed to optimize lead candidates. In the MLTR, optimization is achieved through the qualitative and quantitative assessment of human peripheral blood mononuclear cell (PBMC) responses to engineered allogeneic tumor cells. The MLTR assay permits assessment of proliferation and differentiation by flow cytometry and mass cytometry (CyTOF). Cytotoxicity, can be measured by lactate dehydrogenase (LDH) release assay, and the cytokine profile can be measured by LUMINEX® multiplex assay. In certain embodiments, allogeneic cell pools expressing a single immunomodulatory protein are used in the MLTR. In other embodiments, allogeneic cell pools expressing multiple immunomodulatory proteins are used in the MLTR.

The basic MLTR one day procedure is carried out as follows:

Frozen human PBMC are thawed. Cells are then washed in dPBS. PMBC cells are resuspended at $2.5 \times 10^6$ cell per ml stock in X-VIVO™ serum free media (Invitrogen). The cells are characterized by flow cytometry to document and confirm the phenotypic nature of the cell population.

The MLTR set up in the following fashion:
$2.5 \times 10^5$ cell PBMC (100 µl of stock)
$0.5 \times 10^5$ allogeneic cells (100 µl of stock), when used
Positive control 50 µl of a 6× stock (anti-CD28/CD3)
Total volume 300 µl in a 96-well flat bottom–total volume of a 96-well is 300 ul.
Incubate for 1 day.
100 µl is removed for cytokine analysis by LUMINEX® multiplex assay
CyTOF is conducted on the cellular component.

CyTOF has been previously described, for example in Bendall et al. (Science, Vol. 332, 6 May 2011) and Bendall and Nolan (Nature Biotechnology, Vol. 30 No. 7, July 2012), both of which are incorporated by reference in their entireties herein. Human markers employed in CyTOF staining are shown below in Table 1.

TABLE 1

Human Markers for CyTOF Staining

| | Marker | Clone | Metal |
|---|---|---|---|
| | HLA-DR | L243 | 89Y |
| | CD3 | UCHT1 | 115In |
| | CD27 | O323 | 141Pr |
| | CD19 | HIB 19 | 142Nd |
| | CD134/OX40 | Ber-ACT35 | 143Nd |
| * | Granzyme B | GB11 | 144Nd |
| | CD258/LIGHT | 115520 | 145Nd |
| | CD8A | RPA t8 | 146Nd |
| | CD45RO | UCHL1 | 147Sm |
| | CD226/DNAM-1 | 11A8 | 149Sm |
| | CD194/CCR4 | L291H4 | 150Nd |
| | PD1 (CD279) | EH12.2H7 | 151Eu |
| | CD170 | 1A5 | 152Sm |
| | CD69 | FN50 | 153Eu |
| | CD70 | 113-16 | 154Sm |
| | CD4 | RPA T4 | 155Gd |
| | CD8b | SIDI8BEE | 156Gd |
| | IL-17R | W15177A | 158Gd |
| * | CTLA-4 CD152 | L3D10 | 159Tb |
| | CD278/ICOS | C398.4A | 160Gd |
| * | AHR | FF3399 | 161Dy |
| | CD56 | NCAM16.2 | 162Dy |
| | CD195/CCR5 | J418F1 | 163Dy |
| * | Ki67 | 8D5 | 164Dy |
| * | FoxP3 | Use Ebio | 165Ho |
| | CD40 | 5C3 | 166Er |
| * | Helios | 22F6 | 168Er |
| * | PU.1 | puph13 | 169Tm |
| * | RORgt | 1181A | 170Er |
| | CD127/IL-7R | 40131 | 171Yb |
| | CD38 | HIT2 | 172Yb |
| | CD25 | M-A251 | 173Yb |
| | CD86 | IT2.2 | 174Yb |
| * | T-bet | 4B10 | 175Lu |
| * | Perforin | dG9 | 176Yb |

* denotes intracellular targets while all others are cell surface targets

LUMINEX® Multiplex Assay

The LUMINEX® xMAP technology (formerly LabMAP, FlowMetrix) uses digital signal processing capable of classifying polystyrene beads (microspheres) dyed with distinct proportions of red and near-infrared fluorophores. These proportions define 'spectral addresses' for each bead population. As a result, up to one hundred different detection reactions can be carried out simultaneously on the various bead populations in very small sample volumes (Earley et al. Report from a Workshop on Multianalyte Microsphere Arrays. Cytometry 2002; 50:239-242; Oliver et al. Clin Chem 1998; 44(9):2057-2060; Eishal and McCoy, Methods 38(4): 317-323, April 2006, all of which are incorporated by reference in their entireties herein). The LUMINEX® Multiplex Assay is commercially available and is described at Thermofisher's official website, incorporated by reference in its entirety herein. *Mitomycin C Preparation of Allogeneic Cells for MLTR Assay of Greater than 1 Day Duration.*

Mitomycin C is prepared from dry powder (2 mg per vial) using 400 µl of DMSO (500× stock=5 mg/ml), dissolved completely and aliquoted into 25 ul volumes, and stored at −80C. 20 µl of a single aliquot is used in 10 ml warmed C5 to yield 10 µg/ml final working solution. The solution is filter sterilized.

The solution can be used on resuspended cells or adherent cells in flasks.

Cells are incubated at 37C for 30 minutes in the dark, then washed in warm C5 cell culture media (RPMI, supplemented with non-essential amino acids, glutamine, antibiotics and 5% Fetal calf serum) three times. Cells are resuspended in 1 ml X-VIVO™, counted and final concentration adjusted to $1\times10^6$/ml stock solution in X-VIVO™ (serum free media, Lonza).

Example 2

The described invention provides an approach for restoring immunologic balance in, for example, treating cancer, by targeting multiple immunomodulators with a single cellular platform. This approach enables the simultaneous modulation of multiple signals, and affords a spatially and temporally restricted method of modulating the immune response, an important feature that differentiates this methodology from traditional approaches using systemic administration of biologic agents to act on a single immunomodulatory pathway at a time.

According to one aspect of the disclosed invention, a tumor-type specific cell line variant expressing five or more recombinant peptides may be generated for use as a tumor cell vaccine to treat that cancer type. For example, a tumor cell line may be selected for modification and lentiviral transfection of recombinant immunomodulator sequences may be used to stably integrate immune modulators into the cell genome. Example 3 below describes 7 lentiviral vectors (vector 1, vector 2, vector 3, vector 4, vector 5, vector 6 and vector 7) that may be used to stably integrate immune modulators into the cell genome.

According to some embodiments, two recombinant immunomodulator proteins may be transfected simultaneously, followed by transfections of two more recombinant immunomodulator proteins simultaneously, followed by transfection of a single recombinant immunomodulator protein to achieve the total of five recombinant peptides for use as a tumor cell vaccine. According to some embodiments, two recombinant peptides may be transfected simultaneously, followed by transfection of a single recombinant peptide, followed by transfection of a single recombinant peptide, followed by transfection of a single recombinant peptide to achieve the total of five recombinant peptides for use as a tumor cell vaccine. According to some embodiments, a single recombinant peptide is transfected, followed by transfection of two recombinant peptides simultaneously, followed by transfection of two recombinant peptides simultaneously to achieve a total of five recombinant peptide for use as a tumor cell vaccine.

According to one embodiment of the disclosed invention, combinations of allogeneic cell pools, each expressing a single immunomodulatory protein, are used to model what a single cell expressing multiple immunomodulatory proteins might do (e.g. additivity, synergy, interference).

According to one aspect of the disclosed invention, a tumor cell line variant expressing one, two, three, four, five or more recombinant peptides may be generated for use as a tumor cell vaccine to treat skin cancer. For example, the SK-MEL2 human melanoma cell line (ATCC® HTB-68) may be selected for modification, and lentiviral transfection of recombinant immune modulator sequences may be used to stably integrate immune modulators into the cell genome.

According to one aspect of the disclosed invention, a tumor cell line variant expressing one, two, three, four, five or more recombinant peptides may be generated for use as a tumor cell vaccine to treat a prostate cancer. For example, the DU-145 human prostate carcinoma cell line may be selected for modification, and lentiviral transfection of recombinant immune modulator sequences may be used to stably integrate immune modulators into the cell genome. According to some embodiments, two recombinant immunomodulator proteins may be transfected simultaneously, followed by transfections of two more recombinant immunomodulator proteins simultaneously, followed by transfection of a single recombinant immunomodulator protein to achieve the total of five recombinant peptides for use as a tumor cell vaccine. According to some embodiments, two recombinant peptides may be transfected simultaneously, followed by transfection of a single recombinant peptide, followed by transfection of a single recombinant peptide, followed by transfection of a single recombinant peptide to achieve the total of five recombinant peptides for use as a tumor cell vaccine. According to some embodiments, a single recombinant peptide is transfected, followed by transfection of two recombinant peptides simultaneously, followed by transfection of two recombinant peptides simultaneously to achieve a total of five recombinant peptide for use as a tumor cell vaccine.

According to another aspect of the present invention, two or more tumor cell line variants expressing one or more recombinant peptides may be generated for use as a tumor cell vaccine to treat a prostate cancer. For example, the DU-145 and PC-3 human prostate carcinoma cell line may be selected for modification, and lentiviral transfection of recombinant immune modulator sequences may be used to stably integrate immune modulators into the cell genome.

CD40L Immunomodulator

The CD40L immune modulator cDNA sequence may be cloned into the lentiviral transfer plasmid construct pLentipuro (Addgene Cat. No. 39481) driven by a CMV promoter with puromycin selectable marker. The CD40L immune modulator cDNA sequence may be engineered to be noncleavable, which ultimately keeps the translated CD40L protein in a membrane bound state (e.g. SEQ ID NO: 7).

Each of the lentiviral transfer plasmid, packaging plasmid, and envelope plasmid may be transfected into log phase growth 293T cells using LIPOFECTAMINE™ 2000 (ThermoFisher Cat. No. 11668027). Briefly, cells are seeded at 70% to 90% confluence. On the day of transfection, 12 µl of LIPOFECTAMINE™ reagent is diluted in 150 µl of serum free cell media. 5 µg of DNA for transfection is also diluted in 150 µl of serum free media. The diluted DNA is then added to the diluted LIPOFECTAMINE™ and incubated for 5 minutes at room temperature. The total volume of the mixture is then added dropwise to the media of the seeded 293T cells while swirling. Cells are then incubated for one to three days at 37 degrees.

The 293T cell culture medium comprising virus particle is harvested 3 times every 8-12 hours and centrifuged to pellet detached cells and debris. The culture medium containing virus particles is used directly to infect the DU-145 cell line.

The DU-145 cell line is cultured in Eagle's Minimum Essential Medium (EMEM) with 10% fetal bovine serum to a confluency of about 70%. Hexadimethrine bromide (Sigma-Aldrich Cat No. H9268) is then combined with media containing virus particles to make a final concentration of 8 g/mL Hexadimethrine bromide. Culture media of the DU-145 cells is aspirated and replaced with media containing virus particles and 8 g/mL Hexadimethrine bromide. DU-145 cells are cultured for 18-20 hours followed by media change.

Infected DU-145 cells are then grown in media containing 1 g/mL Puromycin (ThermoFisher Cat. No. A1113802) until cell die off begins after about a week. Multiple surviving colonies of transfected cells are picked for expansion and tested for CD40L expression by Western blot. The Western blot is probed with mouse monoclonal anti-HA primary antibodies (Abcam Cat. No. ab18181) and goat anti-mouse HRP (Abcam Cat. No. ab205719) secondary antibodies to quantify the relative amounts of recombinant CD40L expressed in each clonal line. The highest stably expressing DU-145 line is labeled DU145-Gen1 and selected for further manipulation.

TNF-alpha GM-CSF

The DU145-Gen1 cells transfected to express CD40L are further transfected with a bi-cistronic lentiviral vector comprising TNF-alpha and GM-CSF sequences. Each of TNF-alpha cDNA and GM-CSF cDNA is first cloned into the pEF1α-IRES bicistronic mammalian expression vector (Clontech Cat. No. 631970) under the control of the human elongation factor 1 alpha (EF1α) promoter. A variant of TNF-alpha that cannot be cleaved by TACE is used so that the translated protein remains in membrane bound form. The TNF-alpha sequence is provided with a FLAG tag sequence on the extracellular region of TNF-alpha for easy detection of translated protein. The FLAG tag peptide sequence is DYKDDDDK (SEQ ID NO: 29). GM-CSF sequences capable of forming soluble GM-CSF are used. The entirety of the pEF1 promoter, TNF-alpha sequences, IRES sequences, and GM-CSF sequences is then cloned into the pLenti-puro (Addgene Cat. No. 39481) lentiviral vector (the original CMV promoter from the vector is removed during this process). Packaging plasmid psPAX2 (AddGene Cat. No. 12260) and envelope plasmid pLTR-RD114A (AddGene Cat. No. 17576) are also selected.

Each of the lentiviral transfer plasmid, packaging plasmid, and envelope plasmid is transfected into log phase growth 293T cells using LIPOFECTAMINE™ 2000 (ThermoFisher Cat. No. 11668027). Briefly, cells are seeded at 70% to 90% confluence. On the day of transfection, 12 µl of LIPOFECTAMINE™ reagent is diluted in 150 µl of serum free cell media. 5 µg of DNA for transfection is also diluted in 150 µl of serum free media. The diluted DNA is then added to the diluted LIPOFECTAMINE™ and incubated for 5 minutes at room temperature. The total volume of the mixture is then added dropwise to the media of the seeded 293T cells while swirling. Cells are then incubated for one to three days at 37 degrees.

The 293T cell culture medium comprising virus particle is harvested 3 times every 8-12 hours and centrifuged to pellet detached cells and debris. The culture medium containing virus particles is used directly to infect the DU145-Gen1 cell line.

The DU145-Gen1 cell line is cultured to a confluency of about 70%. Hexadimethrine bromide (Sigma-Aldrich Cat No. H9268) is then combined with media containing virus particles to make a final concentration of 8 g/mL Hexadimethrine bromide. Culture media of the DU145-Gen1 cells is aspirated and replaced with media containing virus particles and 8 g/mL Hexadimethrine bromide. DU145-Gen1 cells are cultured for 18-20 hours followed by media change.

The transduced DU145-Gen1 cells are then selected for clones that stably express the recombinant immune modulators. The selection process is performed by fluorescence activated cell sorting using the FLAG tag on the TNF-alpha to identify cells that have integrated the immune modulators. Live cells are probed with mouse monoclonal anti-FLAG antibody (Sigma Aldrich F3040) and rabbit anti-mouse FITC conjugated secondary antibody (Sigma Aldrich ASB3701170) in PBS with blocking buffer. The highest expressing cells are sorted, isolated, and cultured for further processing. After sorting based on the presence of the FLAG tag, expression of soluble GM-CSF is confirmed by Western blot. Concentrated media of sorted cultured cells is resolved by SDS-PAGE and probed by Western blot with mouse anti-GM-CSF antibody (ThermoFisher Cat. No. 3092) and goat anti-mouse HRP conjugated secondary antibody. Cell lysate may also be resolved by SDS-PAGE and probed for FLAG tag to verify the presence of TNF. Cell cultures that express high levels of recombinant GM-CSF and TNF-alpha are designated DU145-Gen2 and selected for further processing.

Flt-3L

The DU145-Gen2 cells transfected to express CD40L, GM-CSF, and TNF are further transfected with a lentiviral vector comprising Flt-3L immune modulator sequences. The Flt-3L cDNA is cloned into a pEF1α-IRES bicistronic mammalian expression vector (Clontech Cat. No. 631970), along with GFP protein sequences to be used as a marker for integration and expression. The sequence of Flt-3L is translated into a membrane bound peptide, while the GFP remains cytoplasmic. The entirety of the pEF1 promoter, Flt-3L sequences, IRES sequences, and GFP sequences is then cloned into the pLenti-puro (Addgene Cat. No. 39481) lentiviral vector (the original CMV promoter from the vector is removed during this process). Packaging plasmid psPAX2 (AddGene Cat. No. 12260) and envelope plasmid pLTR-RD 114A (AddGene Cat. No. 17576) are also selected.

Each of the lentiviral transfer plasmid, packaging plasmid, and envelope plasmid is transfected into log phase growth 293T cells using LIPOFECTAMINE™ 2000 (ThermoFisher Cat. No. 11668027). Briefly, cells are seeded at 70% to 90% confluence. On the day of transfection, 12 µl of LIPOFECTAMINE™ reagent is diluted in 150 µl of serum free cell media. 5 µg of DNA for transfection is also diluted in 150 µl of serum free media. The diluted DNA is then added to the diluted LIPOFECTAMINE™ and incubated for 5 minutes at room temperature. The total volume of the mixture is then added dropwise to the media of the seeded 293T cells while swirling. Cells are then incubated for one to three days at 37 degrees.

The 293T cell culture medium comprising virus particle is harvested 3 times every 8-12 hours and centrifuged to pellet detached cells and debris. The culture medium containing virus particles is used directly to infect the DU145-Gen2 cell line.

The DU145-Gen2 cell line is cultured to a confluency of about 70%. Hexadimethrine bromide (Sigma-Aldrich Cat No. H9268) is then combined with media containing virus particles to make a final concentration of 8 g/mL Hexadimethrine bromide. Culture media of the DU145-Gen2 cells is aspirated and replaced with media containing virus particles and 8 g/mL Hexadimethrine bromide. DU145-Gen2 cells are cultured for 18-20 hours followed by media change.

The DU145-Gen2 cells are then selected for cells stably expressing the Flt-3L sequences using the GFP marker. The selection process is performed by fluorescence activated cell sorting (FACS) using the GFP marker to identify cells that have integrated the immune modulator. The highest expressing cells are sorted, isolated, and cultured for further processing. After sorting based on the presence of the GFP marker, the expression of Flt-3L is confirmed by Western blot. Cultured cell lysates are resolved by SDS-PAGE and probed by Western blot with rabbit polyclonal anti-Flt-3L antibody (AbCam Cat. No. ab9688) and goat anti-rabbit HRP conjugated secondary antibody (AbCam Cat. No. ab205718). Cell cultures that express high levels of recombinant Flt-3L are designated DU145-Gen3 and are selected for further processing.

IgG Heavy and Light Chains

The DU145-Gen3 cells transfected to express CD40L, GM-CSF, TNF-alpha, and Flt-3L are further transfected with a lentiviral vector comprising IgG 1 (SEQ ID NO: 1), a membrane bound IgG1 heavy chain fragment. The IgG1 heavy chain cDNA is cloned into pEF1α-IRES bicistronic mammalian expression vector (Clontech Cat. No. 631970), along with RFP protein sequences to be used as a marker for integration and expression. The sequence of IgG1 heavy chain is translated into a membrane bound peptide, while the RFP remains cytoplasmic. The entirety of the pEF1 promoter, IgG1 heavy chain sequence, IRES sequence, and RFP sequence is then cloned into the pLenti-puro (Addgene Cat. No. 39481) lentiviral vector (the original CMV promoter from the vector is removed during this process). Packaging plasmid psPAX2 (AddGene Cat. No. 12260) and envelope plasmid pLTR-RD 114A (AddGene Cat. No. 17576) are also selected.

Each of the lentiviral transfer plasmid, packaging plasmid, and envelope plasmid is transfected into log phase growth 293T cells using LIPOFECTAMINE™ 2000 (ThermoFisher Cat. No. 11668027). Briefly, cells are seeded at 70% to 90% confluence. On the day of transfection, 12 µl of LIPOFECTAMINE™ reagent is diluted in 150 µl of serum free cell media. 5 µg of DNA for transfection is also diluted in 150 µl of serum free media. The diluted DNA is then added to the diluted LIPOFECTAMINE™ and incubated for 5 minutes at room temperature. The total volume of the mixture is then added dropwise to the media of the seeded 293T cells while swirling. Cells are then incubated for one to three days at 37 degrees.

The 293T cell culture medium comprising virus particle is harvested 3 times every 8-12 hours and centrifuged to pellet detached cells and debris. The culture medium containing virus particles is used directly to infect the DU145-Gen3 cell line.

The DU145-Gen3 cell line is cultured to a confluency of about 70%. Hexadimethrine bromide (Sigma-Aldrich Cat No. H9268) is then combined with media containing virus particles to make a final concentration of 8 g/mL Hexadimethrine bromide. Culture media of the DU145-Gen2 cells is aspirated and replaced with media containing virus particles and 8 µg/mL Hexadimethrine bromide. DU145-Gen3 cells are cultured for 18-20 hours followed by media change.

The DU145-Gen3 cells are then selected for cells stably expressing the IgG1 heavy chain sequences using the RFP marker. The selection process is performed by fluorescence activated cell sorting (FACS) using the RFP marker to identify cells that have integrated the immune modulator. The highest expressing cells are sorted, isolated, and cultured for further processing. After sorting based on the presence of the RFP marker, the expression of IgG1 heavy chain is confirmed by Western blot. Cell cultures that express high levels of recombinant IgG1 heavy chain are designated DU145-Gen4 and are selected for further processing.

The DU145-Gen4 tumor cell line transfected to express CD40L, GM-CSF, TNF, Flt-3L, and IgG1 heavy chain is characterized by RT-PCR, immunofluorescence, and Western blotting to confirm all recombinant immune modulators are expressed by the cells and are in the right location (e.g. on the membrane of the cell).

Human Mixed Lymphocyte Tumor Reaction (MLTR) Testing

The DU145-Gen4 cells are tested for their immunomodulatory potential by primary and secondary MLTR assay against each of the other generations (i.e. DU145-Gen2 and DU145-Gen3) of modified cells and unmodified DU145 cells.

Peripheral blood mononuclear cells (PBMCs) are obtained from the peripheral blood of healthy individuals and from prostate cancer patients, and the blood cells separated using a FICOLL-PAQUE® gradient. Anticoagulant-treated blood is diluted in the range of 1:2 to 1:4 with PBS/EDTA to reduce aggregation of erythrocytes. The diluted blood is then layered above a FICOLL-PAQUE® solution in a centrifuge tube, without mixing. The layered blood/FICOLL-PAQUE® is centrifuged for 40 minutes at 400×g between 18° and 20° C., without the use of the centrifuge brake, resulting in the formation of blood fractions. The fraction comprising mononuclear cells is selected for further processing.

Each of the cells from the transfected tumor cell line variants and from parental tumor cell line DU-145 (control) is co-cultured with PBMCs for seven days under standard tissue culture conditions, followed by evaluation for immune cell proliferation, immune cell differentiation, measured by flow cytometry and CyTOF, cytokine release profile, and cytotoxicity, measured by LDH release assay.

Example 3

Figure 2A:
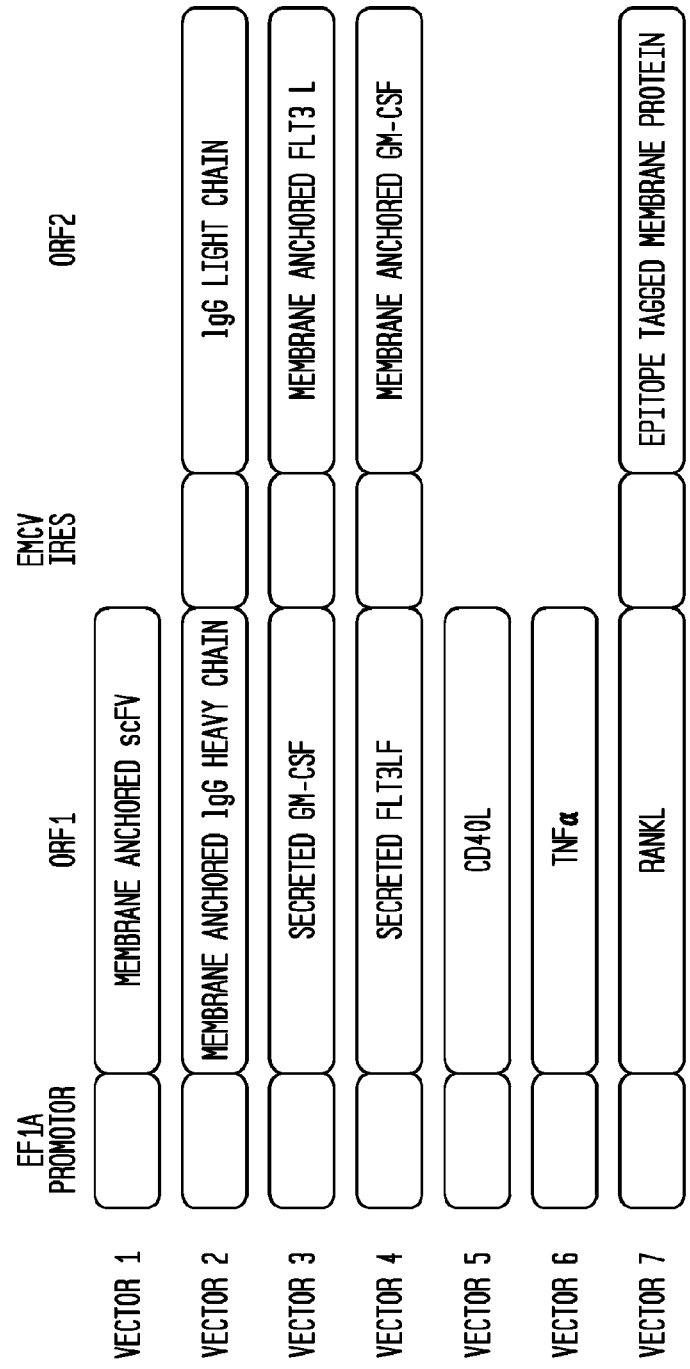
FIG. 2A shows a schematic of the core vectors.
Figure 2B:
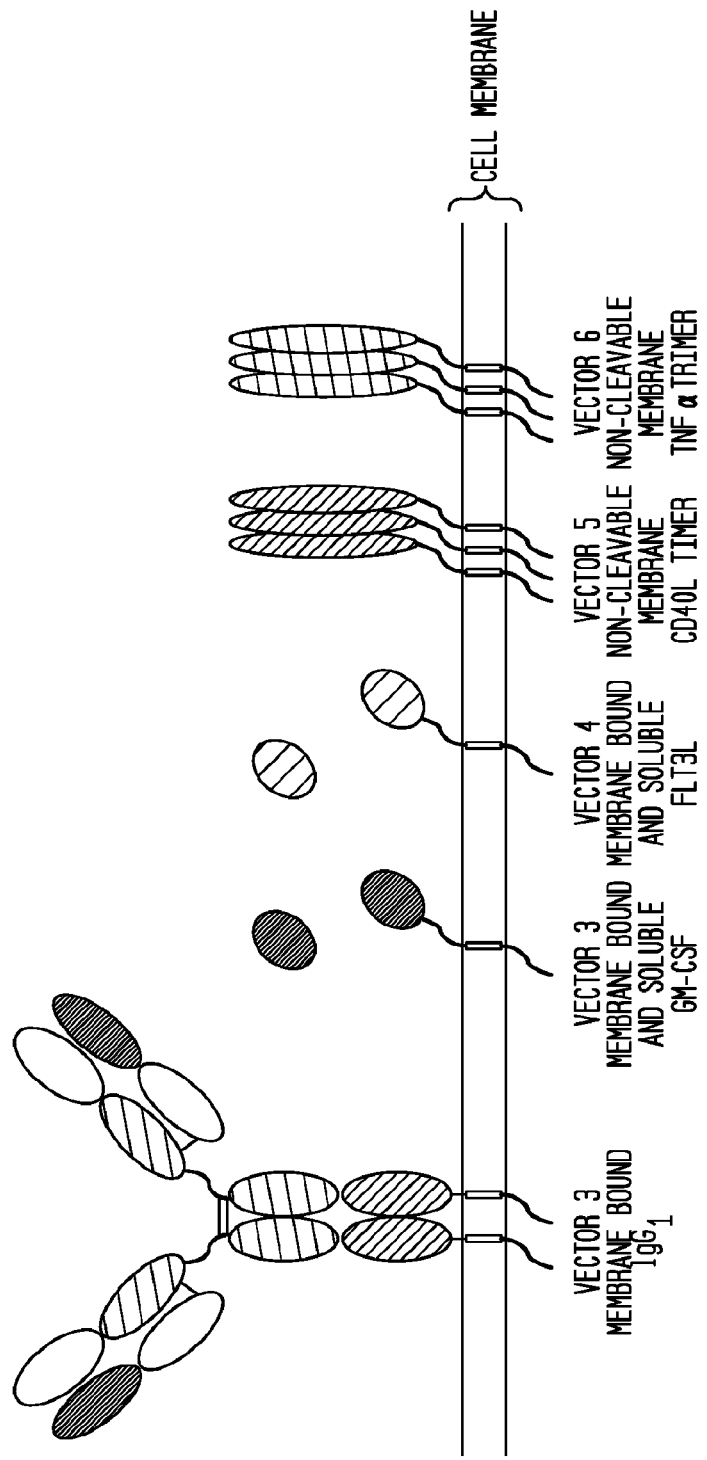
FIG. 2B shows a schematic of the proteins encoded by Vectors 2-6.

A schematic of the core lentiviral vectors employed in the experiments described herein is shown in FIG. 2A and a schematic of the encoded proteins is shown in FIG. 2B. The promoter is human elongation factor 1 alpha (EF1α) promoter and the internal ribosomal entry sequence (IRES) is derived from encephalomyocarditis virus (EMCV). The core vectors are described in detail hereinbelow as follows:

Vector 1. Immunomodulator:
scFv-anti-biotin-G3hinge-mIgG1 (to Generate Surface IgG)

Figure 3A:
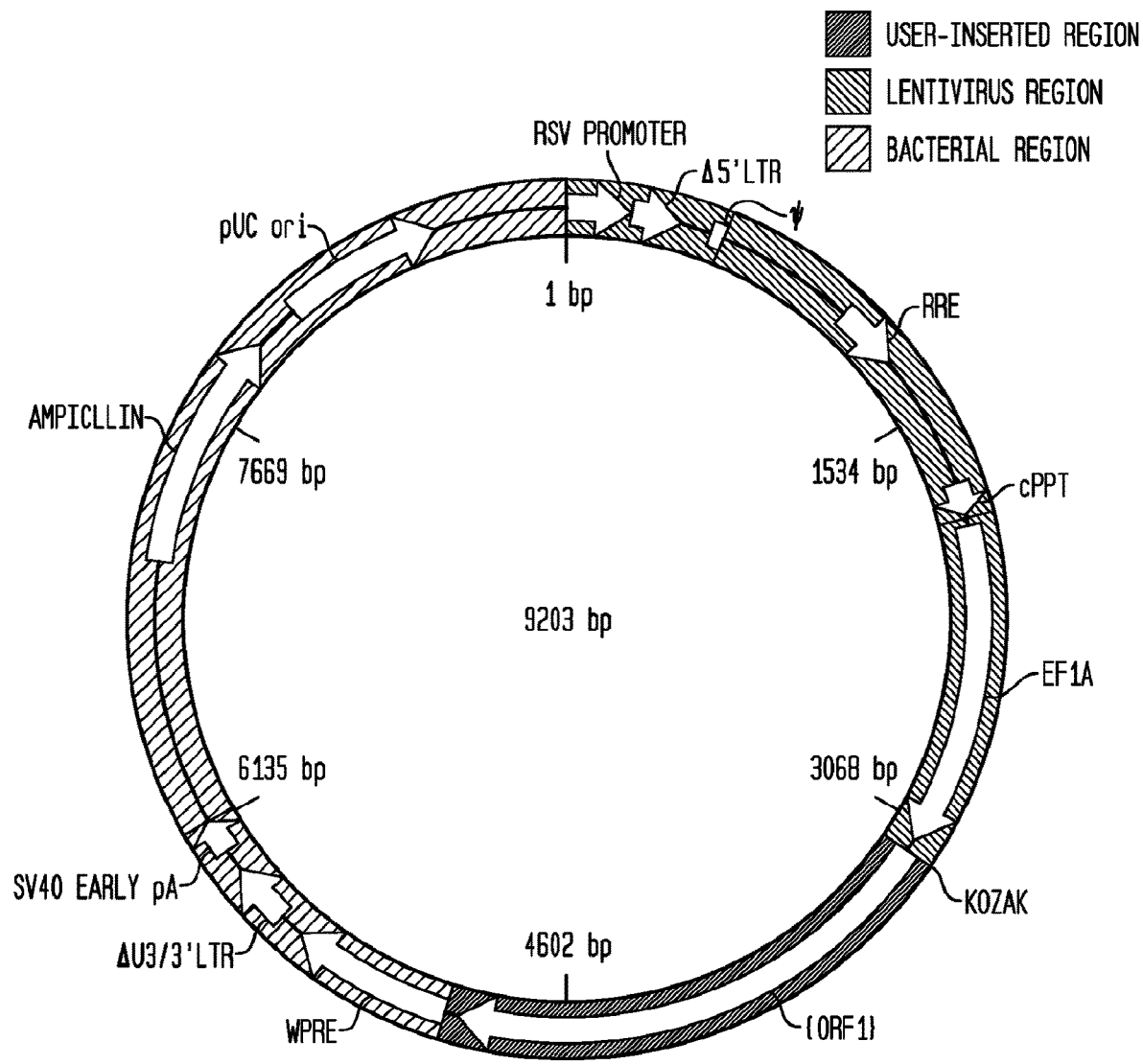
FIG. 3A shows a schematic of the organization of the scFv-anti-biotin-G3hinge-mIgG1 vector.

A schematic of the organization of vector 1, used for the immunomodulator scFv-anti-biotin-G3hinge-mIgG1 is shown in FIG. 3A. The nucleotide sequence of vector 1 (SEQ ID NO: 47) is shown in FIG. 3B. Table 2, below, shows the vector component name, the corresponding nucleotide position in SEQ ID NO: 47, the full name of the component and a description.

TABLE 2

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1959-3137 | EF1A | Component entered by user |
| Kozak | 3162-3167 | Kozak | Component entered by user |
| {ORF1} | 3168-5005 | {ORF1} | Component entered by user |
| WPRE | 5044-5641 | Woodchuck hepatitis virus posttranscriptional regulatory element | Facilitates effective transcription termination at the 3'TLTR.T |
| ΔU3/3' LTR | 5723-5957 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6030-6164 | SV40 early polyadenation signal | Allows transcription termination and polyadenylation of mRNA. |
| Ampicillin | 7118-7978 | Ampicillin resistance gene | Allows selection of the plasmid in *E. coli*. |
| pUC ori | 8149-8737 | pUC origin of replication | Permits high-copy replication and maintenance in *E. coli*. |

When vector 1 is employed, anti-IgG is used for flow detection. A biotin+fluorescent labelled oligodeoxynucleotides (ODN) is used as a secondary detection method.

The following is a description of the immunomodulator scFv-anti-biotin-G3hinge-IgG1-Tm.

Type:
 Immunoglobulin
Annotation:
 H7 heavy chain leader
 Anti-biotin Variable Heavy chain (VH) allows for loading biotin labeled CpG
 Inter-domain disulfide linkage VH44 (G->C) and VL100 (G->C)
 IgG3 hinge to enhance FcyR interaction
 Linkage is standard
 IgG1 (CH2-CH3-Tm-Cyt) used for interaction with FcyR/FcRn and membrane anchoring
 T233A mutation to enhance FcRn and FcyR interaction
 The sequences are shown as follows:

```
H7 heavy chain leader
                                  (SEQ ID NO. 54)
MEFGLSWVFLVALFRGVQC anti-biotin murine vH with inserted Cys for
inter-domain linkage
                                  (SEQ ID NO. 55)
QVKLQESGPG LVAPSQSLSI TCTVSGFSLT AYGVDWVRQP

PGKCLEWLGV IWGGGRTNYN SGLMSRLSIR KDNSKSQVFL

TMNSLQTDDT AKYYCVKHTN WDGGFAYWGQ GTTVTVSS linker
                                  (SEQ ID NO. 56)
GGGGSGGGGS GGGGS Light Chain Variable (human lambda variable)
                                  (SEQ ID NO. 57)
GSPGQSVSIS CSGSSSNIGN NYVYWYQHLP GTAPKLLIYS

DTKRPSGVPD RISGSKSGTS ASLAISGLQS EDEADYYCAS

WDDSLDGPVF GCGTKLTVL

IgG3 hinge for greater accessibility to FcyR
                                  (SEQ ID NO. 58)
LKTPLGDTTHTCPR CPEPKSCDTP PPCPRCPEPK SCDTPPPCPR

CPEPKSCDTP PPCPRCP

IgG1 CH2, CH3 Tm and cytoplasmic tail (T256A)
                                  (SEQ ID NO. 59)
LLGGPSVFLF PPKPKDTLMI SRAPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH

NHYTQKSLSL SPELQLEESC AEAQDGELDG LWTTITIFIT

LFLLSVCYSA TVTFFKVKWI FSSVVDLKQT IIPDYRNMIG

QGA*

The following shows the sequence of scFv-anti-
biotin-G3hinge-IgG1-Tm (598 ORF1)
                                  (SEQ ID NO. 60)
MEFGLSWVFLVALFRGVQCQVKLQESGPGLVAPSQSLSITCTVSGFSLT

AYGVDWVRQPPGKCLEWLGVIWGGGRTNYNSGLMSRLSIRKDNSKSQVF

LTMNSLQTDDTAKYYCVKHTNWDGGFAYWGQGTTVTVSSGGGGSGGGGS

GGGGSGSPGQSVSISCSGSSSNIGNNYVYWYQHLPGTAPKLLIYSDTKR

PSGVPDRISGSKSGTSASLAISGLQSEDEADYYCASWDDSLDGPVFGCG
```

-continued

```
TKLTVLLKTPLGDTTHTCPRCPEPKSCDTPPPCPRCPEPKSCDTPPPCP

RCPEPKSCDTPPPCPRCPAPELLGGPSVFLFPPKPKDTLMISRAPEVTC

VVVDVSHEDPEVKFNWYVDGVEVHNAKTKPREEQYNSTYRVVSVLTVLH

QDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYS

KLTVDKSRWQQGNVFSCSVMHEALHNHYTQKSLSLSPELQLEESCAEAQ

DGELDGLWTTITIFITLFLLSVCYSATVTFFKVKWIFSSVVDLKQTIIP

DYRNMIGQGA*
```

Vector 2. Immunomodulator: Full Anti-Biotin G3hinge-mIgG1 (Using Heavy Chain/Ires/Light Chain)

Figure 4A:
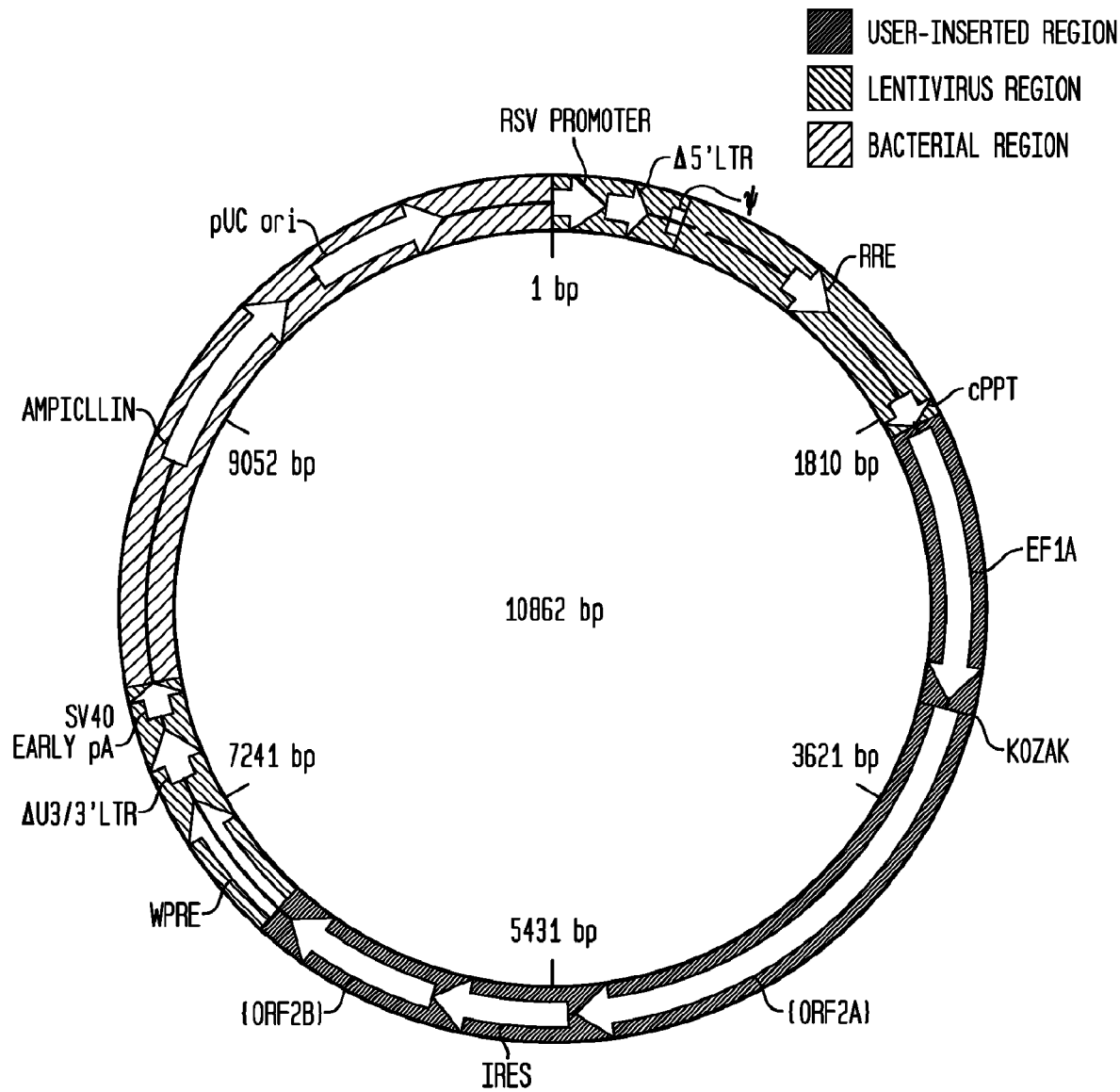
FIG. 4A shows a schematic of the organization of the full anti-biotin—G3hinge-mIgG1 vector.

A schematic of the organization of vector 2, used for the immunomodulator full anti-biotin—G3hinge-mIgG1 is shown in FIG. 4A. Vector 2 is bicistronic. The nucleotide sequence of vector 2 (SEQ ID NO. 48) is shown in FIG. 4B. Table 3, below, shows the vector component name, the corresponding nucleotide position in SEQ ID NO. 48, the full name of the component and a description.

TABLE 3

| Component Name | Nucleotide Position | Full Name | Description |
| --- | --- | --- | --- |
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-56g | HIV-1 psi packaging signal | Allows viral packaging. |
| RRET | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF1} | 3159-5342 | {ORF2A} | Component entered by user |
| WPRE | 6703-7300 | Woodchuck hepatitis virus posttranscriptional regulatory element | Facilitates effective transcription termination at the 3'TLTR.T |
| ΔU3/3' LTR | 7382-7616 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 7689-7823 | SV40 early polyadenation signal | Allows transcription termination and polyadenylation of mRNA. |
| Ampicillin | 8777-9637 | Ampicillin resistance gene | Allows selection of the plasmid in E. coli. |
| pUC ori | 9808-10396 | pUC origin of replication | Permits high-copy replication and maintenance in E. coli. |

When vector 2 is employed, anti-IgG is used for flow detection. Biotin+fluorescent labelled ODN is used as a secondary detection method.

The following is a description of the immunomodulator full anti-biotin—G3hinge-mIgG1 (using heavy chain/ires/light chain).

Type:
  Membrane anchored Immunoglobulin
Annotation:
  H7 heavy chain leader
  IgG3 hinge to enhance FcγR interaction
  T233A mutation to enhance FcRn and FcγR interaction
  Anti-biotin Variable H allows for loading biotin labeled CpG
  CH1 (generic)
  LC Variable (human lambda variable)
  LC Constant Region 1 from Lambda
  Interdomain disulfide linkage VH44 (G->C) and VL100 (G->C) (ref)
  Linkage is standard
  IgG1 (CH2-CH3-Tm-Cyt) for interaction with FcγR/FcRn and membrane anchoring L1 light chain leader (modified for improved IRES expression)
MATDMRVPAQLLGLLLLWLSGARC (SEQ ID NO. 61)

The sequences are shown as follows:

H7 heavy chain leader
(SEQ ID NO. 61)
MEFGLSWVFLVALFRGVQC anti-biotin vH (murine)
(SEQ ID NO. 62)
QVKLQESGPG LVAPSQSLSI TCTVSGFSLT AYGVDWVRQP
PGKGLEWLGV IWGGGRTNYN SGLMSRLSIR KDNSKSQVFL
TMNSLQTDDT AKYYCVKHTN WDGGFAYWGQ GTTVTVSS CH1 (generic)
(SEQ ID NO. 63)
PSVFP LAPSSKSTSG GTAALGCLVK DYFPEPVTVS WNSGALTSGV
HTFPAVLQSS GLYSLSSVVT VPSSSLGTQT YICNVNHKPS
NTKVDKKVE IgG3 hinge for greater accessibility to FcγR
(SEQ ID NO. 64)
LKTP LGDTTHTCPR CPEPKSCDTP PPCPRCPEPK SCDTPPPCPR
CPEPKSCDTP PPCPRCP IgG1 CH2, CH3 Tm and cytoplasmic tail (T256A)
(SEQ ID NO. 65)
APELLGGPSVFLF PPKPKDTLMI SRAPEVTCVV VDVSHEDPEV
KFNWYVDGVE VHNAKTKPRE EQYNSTYRVV SVLTVLHQDW
LNGKEYKCKV SNKALPAPIE KTISKAKGQP REPQVYTLPP
SRDELTKNQV SLTCLVKGFY PSDIAVEWES NGQPENNYKT
TPPVLDSDGS FFLYSKLTVD KSRWQQGNVF SCSVMHEALH
NHYTQKSLSL SPELQLEESC AEAQDGELDG LWTTITIFIT
LFLLSVCYSA TVTFFKVKWI FSSVVDLKQT IIPDYRNMIG
QGA*

Summary (578 ORF2a)
(SEQ ID NO. 66)
MEFGLSWVFLVALFRGVQCQVKLQESGPGLVAPSQSLSITCTVSGFSLTA
YGVDWVRQPPGKGLEWLGVIWGGGRTNYNSGLMSRLSIRKDNSKSQVFLT
MNSLQTDDTAKYYCVKHTNWDGGFAYWGQGTTVTVSSPSVFPLAPSSKST
SGGTAALGCLVKDYFPEPVTVSWNSGALTSGVHTFPAVLQSSGLYSLSSV
VTVPSSSLGTQTYICNVNHKPSNTKVDKKVELKTPLGDTTHTCPRCPEPK
SCDTPPPCPRCPEPKSCDTPPPCPRCPEPKSCDTPPPCPRCPAPELLGGP
SVFLFPPKPKDTLMISRAPEVTCVVVDVSHEDPEVKFNWYVDGVEVHNAK
TKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQ
KSLSLSPELQLEESCAEAQDGELDGLWTTITIFITLFLLSVCYSATVTFF
KVKWIFSSVVDLKQTIIPDYRNMIGQGA*

(SEQ ID NO. 67)
IRES

L1 Signal (modified to be IRES compatible)
(SEQ ID NO. 68)
MATDMR VPAQLLGLLLLWLSGARC LC Variable (human lambda variable)
(SEQ ID NO. 69)
GSPGQSVSIS CSGSSSNIGN NYVYWYQHLP GTAPKLLIYS
DTKRPSGVPD RISGSKSGTS ASLAISGLQS EDEADYYCAS
WDDSLDGPVF GGGTKLTVL LC Constant Region 1 from Lambda (irrelevant)
(SEQ ID NO. 70)
GQPKANPTVT LFPPSSEELQ ANKATLVCLI SDFYPGAVTV
AWKADGSPVK AGVETTKPSK QSNNKYAASS YLSLTPEQWK
SHRSYSCQVT HEGSTVEKTV APTECS*

Summary (229 ORF2b)
(SEQ ID NO. 71)
MATDMRVPAQLLGLLLLWLSGARCGSPGQSVSISCSGSSSNIGNNYVYWY
QHLPGTAPKLLIYSDTKRPSGVPDRISGSKSGTSASLAISGLQSEDEADY
YCASWDDSLDGPVFGGGTKLTVLGQPKANPTVTLFPPSSEELQANKATLV
CLISDFYPGAVTVAWKADGSPVKAGVETTKPSKQSNNKYAASSYLSLTPE
QWKSHRSYSCQVTHEGSTVEKTVAPTECS*

Vector 3. Immunomodulator:
sGM-CSF/ires/mFLT3L

Figure 5A:
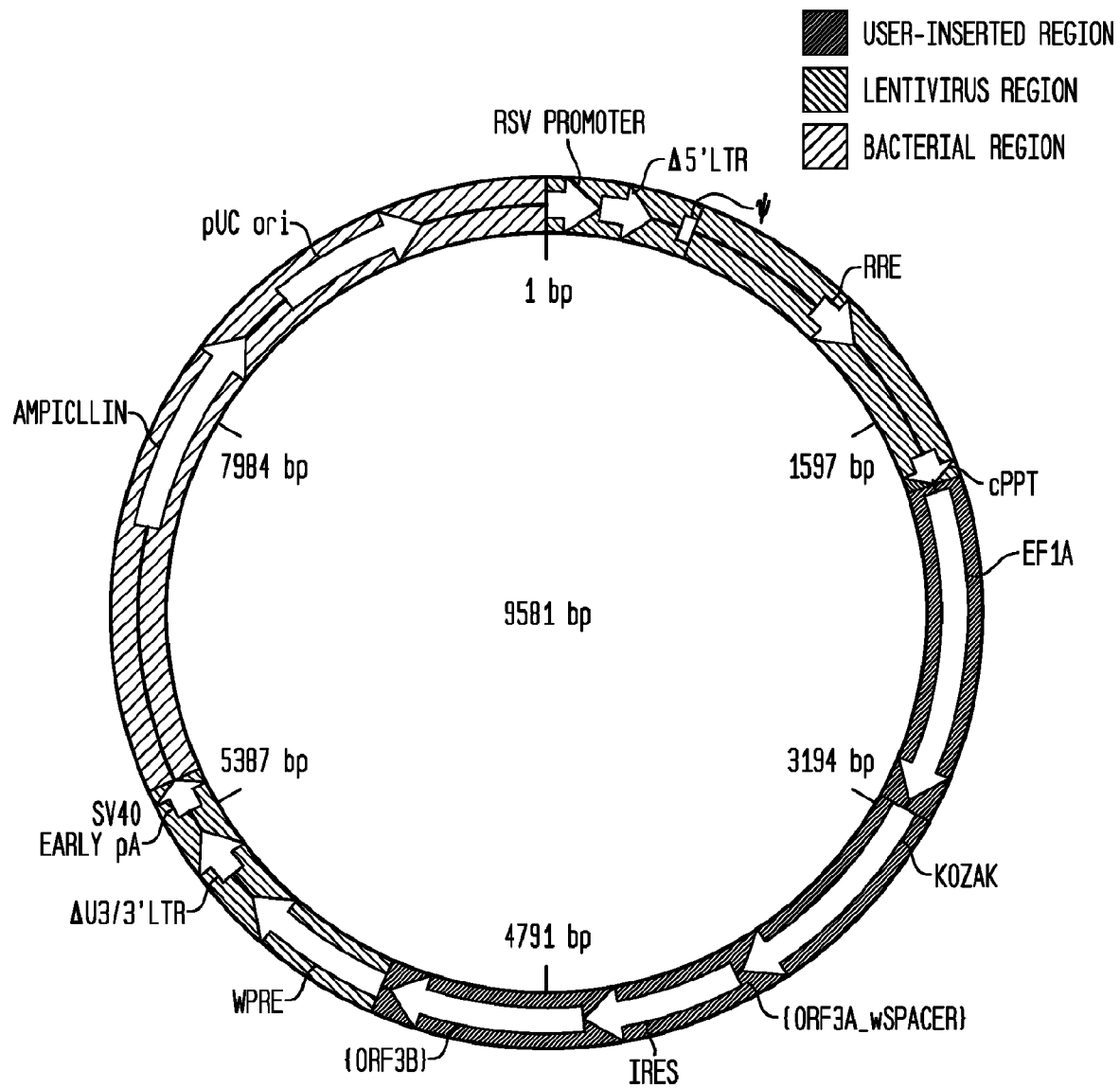
FIG. 5A shows a schematic of the organization of the sGM-CSF/ires/mFLT3L vector.

A schematic of the organization of vector 3, used for the immunomodulator sGM-CSF/ires/mFLT3L is shown in FIG. 5A. Vector 3 is bicistronic. The nucleotide sequence of vector 3 (SEQ ID NO. 49) is shown in FIG. 5B. Table 4, below, shows the vector component name, the corresponding nucleotide position in SEQ ID NO. 49, the full name of the component and a description.

TABLE 4

| Component Name | Nucleotide Position | Full Name | Description |
| --- | --- | --- | --- |
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |

TABLE 4-continued

| Component Name | Nucleotide Position | Full Name | Description |
|---|---|---|---|
| EF1A | 1950-3128 | EF1A | Component entered by user |
| Kozak | 3153-3158 | Kozak | Component entered by user |
| {ORF3A_wSPACER} | 3159-4040 | {ORF3A_wSPACER} | Component entered by user |
| IRES | 4065-4652 | IRES | Component entered by user |
| {ORF3B} | 4653-5392 | {ORF3B} | Component entered by user |
| WPRE | 5422-6019 | Woodchuck hepatitis virus posttranscriptional regulatory element | Facilitates effective transcription termination at the 3' LTR. |
| ΔU3/3' LTR | 6101-6335 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6408-6542 | SV40 early polyadenation signal | Allows transcription termination and polyadenylation of mRNA. |
| Ampicillin | 7496-8356 | Ampicillin resistance gene | Allows selection of the plasmid in *E. coli*. |
| pUC ori | 8527-9115 | pUC origin of replication | Permits high-copy replication and maintenance in *E. coli*. |

When vector 3 is employed, anti-FLT3L is used for flow detection. The highest surface FLT3L expressor will have the highest secreted GM-CSF expression.

The following is a description of the immunomodulator sGM-CSF/ires/mFLT3L.

Type:
  cytokine, growth and differentiation factor

Annotation:
  wild-type sequence

The sequences are shown as follows:

GM-CSF signal sequence
(SEQ ID NO. 72)
MWLQSLLLLG TVACSIS wild type GM-CSF sequence
(SEQ ID NO. 73)
APA RSPSPSTQPW EHVNAIQEAR RLLNLSRDTA AEMNETVEVI

SEMFDLQEPT CLQTRLELYK QGLRGSLTKL KGPLTMMASH

YKQHCPPTPE TSCATQIITF ESFKENLKDF LL VIPFDCWE

PVQE*

(SEQ ID NO. 74)
IRES

FLT3L signal (modified to be IRES friendly)
(SEQ ID NO. 75)
MATVLAPAWSP TTYLLLLLLL SSGLS

FLT3L
(SEQ ID NO. 76)
GTQDC SFQHSPISSD FAVKIRELSD YLLQDYPVTV ASNLQDEELC

GGLWRLVLAQ RWMERLKTVA GSKMQGLLER VNTEIHFVTK

CAFQPPPSCL RFVQTNISRL LQETSEQLVA LKPWITRQNF

SRCLELQCQP DSSTLPPPWS PRPLEATAPT APQPPLLLLL

LLPVGLLLLA AAWCLHWQRT RRRTPRPGEQ VPPVPSPQDL

LLVEH*

-continued

Summary (144 ORF3a)
(SEQ ID NO. 77)
MWLQSLLLLGTVACSISAPARSPSPSTQPWEHVNAIQEARRLLNLSRDT

AAEMNETVEVISEMFDLQEPTCLQTRLELYKQGLRGSLTKLKGPLTMMA

SHYKQHCPPTPETSCATQIITFESFKENLKDFLLVIPFDCWEPVQE*

Summary (236 ORF3b)
(SEQ ID NO. 78)
MATVLAPAWSPTTYLLLLLLLSSGLSGTQDCSFQHSPISSDFAVKIREL

SDYLLQDYPVTVASNLQDEELCGGLWRLVLAQRWMERLKTVAGSKMQGL

LERVNTEIHFVTKCAFQPPPSCLRFVQTNISRLLQETSEQLVALKPWIT

RQNFSRCLELQCQPDSSTLPPPWSPRPLEATAPTAPQPPLLLLLLLPVG

LLLLAAAWCLHWQRTRRRTPRPGEQVPPVPSPQDLLLVEH*

Vector 4. Immunomodulator: sFLT3L/ires/(FLT3 signal-GM-CSF-Tm)

Figure 6A:
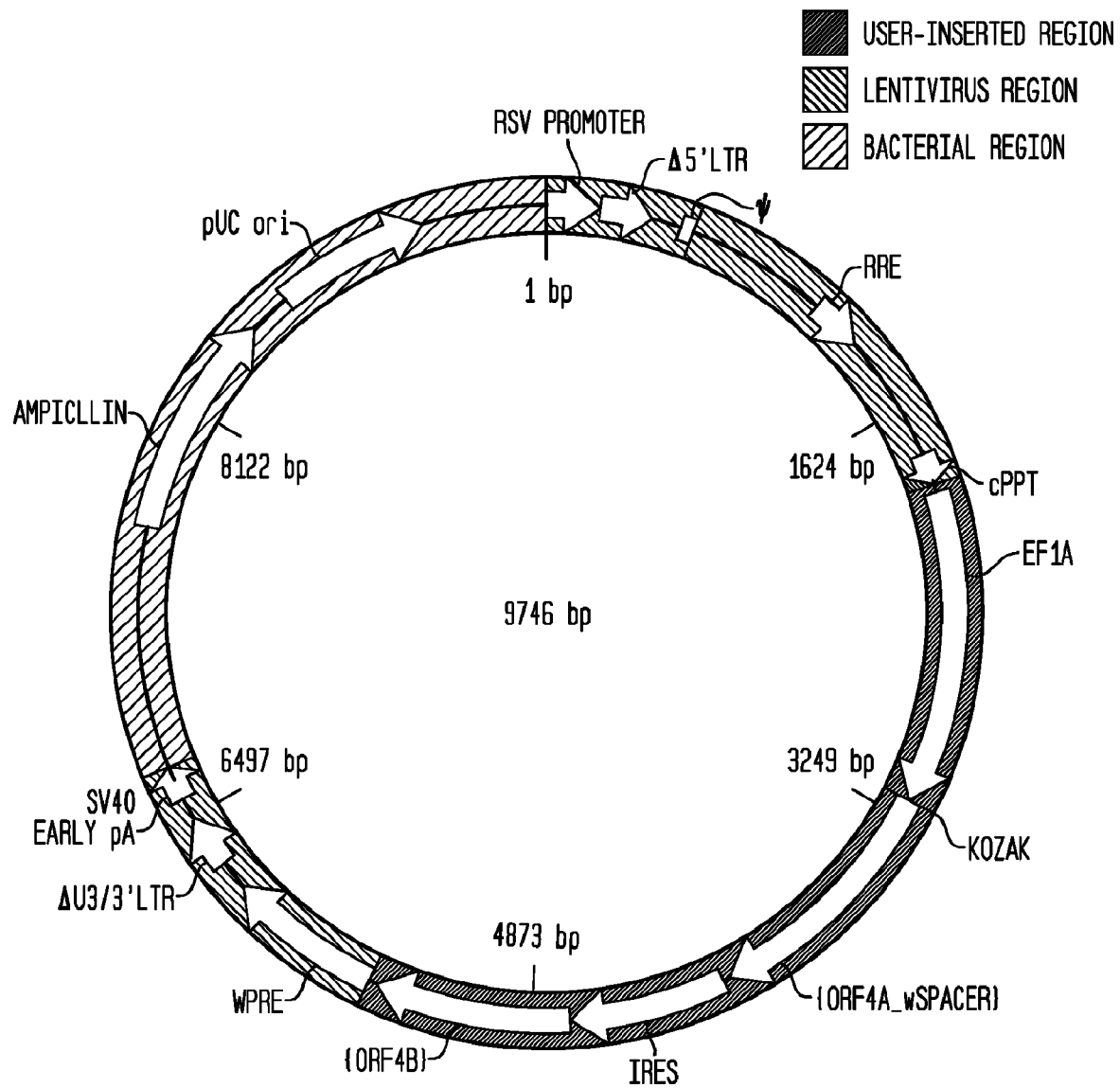
FIG. 6A shows a schematic of the organization of the sFLT3L/ires/(FLT3 signal-GM-CSF-Tm) vector.

A schematic of the organization of vector 4, used for the immunomodulator sFLT3L/ires/(FLT3 signal-GM-CSF-Tm) is shown in FIG. 6A. Vector 4 is bicistronic. The nucleotide sequence of vector 4 (SEQ ID NO. 50) is shown in FIG. 6B. Table 5, below, shows the vector component name, the corresponding nucleotide position in SEQ ID NO. 50, the full name of the component and a description.

TABLE 5

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF4A_wSPACER} | 3159-4157 | {ORF4A_wSPACER} | Component entered by user |
| IRES | 4182-4769 | IRES | Component entered by user |
| {ORF4B} | 4770-5557 | {ORF4B} | Component entered by user |
| WPRE | 5587-6184 | Woodchuck hepatitis virus posttranscriptional regulatory element | Facilitates effective transcription termination at the 3' LTR. |
| ΔU3/3' LTR | 6266-6500 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6573-6707 | SV40 early polyadenation signal | Allows transcription termination and polyadenylation of mRNA. |
| Ampicillin | 7661-8521 | Ampicillin resistance gene | Allows selection of the plasmid in E. coli. |
| pUC ori | 8692-9280 | pUC origin of replication | Permits high-copy replication and maintenance in E. coli. |

When vector 4 is employed, anti-GM-CSF is used for flow detection. The highest surface GMCSF expressor will have highest secreted FLT3L expression.

The following is a description of the immunomodulator sFLT3L/ires/(FLT3 signal-GM-CSF-Tm)
Type:
  cytokine, growth and differentiation factor
Annotation:
  wild-type sequence
  The sequences are shown as follows:

```
wild type FLT3L sequence with transmembrane
deleted
                                    (SEQ ID NO. 79)
MTVLAPAWSP TTYLLLLLLL SSGLSGTQDC SFQHSPISSD

FAVKIRELSD YLLQDYPVTV ASNLQDEELC GGLWRLVLAQ

RWMERLKTVA GSKMQGLLER VNTEIHFVTK CAFQPPPSCL

RFVQTNISRL LQETSEQLVA LKPWITRQNF SRCLELQCQP

DSSTLPPPWS PRPLEATAPT APQ*
                                    (SEQ ID NO. 80)
IRES

FLT3L signal (modified to be IRES friendly)
                                    (SEQ ID NO. 81)
MATVLAPAWSP TTYLLLLLLL SSGLS wild type GM-CSF sequence (minus native signal)
                                    (SEQ ID NO. 82)
APA RSPSPSTQPW EHVNAIQEAR RLLNLSRDTA AEMNETVEVI

SEMFDLQEPT CLQTRLELYK QGLRGSLTKL KGPLTMMASH

YKQHCPPTPE TSCATQIITF ESFKENLKDF LLVIPFDCWE

PVQE

CD8alpha transmembrane and cytoplasmic domain
                                    (SEQ ID NO. 83)
PTTTP APRPPTPAPTIASQPLSLRP EACRPAAGGA VHTRGLDFAC

DIYIWAPLAG TCGVLLLSLVITLYCNHRNR RRVCKCPRPV

VKSGDKPSLS ARYV*

Summary (183 ORF4a)
                                    (SEQ ID NO. 84)
MTVLAPAWSPTTYLLLLLLLSSGLSGTQDCSFQHSPISSDFAVKIRELS

DYLLQDYPVTVASNLQDEELCGGLWRLVLAQRWMERLKTVAGSKMQGLL

ERVNTEIHFVTKCAFQPPPSCLRFVQTNISRLLQETSEQLVALKPWITR

QNFSRCLELQCQPDSSTLPPPWSPRPLEATAPTAPQ*

Summary for CYAGEN (253 ORF4b)
                                    (SEQ ID NO. 85)
MATVLAPAWSPTTYLLLLLLLSSGLSAPARSPSPSTQPWEHVNAIQEAR

RLLNLSRDTAAEMNETVEVISEMFDLQEPTCLQTRLELYKQGLRGSLTK

LKGPLTMMASHYKQHCPPTPETSCATQIITFESFKENLKDFLLVIPFDC

WEPVQEPTTTPAPRPPTPAPTIASQPLSLRPEACRPAAGGAVHTRGLDF

ACDIYIWAPLAGTCGVLLLSLVITLYCNHRNRRRVCKCPRPVVKSGDKP

SLSARYV*
```

Vector 5. Immunomodulator: mCD40L

Figure 7A:
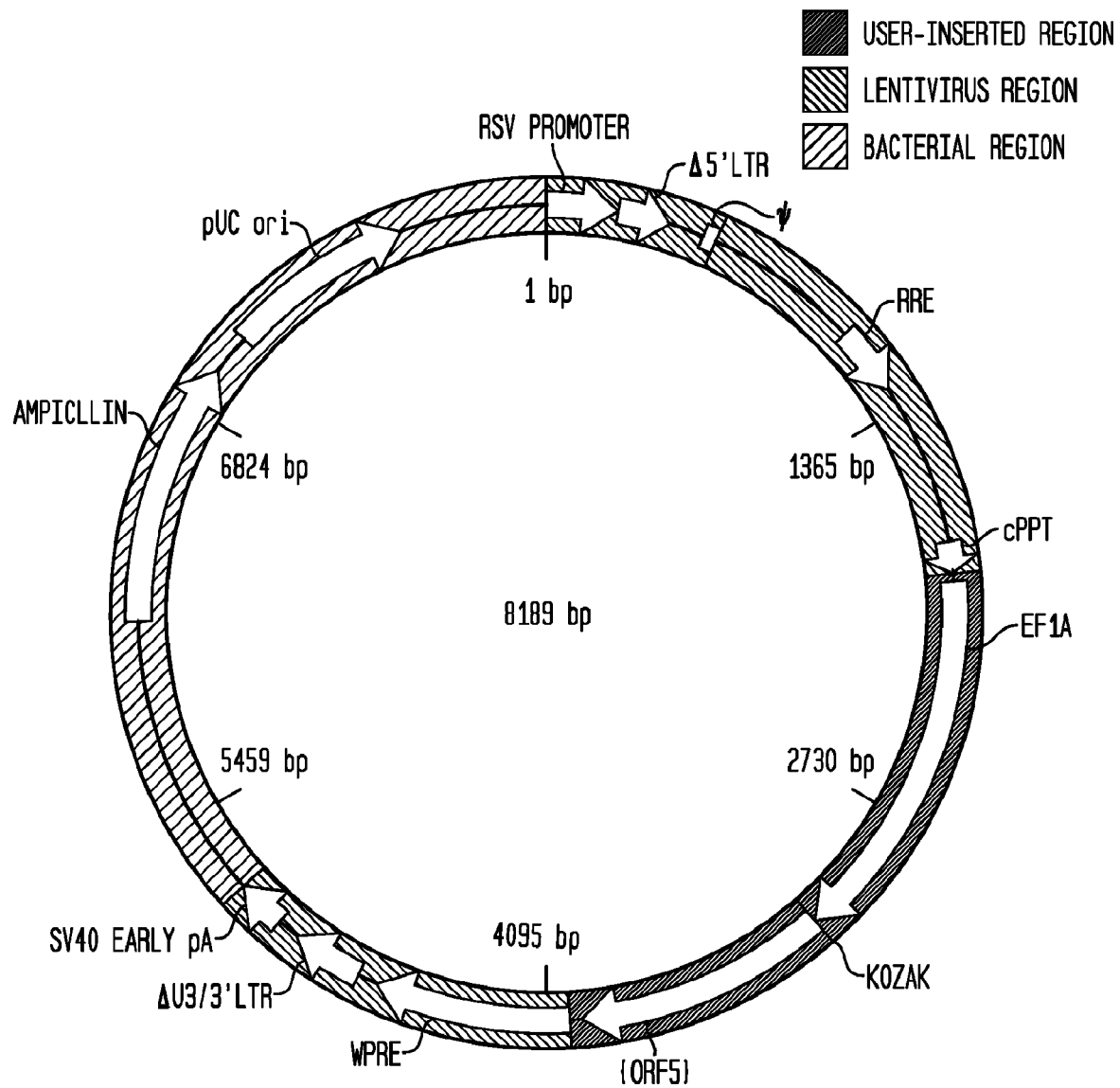
FIG. 7A shows a schematic of the organization of the mCD40L vector.
Figure 8A:
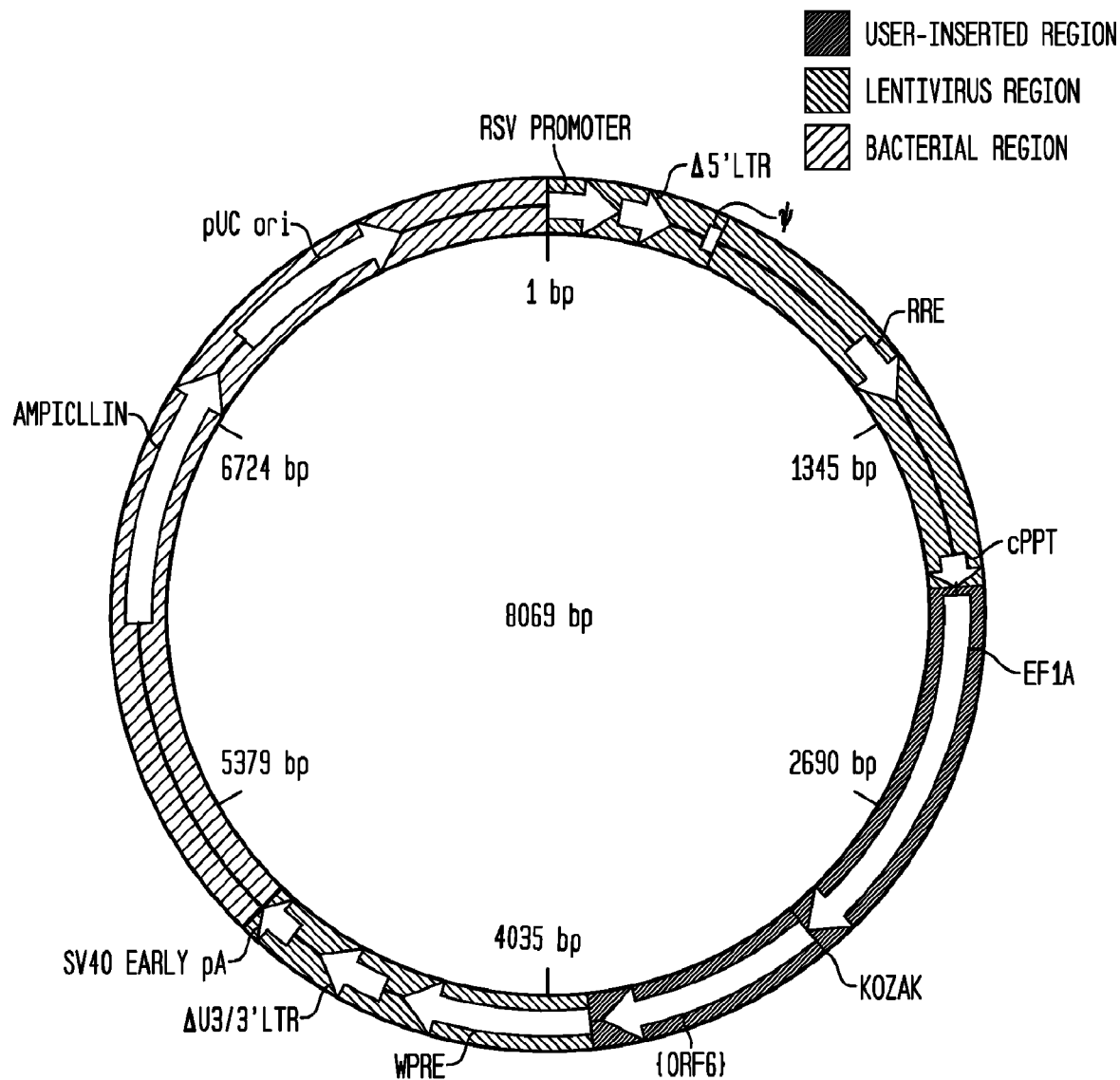
FIG. 8A shows a schematic of the organization of the mTNFa vector.

A schematic of the organization of vector 5, used for the immunomodulator mCD40L is shown in FIG. 7A. Vector 5 is monocistronic. The nucleotide sequence of vector 5 (SEQ ID NO. 51) is shown in FIG. 7B. Table 6, below, shows the vector component name, the corresponding nucleotide position in SEQ ID NO. 51, the full name of the component and a description.

TABLE 6

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1959-3137 | EF1A | Component entered by user |
| Kozak | 3162-3167 | Kozak | Component entered by user |
| {ORF5} | 3168-3991 | {ORF5} | Component entered by user |
| WPRE | 4030-4627 | Woodchuck hepatitis virus posttranscriptional regulatory element | Facilitates effective transcription termination at the 3' LTR. |
| ΔU3/3' LTR | 4709-4943 | HIV-1 truncated 3' LTR | Allows viral packaging but self-inactivates the 5'LTR for biosafety purposes. The TABLE 7-continued

| Component Name | Nucleotide Position | Full Name | Description |
|---|---|---|---|
| EF1A | 1959-3137 | EF1A | Component entered by user |
| Kozak | 3162-3167 | Kozak | Component entered by user |
| {ORF6} | 3168-3871 | {ORF6} | Component entered by user |
| WPRE | 3910-4507 | Woodchuck hepatitis virus posttranscriptional regulatory element | Facilitates effective transcription termination at the 3' LTR. |
| ΔU3/3' LTR | 4859-4823 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 4896-5030 | SV40 early polyadenation signal | Allows transcription termination and polyadenylation of mRNA. |
| Ampicillin | 5984-6844 | Ampicillin resistance gene | Allows selection of the plasmid in *E. coli*. |
| pUC ori | 7015-7603 | pUC origin of replication | Permits high-copy replication and maintenance in *E. coli*. |

When vector 6 is employed, anti-TNFα is used for flow detection.

The following is a description of the immunomodulator mTNFα.

Type:
TNF type II transmembrane protein

Annotation:
Mutations introduced to make a non-cleavable version, as described below in SEQ ID NO. 88

The sequences are shown as follows:

```
Modified to stop cleavage
                                              (SEQ ID NO. 88)
MSTESMIRDV ELAEEALPKK TGGPQGSRRC LFLSLESFLI

VAGATTLFCL LHFGVIGPQR EEFPRDLSLI SPLAQA....

........VA HVVANPQAEG QLQWLNRRAN ALLANGVELR

DNQLVVPSEG LYLIYSQVLF KGQGCPSTHV LLTHTISRIA

VSYQTKVNLL SAIKSPCQRE TPEGAEAKPW YEPIYLGGVF

QLEKGDRLSA EINRPDYLDF AESGQVYFGI IAL*
```

```
Summary (221 ORF6)
                                              (SEQ ID NO. 89)
MSTESMIRDVELAEEALPKKTGGPQGSRRCLFLSLFSFLIVAGATTLFC

LLHFGVIGPQREEFPRDLSLISPLAQAVAHVVANPQAEGQLQWLNRRAN

ALLANGVELRDNQLVVPSEGLYLIYSQVLFKGQGCPSTHVLLTHTISRI

AVSYQTKVNLLSAIKSPCQRETPEGAEAKPWYEPIYLGGVFQLEKGDRL

SAEINRPDYLDFAESGQVYFGIIAL*
```

Vector 7. Immunomodulator: mRANKL/ires/FLT3 signal-V5-scFV anti-biotin-Tm

Figure 9A:
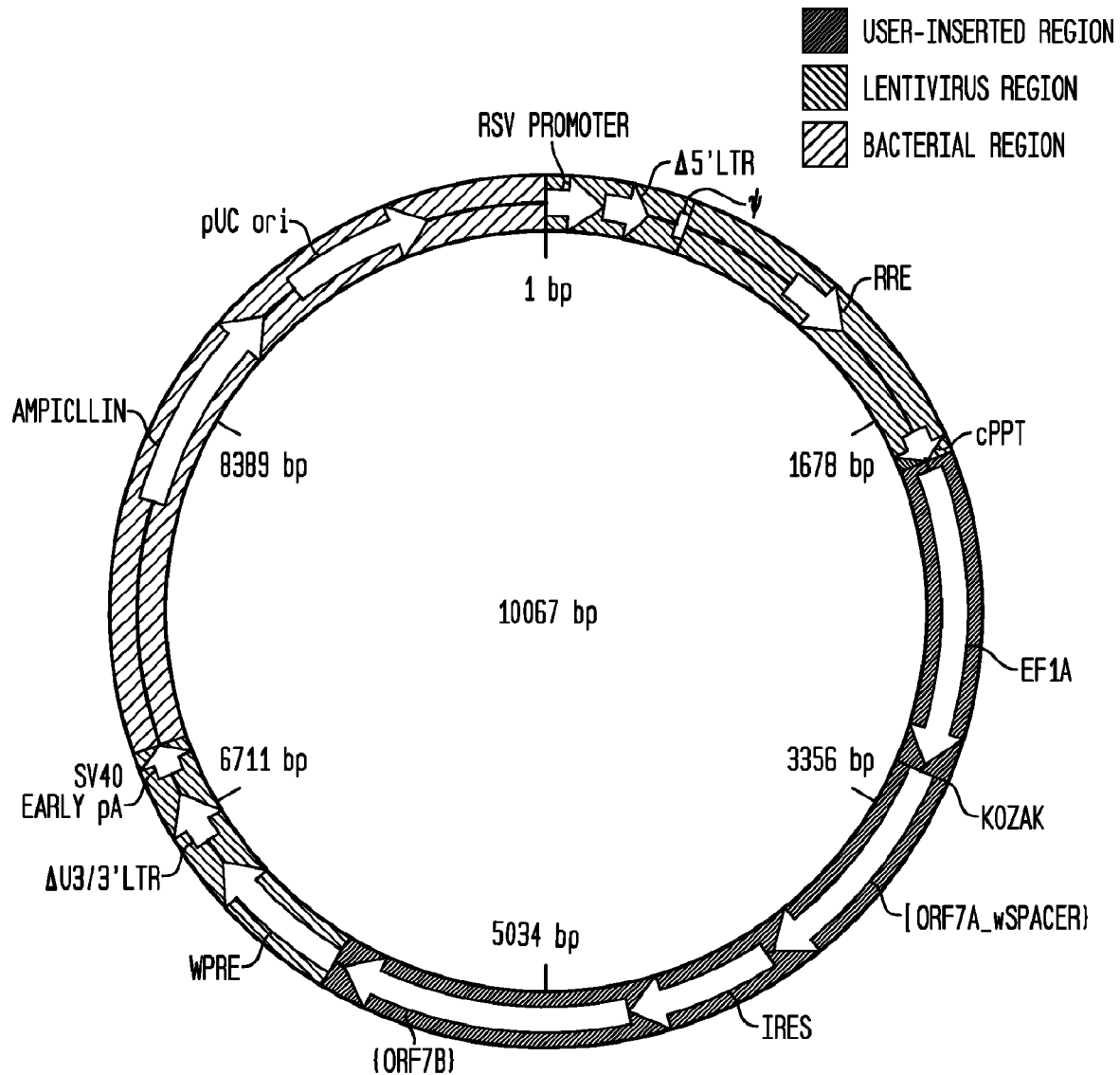
FIG. 9A shows a schematic of the organization of the mRANKL/ires/FLT3 signal-V5-scFV anti-biotin-Tm vector.

A schematic of the organization of vector 7, used for the immunomodulator mRANKL/ires/FLT3 signal-V5-scFV anti-biotin-Tm is shown in FIG. 9A. The nucleotide sequence of vector 7 (SEQ ID NO. 53) is shown in FIG. 9B. Table 8, below, shows the vector component name, the corresponding nucleotide position in SEQ ID NO. 53, the full name of the component and a description.

TABLE 8

| Component Name | Nucleotide Position | Full Name | Description |
|---|---|---|---|
| RSV promoter | 1-229 | Rous sarcoma virus (RSV) enhancer/promoter | Allows Tat-independent production of viral mRNA. |
| Δ5' LTR | 230-410 | HIV-1 truncated 5' LTRT | Permits viral packaging and reverse transcription of the viral mRNA. |
| Ψ | 521-565 | HIV-1 psi packaging signal | Allows viral packaging. |
| RRE | 1075-1308 | HIV-1 Rev response element | Permits Rev-dependent nuclear export of unspliced viral mRNA. |
| cPPT | 1803-1920 | Central polypurine tract | Facilitates the nuclear import of HIV-1 cDNA through a central DNA flap. |
| EF1A | 1950-3128 | EF1A | Component entered by user |
| Kozak | 3153-3158 | Kozak | Component entered by user |
| {ORF7_wSPACER} | 3159-4091 | {ORF7_wSPACER} | Component entered by user |
| IRES | 4116-4703 | IRES | Component entered by user |
| {ORF7B} | 4704-5878 | {ORF7B} | Component entered by user |
| WPRE | 5908-6505 | Woodchuck hepatitis virus posttranscriptional regulatory element | Facilitates effective transcription termination at the 3' LTR. |

TABLE 8-continued

| Component Name | Nucleotide Position | Full Name | Description |
|---|---|---|---|
| ΔU3/3' LTR | 6587-3821 | HIV-1 truncated 3' LTR | Allows viral packaging but self-inactivates the 5'LTR for biosafety purposes. The element also contains apolyadenylation signal for transcription termination and polyadenylation of mRNA in transduced cells. |
| SV40 early pA | 6894-7028 | SV40 early polyadenation signal | Allows transcription termination and polyadenylation of mRNA. |
| Ampicillin | 7982-8842 | Ampicillin resistance gene | Allows selection of the plasmid in *E. coli*. |
| pUC ori | 9013-9601 | pUC origin of replication | Permits high-copy replication and maintenance in *E. coli*. |

When vector 7 is employed, anti-RANKL is used for flow detection. Anti-V5 mAb is used as a secondary detection method.

The following is a description of the immunomodulator mRANKL/ires/FLT3 signal-V5-scFV anti-biotin-Tm.

Type:

TNF type II transmembrane protein

Annotation:

wild-type sequence

The sequences are shown as follows:

```
wild-type
                                       (SEQ ID NO. 90)
MDPNRISEDG THCIYRILRL HENADFQDTT LESQDTKLIP

DSCRRIKQAF QGAVQKELQH IVGSQHIRAE KAMVDGSWLD

LAKRSKLEAQ PFAHLTINAT DIPSGSHKVS LSSWYHDRGW

AKISNMTFSN GKLIVNQDGF YYLYANICFR HHETSGDLAT

EYLQLMVYVT KTSIKIPSSH TLMKGGSTKY WSGNSEFHFY

SINVGGFFKL RSGEEISIEV SNPSLLDPDQ DATYFGAFKV

RDID*"

(SEQ ID NO. 91)
IRES

FLT3L signal (modified to be IRES friendly)
                                       (SEQ ID NO. 92)
MATVLAPAWSP TTYLLLLLLL SSGLS Linker
                                       (SEQ ID NO. 93)
GGGGS V5 epitope tag for flow detection
                                       (SEQ ID NO. 94)
GKPIPNPLLGLDST Linker
                                       (SEQ ID NO. 93)
GGGGS anti-biotin murine vH with inserted Cys for
intralinkage
                                       (SEQ ID NO. 95)
QVKLQESGPG LVAPSQSLSI TCTVSGFSLT AYGVDWVRQP

PGKCLEWLGV IWGGGRTNYN SGLMSRLSIR KDNSKSQVFL

TMNSLQTDDT AKYYCVKHTN WDGGFAYWGQ GTTVTVSS
```

```
                         -continued
linker
                                       (SEQ ID NO. 96)
GGGGSGGGGS GGGGS LC Variable (human lambda variable)
                                       (SEQ ID NO. 97)
GSPGQSVSIS CSGSSSNIGN NYVYWYQHLP GTAPKLLIYS

DTKRPSGVPD RISGSKSGTS ASLAISGLQS EDEADYYCAS

WDDSLDGPVF GCGTKLTVL

CD8alpha transmembrane and cytoplasmic domain
                                       (SEQ ID NO. 98)
PTTTP APRPPTPAPTIASQPLSLRP EACRPAAGGA VHTRGLDFAC

DIYIWAPLAG TCGVLLLSLVITLYCNHRNR RRVCKCPRPV

VKSGDKPSLS ARYV*

Summary (244 ORF7a)
                                       (SEQ ID NO. 99)
MDPNRISEDGTHCIYRILRLHENADFQDTTLESQDTKLIPDSCRRIKQA

FQGAVQKELQHIVGSQHIRAEKAMVDGSWLDLAKRSKLEAQPFAHLTIN

ATDIPSGSHKVSLSSWYHDRGWAKISNMTFSNGKLIVNQDGFYYLYANI

CFRHHETSGDLATEYLQLMVYVTKTSIKIPSSHTLMKGGSTKYWSGNSE

FHFYSINVGGFFKLRSGEEISIEVSNPSLLDPDQDATYFGAFKVRDID*"

Summary (381aa ORF7b)
                                       (SEQ ID NO. 100)
MATVLAPAWSPTTYLLLLLLLSSGLSGGGGSGKPIPNPLLGLDSTGGGG

SQVKLQESGPGLVAPSQSLSITCTVSGFSLTAYGVDWVRQPPGKCLEWL

GVIWGGGRTNYNSGLMSRLSIRKDNSKSQVFLTMNSLQTDDTAKYYCVK

HTNWDGGFAYWGQGTTVTVSSGGGGSGGGGSGGGGSGSPGQSVSISCSG

SSSNIGNNYVYWYQHLPGTAPKLLIYSDTKRPSGVPDRISGSKSGTSAS

LAISGLQSEDEADYYCASWDDSLDGPVFGCGTKLTVLPTTTPAPRPPTP

APTIASQPLSLRPEACRPAAGGAVHTRGLDFACDIYIWAPLAGTCGVLL

LSLVITLYCNHRNRRRVCKCPRPVVKSGDKPSLSARYV*
```

According to one embodiment, a tumor cell line is selected for modification, and vector 2 is used to stably integrate immune modulators into the cell genome.

According to one embodiment, a tumor cell line is selected for modification, and vector 3 is used to stably integrate immune modulators into the cell genome.

According to one embodiment, a tumor cell line is selected for modification, and vector 4 is used to stably integrate immune modulators into the cell genome.

According to one embodiment, a tumor cell line is selected for modification, and vector 5 is used to stably integrate immune modulators into the cell genome.

According to one embodiment, a tumor cell line is selected for modification, and vector 6 is used to stably integrate immune modulators into the cell genome.

According to one embodiment, a tumor cell line is selected for modification, and vector 2 and vector 3 are used to stably integrate immune modulators into the cell genome.

According to one embodiment, a tumor cell line is selected for modification, and vector 2 and vector 4 are used to stably integrate immune modulators into the cell genome.

According to one embodiment, a tumor cell line is selected for modification, and vector 2 and vector 5 are used to stably integrate immune modulators into the cell genome.

According to one embodiment, a tumor cell line is selected for modification, and vector 2 and vector 6 are used to stably integrate immune modulators into the cell genome.

According to one embodiment, a tumor cell line is selected for modification, and vector 3 and vector 4 are used to stably integrate immune modulators into the cell genome.

According to one embodiment, a tumor cell line is selected for modification, and vector 3 and vector 5 are used to stably integrate immune modulators into the cell genome.

According to one embodiment, a tumor cell line is selected for modification, and vector 3 and vector 6 are used to stably integrate immune modulators into the cell genome.

According to one embodiment, a tumor cell line is selected for modification, and vector 2, vector 3 and vector 4 are used to stably integrate immune modulators into the cell genome.

According to one embodiment, a tumor cell line is selected for modification, and vector 2, vector 3 and vector 5 are used to stably integrate immune modulators into the cell genome.

According to one embodiment, a tumor cell line is selected for modification, and vector 2, vector 3 and vector 6 are used to stably integrate immune modulators into the cell genome.

According to one embodiment, a tumor cell line is selected for modification, and vector 2, vector 3 and vector 6 are used to stably integrate immune modulators into the cell genome.

According to one embodiment, a tumor cell line is selected for modification, and vector 3, vector 4 and vector 5 are used to stably integrate immune modulators into the cell genome.

According to one embodiment, a tumor cell line is selected for modification, and vector 3, vector 4 and vector 6 are used to stably integrate immune modulators into the cell genome.

According to one embodiment, a tumor cell line is selected for modification, and vector 2, vector 3, vector 4 and vector 5 are used to stably integrate immune modulators into the cell genome.

According to one embodiment, a tumor cell line is selected for modification, and vector 2, vector 3, vector 4 and vector 6 are used to stably integrate immune modulators into the cell genome.

According to one embodiment, a tumor cell line is selected for modification, and vector 2, vector 3, vector 5 and vector 6 are used to stably integrate immune modulators into the cell genome.

According to one embodiment, a tumor cell line is selected for modification, and vector 3, vector 4, vector 5 and vector 6 are used to stably integrate immune modulators into the cell genome.

According to one embodiment, a tumor cell line is selected for modification, and vector 2, vector 3, vector 4, vector 5 and vector 6 are used to stably integrate immune modulators into the cell genome.

Example 4

Figure 10:
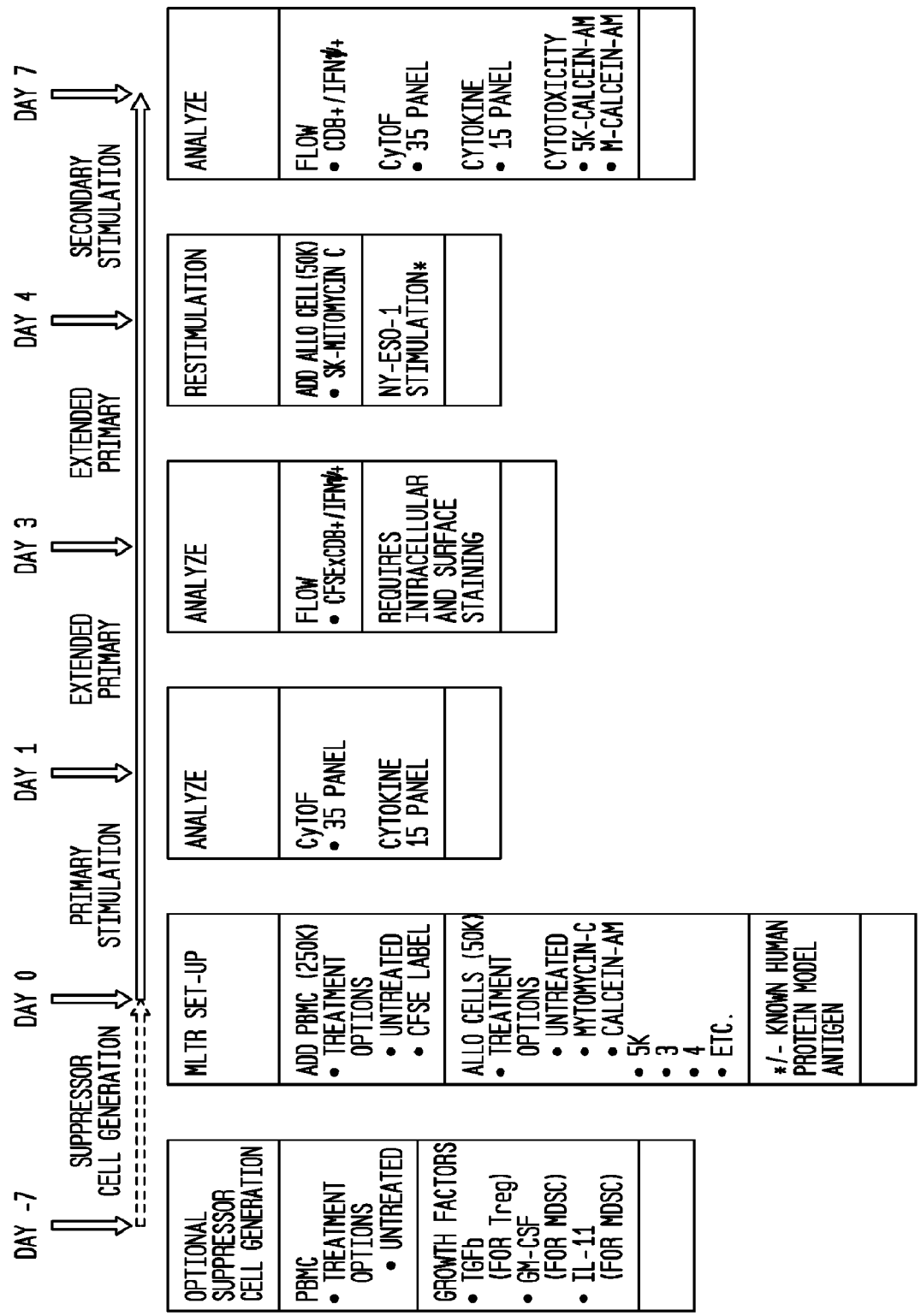
FIG. 10 is a schematic that shows the general experimental format.

Experiments were carried out to demonstrate that the immunomodulators described herein, expressed on the tumor cell line SK-MEL2 differentially impact the proliferation and differentiation of human PBMC. FIG. 10 is a schematic that shows the general experimental design. The following allogeneic cell lines are tested:
  SK-MEL (Parental line) ("SK")
  SK modified with Vector 2 only ("2")
  SK modified with Vector 3 only ("3")
  SK modified with Vector 4 only ("4")
  SK modified with Vector 6 only (6")
  SK modified with Vector 3 and Vector 4 ("3-4")
  SK modified with Vector 3, Vector 4 and Vector 5 ("3-4-5")
  SK modified with Vector 3, Vector 5 and Vector 6 ("3-5-6")

Functional characterization of the allogeneic cell lines was performed using a primary MLTR assay, as described herein. The MLTR assay was set up with 250,000 freshly thawed PBMC and 50,000 of select engineered allogeneic cell lines. The following outputs were measured: 1) Proliferation is measured by flow on CFSE labeled PMBC; 2) Differentiation is measured by CyTOF on unlabeled PMBC; 3) Cytokine profiling is performed by LUMINEX®.

Flow Cytometry Data

The experiments described herein detect hPBMC activation from direct allorecognition of allogeneic cells versus a pan-T-cell activation using anti-CD3 and anti-CD28 mAbs. It was found that hPBMC activation via direct allorecognition of allogeneic cells displays a fundamentally different response compared to pan-T-cell activation with anti-CD3/CD28 treatment. Three key observations were made with regard to this differential hPBMC activation: 1) that ~10% of hPBMC proliferate in response to incubation with allogeneic cells compared to ~50% with anti-CD3/CD28 treatment; 2) that hPBMC proliferate through more cell divisions in response to activation with allogeneic cells compared to activation with anti-CD3/CD28 treatment; 3) that hPBMC take on a more highly varied morphology as measured by side scatter as compared to the the more uniform cell morphology when hPBMC are stimulated with anti-CD3/CD28 treatment.

Figure 11:
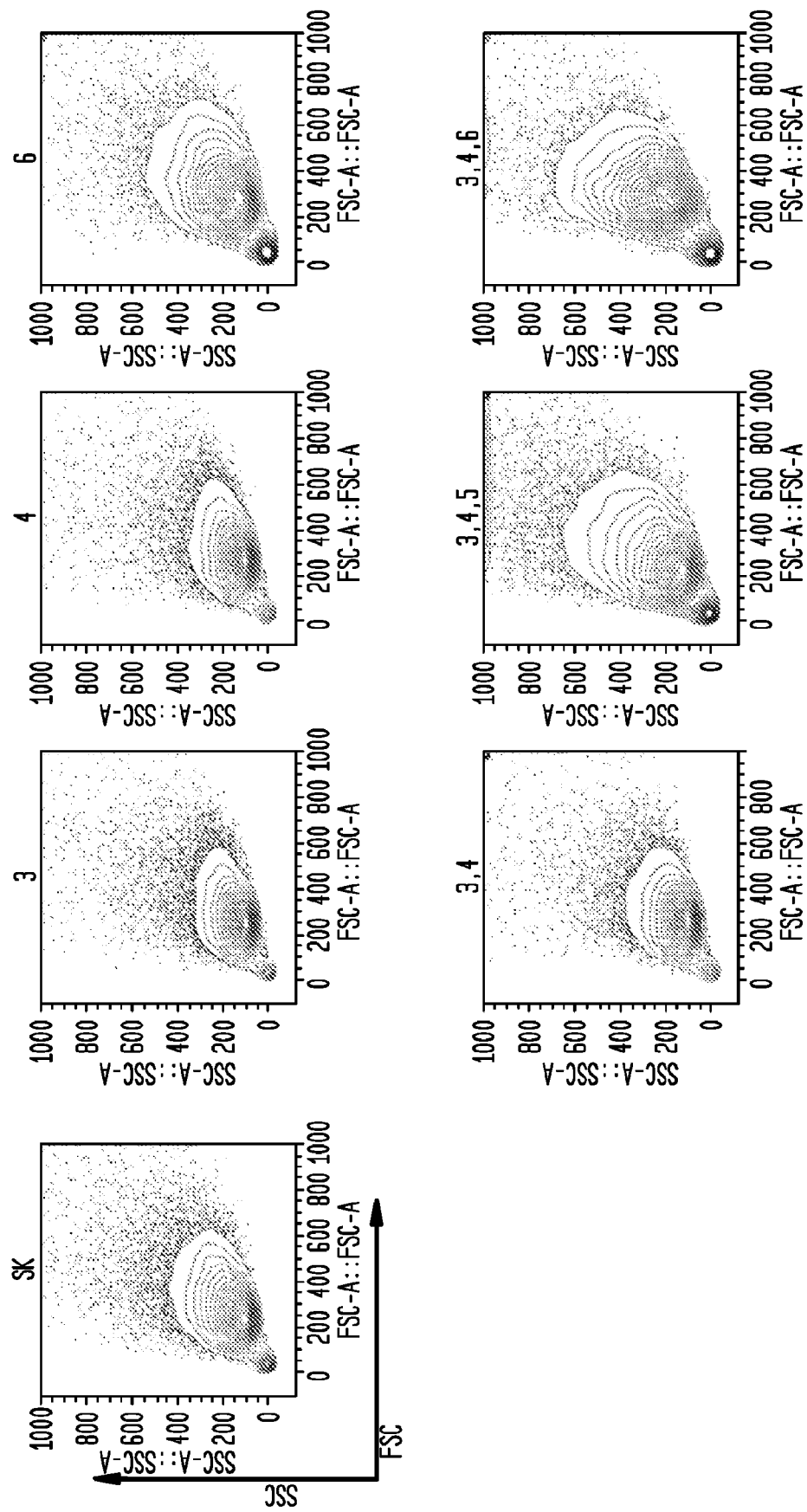
FIG. 11 is a panel of graphs that show the results of flow cytometry experiments. Forward (FSC) and side scatter (SSC) plots for size and granularity. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6. Cell lines 6, 3-4-5 and 3-4-6 display a larger and more granular phenotype likely owing to the presence of receptors for TNF-a and CD40L on cells of epithelial origin

FIG. 11 is a panel of graphs that show the results of flow cytometry experiments. Forward (FSC) and side scatter (SSC) plots for size and granularity are shown. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-alpha; 3-4 is a combination of 3 and 4; 3-4-5 is a combination of 3,4 and 5; and 3-4-6 is a combination of 3,4 and 6. Cell lines 6, 3-4-5 and 3-4-6 display a larger and more granular phenotype likely owing to the presence of receptors for TNF-alpha and CD40L on cells of epithelial origin.

Figure 12:
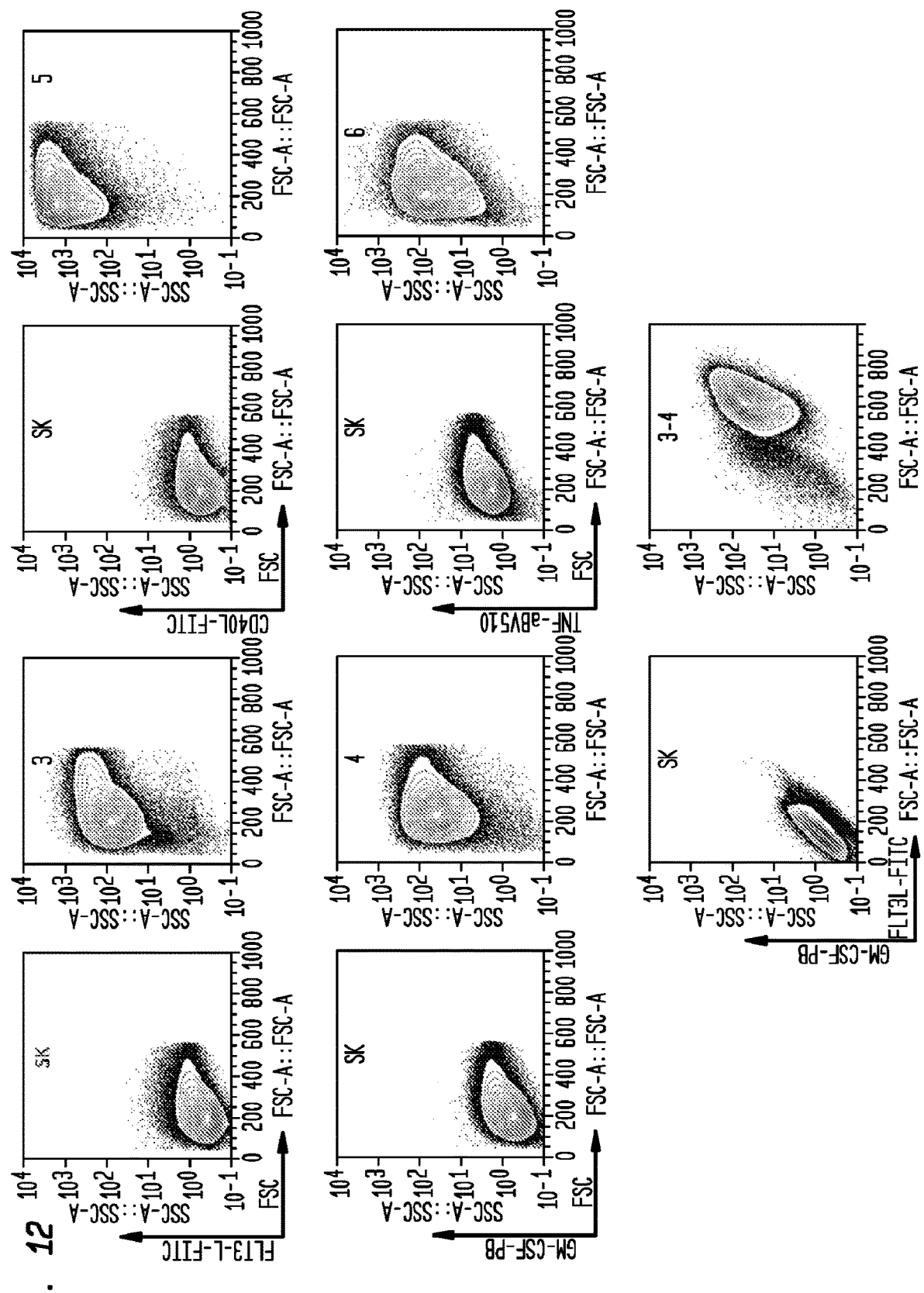
FIG. 12 is a panel of graphs that show representative flow cytometry stains for CD4 cells in hPBMC in response to the indicated engineered cell lines with the indicated immunomodulators SK cell lines are represented by the following code; SK, unmodified parent line; 2, membrane expressed IgG1, 3, secreted GM-CSF and membrane expressed FLT-3L; 4, secreted FLT3L and membrane expressed GM-CSF; 5, a non-cleavable form of CD40L; and 6, a non-cleavable form of TNF.

FIG. 12 is a panel of graphs that show representative flow cytometry stains for the indicated engineered surface markers; GM-CSF, FLT3L, TNF-a and CD40L. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-alpha; 3-4 is a combination of 3 and 4; 3-4-5 is a combination of 3,4 and 5; and 3-4-6 is a combination of 3, 4 and 6.

Figure 13:
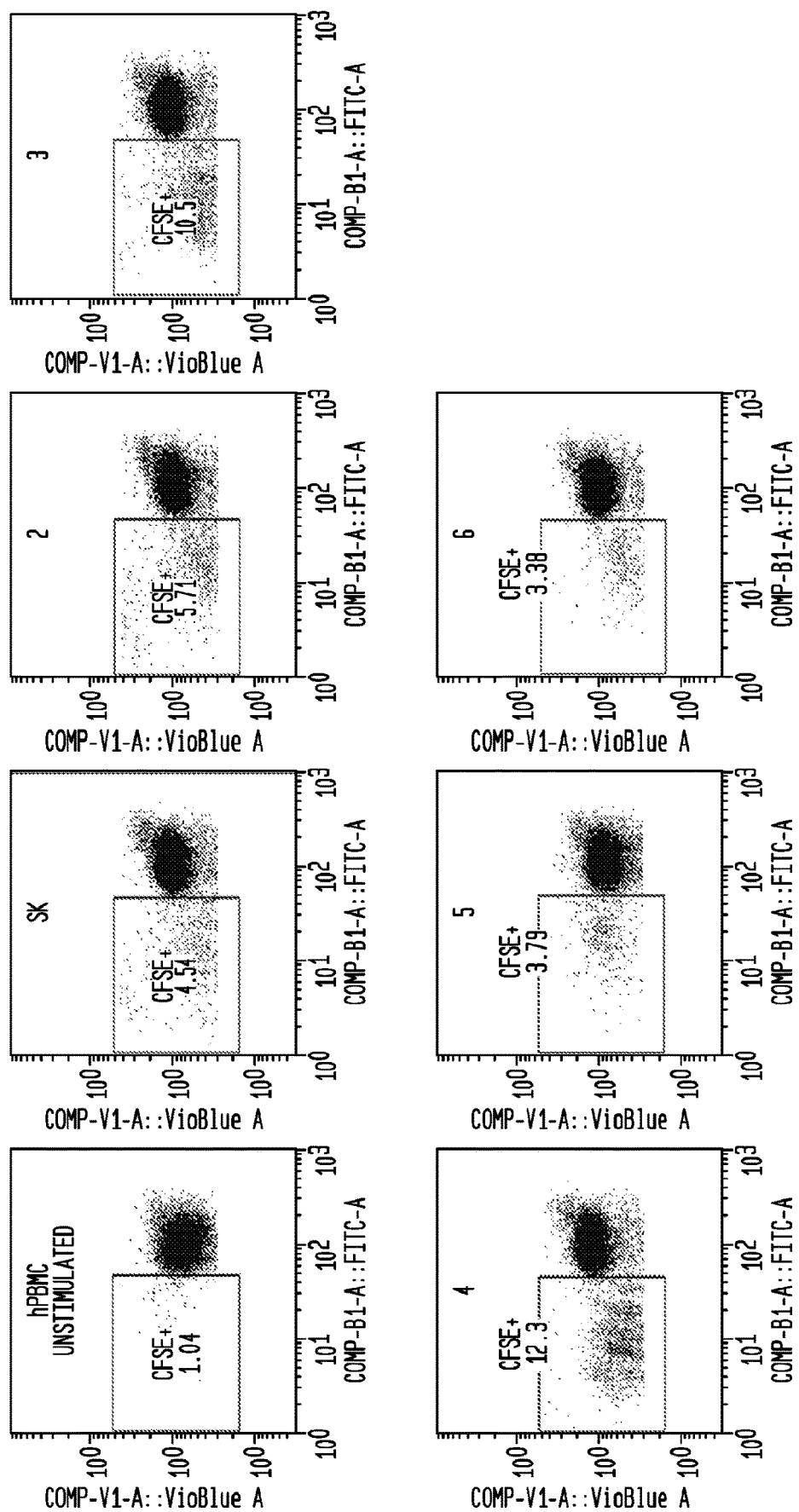
FIG. 13 is a panel of graphs that show representative flow cytometry stains for the indicated engineered surface markers; GM-CSF, FLT3L, TNF-a and CD40L. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.

FIG. 13 is a panel of graphs that show representative flow cytometry stains for the indicated engineered surface markers; GM-CSF, FLT3L, TNF-a and CD40L. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-a; 3-4 is a combination of 3 and 4; 3-4-5 is a combination of 3,4 and 5; and 3-4-6 is a combination of 3,4 and 6.

CyTOF Data

CyTOF mass cytometry single-cell phenotype analysis of hPBMC response to SK melanoma cells with modification by expression of immunomodulatory factors is shown in FIG. 14A and FIG. 14B. The SK melanoma cell line and hPBMCs were cultured for 24 hours. Cells were harvested from cultures and stained with a 32-marker CyTOF antibody panel to detect multiple immune cell subsets as well as cell-surface and intracellular phenotyping markers. CyTOF mass cytometry data was generated on a Helios instrument. The data were normalized for signal using equilibration beads. Cell staining data were analyzed using Cytobank—a cloud computing suite for CyTOF data analysis that includes cell gating functions and an array of data visualization methods.

The data shown in FIG. 14A and FIG. 14B were plotted using viSNE, which is a dimensional reduction method that converts multidimensional staining signals from single cells into plots for visualization. FIG. 14A shows viSNE density contour plots of CyTOF staining data showing relative changes in immune cell subset abundance and phenotype. FIG. 14B shows single-cell phenotype analysis. viSNE density contour plots were generated by viSNE from ungated total PBMCs that were cultured with SK melanoma cells or modified SK melanoma cells. The plots illustrate relative changes in cell density for hPBMC immune cell subsets. The inserted viSNE plot identifies the immune cell subsets that are found within the clusters of the viSNE density plots. The arrows in the density contour plots point to the obvious changes in immune cell subsets between hPBMCs, SK cells, and the modified SK cells.

Figure 15A:
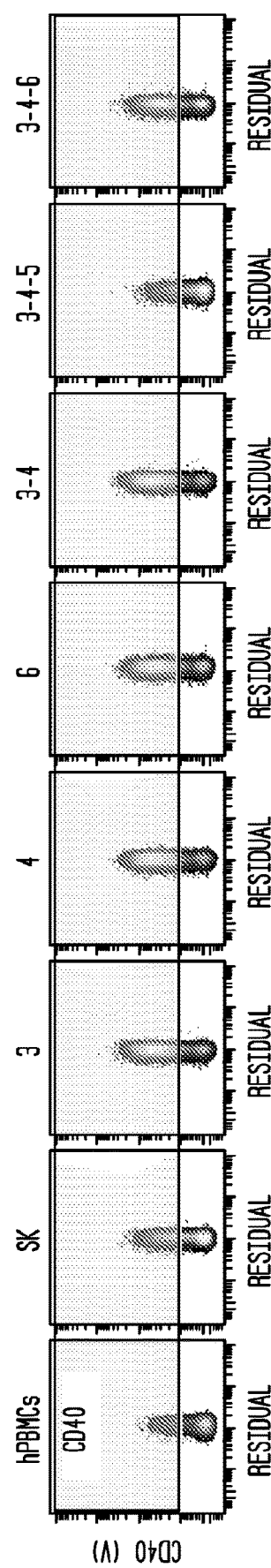
FIG. 15A-FIG. 15D shows CyTOF monocyte cluster analysis of hPBMC indicating changes in the activation markers CD40 (FIG. 15A), CD86 (FIG. 15B), CD69 (FIG. 15C) and CD25 (FIG. 15D) expression following 1 day stimulation with the indicated genetically modified SK lines at a 1:5 cell ratio. SK lines are represented by a number code; SK, unmodified parent line; 3, secreted GM-CSF and membrane expressed FLT-3L; 4, secreted FLT3L and membrane expressed GM-CSF; 5, a non-cleavable form of CD40L; 6, a non-cleavable form of TNF-α; 3-4 is a combination of 3 and 4; 3-4-5 is a combination of 3,4 and 5; and 3-4-6 is a combination of 3,4 and 6.
Figure 15B:
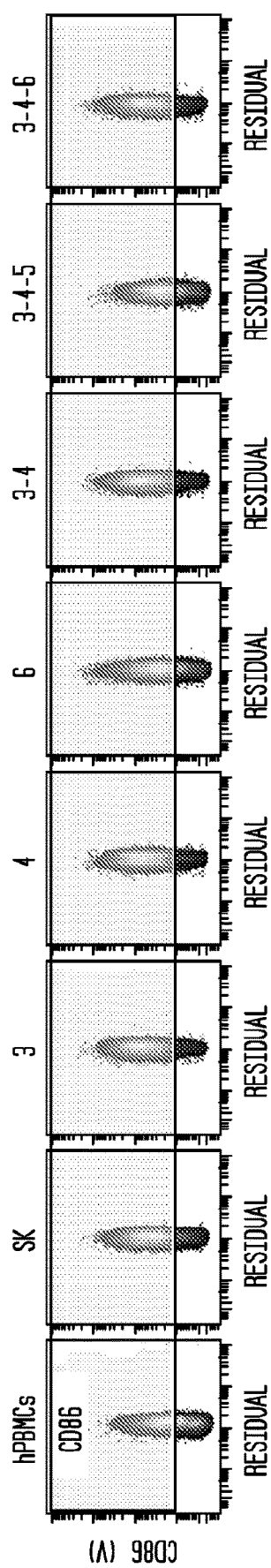
Figure 15C:
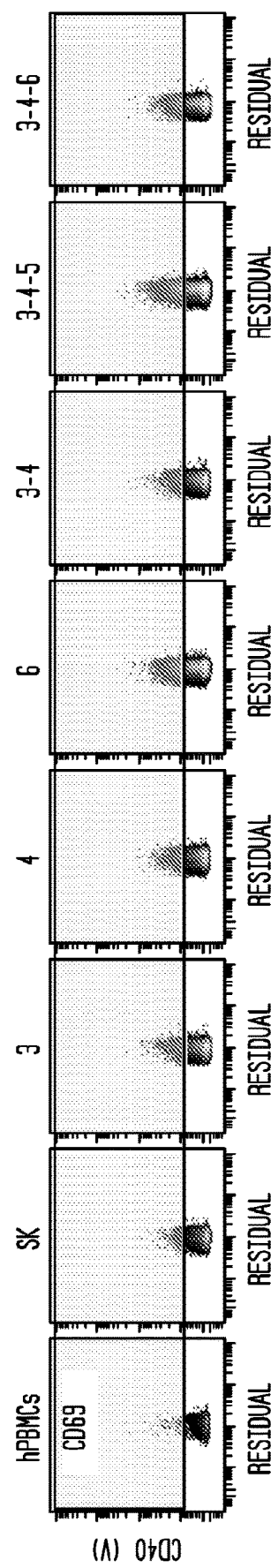
Figure 15D:
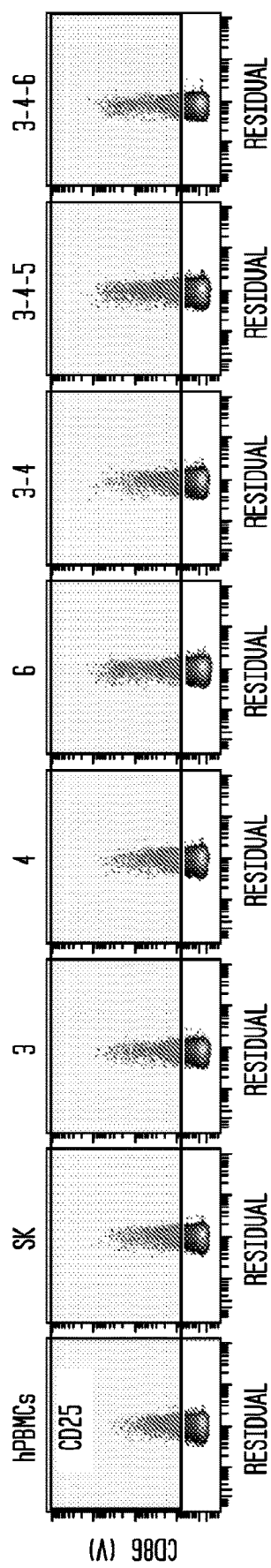
Figure 15E:
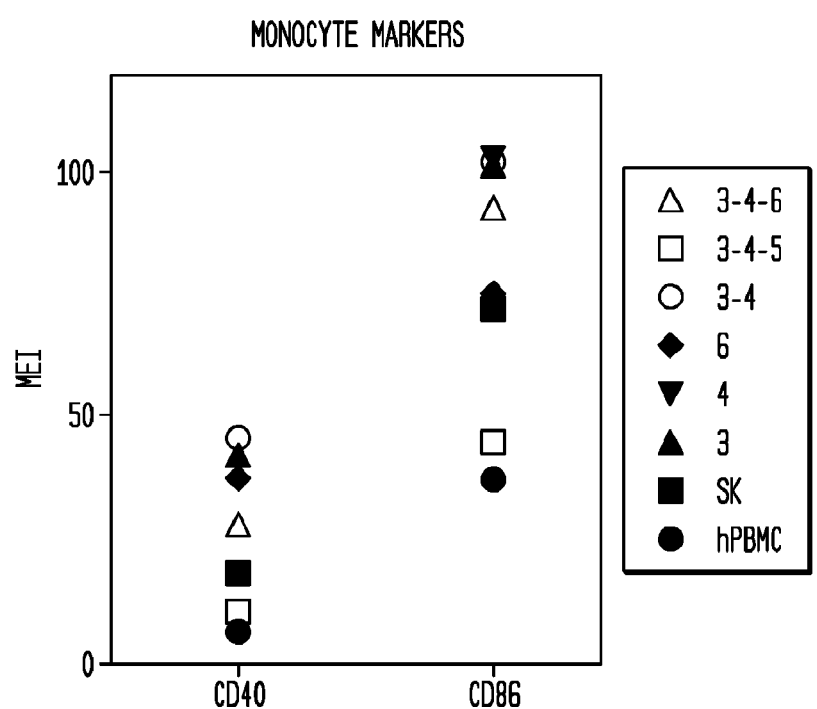
FIG. 15E shows CyTOF monocyte cluster analysis of hPBMC indicating relative median expression levels of monocyte markers CD40 and CD86.

FIGS. 15A-FIG. 15D show CyTOF monocyte cluster analysis of hPBMC indicating changes in the activation markers CD40 (FIG. 15A), CD86 (FIG. 15B), CD69 (FIG. 15C) and CD25 (FIG. 15D) expression following 1 day stimulation with the indicated genetically modified SK lines at a 1:5 cell ratio. FIG. 15E shows CyTOF monocyte cluster analysis of hPBMC indicating relative median expression levels of monocyte markers CD40 and CD86. FIG. 15E shows CyTOF monocyte cluster analysis of hPBMC indicating relative median expression levels of CD4 T cell markers CD69 and CD25.

Cytokine Data

LUMINEX® multiplex cytokine profiling of human PBMC responses to SK parent line and genetically modified SK lines is shown in FIG. 16. SK cells or the indicated modified cell lines were cultured for 24 hours with human PBMCs at a 1:5 cell ratio. Control cultures included SK cells alone, hPBMCs alone, and hPBMCs stimulated with a mixture of anti-CD3 and anti-CD28 antibodies (1 pg/ml final concentration). Supernatants were screened for cytokine levels using a multiplexed LUMINEX® bead array assay to detect IL-1a, IL-1b, IL-1ra, IL-2, IL-4, IL-6, IL-8, IL-10, IL-12p40, IL-12p70, IL-13, IL-17A, IL-23, TNFa, IFNg, G-CSF, GM-CSF, MIP1b, MCP-1, Rantes, Tweak, and TREM-1. Those cytokines found to be specifically induced by the SK parent line and modified SK lines are shown in the plots. Symbols indicate cytokine levels in pg/ml as estimated from a standard curve using recombinant cytokines. Absence of symbols indicates the cytokine was not detected. SK lines are represented by a number code; SK, unmodified parent line; 3, secreted GM-CSF and membrane expressed FLT-3L; 3, secreted FLT3L and membrane expressed GM-CSF; 5, a non-cleavable form of CD40L; 6, a non-cleavable form of TNF-alpha; 3-4 is a combination of 3 and 4; 3-4-5 is a combination of 3,4 and 5; and 3-4-6 is a combination of 3,4 and 6.

The described study provides a proof of concept that the complex combinatorial space of immunomodulators can be rapidly and efficiently assessed using an all human in vitro MLTR assay.

"Allorecognition" is a term used to define immunological recognition of histoincompatible antigens between genetically disparate individuals within the same species. "Direct allorecognition" is a mechanism by which recipient T cells recognize determinants on MHC-molecule-peptide complexes displayed on the surface of transplanted cells without the requirement for antigen processing by recipient APCs. The direct allorecognition response is detected early in the course of the MLTR assay (up to 1 day duration) during which time no antigen processing by host APC is required.

"Indirect allorecognition" refers to recognition of processed antigens of allogeneic cell origin presented by self-HLA on the surface of host antigen presenting cells. The indirect allorecognition response can be deteted later in the course of the MLTR assay (greater than 3 days duration) during which time antigen processing by host APC has occurred.

Approximately 10% of peripheral blood T cells bear a TCR capable of allorecognition of the allogeneic tumor type specific cells used for vaccination. This is called "direct allorecognition" and occurs early in the course of events post vaccination. Direct allorecognition targets a T cell mediated immune response against the allogeneic cells resulting in their death and release of tumor type specific neoantigens (and shared normal antigens). These tumor neoantigens (and normal antigens) are taken up by host antigen presenting cells, processed and presented in the context of host HLA. This "indirect allorecognition" occurs late in the course of events post vaccination. The TCRs activated during indirect allorecognition are different from those involved earlier during direct allorecognition, but both processes occur in a local environment after exposure to allogeneic cells. The presence of genetically introduced immunomodulators on the allogeneic cells altered the allorecognition response in qualitative and quantitative ways.

Epitope spreading is a process of expanding an immune response to include distinct but closely related T cell epitopes. This is generally described as a maturation of the immune response. The differential maturation of the immune response against tumor neoantigens versus self-antigens is driven by the fact that tolerance mechanisms are in place to differentially protect against immune responses against self-antigens. While self-tolerance can be broken, it is more difficult than the response against a tumor neoantigen.

Without being limited by theory, since all tumors of a given type share many antigens, the T-cell mediated response initially driven by indirect allorecognition of the immune response will cross react against the host tumor of the same type. According to some embodiments, since the tumor microenvironment may provide an insurmountable negative immunomodulatory hurdle, this approach may best be used in combination with checkpoint inhibitors in the setting of minimal residual disease after a debulking therapy (e.g. surgery, radiation or oncolytic viruses).

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. An allogeneic tumor cell vaccine used to elicit and stimulate an immune response against a melanoma or prostate cancer comprising:
  (1) a clonally-derived variant of a melanoma tumor cell line or a prostate tumor cell line comprising:
    (a) two or more stably expressed recombinant membrane-bound immunomodulator molecules selected from the group consisting of an IgG1 peptide, a CD40L peptide, a TNF-alpha peptide, and an Flt-3L peptide; and
    (b) a stably expressed recombinant soluble GM-CSF peptide; and
  (2) a pharmaceutically acceptable carrier;
  wherein the clonally-derived variant of the melanoma tumor cell line or the prostate tumor cell line is proliferation-incompetent;
  wherein the clonally-derived variant of the melanoma tumor cell line or the prostate tumor cell line is effective to elicit stimulation of the immune response to a subject's melanoma or prostate cancer, respectively, comprising activation of one or more of T cells, B cells, and dendritic cells as measured by one or more parameters selected from cellular proliferation, cellular subset differentiation, cytokine release profile, and tumor cell lysis that improves overall survival of the subject when compared to a control comprising a non-transfected melanoma tumor cell line or a prostate tumor cell line;
  wherein the clonally-derived variant of the melanoma tumor cell line or the prostate tumor cell line expresses the soluble GM-CSF peptide comprising an amino acid sequence as set forth in SEQ ID NO: 13 and two or more of:
    (a) the membrane-bound IgG1 immunomodulator peptide comprising an amino acid sequence as set forth in SEQ ID NO: 45;
    (b) the membrane-bound CD40L immunomodulator peptide comprising an amino acid sequence as set forth in SEQ ID NO: 7;
    (c) the membrane-bound form of TNF-alpha immunomodulator peptide comprising an amino acid sequence as set forth in SEQ ID NO: 11; and
    (d) the membrane-bound form of Flt-3L immunomodulator peptide comprising an amino acid sequence as set forth in SEQ ID NO: 14;
  wherein the melanoma tumor cell line is SK-MEL2, NIS-G, TRI-G, WIL-G, MRI-H-121B, MRI-H-187, MRI-H-221, or MRI-H-255; and
  wherein the prostate tumor cell line is CWR-22, DU145, PC-3/M, PC-3, VCaP, MDA PCa 2b, or LNCaP clone FGC.

2. The allogeneic tumor cell vaccine of claim 1, wherein the clonally-derived variant of the melanoma tumor cell line or prostate tumor cell line
  comprises a membrane-bound chimeric fusion protein comprising a fusion of the CD40L immunomodulator peptide and the TNF-alpha immunomodulator peptide.

3. The allogeneic tumor cell vaccine of claim 2, wherein the membrane-bound chimeric fusion protein comprises the CD40L immunomodulator peptide as set forth in SEQ ID NO: 9 and the TNF-alpha immunomodulator peptide as set forth in SEQ ID NO: 10.

4. The allogeneic tumor cell vaccine of claim 1, wherein the stably expressed recombinant membrane-bound immunomodulator molecules in (a) include the membrane-bound form of TNF-alpha immunomodulator peptide with an amino acid sequence as set forth in SEQ ID NO: 11.

5. The allogeneic tumor cell vaccine of claim 1, wherein the subject includes a member of an animal species of mammalian origin.

* * * * *

SEQUENCE LISTING

```
<160> NUMBER OF SEQ ID NOS: 104

<210> SEQ ID NO 1
<211> LENGTH: 399
<212> TYPE: PRT
<213> ORGANISM: Artificial Sequence
<220> FEATURE:
<223> OTHER INFORMATION: membrane IgG-1 heavy chain

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Glu Leu Gln Leu Glu Glu Ser Cys
                325                 330                 335

Ala Glu Ala Gln Asp Gly Glu Leu Asp Gly Leu Trp Thr Thr Ile Thr
            340                 345                 350

Ile Phe Ile Thr Leu Phe Leu Leu Ser Val Cys Tyr Ser Ala Thr Val
        355                 360                 365

Thr Phe Phe Lys Val Lys Trp Ile Phe Ser Ser Val Val Asp Leu Lys
    370                 375                 380

Gln Thr Ile Ile Pro Asp Tyr Arg Asn Met Ile Gly Gln Gly Ala
385                 390                 395

<210> SEQ ID NO 2
<211> LENGTH: 330
<212> TYPE: PRT
<213> ORGANISM: Artificial Sequence
<220> FEATURE:
<223> OTHER INFORMATION: secreted IgG-1 heavy chain

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 3
<211> LENGTH: 295
<212> TYPE: PRT
<213> ORGANISM: Artificial Sequence
<220> FEATURE:
<223> OTHER INFORMATION: fragment secreted IgG-1 heavy chain

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Asp Glu Leu Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295
```

<210> SEQ ID NO 4
<211> LENGTH: 377
<212> TYPE: PRT
<213> ORGANISM: Artificial Sequence
<220> FEATURE:
<223> OTHER INFORMATION: IgG-3 heavy chain constant region

<400> SEQUENCE: 4

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365
```

```
Lys Ser Leu Ser Leu Ser Pro Gly Lys
    370                 375

<210> SEQ ID NO 5
<211> LENGTH: 184
<212> TYPE: PRT
<213> ORGANISM: Artificial Sequence
<220> FEATURE:
<223> OTHER INFORMATION: mGM-CSF HLA derived TM and SHORTENED
      cytoplasmic domain

<400> SEQUENCE: 5

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

Glu Leu Ser Ser Gln Pro Thr Ile Pro Ile Val Gly Ile Ile Ala Gly
145                 150                 155                 160

Leu Val Leu Leu Gly Ala Val Ile Thr Gly Ala Val Val Ala Ala Val
                165                 170                 175

Met Trp Arg Arg Lys Ser Ser Asp
            180

<210> SEQ ID NO 6
<211> LENGTH: 261
<212> TYPE: PRT
<213> ORGANISM: Artificial Sequence
<220> FEATURE:
<223> OTHER INFORMATION: CD40L

<400> SEQUENCE: 6

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95
```

```
Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 7
<211> LENGTH: 261
<212> TYPE: PRT
<213> ORGANISM: Artificial Sequence
<220> FEATURE:
<223> OTHER INFORMATION: non-cleavable CD40L

<400> SEQUENCE: 7

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
                100                 105                 110

Met Pro Arg Gly Glu Glu Asp Ser Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190
```

```
Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 8
<211> LENGTH: 233
<212> TYPE: PRT
<213> ORGANISM: Artificial Sequence
<220> FEATURE:
<223> OTHER INFORMATION: TNF

<400> SEQUENCE: 8

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 9
<211> LENGTH: 108
<212> TYPE: PRT
<213> ORGANISM: Artificial Sequence
<220> FEATURE:
<223> OTHER INFORMATION: CD40L piece

<400> SEQUENCE: 9
```

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu
                100                 105

<210> SEQ ID NO 10
<211> LENGTH: 141
<212> TYPE: PRT
<213> ORGANISM: Artificial Sequence
<220> FEATURE:
<223> OTHER INFORMATION: TNF piece

<400> SEQUENCE: 10

Val Ala Asn Pro Gln Ala Glu Gly Gln Leu Gln Trp Leu Asn Arg Arg
1               5                   10                  15

Ala Asn Ala Leu Leu Ala Asn Gly Val Glu Leu Arg Asp Asn Gln Leu
                20                  25                  30

Val Val Pro Ser Glu Gly Leu Tyr Leu Ile Tyr Ser Gln Val Leu Phe
            35                  40                  45

Lys Gly Gln Gly Cys Pro Ser Thr His Val Leu Leu Thr His Thr Ile
        50                  55                  60

Ser Arg Ile Ala Val Ser Tyr Gln Thr Lys Val Asn Leu Leu Ser Ala
65                  70                  75                  80

Ile Lys Ser Pro Cys Gln Arg Glu Thr Pro Glu Gly Ala Glu Ala Lys
                85                  90                  95

Pro Trp Tyr Glu Pro Ile Tyr Leu Gly Gly Val Phe Gln Leu Glu Lys
                100                 105                 110

Gly Asp Arg Leu Ser Ala Glu Ile Asn Arg Pro Asp Tyr Leu Asp Phe
            115                 120                 125

Ala Glu Ser Gly Gln Val Tyr Phe Gly Ile Ile Ala Leu
        130                 135                 140

<210> SEQ ID NO 11
<211> LENGTH: 233
<212> TYPE: PRT
<213> ORGANISM: Artificial Sequence
<220> FEATURE:
<223> OTHER INFORMATION: mTNF-a

<400> SEQUENCE: 11

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
```

```
                    50                  55                  60
Arg Asp Leu Ser Leu Ile Ser Pro Leu Ala Gln Ala Ser Gly Ser Gly
 65                  70                  75                  80

Ser Gly Ser Gly Ser Gly Glu Pro Val Ala His Val Val Ala Asn Pro
                     85                  90                  95

Gln Ala Glu Gly Gln Leu Gln Trp Leu Asn Arg Arg Ala Asn Ala Leu
                100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
        130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230

<210> SEQ ID NO 12
<211> LENGTH: 113
<212> TYPE: PRT
<213> ORGANISM: Artificial Sequence
<220> FEATURE:
<223> OTHER INFORMATION: HC Constant Region 3 from IgG1

<400> SEQUENCE: 12

Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Glu Leu Gln Leu Glu Glu Ser
                100                 105                 110

Cys

<210> SEQ ID NO 13
<211> LENGTH: 144
<212> TYPE: PRT
<213> ORGANISM: Artificial Sequence
<220> FEATURE:
<223> OTHER INFORMATION: native GM-CSF

<400> SEQUENCE: 13

Met Trp Leu Gln Ser Leu Leu Leu Leu Gly Thr Val Ala Cys Ser Ile
```

```
              1               5                  10                 15
            Ser Ala Pro Ala Arg Ser Pro Ser Pro Ser Thr Gln Pro Trp Glu His
                            20                  25                 30
            Val Asn Ala Ile Gln Glu Ala Arg Arg Leu Leu Asn Leu Ser Arg Asp
                            35                  40                 45
            Thr Ala Ala Glu Met Asn Glu Thr Val Glu Val Ile Ser Glu Met Phe
                 50                  55                 60
            Asp Leu Gln Glu Pro Thr Cys Leu Gln Thr Arg Leu Glu Leu Tyr Lys
            65                  70                  75                 80
            Gln Gly Leu Arg Gly Ser Leu Thr Lys Leu Lys Gly Pro Leu Thr Met
                            85                  90                 95
            Met Ala Ser His Tyr Lys Gln His Cys Pro Pro Thr Pro Glu Thr Ser
                            100                 105                110
            Cys Ala Thr Gln Ile Ile Thr Phe Glu Ser Phe Lys Glu Asn Leu Lys
                            115                 120                125
            Asp Phe Leu Leu Val Ile Pro Phe Asp Cys Trp Glu Pro Val Gln Glu
                            130                 135                140
```

<210> SEQ ID NO 14
<211> LENGTH: 235
<212> TYPE: PRT
<213> ORGANISM: Artificial Sequence
<220> FEATURE:
<223> OTHER INFORMATION: Flt3L

<400> SEQUENCE: 14

```
            Met Thr Val Leu Ala Pro Ala Trp Ser Pro Thr Thr Tyr Leu Leu Leu
            1               5                  10                 15
            Leu Leu Leu Leu Ser Ser Gly Leu Ser Gly Thr Gln Asp Cys Ser Phe
                            20                  25                 30
            Gln His Ser Pro Ile Ser Ser Asp Phe Ala Val Lys Ile Arg Glu Leu
                            35                  40                 45
            Ser Asp Tyr Leu Leu Gln Asp Tyr Pro Val Thr Val Ala Ser Asn Leu
                 50                  55                 60
            Gln Asp Glu Glu Leu Cys Gly Gly Leu Trp Arg Leu Val Leu Ala Gln
            65                  70                  75                 80
            Arg Trp Met Glu Arg Leu Lys Thr Val Ala Gly Ser Lys Met Gln Gly
                            85                  90                 95
            Leu Leu Glu Arg Val Asn Thr Glu Ile His Phe Val Thr Lys Cys Ala
                            100                 105                110
            Phe Gln Pro Pro Pro Ser Cys Leu Arg Phe Val Gln Thr Asn Ile Ser
                            115                 120                125
            Arg Leu Leu Gln Glu Thr Ser Glu Gln Leu Val Ala Leu Lys Pro Trp
                            130                 135                140
            Ile Thr Arg Gln Asn Phe Ser Arg Cys Leu Glu Leu Gln Cys Gln Pro
            145                 150                 155                160
            Asp Ser Ser Thr Leu Pro Pro Pro Trp Ser Pro Arg Pro Leu Glu Ala
                            165                 170                175
            Thr Ala Pro Thr Ala Pro Gln Pro Pro Leu Leu Leu Leu Leu Leu Leu
                            180                 185                190
            Pro Val Gly Leu Leu Leu Leu Ala Ala Ala Trp Cys Leu His Trp Gln
                            195                 200                205
            Arg Thr Arg Arg Arg Thr Pro Arg Pro Gly Glu Gln Val Pro Pro Val
                            210                 215                220
            Pro Ser Pro Gln Asp Leu Leu Leu Val Glu His
```

<210> SEQ ID NO 15
<211> LENGTH: 13
<212> TYPE: RNA
<213> ORGANISM: Artificial Sequence
<220> FEATURE:
<223> OTHER INFORMATION: Kozak sequence
<220> FEATURE:
<221> NAME/KEY: misc_feature
<222> LOCATION: (7)..(7)
<223> OTHER INFORMATION: n is A or G

<400> SEQUENCE: 15
gccgccncca ugg                                                         13

<210> SEQ ID NO 16
<211> LENGTH: 377
<212> TYPE: PRT
<213> ORGANISM: Artificial Sequence
<220> FEATURE:
<223> OTHER INFORMATION: IgG-3 heavy chain constant region E213Q

<400> SEQUENCE: 16

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Gln Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

```
Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 17
<211> LENGTH: 377
<212> TYPE: PRT
<213> ORGANISM: Artificial Sequence
<220> FEATURE:
<223> OTHER INFORMATION: IgG-3 heavy chain constant region P221L

<400> SEQUENCE: 17

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

```
Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
    370                 375

<210> SEQ ID NO 18
<211> LENGTH: 377
<212> TYPE: PRT
<213> ORGANISM: Artificial Sequence
<220> FEATURE:
<223> OTHER INFORMATION: IgG-3 heavy chain constant region E224Q

<400> SEQUENCE: 18

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Gln
    210                 215                 220

Gln Tyr Asn Ser Thr Phe Arg Val Val Ser Val Leu Thr Val Leu His
225                 230                 235                 240
```

```
Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
    275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 19
<211> LENGTH: 377
<212> TYPE: PRT
<213> ORGANISM: Artificial Sequence
<220> FEATURE:
<223> OTHER INFORMATION: IgG-3 heavy chain constant region Y226F

<400> SEQUENCE: 19

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220
```

```
Gln Phe Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
        260                 265                 270

Pro Arg Glu Pro Gln Val Tyr Thr Leu Pro Pro Ser Arg Glu Glu Met
    275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
            325                 330                 335

Tyr Ser Lys Leu Thr Val Asp Lys Ser Arg Trp Gln Gln Gly Asn Ile
        340                 345                 350

Phe Ser Cys Ser Val Met His Glu Ala Leu His Asn Arg Phe Thr Gln
    355                 360                 365

Lys Ser Leu Ser Leu Ser Pro Gly Lys
370                 375

<210> SEQ ID NO 20
<211> LENGTH: 377
<212> TYPE: PRT
<213> ORGANISM: Artificial Sequence
<220> FEATURE:
<223> OTHER INFORMATION: IgG-3 heavy chain constant region D242N

<400> SEQUENCE: 20

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205
```

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asn Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
        370                 375

<210> SEQ ID NO 21
<211> LENGTH: 377
<212> TYPE: PRT
<213> ORGANISM: Artificial Sequence
<220> FEATURE:
<223> OTHER INFORMATION: IgG-3 heavy chain constant region N245D

<400> SEQUENCE: 21

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65              70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

```
Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asp Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375

<210> SEQ ID NO 22
<211> LENGTH: 377
<212> TYPE: PRT
<213> ORGANISM: Artificial Sequence
<220> FEATURE:
<223> OTHER INFORMATION: IgG-3 heavy chain constant region T269A

<400> SEQUENCE: 22

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175
```

-continued

```
Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
            210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
            290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375
```

<210> SEQ ID NO 23
<211> LENGTH: 377
<212> TYPE: PRT
<213> ORGANISM: Artificial Sequence
<220> FEATURE:
<223> OTHER INFORMATION: IgG-3 heavy chain constant region S314N

<400> SEQUENCE: 23

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160
```

```
Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
        180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 24
<211> LENGTH: 376
<212> TYPE: PRT
<213> ORGANISM: Artificial Sequence
<220> FEATURE:
<223> OTHER INFORMATION: IgG-3 heavy chain constant region S314 del

<400> SEQUENCE: 24

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140
```

```
Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
        165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Gly Gln Pro Glu Asn Asn Tyr
305                 310                 315                 320

Asn Thr Thr Pro Pro Met Leu Asp Ser Asp Gly Ser Phe Phe Leu Tyr
            325                 330                 335

Ser Lys Leu Thr Val Asp Lys Ser Arg Trp Gln Gln Gly Asn Ile Phe
            340                 345                 350

Ser Cys Ser Val Met His Glu Ala Leu His Asn Arg Phe Thr Gln Lys
        355                 360                 365

Ser Leu Ser Leu Ser Pro Gly Lys
        370                 375

<210> SEQ ID NO 25
<211> LENGTH: 377
<212> TYPE: PRT
<213> ORGANISM: Artificial Sequence
<220> FEATURE:
<223> OTHER INFORMATION: IgG-3 heavy chain constant region F366Y

<400> SEQUENCE: 25

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125
```

```
Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Tyr Thr Gln
                355                 360                 365

Lys Ser Leu Ser Leu Ser Pro Gly Lys
                370                 375

<210> SEQ ID NO 26
<211> LENGTH: 221
<212> TYPE: PRT
<213> ORGANISM: Artificial Sequence
<220> FEATURE:
<223> OTHER INFORMATION: TNF - VRSSSRTPSDKP del

<400> SEQUENCE: 26

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
                35                  40                  45

Cys Leu Leu His Phe Gly Val Ile Gly Pro Gln Arg Glu Glu Phe Pro
            50                  55                  60

Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
                100                 105                 110
```

```
Val Val Pro Ser Glu Gly Leu Tyr Leu Ile Tyr Ser Gln Val Leu Phe
            115                 120                 125

Lys Gly Gln Gly Cys Pro Ser Thr His Val Leu Leu Thr His Thr Ile
130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
                180                 185                 190

Gly Asp Arg Leu Ser Ala Glu Ile Asn Arg Pro Asp Tyr Leu Asp Phe
                195                 200                 205

Ala Glu Ser Gly Gln Val Tyr Phe Gly Ile Ile Ala Leu
    210                 215                 220

<210> SEQ ID NO 27
<211> LENGTH: 212
<212> TYPE: PRT
<213> ORGANISM: Artificial Sequence
<220> FEATURE:
<223> OTHER INFORMATION: TNF - FSFLIVAGATTLFCLLHFGVI del

<400> SEQUENCE: 27

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Gly Pro Gln Arg Glu Glu Phe Pro Arg Asp Leu Ser Leu
            35                  40                  45

Ile Ser Pro Leu Ala Gln Ala Val Arg Ser Ser Ser Arg Thr Pro Ser
50                  55                  60

Asp Lys Pro Val Ala His Val Val Ala Asn Pro Gln Ala Glu Gly Gln
65                  70                  75                  80

Leu Gln Trp Leu Asn Arg Arg Ala Asn Ala Leu Leu Ala Asn Gly Val
                85                  90                  95

Glu Leu Arg Asp Asn Gln Leu Val Val Pro Ser Glu Gly Leu Tyr Leu
                100                 105                 110

Ile Tyr Ser Gln Val Leu Phe Lys Gly Gln Gly Cys Pro Ser Thr His
                115                 120                 125

Val Leu Leu Thr His Thr Ile Ser Arg Ile Ala Val Ser Tyr Gln Thr
            130                 135                 140

Lys Val Asn Leu Leu Ser Ala Ile Lys Ser Pro Cys Gln Arg Glu Thr
145                 150                 155                 160

Pro Glu Gly Ala Glu Ala Lys Pro Trp Tyr Glu Pro Ile Tyr Leu Gly
                165                 170                 175

Gly Val Phe Gln Leu Glu Lys Gly Asp Arg Leu Ser Ala Glu Ile Asn
                180                 185                 190

Arg Pro Asp Tyr Leu Asp Phe Ala Glu Ser Gly Gln Val Tyr Phe Gly
                195                 200                 205

Ile Ile Ala Leu
    210

<210> SEQ ID NO 28
<211> LENGTH: 9
<212> TYPE: PRT
<213> ORGANISM: Artificial Sequence
<220> FEATURE:
```

```
<223> OTHER INFORMATION: HA tag seq

<400> SEQUENCE: 28

Tyr Pro Tyr Asp Val Pro Asp Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: FLAG TAG

<400> SEQUENCE: 29

Asp Tyr Lys Asp Asp Asp Asp Lys
1               5

<210> SEQ ID NO 30
<211> LENGTH: 583
<212> TYPE: PRT
<213> ORGANISM: Artificial Sequence
<220> FEATURE:
<223> OTHER INFORMATION: mIgG Heavy Chain IgG 1/3 hybrid anti-biotin
      heavy chain - E325A mutant

<400> SEQUENCE: 30

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Gly Phe Ala Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Leu Lys Thr Pro
225                 230                 235                 240

Leu Gly Asp Thr Thr His Thr Cys Pro Arg Cys Pro Glu Pro Lys Ser
                245                 250                 255
```

Cys Asp Thr Pro Pro Cys Pro Arg Cys Pro Glu Pro Lys Ser Cys
            260             265             270

Asp Thr Pro Pro Cys Pro Arg Cys Pro Glu Pro Lys Ser Cys Asp
        275             280             285

Thr Pro Pro Pro Cys Pro Arg Cys Pro Ala Pro Glu Leu Leu Gly Gly
    290             295             300

Pro Ser Val Phe Leu Phe Pro Pro Lys Pro Lys Asp Thr Leu Met Ile
305             310             315             320

Ser Arg Thr Pro Ala Val Thr Cys Val Val Val Asp Val Ser His Glu
                325             330             335

Asp Pro Glu Val Lys Phe Asn Trp Tyr Val Asp Gly Val Glu Val His
            340             345             350

Asn Ala Lys Thr Lys Pro Arg Glu Glu Gln Tyr Asn Ser Thr Tyr Arg
        355             360             365

Val Val Ser Val Leu Thr Val Leu His Gln Asp Trp Leu Asn Gly Lys
    370             375             380

Glu Tyr Lys Cys Lys Val Ser Asn Lys Ala Leu Pro Ala Pro Ile Glu
385             390             395             400

Lys Thr Ile Ser Lys Ala Lys Gly Gln Pro Arg Glu Pro Gln Val Tyr
                405             410             415

Thr Leu Pro Pro Ser Arg Asp Glu Leu Thr Lys Asn Gln Val Ser Leu
            420             425             430

Thr Cys Leu Val Lys Gly Phe Tyr Pro Ser Asp Ile Ala Val Glu Trp
        435             440             445

Glu Ser Asn Gly Gln Pro Glu Asn Asn Tyr Lys Thr Thr Pro Pro Val
    450             455             460

Leu Asp Ser Asp Gly Ser Phe Phe Leu Tyr Ser Lys Leu Thr Val Asp
465             470             475             480

Lys Ser Arg Trp Gln Gln Gly Asn Val Phe Ser Cys Ser Val Met His
                485             490             495

Glu Ala Leu His Asn His Tyr Thr Gln Lys Ser Leu Ser Leu Ser Pro
            500             505             510

Glu Leu Gln Leu Glu Glu Ser Cys Ala Glu Ala Gln Asp Gly Glu Leu
        515             520             525

Asp Gly Leu Trp Thr Thr Ile Thr Ile Phe Ile Thr Leu Phe Leu Leu
    530             535             540

Ser Val Cys Tyr Ser Ala Thr Val Thr Phe Phe Lys Val Lys Trp Ile
545             550             555             560

Phe Ser Ser Val Val Asp Leu Lys Gln Thr Ile Ile Pro Asp Tyr Arg
                565             570             575

Asn Met Ile Gly Gln Gly Ala
            580

<210> SEQ ID NO 31
<211> LENGTH: 223
<212> TYPE: PRT
<213> ORGANISM: Artificial Sequence
<220> FEATURE:
<223> OTHER INFORMATION: CD40L-TNFa fusion protein

<400> SEQUENCE: 31

Met Ile Glu Thr Tyr Asn Gln Thr Ser Pro Arg Ser Ala Ala Thr Gly
1               5               10              15

Leu Pro Ile Ser Met Lys Ile Phe Met Tyr Leu Leu Thr Val Phe Leu
            20              25              30

```
Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
 50                  55                  60

Phe Met Lys Thr Ile Gln Arg Cys Asn Thr Gly Glu Arg Pro Val Ala
 65                  70                  75                  80

His Val Val Ala Asn Pro Gln Ala Glu Gly Gln Leu Gln Trp Leu Asn
                 85                  90                  95

Arg Arg Ala Asn Ala Leu Leu Ala Asn Gly Val Glu Leu Arg Asp Asn
                100                 105                 110

Gln Leu Val Val Pro Ser Glu Gly Leu Tyr Leu Ile Tyr Ser Gln Val
                115                 120                 125

Leu Phe Lys Gly Gln Gly Cys Pro Ser Thr His Val Leu Leu Thr His
                130                 135                 140

Thr Ile Ser Arg Ile Ala Val Ser Tyr Gln Thr Lys Val Asn Leu Leu
145                 150                 155                 160

Ser Ala Ile Lys Ser Pro Cys Gln Arg Glu Thr Pro Glu Gly Ala Glu
                165                 170                 175

Ala Lys Pro Trp Tyr Glu Pro Ile Tyr Leu Gly Gly Val Phe Gln Leu
                180                 185                 190

Glu Lys Gly Asp Arg Leu Ser Ala Glu Ile Asn Arg Pro Asp Tyr Leu
                195                 200                 205

Asp Phe Ala Glu Ser Gly Gln Val Tyr Phe Gly Ile Ile Ala Leu
                210                 215                 220

<210> SEQ ID NO 32
<211> LENGTH: 19
<212> TYPE: PRT
<213> ORGANISM: Artificial Sequence
<220> FEATURE:
<223> OTHER INFORMATION: HC Signal

<400> SEQUENCE: 32

Met Glu Phe Gly Leu Ser Trp Val Phe Leu Val Ala Leu Phe Arg Gly
 1               5                  10                  15

Val Gln Cys

<210> SEQ ID NO 33
<211> LENGTH: 118
<212> TYPE: PRT
<213> ORGANISM: Artificial Sequence
<220> FEATURE:
<223> OTHER INFORMATION: HC Variable anti-biotin

<400> SEQUENCE: 33

Gln Val Lys Leu Gln Glu Ser Gly Pro Gly Leu Val Ala Pro Ser Gln
 1               5                  10                  15

Ser Leu Ser Ile Thr Cys Thr Val Ser Gly Phe Ser Leu Thr Ala Tyr
                 20                  25                  30

Gly Val Asp Trp Val Arg Gln Pro Pro Gly Lys Gly Leu Glu Trp Leu
                 35                  40                  45

Gly Val Ile Trp Gly Gly Gly Arg Thr Asn Tyr Asn Ser Gly Leu Met
                 50                  55                  60

Ser Arg Leu Ser Ile Arg Lys Asp Asn Ser Lys Ser Gln Val Phe Leu
 65                  70                  75                  80

Thr Met Asn Ser Leu Gln Thr Asp Asp Thr Ala Lys Tyr Tyr Cys Val
                 85                  90                  95
```

-continued

```
Lys His Thr Asn Trp Asp Gly Gly Phe Ala Tyr Trp Gly Gln Gly Thr
                100                 105                 110
Thr Val Thr Val Ser Ser
        115

<210> SEQ ID NO 34
<211> LENGTH: 99
<212> TYPE: PRT
<213> ORGANISM: Artificial Sequence
<220> FEATURE:
<223> OTHER INFORMATION: HC Constant Region 1 from IgG1

<400> SEQUENCE: 34

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu

<210> SEQ ID NO 35
<211> LENGTH: 61
<212> TYPE: PRT
<213> ORGANISM: Artificial Sequence
<220> FEATURE:
<223> OTHER INFORMATION: HC Hinge Region from IgG3

<400> SEQUENCE: 35

Leu Lys Thr Pro Leu Gly Asp Thr Thr His Thr Cys Pro Arg Cys Pro
1               5                   10                  15
Glu Pro Lys Ser Cys Asp Thr Pro Pro Cys Pro Arg Cys Pro Glu
            20                  25                  30
Pro Lys Ser Cys Asp Thr Pro Pro Cys Pro Arg Cys Pro Glu Pro
        35                  40                  45
Lys Ser Cys Asp Thr Pro Pro Cys Pro Arg Cys Pro
    50                  55                  60

<210> SEQ ID NO 36
<211> LENGTH: 110
<212> TYPE: PRT
<213> ORGANISM: Artificial Sequence
<220> FEATURE:
<223> OTHER INFORMATION: HC Constant Region 2  from IgG1

<400> SEQUENCE: 36

Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
```

```
Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 37
<211> LENGTH: 63
<212> TYPE: PRT
<213> ORGANISM: Artificial Sequence
<220> FEATURE:
<223> OTHER INFORMATION: HC Transmembrane and Cytoplasmic region from
      IgG1

<400> SEQUENCE: 37

Ala Glu Ala Gln Asp Gly Glu Leu Asp Gly Leu Trp Thr Thr Ile Thr
 1               5                  10                  15

Ile Phe Ile Thr Leu Phe Leu Leu Ser Val Cys Tyr Ser Ala Thr Val
                 20                  25                  30

Thr Phe Phe Lys Val Lys Trp Ile Phe Ser Ser Val Val Asp Leu Lys
             35                  40                  45

Gln Thr Ile Ile Pro Asp Tyr Arg Asn Met Ile Gly Gln Gly Ala
         50                  55                  60

<210> SEQ ID NO 38
<211> LENGTH: 22
<212> TYPE: PRT
<213> ORGANISM: Artificial Sequence
<220> FEATURE:
<223> OTHER INFORMATION: LC Signal

<400> SEQUENCE: 38

Met Lys Tyr Leu Leu Pro Thr Ala Ala Ala Gly Leu Leu Leu Leu Ala
 1               5                  10                  15

Ala Gln Pro Ala Met Ala
             20

<210> SEQ ID NO 39
<211> LENGTH: 99
<212> TYPE: PRT
<213> ORGANISM: Artificial Sequence
<220> FEATURE:
<223> OTHER INFORMATION: LC Variable

<400> SEQUENCE: 39

Gly Ser Pro Gly Gln Ser Val Ser Ile Ser Cys Ser Gly Ser Ser Ser
 1               5                  10                  15

Asn Ile Gly Asn Asn Tyr Val Tyr Trp Tyr Gln His Leu Pro Gly Thr
                 20                  25                  30

Ala Pro Lys Leu Leu Ile Tyr Ser Asp Thr Lys Arg Pro Ser Gly Val
             35                  40                  45

Pro Asp Arg Ile Ser Gly Ser Lys Ser Gly Thr Ser Ala Ser Leu Ala
         50                  55                  60

Ile Ser Gly Leu Gln Ser Glu Asp Glu Ala Asp Tyr Tyr Cys Ala Ser
 65                  70                  75                  80

Trp Asp Asp Ser Leu Asp Gly Pro Val Phe Gly Gly Gly Thr Lys Leu
                 85                  90                  95

Thr Val Leu
```

<210> SEQ ID NO 40
<211> LENGTH: 106
<212> TYPE: PRT
<213> ORGANISM: Artificial Sequence
<220> FEATURE:
<223> OTHER INFORMATION: LC Constant Region 1

<400> SEQUENCE: 40

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 41
<211> LENGTH: 583
<212> TYPE: PRT
<213> ORGANISM: Artificial Sequence
<220> FEATURE:
<223> OTHER INFORMATION: mIgG Heavy Chain IgG 1/3 hybrid anti-biotin
      heavy chain - T323A mutant

<400> SEQUENCE: 41

```
Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Phe Ala Tyr Trp Gly
            115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
```

```
            195                 200                 205
Pro Ser Ser Ser Leu Gly Thr Gln Thr Tyr Ile Cys Asn Val Asn His
210                     215                 220

Lys Pro Ser Asn Thr Lys Val Asp Lys Val Glu Leu Lys Thr Pro
225                 230                 235                 240

Leu Gly Asp Thr Thr His Thr Cys Pro Arg Cys Pro Glu Pro Lys Ser
                    245                 250                 255

Cys Asp Thr Pro Pro Pro Cys Pro Arg Cys Pro Glu Pro Lys Ser Cys
                260                 265                 270

Asp Thr Pro Pro Pro Cys Pro Arg Cys Pro Glu Pro Lys Ser Cys Asp
                275                 280                 285

Thr Pro Pro Pro Cys Pro Arg Cys Pro Ala Pro Glu Leu Leu Gly Gly
                290                 295                 300

Pro Ser Val Phe Leu Phe Pro Pro Lys Pro Lys Asp Thr Leu Met Ile
305                 310                 315                 320

Ser Arg Ala Pro Glu Val Thr Cys Val Val Val Asp Val Ser His Glu
                    325                 330                 335

Asp Pro Glu Val Lys Phe Asn Trp Tyr Val Asp Gly Val Glu Val His
                340                 345                 350

Asn Ala Lys Thr Lys Pro Arg Glu Glu Gln Tyr Asn Ser Thr Tyr Arg
                355                 360                 365

Val Val Ser Val Leu Thr Val Leu His Gln Asp Trp Leu Asn Gly Lys
370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
                420                 425                 430

Thr Cys Leu Val Lys Gly Phe Tyr Pro Ser Asp Ile Ala Val Glu Trp
                435                 440                 445

Glu Ser Asn Gly Gln Pro Glu Asn Asn Tyr Lys Thr Thr Pro Pro Val
450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
                500                 505                 510

Glu Leu Gln Leu Glu Glu Ser Cys Ala Glu Ala Gln Asp Gly Glu Leu
                515                 520                 525

Asp Gly Leu Trp Thr Thr Ile Thr Ile Phe Ile Thr Leu Phe Leu Leu
                530                 535                 540

Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
                565                 570                 575

Asn Met Ile Gly Gln Gly Ala
            580

<210> SEQ ID NO 42
<211> LENGTH: 211
<212> TYPE: PRT
<213> ORGANISM: Artificial Sequence
```

<220> FEATURE:
<223> OTHER INFORMATION: GM-CSF - HLA-I fusion peptide

<400> SEQUENCE: 42

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

Glu Leu Ser Ser Gln Pro Thr Ile Pro Ile Val Gly Ile Ile Ala Gly
145                 150                 155                 160

Leu Val Leu Leu Gly Ala Val Ile Thr Gly Ala Val Val Ala Ala Val
                165                 170                 175

Met Trp Arg Arg Lys Ser Ser Asp Arg Lys Gly Gly Ser Tyr Thr Gln
            180                 185                 190

Ala Ala Ser Ser Asp Ser Ala Gln Gly Ser Asp Val Ser Leu Thr Ala
        195                 200                 205

Cys Lys Val
    210

<210> SEQ ID NO 43
<211> LENGTH: 583
<212> TYPE: PRT
<213> ORGANISM: Artificial Sequence
<220> FEATURE:
<223> OTHER INFORMATION: mIgG Heavy Chain IgG 1/3 hybrid anti-biotin
      heavy chain - E325A, T323A mutant

<400> SEQUENCE: 43

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

-continued

Tyr Cys Val Lys His Thr Asn Trp Asp Gly Gly Phe Ala Tyr Trp Gly
                115                 120                 125

Gln Gly Thr Thr Val Thr Val Ser Ser Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Leu Lys Thr Pro
225                 230                 235                 240

Leu Gly Asp Thr Thr His Thr Cys Pro Arg Cys Pro Glu Pro Lys Ser
                245                 250                 255

Cys Asp Thr Pro Pro Cys Pro Arg Cys Pro Glu Pro Lys Ser Cys
        260                 265                 270

Asp Thr Pro Pro Pro Cys Pro Arg Cys Pro Glu Pro Lys Ser Cys Asp
            275                 280                 285

Thr Pro Pro Pro Cys Pro Arg Cys Pro Ala Pro Glu Leu Leu Gly Gly
        290                 295                 300

Pro Ser Val Phe Leu Phe Pro Pro Lys Pro Lys Asp Thr Leu Met Ile
305                 310                 315                 320

Ser Arg Ala Pro Ala Val Thr Cys Val Val Val Asp Val Ser His Glu
                325                 330                 335

Asp Pro Glu Val Lys Phe Asn Trp Tyr Val Asp Gly Val Glu Val His
            340                 345                 350

Asn Ala Lys Thr Lys Pro Arg Glu Glu Gln Tyr Asn Ser Thr Tyr Arg
        355                 360                 365

Val Val Ser Val Leu Thr Val Leu His Gln Asp Trp Leu Asn Gly Lys
    370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
            420                 425                 430

Thr Cys Leu Val Lys Gly Phe Tyr Pro Ser Asp Ile Ala Val Glu Trp
        435                 440                 445

Glu Ser Asn Gly Gln Pro Glu Asn Asn Tyr Lys Thr Thr Pro Pro Val
    450                 455                 460

Leu Asp Ser Asp Gly Ser Phe Phe Leu Tyr Ser Lys Leu Thr Val Asp
465                 470                 475                 480

Lys Ser Arg Trp Gln Gln Gly Asn Val Phe Ser Cys Ser Val Met His
                485                 490                 495

Glu Ala Leu His Asn His Tyr Thr Gln Lys Ser Leu Ser Leu Ser Pro
            500                 505                 510

Gly Leu Gln Leu Glu Glu Ser Cys Ala Glu Ala Gln Asp Gly Glu Leu
        515                 520                 525

Asp Gly Leu Trp Thr Thr Ile Thr Ile Phe Ile Thr Leu Phe Leu Leu

```
                530             535             540
Ser Val Cys Tyr Ser Ala Thr Val Thr Phe Phe Lys Val Lys Trp Ile
545                 550                 555                 560

Phe Ser Ser Val Val Asp Leu Lys Gln Thr Ile Ile Pro Asp Tyr Arg
                565                 570                 575

Asn Met Ile Gly Gln Gly Ala
            580

<210> SEQ ID NO 44
<211> LENGTH: 183
<212> TYPE: PRT
<213> ORGANISM: Artificial Sequence
<220> FEATURE:
<223> OTHER INFORMATION: Soluble Flt3-L

<400> SEQUENCE: 44

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
        50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln
            180

<210> SEQ ID NO 45
<211> LENGTH: 583
<212> TYPE: PRT
<213> ORGANISM: Artificial Sequence
<220> FEATURE:
<223> OTHER INFORMATION: mIgG Heavy Chain IgG 1/3 hybrid anti-biotin
      heavy chain

<400> SEQUENCE: 45

Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
                20                  25                  30

Pro Ser Gln Ser Leu Ser Ile Thr Cys Thr Val Ser Gly Phe Ser Leu
            35                  40                  45

Thr Ala Tyr Gly Val Asp Trp Val Arg Gln Pro Pro Gly Lys Gly Leu
        50                  55                  60
```

```
Glu Trp Leu Gly Val Ile Trp Gly Gly Arg Thr Asn Tyr Asn Ser
 65                  70                  75                  80

Gly Leu Met Ser Arg Leu Ser Ile Arg Lys Asp Asn Ser Lys Ser Gln
                 85                  90                  95

Val Phe Leu Thr Met Asn Ser Leu Gln Thr Asp Thr Ala Lys Tyr
                100                 105                 110

Tyr Cys Val Lys His Thr Asn Trp Asp Gly Phe Ala Tyr Trp Gly
                115                 120                 125

Gln Gly Thr Thr Val Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Lys Val Glu Leu Lys Thr Pro
225                 230                 235                 240

Leu Gly Asp Thr Thr His Thr Cys Pro Arg Cys Pro Glu Pro Lys Ser
                245                 250                 255

Cys Asp Thr Pro Pro Cys Pro Arg Cys Pro Glu Pro Lys Ser Cys
                260                 265                 270

Asp Thr Pro Pro Cys Pro Arg Cys Pro Glu Pro Lys Ser Cys Asp
                275                 280                 285

Thr Pro Pro Pro Cys Pro Arg Cys Pro Ala Pro Glu Leu Leu Gly Gly
                290                 295                 300

Pro Ser Val Phe Leu Phe Pro Pro Lys Pro Lys Asp Thr Leu Met Ile
305                 310                 315                 320

Ser Arg Thr Pro Glu Val Thr Cys Val Val Asp Val Ser His Glu
                325                 330                 335

Asp Pro Glu Val Lys Phe Asn Trp Tyr Val Asp Gly Val Glu Val His
                340                 345                 350

Asn Ala Lys Thr Lys Pro Arg Glu Glu Gln Tyr Asn Ser Thr Tyr Arg
                355                 360                 365

Val Val Ser Val Leu Thr Val Leu His Gln Asp Trp Leu Asn Gly Lys
                370                 375                 380

Glu Tyr Lys Cys Lys Val Ser Asn Lys Ala Leu Pro Ala Pro Ile Glu
385                 390                 395                 400

Lys Thr Ile Ser Lys Ala Lys Gly Gln Pro Arg Glu Pro Gln Val Tyr
                405                 410                 415

Thr Leu Pro Pro Ser Arg Asp Glu Leu Thr Lys Asn Gln Val Ser Leu
                420                 425                 430

Thr Cys Leu Val Lys Gly Phe Tyr Pro Ser Asp Ile Ala Val Glu Trp
                435                 440                 445

Glu Ser Asn Gly Gln Pro Glu Asn Asn Tyr Lys Thr Thr Pro Pro Val
                450                 455                 460

Leu Asp Ser Asp Gly Ser Phe Phe Leu Tyr Ser Lys Leu Thr Val Asp
465                 470                 475                 480
```

```
Lys Ser Arg Trp Gln Gln Gly Asn Val Phe Ser Cys Ser Val Met His
                485                 490                 495
Glu Ala Leu His Asn His Tyr Thr Gln Lys Ser Leu Ser Leu Ser Pro
            500                 505                 510
Glu Leu Gln Leu Glu Glu Ser Cys Ala Glu Ala Gln Asp Gly Glu Leu
            515                 520                 525
Asp Gly Leu Trp Thr Thr Ile Thr Ile Phe Ile Thr Leu Phe Leu Leu
            530                 535                 540
Ser Val Cys Tyr Ser Ala Thr Val Thr Phe Phe Lys Val Lys Trp Ile
545                 550                 555                 560
Phe Ser Ser Val Val Asp Leu Lys Gln Thr Ile Ile Pro Asp Tyr Arg
                565                 570                 575
Asn Met Ile Gly Gln Gly Ala
                580

<210> SEQ ID NO 46
<211> LENGTH: 227
<212> TYPE: PRT
<213> ORGANISM: Artificial Sequence
<220> FEATURE:
<223> OTHER INFORMATION: IgG Light Chain

<400> SEQUENCE: 46

Met Lys Tyr Leu Leu Pro Thr Ala Ala Ala Gly Leu Leu Leu Leu Ala
1               5                   10                  15
Ala Gln Pro Ala Met Ala Gly Ser Pro Gly Gln Ser Val Ser Ile Ser
                20                  25                  30
Cys Ser Gly Ser Ser Ser Asn Ile Gly Asn Asn Tyr Val Tyr Trp Tyr
            35                  40                  45
Gln His Leu Pro Gly Thr Ala Pro Lys Leu Leu Ile Tyr Ser Asp Thr
        50                  55                  60
Lys Arg Pro Ser Gly Val Pro Asp Arg Ile Ser Gly Ser Lys Ser Gly
65                  70                  75                  80
Thr Ser Ala Ser Leu Ala Ile Ser Gly Leu Gln Ser Glu Asp Glu Ala
                85                  90                  95
Asp Tyr Tyr Cys Ala Ser Trp Asp Asp Ser Leu Asp Gly Pro Val Phe
                100                 105                 110
Gly Gly Gly Thr Lys Leu Thr Val Leu Gly Gln Pro Lys Ala Asn Pro
            115                 120                 125
Thr Val Thr Leu Phe Pro Pro Ser Ser Glu Glu Leu Gln Ala Asn Lys
        130                 135                 140
Ala Thr Leu Val Cys Leu Ile Ser Asp Phe Tyr Pro Gly Ala Val Thr
145                 150                 155                 160
Val Ala Trp Lys Ala Asp Gly Ser Pro Val Lys Ala Gly Val Glu Thr
                165                 170                 175
Thr Lys Pro Ser Lys Gln Ser Asn Asn Lys Tyr Ala Ala Ser Ser Tyr
            180                 185                 190
Leu Ser Leu Thr Pro Glu Gln Trp Lys Ser His Arg Ser Tyr Ser Cys
        195                 200                 205
Gln Val Thr His Glu Gly Ser Thr Val Glu Lys Thr Val Ala Pro Thr
    210                 215                 220
Glu Cys Ser
225

<210> SEQ ID NO 47
<211> LENGTH: 9203
```

```
<212> TYPE: DNA
<213> ORGANISM: Artificial Sequence
<220> FEATURE:
<223> OTHER INFORMATION: Vector 1

<400> SEQUENCE: 47
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaa     600
attagatcgc gatgggaaaa aattcggtta aggccagggg gaagaaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaagggggg gattggggggg tacagtgcag gggaaagaat agtagacata    1860
atagcaacag acatacaaac taagaattta caaaaacaaa ttacaaaaat tcaaaatttt    1920
actagtgatt atcggatcaa cttttgtatag aaaagttggg ctccggtgcc cgtcagtggg    1980
cagagcgcac atcgcccaca gtccccgaga gttgggggg aggggtcggc aattgaaccg    2040
gtgcctagag aaggtggcgc ggggtaaact gggaaagtga tgtcgtgtac tggctccgcc    2100
ttttttcccga gggtggggga gaaccgtata taagtgcagt agtcgccgtg aacgttcttt    2160
```

```
ttcgcaacgg gtttgccgcc agaacacagg taagtgccgt gtgtggttcc cgcgggcctg    2220
gcctctttac gggttatggc ccttgcgtgc cttgaattac ttccacctgg ctgcagtacg    2280
tgattcttga tcccgagctt cgggttggaa gtgggtggga gagttcgagg ccttgcgctt    2340
aaggagcccc ttcgcctcgt gcttgagttg aggcctggcc tgggcgctgg ggccgccgcg    2400
tgcgaatctg gtggcacctt cgcgcctgtc tcgctgcttt cgataagtct ctagccattt    2460
aaaattttg atgacctgct gcgacgcttt ttttctggca agatagtctt gtaaatgcgg    2520
gccaagatct gcacactggt atttcggttt ttggggccgc gggcggcgac ggggcccgtg    2580
cgtcccagcg cacatgttcg gcgaggcggg gcctgcgagc gcggccaccg agaatcggac    2640
gggggtagtc tcaagctggc cggcctgctc tggtgcctgg tctcgcgccg ccgtgtatcg    2700
ccccgcccctg gcgggcaagg ctggcccggt cggcaccagt tgcgtgagcg gaaagatggc    2760
cgcttcccgg ccctgctgca gggagctcaa aatggaggac gcggcgctcg ggagagcggg    2820
cgggtgagtc acccacacaa aggaaaaggg cctttccgtc ctcagccgtc gcttcatgtg    2880
actccacgga gtaccgggcg ccgtccaggc acctcgatta gttctcgagc ttttggagta    2940
cgtcgtcttt aggttggggg gaggggtttt atgcgatgga gtttccccac actgagtggg    3000
tggagactga agttaggcca gcttggcact tgatgtaatt ctccttggaa tttgcccttt    3060
ttgagtttgg atcttggttc attctcaagc ctcagacagt ggttcaaagt tttttcttc    3120
catttcaggt gtcgtgacaa gtttgtacaa aaaagcaggc tgccaccatg gagttcggcc    3180
tgagctgggt gttcctggtg gccctgttca gaggcgtgca gtgccaggtg aagctgcagg    3240
agagcggccc cggcctggtg gcccccagcc agagcctgag catcacctgc accgtgagcg    3300
gcttcagcct gaccgcctac ggcgtggact gggtgagaca gccccccggc aagtgcctgg    3360
agtggctggg cgtgatctgg ggcggcggca gaaccaacta caacagcggc ctgatgagca    3420
gactgagcat cagaaaggac aacagcaaga gccaggtgtt cctgaccatg aacagcctgc    3480
agaccgacga caccgccaag tactactgcg tgaagcacac caactgggac ggcggcttcg    3540
cctactgggg ccagggcacc accgtgaccg tgagcagcgg cggcggcggc agcggcggcg    3600
gcggcagcgg cggcggcggc agcggcagcc cggccagag cgtgagcatc agctgcagcg    3660
gcagcagcag caacatcggc aacaactacg tgtactggta ccagcacctg cccggcaccg    3720
cccccaagct gctgatctac agcgacacca gagacccag cggcgtgccc gacagaatca    3780
gcggcagcaa gagcggcacc agcgccagcc tggccatcag cggcctgcag agcgaggacg    3840
aggccgacta ctactgcgcc agctgggacg acagcctgga cggccccgtg ttcggctgcg    3900
gcaccaagct gaccgtgctg ctgaagaccc cctgggcga caccacccac acctgcccca    3960
gatgccccga gccaagagc tgcgacaccc ccccccctg cccagatgc cccgagccca    4020
agagctgcga cacccccccc ccctgcccca gatgcccga gccaagagc tgcgacaccc    4080
cccccctg cccagatgc cccgccccg agctgctggg cggccccagc gtgttcctgt    4140
tcccccccaa gcccaaggac accctgatga tcagcagagc cccgaggtg acctgcgtgg    4200
tggtggacgt gagccacgag gaccccgagg tgaagttcaa ctggtacgtg gacggcgtgg    4260
aggtgcacaa cgccaagacc aagcccgag aggagcagta caacagcacc tacagagtgg    4320
tgagcgtgct gaccgtgctg caccaggact ggctgaacgg caaggagtac aagtgcaagg    4380
tgagcaacaa ggccctgccc gcccccatcg aagagaccat cagcaaggcc aagggccagc    4440
ccagagagcc ccaggtgtac accctgcccc cagcagaga cgagctgacc aagaaccagg    4500
tgagcctgac ctgcctggtg aagggcttct accccagcga catcgccgtg gagtgggaga    4560
```

```
gcaacggcca gcccgagaac aactacaaga ccaccccccc cgtgctggac agcgacggca   4620
gcttcttcct gtacagcaag ctgaccgtgg acaagagcag atggcagcag ggcaacgtgt   4680
tcagctgcag cgtgatgcac gaggccctgc acaaccacta cacccagaag agcctgagcc   4740
tgagccccga gctgcagctg gaggagagct gcgccgaggc ccaggacggc gagctggacg   4800
gcctgtggac caccatcacc atcttcatca ccctgttcct gctgagcgtg tgctacagcg   4860
ccaccgtgac cttcttcaag gtgaagtgga tcttcagcag cgtggtggac ctgaagcaga   4920
ccatcatccc cgactacaga aacatgatcg ccagggcgc ctaaacccag ctttcttgta    4980
caaagtggtg ataatcgaat ctaaacccag ctttcttgt acaaagtggt gataatcgaa    5040
ttccgataat caacctctgg attacaaaat ttgtgaaaga ttgactggta ttcttaacta   5100
tgttgctcct tttacgctat gtggatacgc tgctttaatg cctttgtatc atgctattgc   5160
ttcccgtatg gctttcattt tctcctcctt gtataaatcc tggttgctgt ctctttatga   5220
ggagttgtgg cccgttgtca ggcaacgtgg cgtggtgtgc actgtgtttg ctgacgcaac   5280
ccccactggt tggggcattg ccaccacctg tcagctcctt tccgggactt tcgctttccc   5340
cctccctatt gccacggcgg aactcatcgc cgcctgcctt gcccgctgct ggacaggggc   5400
tcggctgttg ggcactgaca attccgtggt gttgtcgggg aagctgacgt cctttccatg   5460
gctgctcgcc tgtgttgcca cctggattct gcgcgggacg tccttctgct acgtcccttc   5520
ggccctcaat ccagcggacc ttccttcccg cggcctgctg ccggctctgc ggcctcttcc   5580
gcgtcttcgc cttcgccctc agacgagtcg gatctccctt gggccgcct cccgcatcg     5640 ggaattcccg cggttcgctt taagaccaat gacttacaag gcagctgtag atcttagcca   5700
ctttttaaaa gaaagggggg actggaagg gctaattcac tcccaacgaa gacaagatct     5760
gctttttgct tgtactgggt ctctctggtt agaccagatc tgagcctggg agctctctgg   5820
ctaactaggg aacccactgc ttaagcctca ataaagcttg ccttgagtgc ttcaagtagt   5880
gtgtgcccgt ctgttgtgtg actctggtaa ctagagatcc ctcagaccct tttagtcagt   5940
gtggaaaatc tctagcagta gtagttcatg tcatcttatt attcagtatt tataacttgc   6000
aaagaaatga atatcagaga gtgagaggaa cttgtttatt gcagcttata atggttacaa   6060
ataaagcaat agcatcacaa atttcacaaa taaagcattt ttttcactgc attctagttg   6120
tggtttgtcc aaactcatca atgtatctta tcatgtctgg ctctagctat cccgccccta   6180
actccgccca tcccgcccct aactccgccc agttccgccc attctccgcc ccatggctga   6240 ctaattttt tatttatgc agaggccgag gccgcctcgg cctctgagct attccagaag    6300
tagtgaggag gcttttttgg aggcctaggg acgtacccaa ttcgccctat agtgagtcgt   6360
attacgcgcg ctcactggcc gtcgttttac aacgtcgtga ctgggaaaac cctggcgtta   6420
cccaacttaa tcgccttgca gcacatcccc ctttcgccag ctggcgtaat agcgaagagg   6480
cccgcaccga tcgcccttcc caacagttgc gcagcctgaa tggcgaatgg gacgcgccct   6540
gtagcggcgc attaagcgcg gcgggtgtgg tggttacgcg cagcgtgacc gctacacttg   6600
ccagcgccct agcgcccgct cctttcgctt tcttcccttc ctttctcgcc acgttcgccg   6660
gctttccccg tcaagctcta aatcggggc tcccttagg gttccgattt agtgctttac     6720
ggcacctcga cccaaaaaa cttgattagg gtgatggttc acgtagtggg ccatcgccct    6780
gatagacggt ttttcgccct ttgacgttgg agtccacgtt ctttaatagt ggactcttgt   6840
tccaaactgg aacaacactc aaccctatct cggtctattc ttttgattta agggatttt    6900
```

```
tgccgatttc ggcctattgg ttaaaaaatg agctgattta caaaaatttt aacgcgaatt      6960
ttaacaaaat attaacgctt acaatttagg tggcacttttt cggggaaatg tgcgcggaac     7020
ccctatttgt ttattttct aaatacattc aaatatgtat ccgctcatga caataacc        7080 ctgataaatg cttcaataat attgaaaaag gaagagtatg agtattcaac atttccgtgt     7140
cgcccttatt ccctttttg cggcatttttg ccttcctgtt tttgctcacc cagaaacgct     7200
ggtgaaagta aaagatgctg aagatcagtt gggtgcacga gtgggttaca tcgaactgga     7260
tctcaacagc ggtaagatcc ttgagagttt tcgccccgaa gaacgttttc caatgatgag     7320
cacttttaaa gttctgctat gtggcgcggt attatcccgt attgacgccg ggcaagagca     7380
actcggtcgc cgcatacact attctcagaa tgacttggtt gagtactcac cagtcacaga     7440
aaagcatctt acgatggca tgacagtaag agaattatgc agtgctgcca taaccatgag     7500
tgataacact gcggccaact tacttctgac aacgatcgga ggaccgaagg agctaaccgc     7560 tttttttgcac aacatggggg atcatgtaac tcgccttgat cgttgggaac cggagctgaa     7620
tgaagccata ccaaacgacg agcgtgacac cacgatgcct gtagcaatgg caacaacgtt     7680
gcgcaaacta ttaactggcg aactacttac tctagcttcc cggcaacaat taatagactg     7740
gatggaggcg gataaagttg caggaccact tctgcgctcg gcccttccgg ctggctggtt     7800
tattgctgat aaatctggag ccggtgagcg tgggtctcgc ggtatcattg cagcactggg     7860
gccagatggt aagccctccc gtatcgtagt tatctacacg acggggagtc aggcaactat     7920
ggatgaacga atagacaga tcgctgagat aggtgcctca ctgattaagc attggtaact     7980
gtcagaccaa gtttactcat atatacttta gattgattta aaacttcatt tttaatttaa     8040
aaggatctag gtgaagatcc tttttgataa tctcatgacc aaaatccctt aacgtgagtt     8100
ttcgttccac tgagcgtcag accccgtaga aagatcaaa ggatcttctt gagatccttt      8160
ttttctgcgc gtaatctgct gcttgcaaac aaaaaaacca ccgctaccag cggtggtttg     8220
tttgccggat caagagctac caactctttt tccgaaggta actggcttca gcagagcgca     8280
gataccaaat actgttcttc tagtgtagcc gtagttaggc caccacttca agaactctgt     8340
agcaccgcct acatacctcg ctctgctaat cctgttacca gtggctgctg ccagtggcga     8400
taagtcgtgt cttaccgggt tggactcaag acgatagtta ccggataagg cgcagcggtc     8460
gggctgaacg ggggtttcgt gcacacagcc cagcttggag cgaacgacct acaccgaact     8520
gagataccta cagcgtgagc tatgagaaag cgccacgctt cccgaagaga aaaggcgga     8580 caggtatccg gtaagcggca gggtcggaac aggagagcgc acgagggagc ttccagggg     8640 aaacgcctgg tatctttata gtcctgtcgg gtttcgccac ctctgacttg agcgtcgatt     8700
tttgtgatgc tcgtcagggg ggcggagcct atggaaaaac gccagcaacg cggcctttt      8760 acggttcctg gccttttgct ggccttttgc tcacatgttc tttcctgcgt tatccctga      8820 ttctgtggat aaccgtatta ccgcctttga gtgagctgat accgctcgcc gcagccgaac     8880
gaccgagcgc agcgagtcag tgagcgagga agcggaagag cgcccaatac gcaaaccgcc     8940
tctccccgcg cgttggccga ttcattaatg cagctggcac gacaggtttc ccgactggaa     9000
agcgggcagt gagcgcaacg caattaatgt gagttagctc actcattagg caccccaggc     9060
tttacacttt atgcttccgg ctcgtatgtt gtgtggaatt gtgagcggat aacaatttca     9120
cacaggaaac agctatgacc atgattacgc caagcgcgca attaaccctc actaaaggga     9180
acaaaagctg gagctgcaag ctt                                              9203
```

```
<210> SEQ ID NO 48
<211> LENGTH: 10862
<212> TYPE: DNA
<213> ORGANISM: Artificial Sequence
<220> FEATURE:
<223> OTHER INFORMATION: Vector 2

<400> SEQUENCE: 48
```

| | | | | | |
|---|---|---|---|---|---|
| aatgtagtct | tatgcaatac | tcttgtagtc | ttgcaacatg | gtaacgatga | gttagcaaca | 60 |
| tgccttacaa | ggagagaaaa | agcaccgtgc | atgccgattg | gtggaagtaa | ggtggtacga | 120 |
| tcgtgcctta | ttaggaaggc | aacagacggg | tctgacatgg | attggacgaa | ccactgaatt | 180 |
| gccgcattgc | agagatattg | tatttaagtg | cctagctcga | tacataaacg | ggtctctctg | 240 |
| gttagaccag | atctgagcct | gggagctctc | tggctaacta | gggaacccac | tgcttaagcc | 300 |
| tcaataaagc | ttgccttgag | tgcttcaagt | agtgtgtgcc | cgtctgttgt | gtgactctgg | 360 |
| taactagaga | tccctcagac | ccttttagtc | agtgtggaaa | atctctagca | gtggcgcccg | 420 |
| aacagggact | tgaaagcgaa | agggaaacca | gaggagctct | ctcgacgcag | gactcggctt | 480 |
| gctgaagcgc | gcacggcaag | aggcgagggg | cggcgactgg | tgagtacgcc | aaaaattttg | 540 |
| actagcggag | gctagaagga | gagagatggg | tgcgagagcg | tcagtattaa | gcggggagaa | 600 |
| attagatcgc | gatgggaaaa | aattcggtta | aggccagggg | gaaagaaaaa | atataaatta | 660 |
| aaacatatag | tatgggcaag | cagggagcta | gaacgattcg | cagttaatcc | tggcctgtta | 720 |
| gaaacatcag | aaggctgtag | acaaatactg | ggacagctac | aaccatccct | tcagacagga | 780 |
| tcagaagaac | ttagatcatt | atataataca | gtagcaaccc | tctattgtgt | gcatcaaagg | 840 |
| atagagataa | aagacaccaa | ggaagcttta | gacaagatag | aggaagagca | aaacaaaagt | 900 |
| aagaccaccg | cacagcaagc | ggccgctgat | cttcagacct | ggaggaggag | atatgaggga | 960 |
| caattggaga | agtgaattat | ataaatataa | agtagtaaaa | attgaaccat | taggagtagc | 1020 |
| acccaccaag | gcaaagagaa | gagtggtgca | gagagaaaaa | agagcagtgg | gaataggagc | 1080 |
| tttgttcctt | gggttcttgg | gagcagcagg | aagcactatg | ggcgcagcgt | caatgacgct | 1140 |
| gacggtacag | gccagacaat | tattgtctgg | tatagtgcag | cagcagaaca | atttgctgag | 1200 |
| ggctattgag | gcgcaacagc | atctgttgca | actcacagtc | tggggcatca | agcagctcca | 1260 |
| ggcaagaatc | ctggctgtgg | aaagatacct | aaaggatcaa | cagctcctgg | ggatttgggg | 1320 |
| ttgctctgga | aaactcattt | gcaccactgc | tgtgccttgg | aatgctagtt | ggagtaataa | 1380 |
| atctctggaa | cagatttgga | atcacacgac | ctggatggag | tgggacagag | aaattaacaa | 1440 |
| ttacacaagc | ttaatacact | ccttaattga | agaatcgcaa | aaccagcaag | aaaagaatga | 1500 |
| acaagaatta | ttggaattag | ataaatgggc | aagtttgtgg | aattggttta | acataacaaa | 1560 |
| ttggctgtgg | tatataaaat | tattcataat | gatagtagga | ggcttggtag | gtttaagaat | 1620 |
| agttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggtatcgcta | 1800 |
| gcttttaaaa | gaaaggggg | gattggggg | tacagtgcag | gggaaagaat | agtagacata | 1860 |
| atagcaacag | acatacaaac | taagaattac | aaaaacaaa | ttacaaaaat | tcaaaatttt | 1920 |
| actagtatca | actttgtata | gaaaagttgg | gctccggtgc | ccgtcagtgg | gcagagcgca | 1980 |
| catcgcccac | agtccccgag | aagttggggg | gaggggtcgg | caattgaacc | ggtgcctaga | 2040 |
| gaaggtggcg | cggggtaaac | tgggaaagtg | atgtcgtgta | ctggctccgc | cttttcccg | 2100 |

```
agggtgggggg agaaccgtat ataagtgcag tagtcgccgt gaacgttctt tttcgcaacg    2160
ggtttgccgc cagaacacag gtaagtgccg tgtgtggttc ccgcgggcct ggcctcttta    2220
cgggttatgg cccttgcgtg ccttgaatta cttccacctg gctgcagtac gtgattcttg    2280
atcccgagct tcgggttgga agtgggtggg agagttcgag gccttgcgct taaggagccc    2340
cttcgcctcg tgcttgagtt gaggcctggc ctgggcgctg gggccgccgc gtgcgaatct    2400
ggtggcacct tcgcgcctgt ctcgctgctt tcgataagtc tctagccatt taaaattttt    2460
gatgacctgc tgcgacgctt ttttctggc aagatagtct tgtaaatgcg ggccaagatc    2520
tgcacactgg tatttcggtt tttggggccg cgggcggcga cggggcccgt gcgtcccagc    2580
gcacatgttc ggcgaggcgg ggcctgcgag cgcggccacc gagaatcgga cgggggtagt    2640
ctcaagctgg ccggcctgct ctggtgcctg gtctcgcgcc gccgtgtatc gccccgccct    2700
gggcggcaag gctggcccgg tcggcaccag ttgcgtgagc ggaaagatgg ccgcttcccg    2760
gccctgctgc agggagctca aaatggagga cgcggcgctc gggagagcgg gcgggtgagt    2820
cacccacaca aaggaaaagg gccttttccgt cctcagccgt cgcttcatgt gactccacgg    2880
agtaccgggc gccgtccagg cacctcgatt agttctcgag cttttggagt acgtcgtctt    2940
taggttgggg ggaggggttt tatgcgatgg agtttcccca cactgagtgg gtggagactg    3000
aagttaggcc agcttggcac ttgatgtaat tctccttgga atttgcccct tttgagtttg    3060
gatcttggtt cattctcaag cctcagacag tggttcaaag ttttttttctt ccatttcagg    3120
tgtcgtgaca agtttgtaca aaaaagcagg ctgccaccat ggagttcggc ctgagctggg    3180
tgttcctggt ggccctgttc agaggcgtgc agtgccaggt gaagctgcag gagagcggcc    3240
ccggcctggt ggcccccagc cagagcctga gcatcacctg caccgtgagc ggcttcagcc    3300
tgaccgccta cggcgtggac tgggtgagac agccccccgg caagggcctg gagtggctgg    3360
gcgtgatctg gggcggcggc agaaccaact acaacagcgg cctgatgagc agactgagca    3420
tcagaaagga caacagcaag agccaggtgt tcctgaccat gaacagcctg cagaccgacg    3480
acaccgccaa gtactactgc gtgaagcaca ccaactggga cggcggcttc gcctactggg    3540
gccagggcac caccgtgacc gtgagcagcc ccagcgtgtt cccccctggcc cccagcagca    3600
agagcaccag cggcggcacc gccgccctgg gctgcctggt gaaggactac ttccccgagc    3660
ccgtgaccgt gagctggaac agcggcgccc tgaccagcgg cgtgcacacc ttccccgccg    3720
tgctgcagag cagcggcctg tacagcctga gcagcgtggt gaccgtgccc agcagcagcc    3780
tgggcaccca gacctacatc tgcaacgtga accacaagcc cagcaacacc aaggtggaca    3840
agaaggtgga gctgaagacc cccctgggcg acaccaccca cacctgcccc agatgccccg    3900
agcccaagag ctgcgacacc cccccccct gccccagatg ccccgagccc aagagctgcg    3960
acaccccccc ccctgcccc agatgccccg agcccaagag ctgcgacacc cccccccct    4020
gccccagatg cccccgccccc gagctgctgg gcggccccag cgtgttcctg ttccccccca    4080
agcccaagga caccctgatg atcagcagag cccccgaggt gacctgcgtg gtggtggacg    4140
tgagccacga ggaccccgag gtgaagttca actggtacgt ggacggcgtg gaggtgcaca    4200
acgccaagac caagcccaga gaggagcagt acaacagcac ctacagagtg gtgagcgtgc    4260
tgaccgtgct gcaccaggac tggctgaacg gcaaggagta caagtgcaag gtgagcaaca    4320
aggcccctgcc cgccccatc gagaagacca tcagcaaggc caagggccag ccagagagc    4380
cccaggtgta caccctgccc cccagcagag acgagctgac caagaaccag gtgagcctga    4440
cctgcctggt gaagggcttc tacccagcg acatcgccgt ggagtgggag agcaacggcc    4500
```

-continued

```
agcccgagaa caactacaag accaccccc  ccgtgctgga cagcgacggc agcttcttcc   4560
tgtacagcaa gctgaccgtg gacaagagca gatggcagca gggcaacgtg ttcagctgca   4620
gcgtgatgca cgaggccctg cacaaccact acacccagaa gagcctgagc ctgagccccg   4680
agctgcagct ggaggagagc tgcgccgagc ccaggacgg  cgagctggac ggcctgtgga   4740
ccaccatcac catcttcatc accctgttcc tgctgagcgt gtgctacagc gccaccgtga   4800
ccttcttcaa ggtgaagtgg atcttcagca gcgtggtgga cctgaagcag accatcatcc   4860
ccgactacag aaacatgatc ggccagggcg cctaaaacaa caacaattgc attcatttta   4920
tgtttcaggt tcaggggag  gtgtgggagg tttttaaag  caagtaaaac ctctacaaat   4980
gtggtacgcg ttaacaacaa caattgcatt cattttatgt ttcaggttca ggggaggtg   5040 tgggaggttt tttaaagcaa gtaaaacctc tacaaatgtg gtacgcgtta cccagctttc   5100
ttgtacaaag tggtaaatag atagaacaac aacaattgca ttcattttg  atttcaggtt   5160 caggggagg  tgtgggaggt tttttaaagc aagtaaaacc tctacactga cggtacgcgt   5220
taacaacaac aattgcattc atttgtagtt tcaggttcag ggggaggtgt gggaggtttt   5280
ttaaagcaag ttaaacctct aaaatagtgg tacgcgttac ccagctttct tgtacaaagt   5340
ggacccagct ttcttgtaca agtgggccc  ctctccctcc ccccccccta acgttactgg   5400
ccgaagccgc ttggaataag gccggtgtgc gtttgtctat atgttatttt ccaccatatt   5460
gccgtctttt ggcaatgtga gggcccggaa acctggccct gtcttcttga cgagcattcc   5520
taggggtctt tcccctctcg ccaaaggaat gcaaggtctg ttgaatgtcg tgaaggaagc   5580
agttcctctg gaagcttctt gaagacaaac aacgtctgta gcgacccttt gcaggcagcg   5640 gaaccccca  cctggcgaca ggtgcctctg cggccaaaag ccacgtgtat aagatacacc   5700
tgcaaaggcg gcacaacccc agtgccacgt tgtgagttgg atagttgtgg aaagagtcaa   5760
atggctctcc tcaagcgtat caacaaggg  gctgaaggat gcccagaagg tacccattg   5820 tatgggatct gatctggggc ctcggtgcac atgctttaca tgtgtttagt cgaggttaaa   5880
aaaacgtcta ggccccccga accacgggga cgtggttttc ctttgaaaaa cacgatgata   5940
atatggccac aaccatggcc accgacatga gagtgcccgc ccagctgctg ggcctgctgc   6000
tgctgtggct gagcggcgcc agatgcggca gccccggcca gagcgtgagc atcagctgca   6060
gcggcagcag cagcaacatc ggcaacaact acgtgtactg gtaccagcac ctgccggca   6120 ccgcccccaa gctgctgatc tacagcgaca ccaagagacc cagcggcgtg cccgacagaa   6180
tcagcggcag caagagcggc accagcgcca gcctggccat cagcggcctg cagagcgagg   6240
acgaggccga ctactactgc gccagctggg acgacagcct ggacggcccc gtgttcggcg   6300
gcggcaccaa gctgaccgtg ctgggccagc ccaaggccaa ccccaccgtg accctgttcc   6360
cccccagcag cgaggagctg caggccaaca aggccaccct ggtgtgcctg atcagcgact   6420
tctaccccgg cgccgtgacc gtggcctgga aggccgacgg cagccccgtg aaggccggcg   6480
tggagaccac caagcccagc aagcagagca acaacaagta cgccgccagc agctacctga   6540
gcctgacccc cgagcagtgg aagagccaca gaagctacag ctgccaggtg acccacgagg   6600
gcagcaccgt ggagaagacc gtggcccca  ccgagtgcag ctaacaactt tattatacat   6660
agttgatcaa ttccaacttt attatacata gttgatcaat tccgataatc aacctctgga   6720
ttacaaaatt tgtgaaagat tgactggtat tcttaactat gttgctcctt ttacgctatg   6780
tggatacgct gctttaatgc ctttgtatca tgctattgct tcccgtatgg ctttcatttt   6840
```

```
ctcctccttg tataaatcct ggttgctgtc tctttatgag gagttgtggc ccgttgtcag    6900
gcaacgtggc gtggtgtgca ctgtgtttgc tgacgcaacc cccactggtt ggggcattgc    6960
caccacctgt cagctccttt ccgggacttt cgctttcccc ctccctattg ccacggcgga    7020
actcatcgcc gcctgccttg cccgctgctg acaggggct cggctgttgg gcactgacaa     7080
ttccgtggtg ttgtcgggga agctgacgtc ctttccatgg ctgctcgcct gtgttgccac    7140
ctggattctg cgcgggacgt ccttctgcta cgtcccttcg ccctcaatc cagcggacct     7200
tccttcccgc ggcctgctgc cggctctgcg gcctcttccg cgtcttcgcc ttcgccctca    7260
gacgagtcgg atctcccttt gggccgcctc ccgcatcgg gaattcccgc ggttcgcttt     7320
aagaccaatg acttacaagg cagctgtaga tcttagccac tttttaaaag aaaaggggg     7380
actggaaggg ctaattcact cccaacgaag acaagatctg cttttgctt gtactgggtc     7440
tctctggtta gaccagatct gagcctggga gctctctggc taactaggga acccactgct    7500
taagcctcaa taaagcttgc cttgagtgct tcaagtagtg tgtgcccgtc tgttgtgtga    7560
ctctggtaac tagagatccc tcagacccctt ttagtcagtg tggaaaatct ctagcagtag   7620
tagttcatgt catcttatta ttcagtattt ataacttgca aagaaatgaa tatcagagag    7680
tgagaggaac ttgtttattg cagcttataa tggttacaaa taaagcaata gcatcacaaa    7740
tttcacaaat aaagcatttt tttcactgca ttctagttgt ggtttgtcca aactcatcaa    7800
tgtatcttat catgtctggc tctagctatc ccgcccctaa ctccgcccat cccgccccta    7860
actccgccca gttccgccca ttctccgccc catggctgac taattttttt tatttatgca    7920
gaggccgagg ccgcctcggc ctctgagcta ttccagaagt agtgaggagg ctttttggga    7980
ggcctaggga cgtacccaat tcgccctata gtgagtcgta ttacgcgcgc tcactggccg    8040
tcgttttaca acgtcgtgac tgggaaaacc ctggcgttac ccaacttaat cgccttgcag    8100
cacatccccc tttcgccagc tggcgtaata gcgaagaggc ccgcaccgat cgcccttccc    8160
aacagttgcg cagcctgaat ggcgaatggg acgcgcctg tagcggcgca ttaagcgcgg     8220
cgggtgtggt ggttacgcgc agcgtgaccg ctacacttgc cagcgcccta gcgcccgctc    8280
cttcgctt cttcccttcc tttctcgcca cgttcgccgg cttcccccgt caagctctaa      8340
atcgggggct ccctttaggg ttccgattta gtgctttacg gcacctcgac cccaaaaaac    8400
ttgattaggg tgatggttca cgtagtgggc catcgccctg atagacggtt tttcgccctt    8460
tgacgttgga gtccacgttc tttaatagtg gactcttgtt ccaaactgga caacactca    8520
accctatctc ggtctattct tttgatttat aagggatttt gccgatttcg gcctattggt    8580
taaaaatga gctgatttaa caaaaattta acgcgaattt taacaaaata ttaacgctta    8640
caatttaggt ggcactttc ggggaaatgt gcgcggaacc cctatttgtt tatttttcta    8700
aatacattca aatatgtatc cgctcatgag acaataaccc tgataaatgc ttcaataata    8760
ttgaaaaagg aagagtatga gtattcaaca tttccgtgtc gcccttattc ccttttttgc    8820
ggcattttgc cttcctgttt ttgctcaccc agaaacgctg gtgaaagtaa aagatgctga    8880
agatcagttg ggtgcacgag tgggttacat cgaactggat ctcaacagcg gtaagatcct    8940
tgagagtttt cgccccgaag aacgttttcc aatgatgagc acttttaaag ttctgctatg    9000
tggcgcggta ttatcccgta ttgacgccgg gcaagagcaa ctcggtcgcc gcatacacta    9060
ttctcagaat gacttggttg agtactcacc agtcacagaa aagcatctta cggatggcat    9120
gacagtaaga gaattatgca gtgctgccat aaccatgagt gataacactg cggccaactt    9180
acttctgaca acgatcggag gaccgaagga gctaaccgct tttttgcaca acatggggga    9240
```

```
tcatgtaact cgccttgatc gttgggaacc ggagctgaat gaagccatac caaacgacga    9300
gcgtgacacc acgatgcctg tagcaatggc aacaacgttg cgcaaactat taactggcga    9360
actacttact ctagcttccc ggcaacaatt aatagactgg atggaggcgg ataaagttgc    9420
aggaccactt ctgcgctcgg cccttccggc tggctggttt attgctgata aatctggagc    9480
cggtgagcgt gggtctcgcg gtatcattgc agcactgggg ccagatggta agccctcccg    9540
tatcgtagtt atctcacacga cggggagtca ggcaactatg gatgaacgaa atagacagat    9600
cgctgagata ggtgcctcac tgattaagca ttggtaactg tcagaccaag tttactcata    9660
tatactttag attgatttaa aacttcattt ttaatttaaa aggatctagg tgaagatcct    9720
ttttgataat ctcatgacca aaatccctta acgtgagttt tcgttccact gagcgtcaga    9780
ccccgtagaa aagatcaaag gatcttcttg agatcctttt tttctgcgcg taatctgctg    9840
cttgcaaaca aaaaaaccac cgctaccagc ggtggtttgt ttgccggatc aagagctacc    9900
aactcttttt ccgaaggtaa ctggcttcag cagagcgcag ataccaaata ctgttcttct    9960
agtgtagccg tagttaggcc accacttcaa gaactctgta gcaccgccta catacctcgc   10020
tctgctaatc ctgttaccag tggctgctgc cagtggcgat aagtcgtgtc ttaccgggtt   10080
ggactcaaga cgatagttac cggataaggc gcagcggtcg ggctgaacgg ggggttcgtg   10140
cacacagccc agcttggagc gaacgaccta caccgaactg agatacctac agcgtgagct   10200
atgagaaagc gccacgcttc ccgaagagag aaaggcggac aggtatccgg taagcggcag   10260
ggtcggaaca ggagagcgca cgagggagct tccaggggga aacgcctggt atctttatag   10320
tcctgtcggg tttcgccacc tctgacttga gcgtcgattt ttgtgatgct cgtcaggggg   10380
gcggagccta tggaaaaacg ccagcaacgc ggcctttttta cggttcctgg ccttttgctg   10440
gccttttgct cacatgttct ttcctgcgtt atccctgat tctgtggata accgtattac   10500
cgcctttgag tgagctgata ccgctcgccg cagccgaacg accgagcgca gcgagtcagt   10560
gagcgaggaa gcggaagagc gcccaatacg caaaccgcct ctccccgcgc gttggccgat   10620
tcattaatgc agctggcacg acaggtttcc cgactggaaa gcgggcagtg agcgcaacgc   10680
aattaatgtg agttagctca ctcattaggc accccaggct ttacacttta tgcttccggc   10740
tcgtatgttg tgtggaattg tgagcggata acaatttcac acaggaaaca gctatgacca   10800
tgattacgcc aagcgcgcaa ttaaccctca ctaaagggaa caaagctggg agctgcaagc   10860
tt                                                                   10862
```

<210> SEQ ID NO 49
<211> LENGTH: 9581
<212> TYPE: DNA
<213> ORGANISM: Artificial Sequence
<220> FEATURE:
<223> OTHER INFORMATION: Vector 3

<400> SEQUENCE: 49

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
```

```
taactagaga tccctcagac cctttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaa     600
attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct gaggaggag atatgaggga     960 caattggaga agtgaattat ataaatataa agtagtaaaa attgaaccat taggagtagc    1020
acccaccaag gcaaagagaa gagtggtgca gagagaaaaa agagcagtgg aataggagc    1080 tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta cataacaaa    1560 ttggctgtgg tatataaaat tattcataat gatagtagga ggcttggtag gtttaagaat    1620
agtttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaagaat agtagacata    1860 atagcaacag acatacaaac taaagaatta caaaaacaaa ttacaaaaat tcaaaatttt    1920
actagtatca actttgtata gaaaagttgg ctccggtgc ccgtcagtgg gcagagcgca    1980
catcgcccac agtccccgag aagttggggg gaggggtcgg caattgaacc ggtgcctaga    2040
gaaggtggcg cggggtaaac tgggaaagtg atgtcgtgta ctggctccgc cttttcccg    2100 agggtggggg agaaccgtat ataagtgcag tagtcgccgt gaacgttctt tttcgcaacg    2160
ggtttgccgc cagaacacag gtaagtgccg tgtgtggttc ccgcgggcct ggcctcttta    2220
cgggttatgg cccttgcgtg ccttgaatta cttccacctg gctgcagtac gtgattcttg    2280
atcccgagct tcgggttgga agtgggtggg agagttcgag gccttgcgct taaggagccc    2340
cttcgcctcg tgcttgagtt gaggcctggc ctgggcgctg gggccgccgc gtgcgaatct    2400
ggtggcacct tcgcgcctgt ctcgctgctt tcgataagtc tctagccatt taaattttt    2460 gatgacctgc tgcgacgctt ttttctggc aagatagtct tgtaaatgcg ggccaagatc    2520
tgcacactgg tatttcggtt tttggggccg cgggcggcga cggggcccgt gcgtcccagc    2580
gcacatgttc ggcgaggcgg ggcctgcgag cgcggccacc gagaatcgga cgggggtagt    2640
ctcaagctgc ccgccctgct ctggtgcctg gtctcgcgcc gccgtgtatc gccccgccct    2700
gggcggcaag gctggcccgg tcggcaccag ttgcgtgagc ggaaagatgg ccgcttcccg    2760
```

```
gccctgctgc agggagctca aaatggagga cgcggcgctc gggagagcgg gcgggtgagt    2820
cacccacaca aaggaaaagg gcctttccgt cctcagccgt cgcttcatgt gactccacgg    2880
agtaccgggc gccgtccagg cacctcgatt agttctcgag cttttggagt acgtcgtctt    2940
taggttgggg ggaggggttt tatgcgatgg agtttcccca cactgagtgg gtggagactg    3000
aagttaggcc agcttggcac ttgatgtaat tctccttgga atttgccctt tttgagtttg    3060
gatcttggtt cattctcaag cctcagacag tggttcaaag ttttttttctt ccatttcagg    3120
tgtcgtgaca agtttgtaca aaaaagcagg ctgccaccat gtggctgcag agcctgctgc    3180
tgctgggcac cgtggcctgc agcatcagcg ccccgccag aagccccagc ccagcaccc      3240
agccctggga gcacgtgaac gccatccagg aggccagaag actgctgaac ctgagcagag    3300
acaccgccgc cgagatgaac gagaccgtgg aggtgatcag cgagatgttc gacctgcagg    3360
agcccacctg cctgcagacc agactggagc tgtacaagca gggcctgaga ggcagcctga    3420
ccaagctgaa gggcccctg accatgatgg ccagccacta caagcagcac tgcccccca    3480
cccccgagac cagctgcgcc acccagatca tcaccttcga gagcttcaag gagaacctga    3540
aggacttcct gctggtgatc cccttcgact gctgggagcc cgtgcaggag taaaacaaca    3600
acaattgcat tcattttatg tttcaggttc aggggaggt gtgggaggtt ttttaaagca     3660
agtaaaacct ctacaaatgt ggtacgcgtt aacaacaaca attgcattca ttttatgttt    3720
caggttcagg gggaggtgtg ggaggttttt taaagcaagt aaaacctcta caaatgtggt    3780
acgcgttacc cagcttttctt gtacaaagtg gtaaatagat agaacaacaa caattgcatt    3840
cattttttgat ttcaggttca gggggaggtg tgggaggttt tttaaagcaa gtaaaacctc    3900
tacactgacg gtacgcgtta acaacaacaa ttgcattcat ttgtagtttc aggttcaggg    3960
ggaggtgtgg gaggtttttt aaagcaagtt aaacctctaa aatagtggta cgcgttaccc    4020
agctttcttg tacaaagtgg acccagcttt cttgtacaaa gtgggcccct ctccctcccc    4080
ccccctaac gttactggcc gaagccgctt ggaataaggc cggtgtgcgt ttgtctatat      4140
gttattttcc accatattgc cgtcttttgg caatgtgagg gcccggaaac ctggccctgt    4200
cttcttgacg agcattccta ggggtctttc ccctctcgcc aaaggaatgc aaggtctgtt    4260
gaatgtcgtg aaggaagcag ttcctctgga agcttcttga agacaaacaa cgtctgtagc    4320
gaccctttgc aggcagcgga acccccacc tggcgacagg tgcctctgcg gccaaaagcc     4380
acgtgtataa gatacacctg caaaggcggc acaaccccag tgccacgttg tgagttggat    4440
agttgtggaa agagtcaaat ggctctcctc aagcgtattc aacaagggc tgaaggatgc     4500
ccagaaggta ccccattgta tgggatctga tctgggcct cggtgcacat gctttacatg     4560
tgtttagtcg aggttaaaaa aacgtctagg ccccccgaac cacggggacg tggttttcct    4620
ttgaaaaaca cgatgataat atggccacaa ccatggccac cgtgctggcc cccgcctgga    4680
gccccaccac ctacctgctg ctgctgctgc tgctgagcag cggcctgagc ggcacccagg    4740
actgcagctt ccagcacagc cccatcagca gcgacttcgc cgtgaagatc agagagctga    4800
gcgactacct gctgcaggac taccccgtga ccgtggccag caacctgcag gacgaggagc    4860
tgtgcggcgg cctgtggaga ctggtgctgg cccagagatg gatggagaga ctgaagaccg    4920
tggccggcag caagatgcag ggcctgctgg agagagtgaa caccgagatc cacttcgtga    4980
ccaagtgcgc cttccagccc ccccccagct gcctgagatt cgtgcagacc aacatcagca    5040
gactgctgca ggagaccagc gagcagctgg tggccctgaa gccctggatc accagacaga    5100
```

-continued

| | |
|---|---|
| acttcagcag atgcctggag ctgcagtgcc agcccgacag cagcaccctg ccccccccct | 5160 |
| ggagccccag acccctggag gccaccgccc ccaccgcccc ccagcccccc ctgctgctgc | 5220 |
| tgctgctgct gcccgtgggc tgctgctgc tggccgccgc ctggtgcctg cactggcaga | 5280 |
| gaaccagaag aagaaccccc agacccggcg agcaggtgcc ccccgtgccc agccccagg | 5340 |
| acctgctgct ggtggagcac taacaacttt attatacata gttgatcaat ccaacttta | 5400 |
| ttatacatag ttgatcaatt ccgataatca acctctggat tacaaaattt gtgaaagatt | 5460 |
| gactggtatt cttaactatg ttgctccttt tacgctatgt ggatacgctg ctttaatgcc | 5520 |
| tttgtatcat gctattgctt cccgtatggc tttcattttc tcctccttgt ataaatcctg | 5580 |
| gttgctgtct ctttatgagg agttgtggcc cgttgtcagg caacgtggcg tggtgtgcac | 5640 |
| tgtgtttgct gacgcaaccc ccactggttg gggcattgcc accacctgtc agctcctttc | 5700 |
| cgggactttc gctttccccc tccctattgc cacggcggaa ctcatcgccg cctgccttgc | 5760 |
| ccgctgctgg acaggggctc ggctgttggg cactgacaat tccgtggtgt tgtcggggaa | 5820 |
| gctgacgtcc tttccatggc tgctcgcctg tgttgccacc tggattctgc gcgggacgtc | 5880 |
| cttctgctac gtcccttcgg ccctcaatcc agcggacctt ccttcccgcg gcctgctgcc | 5940 |
| ggctctgcgg cctcttccgc gtcttcgcct tcgcctcag acgagtcgga tctccctttg | 6000 |
| ggccgcctcc ccgcatcggg aattcccgcg gttcgcttta agaccaatga cttacaaggc | 6060 |
| agctgtagat cttagccact ttttaaaaga aaggggggga ctggaagggc taattcactc | 6120 |
| ccaacgaaga caagatctgc tttttgcttg tactgggtct ctctggttag accagatctg | 6180 |
| agcctgggag ctctctggct aactagggaa cccactgctt aagcctcaat aaagcttgcc | 6240 |
| ttgagtgctt caagtagtgt gtgcccgtct gttgtgtgac tctggtaact agagatccct | 6300 |
| cagacccttt tagtcagtgt ggaaaatctc tagcagtagt agttcatgtc atcttattat | 6360 |
| tcagtattta aacttgcaa agaaatgaat atcagagagt gagaggaact tgtttattgc | 6420 |
| agcttataat ggttacaaat aaagcaatag catcacaaat ttcacaaata aagcattttt | 6480 |
| ttcactgcat tctagttgtg gtttgtccaa actcatcaat gtatcttatc atgtctggct | 6540 |
| ctagctatcc cgcccctaac tccgcccatc ccgcccctaa ctccgcccag ttccgcccat | 6600 |
| tctccgcccc atggctgact aattttttt atttatgcag aggccgaggc cgcctcggcc | 6660 |
| tctgagctat tccagaagta gtgaggaggc ttttttggag gcctagggac gtacccaatt | 6720 |
| cgccctatag tgagtcgtat tacgcgcgct cactggccgt cgttttacaa cgtcgtgact | 6780 |
| gggaaaaccc tggcgttacc caacttaatc gccttgcagc acatccccct ttcgccagct | 6840 |
| ggcgtaatag cgaagaggcc cgcaccgatc gcccttccca acagttgcgc agcctgaatg | 6900 |
| gcgaatggga cgcgccctgt agcggcgcat taagcgcggc gggtgtggtg gttacgcgca | 6960 |
| gcgtgaccgc tacacttgcc agcgccctag cgcccgctcc tttcgctttc ttcccttcct | 7020 |
| ttctcgccac gttcgccggc tttccccgtc aagctctaaa tcggggggctc cctttagggt | 7080 |
| tccgatttag tgctttacgg cacctcgacc ccaaaaaact tgattagggt gatggttcac | 7140 |
| gtagtgggcc atcgccctga tagacggttt ttcgcccttt gacgttggag tccacgttct | 7200 |
| ttaatagtgg actcttgttc caaactggaa caacactcaa ccctatctcg gtctattctt | 7260 |
| ttgatttata agggattttg ccgatttcgg cctattggtt aaaaaatgag ctgatttaac | 7320 |
| aaaaatttaa cgcgaatttt aacaaaatat taacgcttac aatttaggtg cacttttcg | 7380 |
| gggaaatgtg cgcggaaccc ctatttgttt atttttctaa atacattcaa atatgtatcc | 7440 |
| gctcatgaga caataaccct gataaatgct tcaataatat tgaaaaagga agagtatgag | 7500 |

```
tattcaacat ttccgtgtcg cccttattcc cttttttgcg gcatttttgcc ttcctgtttt    7560 tgctcaccca gaaacgctgg tgaaagtaaa agatgctgaa gatcagttgg gtgcacgagt    7620
gggttacatc gaactggatc tcaacagcgg taagatcctt gagagttttc gccccgaaga    7680
acgttttcca atgatgagca cttttaaagt tctgctatgt ggcgcggtat tatcccgtat    7740
tgacgccggg caagagcaac tcggtcgccg catacactat tctcagaatg acttggttga    7800
gtactcacca gtcacagaaa agcatcttac ggatggcatg acagtaagag aattatgcag    7860
tgctgccata accatgagtg ataacactgc ggccaactta cttctgacaa cgatcggagg    7920
accgaaggag ctaaccgctt ttttgcacaa catgggggat catgtaactc gccttgatcg    7980
ttgggaaccg gagctgaatg aagccatacc aaacgacgag cgtgacacca cgatgcctgt    8040
agcaatggca acaacgttgc gcaaactatt aactggcgaa ctacttactc tagcttcccg    8100
gcaacaatta atagactgga tggaggcgga taaagttgca ggaccacttc tgcgctcggc    8160
ccttccggct ggctggttta ttgctgataa atctggagcc ggtgagcgtg gtctcgcgg    8220 tatcattgca gcactggggc cagatggtaa gccctcccgt atcgtagtta tctacacgac    8280
ggggagtcag gcaactatgg atgaacgaaa tagacagatc gctgagatag gtgcctcact    8340
gattaagcat tggtaactgt cagaccaagt ttactcatat atactttaga ttgatttaaa    8400
acttcatttt taatttaaaa ggatctaggt gaagatcctt tttgataatc tcatgaccaa    8460
aatcccttaa cgtgagtttt cgttccactg agcgtcagac cccgtagaaa agatcaaagg    8520
atcttcttga tccttttttt ttctgcgcgt aatctgctgc ttgcaaacaa aaaaaccacc    8580
gctaccagcg gtggtttgtt tgccggatca agagctacca actcttttc cgaaggtaac    8640 tggcttcagc agagcgcaga taccaaatac tgttcttcta gtgtagccgt agttaggcca    8700
ccacttcaag aactctgtag caccgcctac atacctcgct ctgctaatcc tgttaccagt    8760
ggctgctgcc agtggcgata gtcgtgtct taccggggttg gactcaagac gatagttacc    8820
ggataaggcg cagcggtcgg gctgaacggg gggttcgtgc acacagccca gcttggagcg    8880
aacgacctac accgaactga gatacctaca gcgtgagcta tgagaaagcg ccacgcttcc    8940
cgaagagaga aaggcggaca ggtatccggt aagcggcagg gtcggaacag gagagcgcac    9000
gagggagctt ccagggggaa acgcctggta tctttatagt cctgtcgggt ttcgccacct    9060
ctgacttgag cgtcgatttt tgtgatgctc gtcaggggg cggagcctat ggaaaaacgc    9120
cagcaacgcg gcctttttac ggttcctggc cttttgctgg ccttttgctc acatgttctt    9180
tcctgcgtta tcccctgatt ctgtggataa ccgtattacc gcctttgagt gagctgatac    9240
cgctcgccgc agccgaacga ccgagcgcag cgagtcagtg agcgaggaag cggaagagcg    9300
cccaatacgc aaaccgcctc tccccgcgcg ttggccgatt cattaatgca gctggcacga    9360
caggtttccc gactggaaag cgggcagtga gcgcaacgca attaatgtga gttagctcac    9420
tcattaggca ccccaggctt tacactttat gcttccggct cgtatgttgt gtggaattgt    9480
gagcggataa caatttcaca caggaaacag ctatgaccat gattacgcca agcgcgcaat    9540
taaccctcac taaagggaac aaaagctgga gctgcaagct t                       9581
```

<210> SEQ ID NO 50
<211> LENGTH: 9746
<212> TYPE: DNA
<213> ORGANISM: Artificial Sequence
<220> FEATURE:
<223> OTHER INFORMATION: Vector 4

```
<400> SEQUENCE: 50
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggggaga    600 attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta acaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaaagaat agtagacata    1860
atagcaacag acatacaaac taagaatta caaaaacaaa ttacaaaaat tcaaaatttt     1920
actagtatca actttgtata gaaaagttgg ctccggtgc ccgtcagtgg gcagagcgca    1980
catcgcccac agtccccgag aagttggggg gaggggtcgg caattgaacc ggtgcctaga    2040
gaaggtggcg cggggtaaac tgggaaagtg atgtcgtgta ctggctccgc ctttttcccg    2100 agggtgggggg agaaccgtat ataagtgcag tagtcgccgt gaacgttctt tttcgcaacg    2160
ggtttgccgc cagaacacag gtaagtgccg tgtgtggttc ccgcgggcct ggcctcttta    2220
cgggttatgg cccttgcgtg ccttgaatta cttccacctg gctgcagtac gtgattcttg    2280
atcccgagct tcgggttgga agtgggtggg agagttcgag gccttgcgct taaggagccc    2340
```

```
cttcgcctcg tgcttgagtt gaggcctggc ctgggcgctg gggccgccgc gtgcgaatct      2400
ggtggcacct tcgcgcctgt ctcgctgctt tcgataagtc tctagccatt taaaattttt      2460
gatgacctgc tgcgacgctt ttttctggc aagatagtct tgtaaatgcg ggccaagatc       2520
tgcacactgg tatttcggtt tttggggccg cggggcggcga cggggcccgt gcgtcccagc     2580
gcacatgttc ggcgaggcgg ggcctgcgag cgcggccacc gagaatcgga cggggggtagt    2640 ctcaagctgg ccggcctgct ctggtgcctg gtctcgcgcc gccgtgtatc gccccgccct      2700
gggcggcaag gctggcccgg tcggcaccag ttgcgtgagc ggaaagatgg ccgcttcccg     2760
gccctgctgc agggagctca aaatggagga cgcggcgctc gggagagcgg gcgggtgagt     2820
cacccacaca aaggaaaagg gccttccgt cctcagccgt cgcttcatgt gactccacgg       2880
agtaccgggc gccgtccagg cacctcgatt agttctcgag cttttggagt acgtcgtctt      2940
taggttgggg ggaggggttt tatgcgatgg agtttcccca cactgagtgg gtggagactg    3000
aagttaggcc agcttggcac ttgatgtaat tctccttgga atttgccctt tttgagtttg     3060
gatcttggtt cattctcaag cctcagacag tggttcaaag ttttttttctt ccatttcagg    3120 tgtcgtgaca agtttgtaca aaaaagcagg ctgccaccat gaccgtgctg gcccccgcct     3180
ggagccccac cacctacctg ctgctgctgc tgctgctgag cagcggcctg agcggcaccc     3240
aggactgcag cttccagcac agccccatca gcagcgactt cgccgtgaag atcagagagc     3300
tgagcgacta cctgctgcag gactaccccg tgaccgtggc cagcaacctg caggacgagg     3360
agctgtgcgg cggcctgtgg agactggtgc tggcccagag atggatggag agactgaaga    3420
ccgtggccgg cagcaagatg cagggcctgc tggagagagt gaacaccgag atccacttcg     3480
tgaccaagtg cgccttccag cccccccccca gctgcctgag attcgtgcag accaacatca    3540
gcagactgct gcaggagacc agcgagcagc tggtggccct gaagccctgg atcaccagac    3600
agaacttcag cagatgcctg gagctgcagt gccagcccga cagcagcacc ctgccccccc     3660
cctggagccc cagacccctg gaggccaccg ccccccaccgc ccccccagtaa aacaacaaca     3720 attgcattca ttttatgttt caggttcagg gggaggtgtg ggaggttttt taaagcaagt     3780
aaaacctcta caaatgtggt acgcgttaac aacaacaatt gcattcattt tatgtttcag    3840
gttcaggggg aggtgtggga ggtttttttaa agcaagtaaa acctctacaa atgtggtacg    3900
cgttacccag cttctttcttgta caaagtggta aatagataga caacaacaa ttgcattcat    3960 ttttgatttc aggttcaggg ggaggtgtgg gaggtttttt aaagcaagta aaacctctac    4020
actgacggta cgcgttaaca acaacaattg cattcatttg tagtttcagg ttcaggggga     4080
ggtgtgggag ttttttaaa gcaagttaaa cctctaaaat agtggtacgc gttacccagc     4140
tttcttgtac aaagtggacc cagctttctt gtacaaagtg ggcccctctc cctccccccc    4200
ccctaacgtt actggccgaa gccgcttgga ataaggccgg tgtgcgtttg tctatatgtt     4260 atttccacc atattgccgt cttttggcaa tgtgagggcc cggaaacctg gcctgtctt       4320 cttgacgagc attcctaggg gtctttcccc tctcgccaaa ggaatgcaag gtctgttgaa    4380
tgtcgtgaag gaagcagttc ctctggaagc ttcttgaaga caaacaacgt ctgtagcgac    4440
cctttgcagg cagcggaacc ccccacctgg cgacaggtgc tctgcggcc aaaagccacg     4500 tgtataagat acacctgcaa aggcggcaca accccagtgc cacgttgtga gttggatagt     4560
tgtggaaaga gtcaaatggc tctcctcaag cgtattcaac aaggggctga aggatgccca    4620
gaaggtaccc cattgtatgg gatctgatct ggggcctcgg tgcacatgct ttacatgtgt     4680
```

```
ttagtcgagg ttaaaaaaac gtctaggccc cccgaaccac ggggacgtgg ttttcctttg    4740
aaaaacacga tgataatatg gccacaacca tggccaccgt gctggccccc gcctggagcc    4800
ccaccaccta cctgctgctg ctgctgctgc tgagcagcgg cctgagcgcc cccgccagaa    4860
gccccagccc cagcacccag ccctgggagc acgtgaacgc catccaggag gccagaagac    4920
tgctgaacct gagcagagac accgccgccg agatgaacga gaccgtggag gtgatcagcg    4980
agatgttcga cctgcaggag cccacctgcc tgcagaccag actggagctg tacaagcagg    5040
gcctgagagg cagcctgacc aagctgaagg gccccctgac catgatggcc agccactaca    5100
agcagcactg ccccccccac cccgagacca gctgcgccac ccagatcatc accttcgaga    5160
gcttcaagga gaacctgaag gacttcctgc tggtgatccc cttcgactgc tgggagcccg    5220
tgcaggagcc caccaccacc cccgccccca gaccccccac cccgcccccc accatcgcca    5280
gccagcccct gagcctgaga cccgaggcct gcagacccgc cgcggcggc gccgtgcaca    5340
ccagaggcct ggacttcgcc tgcgacatct acatctgggc ccccctggcc ggcacctgcg    5400
gcgtgctgct gctgagcctg gtgatcaccc tgtactgcaa ccacagaaac agaagaagag    5460
tgtgcaagtg ccccagaccc gtggtgaaga gcggcgacaa gcccagcctg agcgccagat    5520
acgtgtaaca actttattat acatagttga tcaattccaa ctttattata catagttgat    5580
caattccgat aatcaacctc tggattacaa aatttgtgaa agattgactg gtattcttaa    5640
ctatgttgct ccttttacgc tatgtggata cgctgcttta atgcctttgt atcatgctat    5700
tgcttcccgt atggctttca ttttctcctc cttgtataaa tcctggttgc tgtctcttta    5760
tgaggagttg tggcccgttg tcaggcaacg tggcgtggtg tgcactgtgt ttgctgacgc    5820
aacccccact ggttggggca ttgccaccac ctgtcagctc cttccggga ctttcgcttt    5880
ccccctccct attgccacgg cggaactcat cgccgcctgc cttgcccgct gctggacagg    5940
ggctcggctg ttgggcactg acaattccgt ggtgttgtcg gggaagctga cgtccttttcc    6000
atggctgctc gcctgtgttg ccacctggat tctgcgcggg acgtccttct gctacgtccc    6060
ttcggccctc aatccagcgg accttccttc ccgcggcctg ctgccggctc tgcggcctct    6120
tccgcgtctt cgccttcgcc ctcagacgag tcggatctcc ctttgggccg cctccccgca    6180
tcgggaattc ccgcggttcg ctttaagacc aatgacttac aaggcagctg tagatcttag    6240
ccacttttta aaagaaaagg ggggactgga agggctaatt cactcccaac gaagacaaga    6300
tctgctttttt gcttgtactg ggtctctctg gttagaccag atctgagcct gggagctctc    6360
tggctaacta gggaacccac tgcttaagcc tcaataaagc ttgccttgag tgcttcaagt    6420
agtgtgtgcc cgtctgttgt gtgactctgg taactagaga tccctcagac ccttttagtc    6480
agtgtggaaa atctctagca gtagtagttc atgtcatctt attattcagt atttataact    6540
tgcaaagaaa tgaatatcag agagtgagag gaacttgttt attgcagctt ataatggtta    6600
caaataaagc aatagcatca caaatttcac aaataaagca ttttttcac tgcattctag    6660
ttgtggtttg tccaaactca tcaatgtatc ttatcatgtc tggctctagc tatcccgccc    6720
ctaactccgc ccatcccgcc cctaactccg cccagttccg cccattctcc gccccatggc    6780
tgactaattt ttttatttta tgcagaggcc gaggccgcct cggcctctga gctattccag    6840
aagtagtgag gaggcttttt tggaggccta gggacgtacc caattcgccc tatagtgagt    6900
cgtattacgc gcgctcactg gccgtcgttt tacaacgtcg tgactgggaa aaccctggcg    6960
ttacccaact taatcgcctt gcagcacatc cccctttcgc cagctggcgt aatagcgaag    7020
aggcccgcac cgatcgccct tcccaacagt tgcgcagcct gaatggcgaa tgggacgcgc    7080
```

```
cctgtagcgg cgcattaagc gcggcgggtg tggtggttac gcgcagccgtg accgctacac   7140
ttgccagcgc cctagcgccc gctcctttcg ctttcttccc ttcctttctc gccacgttcg   7200
ccggctttcc ccgtcaagct ctaaatcggg ggctcccttt agggttccga tttagtgctt   7260
tacggcacct cgaccccaaa aaacttgatt agggtgatgg ttcacgtagt gggccatcgc   7320
cctgatagac ggttttttcgc cctttgacgt tggagtccac gttctttaat agtggactct   7380
tgttccaaac tggaacaaca ctcaacccta tctcggtcta ttcttttgat ttataaggga   7440
ttttgccgat ttcggcctat tggttaaaaa atgagctgat ttaacaaaaa tttaacgcga   7500
attttaacaa aatattaacg cttacaattt aggtggcact tttcggggaa atgtgcgcgg   7560
aaccccctatt tgtttatttt tctaaataca ttcaaatatg tatccgctca tgagacaata   7620
accctgataa atgcttcaat aatattgaaa aaggaagagt atgagtattc aacatttccg   7680
tgtcgccctt attccctttt ttgcggcatt ttgccttcct gttttgctc acccagaaac   7740
gctggtgaaa gtaaaagatg ctgaagatca gttgggtgca cgagtgggtt acatcgaact   7800
ggatctcaac agcggtaaga tccttgagag ttttcgcccc gaagaacgtt ttccaatgat   7860
gagcactttt aaagttctgc tatgtggcgc ggtattatcc cgtattgacg ccgggcaaga   7920
gcaactcggt cgccgcatac actattctca gaatgacttg gttgagtact caccagtcac   7980
agaaaagcat cttacggatg gcatgacagt aagagaatta tgcagtgctg ccataaccat   8040
gagtgataac actgcggcca acttacttct gacaacgatc ggaggaccga aggagctaac   8100
cgcttttttg cacaacatgg gggatcatgt aactcgcctt gatcgttggg aaccggagct   8160
gaatgaagcc ataccaaacg acgagcgtga caccacgatg cctgtagcaa tggcaacaac   8220
gttgcgcaaa ctattaactg gcgaactact tactctagct tcccggcaac aattaataga   8280
ctggatggag gcggataaag ttgcaggacc acttctgcgc tcggcccttc cggctggctg   8340
gtttattgct gataaatctg gagccggtga gcgtgggtct cgcggtatca ttgcagcact   8400
ggggccagat ggtaagccct cccgtatcgt agttatctac acgacgggga gtcaggcaac   8460
tatgatgaa cgaaatagac agatcgctga gataggtgcc tcactgatta agcattggta   8520
actgtcagac caagtttact catatatact ttagattgat ttaaaacttc attttaatt   8580
taaaaggatc taggtgaaga tccttttga taatctcatg accaaaatcc cttaacgtga   8640
gttttcgttc cactgagcgt cagaccccgt agaaaagatc aaaggatctt cttgagatcc   8700
ttttttttctg cgcgtaatct gctgcttgca acaaaaaaa ccaccgctac cagcggtggt   8760
ttgtttgccg gatcaagagc taccaactct ttttccgaag gtaactggct tcagcagagc   8820
gcagatacca aatactgttc ttctagtgta gccgtagtta ggccaccact tcaagaactc   8880
tgtagcaccg cctacatacc tcgctctgct aatcctgtta ccagtggctg ctgccagtgg   8940
cgataagtcg tgtcttaccg ggttggactc aagacgatag ttaccggata aggcgcagcg   9000
gtcgggctga acggggggtt cgtgcacaca gcccagcttg gagcgaacga cctacaccga   9060
actgagatac ctacagcgtg agctatgaga aagcgccacg cttcccgaag agagaaaggc   9120
ggacaggtat ccggtaagcg gcagggtcgg aacaggagag cgcacgaggg agcttccagg   9180
gggaaacgcc tggtatcttt atagtcctgt cgggtttcgc cacctctgac ttgagcgtcg   9240
atttttgtga tgctcgtcag gggggcggag cctatggaaa aacgccagca acgcggcctt   9300
tttacggttc ctggcctttt gctggccttt tgctcacatg ttctttcctg cgttatcccc   9360
tgattctgtg gataaccgta ttaccgcctt tgagtgagct gataccgctc gccgcagccg   9420
```

| | |
|---|---|
| aacgaccgag cgcagcgagt cagtgagcga ggaagcggaa gagcgcccaa tacgcaaacc | 9480 |
| gcctctcccc gcgcgttggc cgattcatta atgcagctgg cacgacaggt ttcccgactg | 9540 |
| gaaagcgggc agtgagcgca acgcaattaa tgtgagttag ctcactcatt aggcacccca | 9600 |
| ggctttacac tttatgcttc cggctcgtat gttgtgtgga attgtgagcg ataacaatt | 9660 |
| tcacacagga acagctatg accatgatta cgccaagcgc gcaattaacc ctcactaaag | 9720 |
| ggaacaaaag ctggagctgc aagctt | 9746 |

```
<210> SEQ ID NO 51
<211> LENGTH: 8189
<212> TYPE: DNA
<213> ORGANISM: Artificial Sequence
<220> FEATURE:
<223> OTHER INFORMATION: Vector 5

<400> SEQUENCE: 51
```

| | |
|---|---|
| aatgtagtct tatgcaatac tcttgtagtc ttgcaacatg gtaacgatga gttagcaaca | 60 |
| tgccttacaa ggagagaaaa agcaccgtgc atgccgattg gtggaagtaa ggtggtacga | 120 |
| tcgtgcctta ttaggaaggc aacagacggg tctgacatgg attggacgaa ccactgaatt | 180 |
| gccgcattgc agagatattg tatttaagtg cctagctcga tacataaacg ggtctctctg | 240 |
| gttagaccag atctgagcct gggagctctc tggctaacta gggaacccac tgcttaagcc | 300 |
| tcaataaagc ttgccttgag tgcttcaagt agtgtgtgcc cgtctgttgt gtgactctgg | 360 |
| taactagaga tccctcagac cctttagtc agtgtggaaa atctctagca gtggcgcccg | 420 |
| aacagggact tgaaagcgaa agggaaacca gaggagctct ctcgacgcag gactcggctt | 480 |
| gctgaagcgc gcacggcaag aggcgagggg cggcgactgg tgagtacgcc aaaaattttg | 540 |
| actagcggag gctagaagga gagagatggg tgcgagagcg tcagtattaa gcgggggaga | 600 |
| attagatcgc gatgggaaaa aattcggtta aggccagggg gaaagaaaaa atataaatta | 660 |
| aaacatatag tatgggcaag cagggagcta gaacgattcg cagttaatcc tggcctgtta | 720 |
| gaaacatcag aaggctgtag acaaatactg ggacagctac aaccatccct tcagacagga | 780 |
| tcagaagaac ttagatcatt atataataca gtagcaaccc tctattgtgt gcatcaaagg | 840 |
| atagagataa aagacaccaa ggaagcttta gacaagatag aggaagagca aaacaaaagt | 900 |
| aagaccaccg cacagcaagc ggccgctgat cttcagacct ggaggaggag atatgaggga | 960 |
| caattggaga agtgaattat ataaatataa agtagtaaaa attgaaccat taggagtagc | 1020 |
| acccaccaag gcaaagagaa gagtggtgca gagagaaaaa agagcagtgg gaataggagc | 1080 |
| tttgttcctt gggttcttgg gagcagcagg aagcactatg ggcgcagcgt caatgacgct | 1140 |
| gacggtacag gccagacaat tattgtctgg tatagtgcag cagcagaaca atttgctgag | 1200 |
| ggctattgag gcgcaacagc atctgttgca actcacagtc tggggcatca agcagctcca | 1260 |
| ggcaagaatc ctggctgtgg aaagatacct aaaggatcaa cagctcctgg gatttgggg | 1320 |
| ttgctctgga aaactcattt gcaccactgc tgtgccttgg aatgctagtt ggagtaataa | 1380 |
| atctctggaa cagatttgga atcacacgac ctggatggag tgggacagag aaattaacaa | 1440 |
| ttacacaagc ttaatacact ccttaattga agaatcgcaa aaccagcaag aaaagaatga | 1500 |
| acaagaatta ttggaattag ataaatgggc aagtttgtgg aattggttta acataacaaa | 1560 |
| ttggctgtgg tatataaaat tattcataat gatagtagga ggcttggtag gtttaagaat | 1620 |
| agttttgct gtactttcta tagtgaatag agttaggcag ggatattcac cattatcgtt | 1680 |
| tcagacccac ctcccaaccc cgaggggacc cgacaggccc gaaggaatag aagaagaagg | 1740 |

```
tggagagaga gacagagaca gatccattcg attagtgaac ggatctcgac ggtatcgcta   1800
gcttttaaaa gaaaaggggg gattgggggg tacagtgcag gggaaagaat agtagacata   1860
atagcaacag acatacaaac taaagaatta caaaaacaaa ttacaaaaat tcaaaatttt   1920
actagtgatt atcggatcaa ctttgtatag aaaagttggg ctccggtgcc cgtcagtggg   1980
cagagcgcac atcgcccaca gtccccgaga agttggggg aggggtcggc aattgaaccg    2040
gtgcctagag aaggtggcgc ggggtaaact gggaaagtga tgtcgtgtac tggctccgcc   2100
ttttccccga gggtggggga gaaccgtata taagtgcagt agtcgccgtg aacgttcttt   2160
ttcgcaacgg gtttgccgcc agaacacagg taagtgccgt gtgtggttcc cgcgggcctg   2220
gcctctttac gggttatggc ccttgcgtgc cttgaattac ttccacctgg ctgcagtacg   2280
tgattcttga tcccgagctt cgggttggaa gtgggtggga gagttcgagg ccttgcgctt   2340
aaggagcccc ttcgcctcgt gcttgagttg aggcctggcc tgggcgctgg ggccgccgcg   2400
tgcgaatctg gtggcacctt cgcgcctgtc tcgctgcttt cgataagtct ctagccattt   2460
aaaattttg atgacctgct gcgacgcttt ttttctggca agatagtctt gtaaatgcgg    2520
gccaagatct gcacactggt atttcggttt ttggggccgc gggcggcgac ggggcccgtg   2580
cgtcccagcg cacatgttcg gcgaggcggg gcctgcgagc gcggccaccg agaatcggac   2640
gggggtagtc tcaagctggc cggcctgctc tggtgcctgg tctcgcgccg ccgtgtatcg   2700
cccccgccctg ggcggcaagg ctggcccggt cggcaccagt tgcgtgagcg gaaagatggc  2760
cgcttcccgg ccctgctgca gggagctcaa aatggaggac gcggcgctcg ggagagcggg   2820
cgggtgagtc acccacacaa aggaaaaggg cctttccgtc ctcagccgtc gcttcatgtg   2880
actccacgga gtaccgggcg ccgtccaggc acctcgatta gttctcgagc ttttggagta   2940
cgtcgtcttt aggttggggg gagggttttt atgcgatgga gtttccccac actgagtggg   3000
tggagactga agttaggcca gcttggcact tgatgtaatt ctccttggaa tttgcccttt   3060
ttgagtttgg atcttggttc attctcaagc ctcagacagt ggttcaaagt ttttttcttc   3120
catttcaggt gtcgtgacaa gtttgtacaa aaaagcaggc tgccaccatg atcgagacct   3180
acaaccagac cagccccaga agcgccgcca ccggcctgcc catcagcatg aagatcttca   3240
tgtacctgct gaccgtgttc ctgatcaccc agatgatcgg cagcgccctg ttcgccgtgt   3300
acctgcacag aagactggac aagatcgagg acgagagaaa cctgcacgag gacttcgtgt   3360
tcatgaagac catccagaga tgcaacaccg gcgagagaag cctgagcctg ctgaactgcg   3420
aggagatcaa gagccagttc gagggcttcg tgaaggacat catgctgaac aaggaggaga   3480
ccaagaagga gaacagcttc gagatgccca gaggcgagga ggacagccag atcgccgccc   3540
acgtgatcag cgaggccagc agcaagacca ccagcgtgct gcagtgggcc gagaagggct   3600
actacaccat gagcaacaac ctggtgaccc tggagaacgg caagcagctg accgtgaaga   3660
gacagggcct gtactacatc tacgcccagg tgaccttctg cagcaacaga gaggccagca   3720
gccaggcccc cttcatcgcc agcctgtgcc tgaagagccc cggcagattc gagagaatcc   3780
tgctgagagc cgccaacacc cacagcagcc ccagccctg cggccagcag agcatccacc    3840
tgggcggcgt gttcgagctg cagcccgcg ccagcgtgtt cgtgaacgtg accgacccca    3900
gccaggtgag ccacggcacc ggcttcacca gcttcggcct gctgaagctg taaacccagc   3960
tttcttgtac aaagtggtga taatcgaatt cacccagctt tcttgtacaa agtggtgata   4020
atcgaattcc gataatcaac ctctggatta caaaatttgt gaaagattga ctggtattct   4080
```

```
taactatgtt gctccttta cgctatgtgg atacgctgct ttaatgcctt tgtatcatgc    4140
tattgcttcc cgtatggctt tcattttctc ctccttgtat aaatcctggt tgctgtctct    4200
ttatgaggag ttgtggcccg ttgtcaggca acgtggcgtg gtgtgcactg tgtttgctga    4260
cgcaacccc actggttggg gcattgccac cacctgtcag ctcctttccg ggactttcgc    4320
tttccccctc cctattgcca cggcggaact catcgccgcc tgccttgccc gctgctggac    4380
aggggctcgg ctgttgggca ctgacaattc cgtggtgttg tcggggaagc tgacgtcctt    4440
tccatggctg ctcgcctgtg ttgccacctg gattctgcgc gggacgtcct tctgctacgt    4500
cccttcggcc ctcaatccag cggaccttcc ttcccgcggc ctgctgccgg ctctgcggcc    4560
tcttccgcgt cttcgccttc gccctcagac gagtcggatc tccctttggg ccgcctcccc    4620
gcatcgggaa ttcccgcggt tcgctttaag accaatgact acaaggcag ctgtagatct    4680
tagccacttt ttaaaagaaa aggggggact ggaagggcta attcactccc aacgaagaca    4740
agatctgctt tttgcttgta ctgggtctct ctggttagac cagatctgag cctgggagct    4800
ctctggctaa ctagggaacc cactgcttaa gcctcaataa agcttgcctt gagtgcttca    4860
agtagtgtgt gcccgtctgt tgtgtgactc tggtaactag agatccctca gacccttta    4920
gtcagtgtgg aaaatctcta gcagtagtag ttcatgtcat cttattattc agtatttata    4980
acttgcaaag aaatgaatat cagagagtga gaggaacttg tttattgcag cttataatgg    5040
ttacaaataa agcaatagca tcacaaattt cacaaataaa gcattttttt cactgcattc    5100
tagttgtggt ttgtccaaac tcatcaatgt atcttatcat gtctggctct agctatcccg    5160
cccctaactc cgcccatccc gcccctaact ccgcccagtt ccgcccattc tccgccccat    5220
ggctgactaa ttttttttat ttatgcagag gccgaggccg cctcggcctc tgagctattc    5280
cagaagtagt gaggaggctt ttttggaggc ctagggacgt acccaattcg ccctatagtg    5340
agtcgtatta cgcgcgctca ctggccgtcg ttttacaacg tcgtgactgg gaaaaccctg    5400
gcgttaccca acttaatcgc cttgcagcac atccccctt cgccagctgg cgtaatagcg    5460
aagaggcccg caccgatcgc ccttcccaac agttgcgcag cctgaatggc gaatgggacg    5520
cgccctgtag cggcgcatta agcgcggcgg gtgtggtggt tacgcgcagc gtgaccgcta    5580
cacttgccag cgccctagcg cccgctcctt tcgctttctt cccttccttt ctcgccacgt    5640
tcgccggctt tccccgtcaa gctctaaatc ggggctccc tttagggttc cgatttagtg    5700
ctttacggca cctcgacccc aaaaaacttg attagggtga tggttcacgt agtgggccat    5760
cgccctgata gacggttttt cgccctttga cgttggagtc cacgttcttt aatagtggac    5820
tcttgttcca aactggaaca acactcaacc ctatctcggt ctattctttt gatttataag    5880
ggattttgcc gatttcggcc tattggttaa aaaatgagct gatttaacaa aaatttaacg    5940
cgaattttaa caaaatatta acgcttacaa tttaggtggc acttttcggg gaaatgtgcg    6000
cggaacccct atttgtttat ttttctaaat acattcaaat atgtatccgc tcatgagaca    6060
ataaccctga taaatgcttc aataatattg aaaaaggaag agtatgagta ttcaacattt    6120
ccgtgtcgcc cttattccct tttttgcggc attttgcctt cctgtttttg ctcacccaga    6180
aacgctggtg aaagtaaaag atgctgaaga tcagttgggt gcacgagtgg gttacatcga    6240
actggatctc aacagcggta agatccttga gagttttcgc cccgaagaac gttttccaat    6300
gatgagcact ttaaagttc tgctatgtgg cgcggtatta tcccgtattg acgccgggca    6360
agagcaactc ggtcgccgca tacactattc tcagaatgac ttggttgagt actcaccagt    6420
cacagaaaag catcttacgg atggcatgac agtaagagaa ttatgcagtg ctgccataac    6480
```

```
catgagtgat aacactgcgg ccaacttact tctgacaacg atcggaggac cgaaggagct      6540
aaccgctttt ttgcacaaca tgggggatca tgtaactcgc cttgatcgtt gggaaccgga      6600
gctgaatgaa gccataccaa acgacgagcg tgacaccacg atgcctgtag caatggcaac      6660
aacgttgcgc aaactattaa ctggcgaact acttactcta gcttcccggc aacaattaat      6720
agactggatg gaggcggata aagttgcagg accacttctg cgctcggccc ttccggctgg      6780
ctggtttatt gctgataaat ctggagccgg tgagcgtggg tctcgcggta tcattgcagc      6840
actggggcca gatggtaagc cctcccgtat cgtagttatc tacacgacgg ggagtcaggc      6900
aactatggat gaacgaaata gacagatcgc tgagataggt gcctcactga ttaagcattg      6960
gtaactgtca gaccaagttt actcatatat actttagatt gatttaaaac ttcattttta      7020
atttaaaagg atctaggtga agatcctttt tgataatctc atgaccaaaa tcccttaacg      7080
tgagttttcg ttccactgag cgtcagaccc cgtagaaaag atcaaaggat cttcttgaga      7140 tcctttttt ctgcgcgtaa tctgctgctt gcaaacaaaa aaaccaccgc taccagcggt       7200
ggtttgtttg ccggatcaag agctaccaac tctttttccg aaggtaactg gcttcagcag      7260
agcgcagata ccaaatactg ttcttctagt gtagccgtag ttaggccacc acttcaagaa      7320
ctctgtagca ccgcctacat acctcgctct gctaatcctg ttaccagtgg ctgctgccag      7380
tggcgataag tcgtgtctta ccgggttgga ctcaagacga tagttaccgg ataaggcgca      7440
gcggtcgggc tgaacggggg gttcgtgcac acagcccagc ttggagcgaa cgacctacac      7500
cgaactgaga tacctacagc gtgagctatg agaaagcgcc acgcttcccg aagagagaaa      7560
ggcggacagg tatccggtaa gcggcagggt cggaacagga gagcgcacga gggagcttcc      7620 aggggggaaac gcctggtatc tttatagtcc tgtcgggttt cgccacctct gacttgagcg      7680
tcgatttttg tgatgctcgt caggggggcg gagcctatgg aaaaacgcca gcaacgcggc      7740 cttttttacgg ttcctggcct tttgctggcc ttttgctcac atgttctttc ctgcgttatc      7800
ccctgattct gtggataacc gtattaccgc ctttgagtga gctgataccg ctcgccgcag      7860
ccgaacgacc gagcgcagcg agtcagtgag cgaggaagcg gaagagcgcc caatacgcaa      7920
accgcctctc cccgcgcgtt ggccgattca ttaatgcagc tggcacgaca ggtttcccga      7980
ctggaaagcg ggcagtgagc gcaacgcaat taatgtgagt tagctcactc attaggcacc      8040
ccaggcttta cactttatgc ttccggctcg tatgttgtgt ggaattgtga gcggataaca      8100
atttcacaca ggaaacagct atgaccatga ttacgccaag cgcgcaatta accctcacta      8160
aagggaacaa aagctggagc tgcaagctt                                       8189

<210> SEQ ID NO 52
<211> LENGTH: 8069
<212> TYPE: DNA
<213> ORGANISM: Artificial Sequence
<220> FEATURE:
<223> OTHER INFORMATION: Vector 6

<400> SEQUENCE: 52
aatgtagtct tatgcaatac tcttgtagtc ttgcaacatg gtaacgatga gttagcaaca        60
tgccttacaa ggagagaaaa agcaccgtgc atgccgattg gtggaagtaa ggtggtacga       120
tcgtgcctta ttaggaaggc aacagacggg tctgacatgg attggacgaa ccactgaatt       180
gccgcattgc agagatattg tatttaagtg cctagctcga tacataaacg ggtctctctg       240
gttagaccag atctgagcct gggagctctc tggctaacta gggaacccac tgcttaagcc       300
```

```
tcaataaagc ttgccttgag tgcttcaagt agtgtgtgcc cgtctgttgt gtgactctgg      360
taactagaga tccctcagac ccttttagtc agtgtggaaa atctctagca gtggcgcccg      420
aacagggact tgaaagcgaa agggaaacca gaggagctct ctcgacgcag gactcggctt      480
gctgaagcgc gcacggcaag aggcgagggg cggcgactgg tgagtacgcc aaaaattttg      540
actagcggag gctagaagga gagagatggg tgcgagagcg tcagtattaa gcggggagaa      600
attagatcgc gatgggaaaa aattcggtta aggccagggg gaagaaaaaa atataaatta      660
aaacatatag tatgggcaag cagggagcta gaacgattcg cagttaatcc tggcctgtta      720
gaaacatcag aaggctgtag acaaatactg ggacagctac aaccatccct cagacagga      780 tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg gagcagcagg aagcactatg ggcgcagcgt caatgacgct     1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
ttgctctgga aaactcattt gcaccactgc tgtgccttgg aatgctagtt ggagtaataa     1380
atctctggaa cagatttgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta cataacaaa     1560 ttggctgtgg tatataaaat tattcataat gatagtagga ggcttggtag gtttaagaat     1620 agttttgct gtacttcta tagtgaatag agttaggcag ggatattcac cattatcgtt     1680
tcagacccac ctcccaaccc cgaggggacc cgacaggccc gaaggaatag aagaagaagg     1740
tggagagaga gacagagaca gatccattcg attagtgaac ggatctcgac ggtatcgcta     1800
gcttttaaaa gaaaaggggg gattggggg tacagtgcag gggaaagaat agtagacata     1860
atagcaacag acatacaaac taagaatta caaaacaaa ttacaaaaat tcaaaatttt     1920
actagtgatt atcggatcaa cttttgtatag aaaagttggg ctccggtgcc cgtcagtggg     1980
cagagcgcac atcgcccaca gtccccgaga agttggggg aggggtcggc aattgaaccg     2040
gtgcctagag aaggtggcgc ggggtaaact gggaaagtga tgtcgtgtac tggctccgcc     2100
tttttcccga gggtggggga aaccgtata taagtgcagt agtcgccgtg aacgttcttt     2160
ttcgcaacgg gtttgccgcc agaacacagg taagtgccgt gtgtggttcc cgcgggcctg     2220
gcctctttac gggttatggc ccttgcgtgc cttgaattac ttccacctgg ctgcagtacg     2280
tgattcttga tcccgagctt cgggttggaa gtgggtggga gagttcgagg ccttgcgctt     2340
aaggagcccc ttcgcctcgt gcttgagttg aggcctggcc tgggcgctgg ggccgccgcg     2400
tgcgaatctg gtggcacctt cgcgcctgtc tcgctgcttt cgataagtct ctagccattt     2460 aaaattttg atgacctgct gcgacgcttt ttttctggca agatagtctt gtaaatgcgg     2520
gccaagatct gcacactggt atttcggttt tgggccgc gggcggcgac ggggcccgtg     2580
cgtcccagcg cacatgttcg gcgaggcggg gcctgcgagc gcggccaccg agaatcggac     2640 ggggggtagtc tcaagctggc cggcctgctc tggtgcctgg tctcgcgccg ccgtgtatcg     2700
```

-continued

```
ccccgccctg ggcggcaagg ctggcccggt cggcaccagt tgcgtgagcg gaaagatggc    2760
cgcttcccgg ccctgctgca gggagctcaa aatggaggac gcggcgctcg ggagagcggg    2820
cgggtgagtc acccacacaa aggaaaaggg cctttccgtc ctcagccgtc gcttcatgtg    2880
actccacgga gtaccgggcg ccgtccaggc acctcgatta gttctcgagc ttttggagta    2940
cgtcgtcttt aggttggggg gaggggtttt atgcgatgga gtttccccac actgagtggg    3000
tggagactga agttaggcca gcttggcact tgatgtaatt ctccttggaa tttgcccttt    3060
ttgagtttgg atcttggttc attctcaagc ctcagacagt ggttcaaagt ttttttcttc    3120
catttcaggt gtcgtgacaa gtttgtacaa aaaagcaggc tgccaccatg agcaccgaga    3180
gcatgatcag agacgtggag ctggccgagg aggccctgcc caagaagacc ggcggccccc    3240
agggcagcag aagatgcctg ttcctgagcc tgttcagctt cctgatcgtg gccggcgcca    3300
ccaccctgtt ctgcctgctg cacttcggcg tgatcggccc ccagagagag gagttcccca    3360
gagacctgag cctgatcagc cccctggccc aggccgtggc ccacgtggtg gccaaccccc    3420
aggccgaggg ccagctgcag tggctgaaca aagagagcca cgccctgctg ccaacggcg    3480
tggagctgag agacaaccag ctggtggtgc cagcgagggg cctgtacctg atctacagcc    3540
aggtgctgtt caagggccag ggctgcccca gcacccacgt gctgctgacc cacaccatca    3600
gcagaatcgc cgtgagctac cagaccaagg tgaacctgct gagcgccatc aagagccct    3660
gccagagaga ccccgag ggcgccgagg ccaagccctg gtacgagccc atctacctgg    3720
gcggcgtgtt ccagctggag aagggcgaca gactgagcgc cgagatcaac agacccgact    3780
acctggactt cgccgagagc ggccaggtgt acttcggcat catcgccctg taaacccagc    3840
tttcttgtac aaagtggtga taatcgaatt cacccagctt tcttgtacaa agtggtgata    3900
atcgaattcc gataatcaac ctctggatta caaaatttgt gaaagattga ctggtattct    3960
taactatgtt gctcctttta cgctatgtgg atacgctgct ttaatgcctt tgtatcatgc    4020
tattgcttcc cgtatggctt tcattttctc ctccttgtat aaatcctggt tgctgtctct    4080
ttatgaggag ttgtggcccg ttgtcaggca acgtggcgtg gtgtgcactg tgtttgctga    4140
cgcaacccc actggttggg gcattgccac cacctgtcag ctcctttccg ggactttcgc    4200
tttccccctc cctattgcca cggcggaact catcgccgcc tgccttgccc gctgctggac    4260
aggggctcgg ctgttgggca ctgacaattc cgtggtgttg tcggggaagc tgacgtcctt    4320
tccatggctg ctcgcctgtg ttgccacctg gattctgcgc gggacgtcct tctgctacgt    4380
cccttcggcc ctcaatccag cggaccttcc ttcccgcggc ctgctgccgg ctctgcggcc    4440
tcttccgcgt cttcgccttc gccctcagac gagtcggatc ccctttggg ccgcctcccc    4500
gcatcgggaa ttcccgcggt tcgctttaag accaatgact acaaggcag ctgtagatct    4560
tagccacttt ttaaaagaaa aggggggact ggaagggcta attcactccc aacgaagaca    4620
agatctgctt tttgcttgta ctgggtctct ctggttagac cagatctgag cctgggagct    4680
ctctggctaa ctagggaacc cactgcttaa gcctcaataa agcttgcctt gagtgcttca    4740
agtagtgtgt gcccgtctgt tgtgtgactc tggtaactag agatccctca gaccctttta    4800
gtcagtgtgg aaaatctcta gcagtagtag ttcatgtcat cttattattc agtatttata    4860
acttgcaaag aaatgaatat cagagagtga gaggaacttg tttattgcag cttataatgg    4920
ttacaaataa agcaatagca tcacaaattt cacaaataaa gcattttttt cactgcattc    4980
tagttgtggt ttgtccaaac tcatcaatgt atcttatcat gtctggctct agctatcccg    5040
```

```
cccctaactc cgcccatccc gccctaact ccgcccagtt ccgcccattc tccgcccat    5100
ggctgactaa tttttttat ttatgcagag gccgaggccg cctcggcctc tgagctattc    5160
cagaagtagt gaggaggctt ttttggaggc ctagggacgt acccaattcg ccctatagtg   5220
agtcgtatta cgcgcgctca ctggccgtcg ttttacaacg tcgtgactgg gaaaaccctg   5280
gcgttaccca acttaatcgc cttgcagcac atccccttt cgccagctgg cgtaatagcg    5340
aagaggcccg caccgatcgc ccttcccaac agttgcgcag cctgaatggc gaatgggacg   5400
cgccctgtag cggcgcatta agcgcggcgg gtgtggtggt tacgcgcagc gtgaccgcta   5460
cacttgccag cgccctagcg cccgctcctt tcgctttctt cccttccttt ctcgccacgt   5520
tcgccggctt tccccgtcaa gctctaaatc ggggctccc tttagggttc cgatttagtg    5580
ctttacggca cctcgacccc aaaaaacttg attagggtga tggttcacgt agtgggccat   5640
cgccctgata cggttttt cgcccttga cgttggagtc cacgttcttt aatagtggac      5700
tcttgttcca aactgaaca acactcaacc ctatctcggt ctattctttt gatttataag    5760
ggattttgcc gatttcggcc tattggttaa aaaatgagct gatttaacaa aaatttaacg   5820
cgaatttaa caaatatta acgcttacaa tttaggtggc acttttcggg gaaatgtgcg     5880
cggaacccct atttgtttat ttttctaaat acattcaaat atgtatccgc tcatgagaca   5940
ataaccctga taaatgcttc aataatattg aaaaaggaag agtatgagta ttcaacattt   6000
ccgtgtcgcc cttattccct tttttgcggc attttgcctt cctgttttg ctcacccaga    6060
aacgctggtg aaagtaaaag atgctgaaga tcagttgggt gcacgagtgg gttacatcga   6120
actggatctc aacagcggta agatccttga gtttttcgc cccgaagaac gttttccaat    6180
gatgagcact tttaaagttc tgctatgtgg cgcggtatta tcccgtattg acgccgggca   6240
agagcaactc ggtcgccgca tacactattc tcagaatgac ttggttgagt actcaccagt   6300
cacagaaaag catcttacgg atggcatgac agtaagagaa ttatgcagtg ctgccataac   6360
catgagtgat aacactgcgg ccaacttact tctgacaacg atcggaggac cgaaggagct   6420
aaccgctttt ttgcacaaca tgggggatca tgtaactcgc cttgatcgtt gggaaccgga   6480
gctgaatgaa gccataccaa acgacgagcg tgacaccacg atgcctgtag caatggcaac   6540
aacgttgcgc aaactattaa ctggcgaact acttactcta gcttcccggc aacaattaat   6600
agactggatg gaggcggata aagttgcagg accacttctg cgctcggccc ttccggctgg   6660
ctggtttatt gctgataaat ctggagccgg tgagcgtggg tctcgcggta tcattgcagc   6720
actggggcca gatggtaagc cctcccgtat cgtagttatc tacacgacgg ggagtcaggc   6780
aactatggat gaacgaaata gacagatcgc tgagataggt gcctcactga ttaagcattg   6840
gtaactgtca gaccaagttt actcatatat actttagatt gatttaaaac ttcatttta    6900
atttaaaagg atctaggtga agatcctttt tgataatctc atgaccaaaa tcccttaacg   6960
tgagttttcg ttccactgag cgtcagaccc cgtagaaaag atcaaaggat cttcttgaga   7020
tccttttttt ctgcgcgtaa tctgctgctt gcaaacaaaa aaaccaccgc taccagcggt   7080
ggtttgtttg ccggatcaag agctaccaac tcttttccg aaggtaactg gcttcagcag    7140
agcgcagata ccaaatactg ttcttctagt gtagccgtag ttaggccacc acttcaagaa   7200
ctctgtagca ccgcctacat acctcgctct gctaatcctg ttaccagtgg ctgctgccag   7260
tggcgataag tcgtgtctta ccgggttgga ctcaagacga tagttaccgg ataaggcgca   7320
gcggtcgggc tgaacggggg gttcgtgcac acagcccagc ttggagcgaa cgacctacac   7380
cgaactgaga tacctacagc gtgagctatg agaaagcgcc acgcttcccg aagagagaaa   7440
```

```
ggcggacagg tatccggtaa gcggcagggt cggaacagga gagcgcacga gggagcttcc    7500
agggggaaac gcctggtatc tttatagtcc tgtcgggttt cgccacctct gacttgagcg    7560 tcgattttg tgatgctcgt caggggggcg gagcctatgg aaaaacgcca gcaacgcggc    7620 cttttacgg ttcctggcct tttgctggcc ttttgctcac atgttctttc ctgcgttatc     7680
ccctgattct gtggataacc gtattaccgc ctttgagtga gctgataccg ctcgccgcag    7740
ccgaacgacc gagcgcagcg agtcagtgag cgaggaagcg gaagagcgcc caatacgcaa    7800
accgcctctc cccgcgcgtt ggccgattca ttaatgcagc tggcacgaca ggtttcccga    7860
ctggaaagcg ggcagtgagc gcaacgcaat taatgtgagt tagctcactc attaggcacc    7920
ccaggcttta cactttatgc ttccggctcg tatgttgtgt ggaattgtga gcggataaca    7980
atttcacaca ggaaacagct atgaccatga ttacgccaag cgcgcaatta accctcacta    8040
aagggaacaa aagctggagc tgcaagctt                                       8069
```

<210> SEQ ID NO 53
<211> LENGTH: 10067
<212> TYPE: DNA
<213> ORGANISM: Artificial Sequence
<220> FEATURE:
<223> OTHER INFORMATION: Vector 7

<400> SEQUENCE: 53

```
aatgtagtct tatgcaatac tcttgtagtc ttgcaacatg gtaacgatga gttagcaaca      60
tgccttacaa ggagagaaaa agcaccgtgc atgccgattg gtggaagtaa ggtggtacga     120
tcgtgcctta ttaggaaggc aacagacggg tctgacatgg attggacgaa ccactgaatt     180
gccgcattgc agagatattg tatttaagtg cctagctcga tacataaacg ggtctctctg     240
gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac ccttttagtc agtgtggaaa atctctagca gtggcgcccg     420
aacagggact tgaaagcgaa agggaaacca gaggagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaa     600
attagatcgc gatgggaaaa aattcggtta aggccagggg gaagaaaaa atataaatta      660 aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga    960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg gatttgggg    1320 ttgctctgga aaactcattt gcaccactgc tgtgccttgg aatgctagtt ggagtaataa    1380
```

```
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agttttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaaaggggg gattgggggg tacagtgcag gggaaagaat agtagacata    1860
atagcaacag acatacaaac taagaatta caaaaacaaa ttacaaaaat tcaaaatttt    1920
actagtatca acttttgtata gaaaagttgg gctccggtgc ccgtcagtgg gcagagcgca    1980
catcgcccac agtccccgag aagttggggg gaggggtcgg caattgaacc ggtgcctaga    2040
gaaggtggcg cggggtaaac tgggaaagtg atgtcgtgta ctggctccgc ctttttcccg    2100
agggtggggg agaaccgtat ataagtgcag tagtcgccgt gaacgttctt tttcgcaacg    2160
ggtttgccgc cagaacacag gtaagtgccg tgtgtggttc ccgcgggcct ggcctcttta    2220
cgggttatgg cccttgcgtg ccttgaatta cttccacctg gctgcagtac gtgattcttg    2280
atcccgagct tcgggttgga agtgggtggg agagttcgag gccttgcgct taaggagccc    2340
cttcgcctcg tgcttgagtt gaggcctggc ctgggcgctg gggccgccgc gtgcgaatct    2400
ggtggcacct tcgcgcctgt ctcgctgctt tcgataagtc tctagccatt taaaattttt    2460
gatgacctgc tgcgacgctt tttttctggc aagatagtct tgtaaatgcg gccaagatc    2520
tgcacactgg tatttcggtt tttggggccg cgggcggcga cggggcccgt gcgtcccagc    2580
gcacatgttc ggcgaggcgg ggcctgcgag cgcggccacc gagaatcgga cggggggtagt    2640
ctcaagctgg ccggcctgct ctggtgcctg gtctcgcgcc gccgtgtatc gccccgccct    2700
gggcggcaag gctggcccgg tcggcaccag ttgcgtgagc ggaaagatgg ccgcttcccg    2760
gccctgctgc agggagctca aaatggagga cgcggcgctc gggagagcgg gcgggtgagt    2820
cacccacaca aaggaaaagg gccttttccgt cctcagccgt cgcttcatgt gactccacgg    2880
agtaccgggc gccgtccagg cacctcgatt agttctcgag ctttttggagt acgtcgtctt    2940
taggttgggg ggagggggttt tatgcgatgg agtttcccca cactgagtgg gtggagactg    3000
aagttaggcc agcttggcac ttgatgtaat tctccttgga atttgccctt tttgagtttg    3060
gatcttggtt cattctcaag cctcagacag tggttcaaag ttttttttctt ccatttcagg    3120
tgtcgtgaca agtttgtaca aaaaagcagg ctgccaccat gagcaccgag agcatgatca    3180
gagacgtgga gctggccgag gaggccctgc ccaagaagac cggcggcccc cagggcagca    3240
gaagatgcct gttcctgagc ctgttcagct tcctgatcgt ggccggcgcc accaccctgt    3300
tctgcctgct gcacttcggc gtgatcggcc cccagagaga ggagttcccc agagacctga    3360
gcctgatcag ccccctggcc caggccgtgg cccacgtggt ggccaacccc caggccgagg    3420
gccagctgca gtggctgaac agaagagcca acgccctgct ggccaacggc gtggagctga    3480
gagacaacca gctggtggtg cccagcgagg gcctgtacct gatctacagc caggtgctgt    3540
tcaagggcca gggctgcccc agcacccacg tgctgctgac ccacaccatc agcagaatcg    3600
ccgtgagcta ccagaccaag gtgaacctgc tgagcgccat caagagcccc tgccagagag    3660
agaccccga gggcgccgag gccaagccct ggtacgagcc catctacctg ggcggcgtgt    3720
tccagctgga aagggcgac agactgagcg ccgagatcaa cagacccgac tacctggact    3780
```

```
tcgccgagag cggccaggtg tacttcggca tcatcgccct gtaaacccag ctttcttgta   3840
caaagtggtg ataatcgaat tctaaataga tagaacaaca acaattgcat tcattttttga   3900 tttcaggttc aggggggaggt gtgggaggtt ttttaaagca agtaaaacct ctacactgac   3960
ggtacgcgtt aacaacaaca attgcattca tttgtagttt caggttcagg gggaggtgtg   4020
ggaggttttt taaagcaagt taaacctcta aatagtggt acgcgttacc cagctttctt   4080
gtacaaagtg gacccagctt tcttgtacaa agtgggcccc tctccctccc cccccctaa    4140 cgttactggc cgaagccgct tggaataagg ccggtgtgcg tttgtctata tgttattttc   4200
caccatattg ccgtcttttg gcaatgtgag ggcccggaaa cctggccctg tcttcttgac   4260
gagcattcct aggggtcttt cccctctcgc caaaggaatg caaggtctgt tgaatgtcgt   4320
gaaggaagca gttcctctgg aagcttcttg aagacaaaca acgtctgtag cgaccctttg   4380
caggcagcgg aaccccccac ctggcgacag gtgcctctgc ggccaaaagc cacgtgtata   4440
agatacacct gcaaaggcgg cacaaccccca gtgccacgtt gtgagttgga tagttgtgga   4500
aagagtcaaa tggctctcct caagcgtatt caacaagggg ctgaaggatg cccagaaggt   4560 acccccattgt atgggatctg atctgggggcc tcggtgcaca tgctttacat gtgtttagtc   4620
gaggttaaaa aaacgtctag gcccccccgaa ccacggggac gtggttttcc tttgaaaaac   4680
acgatgataa tatggccaca accatggcca ccgtgctggc cccgcctgg agccccacca   4740 cctacctgct gctgctgctg ctgctgagca gcggcctgag cggcggcggc ggcagcggca   4800
agcccatccc caaccccctg ctgggcctgg acagcaccgg cggcggcggc agccaggtga   4860
agctgcagga gagcggcccc ggcctggtgg cccccagcca gagcctgagc atcacctgca   4920
ccgtgagcgg cttcagcctg accgcctacg gcgtggactg ggtgagacag ccccccggca   4980
agtgcctgga gtggctgggc gtgatctggg gcggcggcag aaccaactac aacagcggcc   5040
tgatgagcag actgagcatc agaaaggaca acagcaagag ccaggtgttc ctgaccatga   5100
acagcctgca gaccgacgac accgccaagt actactgcgt gaagcacacc aactgggacg   5160
gcggcttcgc ctactggggc caggcaccaa ccgtgaccgt gagcagcggc ggcggcggca   5220
gcggcggcgc cggcagcggc ggcggcggca gcggcagccc cggccagagc gtgagcatca   5280
gctgcagcgg cagcagcagc aacatcggca caaactacgt gtactggtac cagcacctgc   5340
ccggcaccgc cccaagctg ctgatctaca gcgacaccaa gagacccagc ggcgtgcccg   5400
acagaatcag cggcagcaag agcggcacca cgccagcct ggccatcagc ggcctgcaga   5460
gcgaggacga ggccgactac tactgcgcca gctgggacga cagcctggac ggccccgtgt   5520
tcggctgcgg caccaagctg accgtgctgc ccaccaccac ccccgccccc agacccccca   5580
cccccgcccc caccatcgcc agccagcccc tgagcctgag acccgaggcc tgcagacccg   5640
ccgccggcgg cgccgtgcac accagaggcc tggacttcgc ctgcgacatc tacatctggg   5700
cccccctggc cggcacctgc ggcgtgctgc tgctgagcct ggtgatcacc ctgtactgca   5760
accacagaaa cagaagaaga gtgtgcaagt gccccagacc cgtggtgaag agcggcgaca   5820
agcccagcct gagcgccaga tacgtgtaac aactttatta tacatagttg atcaattcca   5880
actttattat acatagttga tcaattccga taatcaacct ctggattaca aaatttgtga   5940
aagattgact ggtattctta actatgttgc tccttttacg ctatgtggat acgctgcttt   6000
aatgcctttg tatcatgcta ttgcttcccg tatggctttc attttctcct ccttgtataa   6060
atcctggttg ctgtctcttt atgaggagtt gtggcccgtt gtcaggcaac gtggcgtggt   6120
```

```
gtgcactgtg tttgctgacg caaccccccac tggttggggc attgccacca cctgtcagct    6180
cctttccggg actttcgctt tcccctccc  tattgccacg gcggaactca tcgccgcctg    6240
ccttgcccgc tgctggacag gggctcggct gttgggcact gacaattccg tggtgttgtc    6300
ggggaagctg acgtcctttc catggctgct cgcctgtgtt gccacctgga ttctgcgcgg    6360
gacgtccttc tgctacgtcc cttcggccct caatccagcg gaccttcctt cccgcggcct    6420
gctgccggct ctgcggcctc ttccgcgtct tcgccttcgc cctcagacga gtcggatctc    6480
cctttgggcc gcctccccgc atcgggaatt cccgcggttc gctttaagac caatgactta    6540
caaggcagct gtagatctta gccactttt  aaaagaaaag gggggactgg aagggctaat    6600
tcactcccaa cgaagacaag atctgctttt tgcttgtact gggtctctct ggttagacca    6660
gatctgagcc tgggagctct ctggctaact agggaaccca ctgcttaagc ctcaataaag    6720
cttgccttga gtgcttcaag tagtgtgtgc ccgtctgttg tgtgactctg gtaactagag    6780
atccctcaga cccttttagt cagtgtggaa atctctagc  agtagtagtt catgtcatct    6840
tattattcag tatttataac ttgcaaagaa atgaatatca gagagtgaga ggaacttgtt    6900
tattgcagct tataatggtt acaaataaag caatagcatc acaaatttca caaataaagc    6960
atttttttca ctgcattcta gttgtggttt gtccaaactc atcaatgtat cttatcatgt    7020
ctggctctag ctatcccgcc cctaactccg cccatcccgc ccctaactcc gcccagttcc    7080
gcccattctc cgccccatgg ctgactaatt tttttatt  atgcagaggc cgaggccgcc    7140
tcggcctctg agctattcca gaagtagtga ggaggctttt ttggaggcct agggacgtac    7200
ccaattcgcc ctatagtgag tcgtattacg cgcgctcact ggccgtcgtt ttacaacgtc    7260
gtgactggga aaaccctggc gttacccaac ttaatcgcct tgcagcacat ccccctttcg    7320
ccagctggcg taatagcgaa gaggcccgca ccgatcgccc ttcccaacag ttgcgcagcc    7380
tgaatggcga atgggacgcg ccctgtagcg gcgcattaag cgcggcgggt gtggtggtta    7440
cgcgcagcgt gaccgctaca cttgccagcg ccctagcgcc cgctcctttc gctttcttcc    7500
cttcctttct cgccacgttc gccggctttc cccgtcaagc tctaaatcgg ggctccctt    7560
tagggttccg atttagtgct ttacggcacc tcgaccccaa aaaacttgat tagggtgatg    7620
gttcacgtag tgggccatcg ccctgataga cggtttttcg ccctttgacg ttggagtcca    7680
cgttctttaa tagtggactc ttgttccaaa ctggaacaac actcaaccct atctcggtct    7740
attctttga  tttataaggg attttgccga tttcggccta ttggttaaaa atgagctga    7800
tttaacaaaa atttaacgcg aattttaaca aatattaac  gcttacaatt taggtggcac    7860
ttttcgggga aatgtgcgcg gaaccccctat ttgtttattt ttctaaatac attcaaatat    7920
gtatccgctc atgagacaat aaccctgata aatgcttcaa taatattgaa aaaggaagag    7980
tatgagtatt caacatttcc gtgtcgccct tattcccttt tttgcggcat tttgccttcc    8040
tgttttttgct cacccagaaa cgctggtgaa agtaaaagat gctgaagatc agttgggtgc    8100
acgagtgggt tacatcgaac tggatctcaa cagcggtaag atccttgaga gttttcgccc    8160
cgaagaacgt tttccaatga tgagcacttt taaagttctg ctatgtggcg cggtattatc    8220
ccgtattgac gccgggcaag agcaactcgg tcgccgcata cactattctc agaatgactt    8280
ggttgagtac tcaccagtca cagaaaagca tcttacggat ggcatgacag taagagaatt    8340
atgcagtgct gccataacca tgagtgataa cactgcggcc aacttacttc tgacaacgat    8400
cggaggaccg aaggagctaa ccgcttttt  gcacaacatg ggggatcatg taactcgcct    8460
tgatcgttgg gaaccggagc tgaatgaagc cataccaaac gacgagcgtg acaccacgat    8520
```

-continued

```
gcctgtagca atggcaacaa cgttgcgcaa actattaact ggcgaactac ttactctagc    8580
ttcccggcaa caattaatag actggatgga ggcggataaa gttgcaggac cacttctgcg    8640
ctcggccctt ccggctggct ggtttattgc tgataaatct ggagccggtg agcgtgggtc    8700
tcgcggtatc attgcagcac tggggccaga tggtaagccc tcccgtatcg tagttatcta    8760
cacgacgggg agtcaggcaa ctatggatga cgaaataga cagatcgctg agataggtgc    8820
ctcactgatt aagcattggt aactgtcaga ccaagtttac tcatatatac tttagattga    8880
tttaaaactt cattttttaat taaaaggat ctaggtgaag atccttttg ataatctcat    8940
gaccaaaatc ccttaacgtg agttttcgtt ccactgagcg tcagaccccg tagaaaagat    9000
caaaggatct tcttgagatc ctttttttct gcgcgtaatc tgctgcttgc aaacaaaaaa    9060
accaccgcta ccagcggtgg tttgtttgcc ggatcaagag ctaccaactc ttttccgaa    9120
ggtaactggc ttcagcagag cgcagatacc aaatactgtt cttctagtgt agccgtagtt    9180
aggccaccac ttcaagaact ctgtagcacc gcctacatac ctcgctctgc taatcctgtt    9240
accagtggct gctgccagtg gcgataagtc gtgtcttacc gggttggact caagacgata    9300
gttaccggat aaggcgcagc ggtcgggctg aacggggggt tcgtgcacac agcccagctt    9360
ggagcgaacg acctacaccg aactgagata cctacagcgt gagctatgag aaagcgccac    9420
gcttcccgaa gagagaaagg cggacaggta tccggtaagc ggcagggtcg gaacaggaga    9480
gcgcacgagg gagcttccag ggggaaacgc ctggtatctt tatagtcctg tcgggtttcg    9540
ccacctctga cttgagcgtc gatttttgtg atgctcgtca gggggggcgga gcctatggaa    9600
aaacgccagc aacgcggcct ttttacggtt cctggccttt tgctggcctt ttgctcacat    9660
gttctttcct gcgttatccc ctgattctgt ggataaccgt attaccgcct ttgagtgagc    9720
tgataccgct cgccgcagcc gaacgaccga gcgcagcgag tcagtgagcg aggaagcgga    9780
agagcgccca atacgcaaac cgcctctccc cgcgcgttgg ccgattcatt aatgcagctg    9840
gcacgacagg tttcccgact ggaaagcggg cagtgagcgc aacgcaatta atgtgagtta    9900
gctcactcat taggcacccc aggctttaca ctttatgctt ccggctcgta tgttgtgtgg    9960
aattgtgagc ggataacaat ttcacacagg aaacagctat gaccatgatt acgccaagcg   10020
cgcaattaac cctcactaaa gggaacaaaa gctggagctg caagctt                 10067
```

<210> SEQ ID NO 54
<211> LENGTH: 24
<212> TYPE: PRT
<213> ORGANISM: Artificial Sequence
<220> FEATURE:
<223> OTHER INFORMATION: L1 light chain leader

<400> SEQUENCE: 54

Met Ala Thr Asp Met Arg Val Pro Ala Gln Leu Leu Gly Leu Leu Leu
1               5                   10                  15

Leu Trp Leu Ser Gly Ala Arg Cys
            20

<210> SEQ ID NO 55
<211> LENGTH: 118
<212> TYPE: PRT
<213> ORGANISM: Artificial Sequence
<220> FEATURE:
<223> OTHER INFORMATION: anti-biotin murine vH with inserted Cys for
      inter-domain linkage

<400> SEQUENCE: 55

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asp Trp Val Arg Gln Pro Pro Gly Lys Cys Leu Glu Trp Leu
            35                  40                  45

Gly Val Ile Trp Gly Gly Arg Thr Asn Tyr Asn Ser Leu Met
50                  55                  60

Ser Arg Leu Ser Ile Arg Lys Asp Asn Ser Lys Ser Gln Val Phe Leu
65              70                  75                  80

Thr Met Asn Ser Leu Gln Thr Asp Thr Ala Lys Tyr Tyr Cys Val
                85                  90                  95

Lys His Thr Asn Trp Asp Gly Phe Ala Tyr Trp Gly Gln Gly Thr
                100                 105                 110

Thr Val Thr Val Ser Ser
        115

<210> SEQ ID NO 56
<211> LENGTH: 15
<212> TYPE: PRT
<213> ORGANISM: Artificial Sequence
<220> FEATURE:
<223> OTHER INFORMATION: linker

<400> SEQUENCE: 56

Gly Gly Gly Gly Ser Gly Gly Gly Ser Gly Gly Gly Gly Ser
1               5                   10                  15

<210> SEQ ID NO 57
<211> LENGTH: 99
<212> TYPE: PRT
<213> ORGANISM: Artificial Sequence
<220> FEATURE:
<223> OTHER INFORMATION: Light Chain Variable (human lambda variable)

<400> SEQUENCE: 57

Gly Ser Pro Gly Gln Ser Val Ser Ile Ser Cys Ser Gly Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
            35                  40                  45

Pro Asp Arg Ile Ser Gly Ser Lys Ser Gly Thr Ser Ala Ser Leu Ala
50                  55                  60

Ile Ser Gly Leu Gln Ser Glu Asp Glu Ala Asp Tyr Tyr Cys Ala Ser
65              70                  75                  80

Trp Asp Asp Ser Leu Asp Gly Pro Val Phe Gly Cys Gly Thr Lys Leu
                85                  90                  95

Thr Val Leu

<210> SEQ ID NO 58
<211> LENGTH: 61
<212> TYPE: PRT
<213> ORGANISM: Artificial Sequence
<220> FEATURE:
<223> OTHER INFORMATION: IgG3 hinge for greater accessibility to FcγR

<400> SEQUENCE: 58

Leu Lys Thr Pro Leu Gly Asp Thr Thr His Thr Cys Pro Arg Cys Pro

```
                1               5                  10                 15
            Glu Pro Lys Ser Cys Asp Thr Pro Pro Cys Pro Arg Cys Pro Glu
                         20                  25                 30

Pro Lys Ser Cys Asp Thr Pro Pro Cys Pro Arg Cys Pro Glu Pro
                         35                  40                 45

Lys Ser Cys Asp Thr Pro Pro Cys Pro Arg Cys Pro
                 50                  55                 60

<210> SEQ ID NO 59
<211> LENGTH: 283
<212> TYPE: PRT
<213> ORGANISM: Artificial Sequence
<220> FEATURE:
<223> OTHER INFORMATION: IgG1 CH2, CH3 Tm and cytoplasmic tail (T256A)

<400> SEQUENCE: 59

Leu Leu Gly Gly Pro Ser Val Phe Leu Phe Pro Pro Lys Pro Lys Asp
1               5                   10                  15

Thr Leu Met Ile Ser Arg Ala Pro Glu Val Thr Cys Val Val Val Asp
            20                  25                  30

Val Ser His Glu Asp Pro Glu Val Lys Phe Asn Trp Tyr Val Asp Gly
        35                  40                  45

Val Glu Val His Asn Ala Lys Thr Lys Pro Arg Glu Glu Gln Tyr Asn
    50                  55                  60

Ser Thr Tyr Arg Val Val Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys Gly Gln Pro Arg Glu
            100                 105                 110

Pro Gln Val Tyr Thr Leu Pro Pro Ser Arg Asp Glu Leu Thr Lys Asn
        115                 120                 125

Gln Val Ser Leu Thr Cys Leu Val Lys Gly Phe Tyr Pro Ser Asp Ile
    130                 135                 140

Ala Val Glu Trp Glu Ser Asn Gly Gln Pro Glu Asn Asn Tyr Lys Thr
145                 150                 155                 160

Thr Pro Pro Val Leu Asp Ser Asp Gly Ser Phe Phe Leu Tyr Ser Lys
                165                 170                 175

Leu Thr Val Asp Lys Ser Arg Trp Gln Gln Gly Asn Val Phe Ser Cys
            180                 185                 190

Ser Val Met His Glu Ala Leu His Asn His Tyr Thr Gln Lys Ser Leu
        195                 200                 205

Ser Leu Ser Pro Glu Leu Gln Leu Glu Glu Ser Cys Ala Glu Ala Gln
    210                 215                 220

Asp Gly Glu Leu Asp Gly Leu Trp Thr Thr Ile Thr Ile Phe Ile Thr
225                 230                 235                 240

Leu Phe Leu Leu Ser Val Cys Tyr Ser Ala Thr Val Thr Phe Phe Lys
                245                 250                 255

Val Lys Trp Ile Phe Ser Ser Val Val Asp Leu Lys Gln Thr Ile Ile
            260                 265                 270

Pro Asp Tyr Arg Asn Met Ile Gly Gln Gly Ala
        275                 280

<210> SEQ ID NO 60
<211> LENGTH: 598
<212> TYPE: PRT
```

<213> ORGANISM: Artificial Sequence
<220> FEATURE:
<223> OTHER INFORMATION: scFv-anti-biotin-G3hinge-IgG1-Tm (598 ORF1)

<400> SEQUENCE: 60

```
Met Glu Phe Gly Leu Ser Trp Val Phe Leu Val Ala Leu Phe Arg Gly
1               5                   10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Cys Leu
    50                  55                  60

Glu Trp Leu Gly Val Ile Trp Gly Gly Gly Arg Thr Asn Tyr Asn Ser
65                  70                  75                  80

Gly Leu Met Ser Arg Leu Ser Ile Arg Lys Asp Asn Ser Lys Ser Gln
                85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Gly Phe Ala Tyr Trp Gly
        115                 120                 125

Gln Gly Thr Thr Val Thr Val Ser Ser Gly Gly Gly Ser Gly Gly
    130                 135                 140

Gly Gly Ser Gly Gly Gly Ser Gly Ser Pro Gly Gln Ser Val Ser
145                 150                 155                 160

Ile Ser Cys Ser Gly Ser Ser Asn Ile Gly Asn Asn Tyr Val Tyr
        165                 170                 175

Trp Tyr Gln His Leu Pro Gly Thr Ala Pro Lys Leu Leu Ile Tyr Ser
            180                 185                 190

Asp Thr Lys Arg Pro Ser Gly Val Pro Asp Arg Ile Ser Gly Ser Lys
        195                 200                 205

Ser Gly Thr Ser Ala Ser Leu Ala Ile Ser Gly Leu Gln Ser Glu Asp
    210                 215                 220

Glu Ala Asp Tyr Tyr Cys Ala Ser Trp Asp Asp Ser Leu Asp Gly Pro
225                 230                 235                 240

Val Phe Gly Cys Gly Thr Lys Leu Thr Val Leu Leu Lys Thr Pro Leu
            245                 250                 255

Gly Asp Thr Thr His Thr Cys Pro Arg Cys Pro Glu Pro Lys Ser Cys
        260                 265                 270

Asp Thr Pro Pro Pro Cys Pro Arg Cys Pro Glu Pro Lys Ser Cys Asp
    275                 280                 285

Thr Pro Pro Pro Cys Pro Arg Cys Pro Glu Pro Lys Ser Cys Asp Thr
290                 295                 300

Pro Pro Pro Cys Pro Arg Cys Pro Ala Pro Glu Leu Leu Gly Gly Pro
            305                 310                 315                 320

Ser Val Phe Leu Phe Pro Pro Lys Pro Lys Asp Thr Leu Met Ile Ser
                325                 330                 335

Arg Ala Pro Glu Val Thr Cys Val Val Val Asp Val Ser His Glu Asp
            340                 345                 350

Pro Glu Val Lys Phe Asn Trp Tyr Val Asp Gly Val Glu Val His Asn
        355                 360                 365

Ala Lys Thr Lys Pro Arg Glu Glu Gln Tyr Asn Ser Thr Tyr Arg Val
    370                 375                 380

Val Ser Val Leu Thr Val Leu His Gln Asp Trp Leu Asn Gly Lys Glu
```

```
                385                 390                 395                 400
        Tyr Lys Cys Lys Val Ser Asn Lys Ala Leu Pro Ala Pro Ile Glu Lys
                        405                 410                 415

Thr Ile Ser Lys Ala Lys Gly Gln Pro Arg Glu Pro Gln Val Tyr Thr
                        420                 425                 430

Leu Pro Pro Ser Arg Asp Glu Leu Thr Lys Asn Gln Val Ser Leu Thr
                        435                 440                 445

Cys Leu Val Lys Gly Phe Tyr Pro Ser Asp Ile Ala Val Glu Trp Glu
                        450                 455                 460

Ser Asn Gly Gln Pro Glu Asn Asn Tyr Lys Thr Thr Pro Pro Val Leu
        465                 470                 475                 480

Asp Ser Asp Gly Ser Phe Phe Leu Tyr Ser Lys Leu Thr Val Asp Lys
                        485                 490                 495

Ser Arg Trp Gln Gln Gly Asn Val Phe Ser Cys Ser Val Met His Glu
                        500                 505                 510

Ala Leu His Asn His Tyr Thr Gln Lys Ser Leu Ser Leu Ser Pro Glu
                        515                 520                 525

Leu Gln Leu Glu Glu Ser Cys Ala Glu Ala Gln Asp Gly Glu Leu Asp
                        530                 535                 540

Gly Leu Trp Thr Thr Ile Thr Ile Phe Ile Thr Leu Phe Leu Leu Ser
        545                 550                 555                 560

Val Cys Tyr Ser Ala Thr Val Thr Phe Phe Lys Val Lys Trp Ile Phe
                        565                 570                 575

Ser Ser Val Val Asp Leu Lys Gln Thr Ile Ile Pro Asp Tyr Arg Asn
                        580                 585                 590

Met Ile Gly Gln Gly Ala
                        595

<210> SEQ ID NO 61
<211> LENGTH: 19
<212> TYPE: PRT
<213> ORGANISM: Artificial Sequence
<220> FEATURE:
<223> OTHER INFORMATION: H7 heavy chain leader

<400> SEQUENCE: 61

Met Glu Phe Gly Leu Ser Trp Val Phe Leu Val Ala Leu Phe Arg Gly
1               5                   10                  15

Val Gln Cys

<210> SEQ ID NO 62
<211> LENGTH: 118
<212> TYPE: PRT
<213> ORGANISM: Artificial Sequence
<220> FEATURE:
<223> OTHER INFORMATION: anti-biotin vH

<400> SEQUENCE: 62

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
                20                  25                  30

Gly Val Asp Trp Val Arg Gln Pro Pro Gly Lys Gly Leu Glu Trp Leu
                35                  40                  45

Gly Val Ile Trp Gly Gly Gly Arg Thr Asn Tyr Asn Ser Gly Leu Met
                50                  55                  60

Ser Arg Leu Ser Ile Arg Lys Asp Asn Ser Lys Ser Gln Val Phe Leu
```

```
                65                  70                  75                  80
Thr Met Asn Ser Leu Gln Thr Asp Asp Thr Ala Lys Tyr Tyr Cys Val
                    85                  90                  95

Lys His Thr Asn Trp Asp Gly Gly Phe Ala Tyr Trp Gly Gln Gly Thr
                100                 105                 110

Thr Val Thr Val Ser Ser
            115

<210> SEQ ID NO 63
<211> LENGTH: 94
<212> TYPE: PRT
<213> ORGANISM: Artificial Sequence
<220> FEATURE:
<223> OTHER INFORMATION: CH1

<400> SEQUENCE: 63

Pro Ser Val Phe Pro Leu Ala Pro Ser Ser Lys Ser Thr Ser Gly Gly
1               5                   10                  15

Thr Ala Ala Leu Gly Cys Leu Val Lys Asp Tyr Phe Pro Glu Pro Val
            20                  25                  30

Thr Val Ser Trp Asn Ser Gly Ala Leu Thr Ser Gly Val His Thr Phe
        35                  40                  45

Pro Ala Val Leu Gln Ser Ser Gly Leu Tyr Ser Leu Ser Ser Val Val
    50                  55                  60

Thr Val Pro Ser Ser Ser Leu Gly Thr Gln Thr Tyr Ile Cys Asn Val
65                  70                  75                  80

Asn His Lys Pro Ser Asn Thr Lys Val Asp Lys Lys Val Glu
                85                  90

<210> SEQ ID NO 64
<211> LENGTH: 61
<212> TYPE: PRT
<213> ORGANISM: Artificial Sequence
<220> FEATURE:
<223> OTHER INFORMATION: IgG3 hinge

<400> SEQUENCE: 64

Leu Lys Thr Pro Leu Gly Asp Thr Thr His Thr Cys Pro Arg Cys Pro
1               5                   10                  15

Glu Pro Lys Ser Cys Asp Thr Pro Pro Cys Pro Arg Cys Pro Glu
            20                  25                  30

Pro Lys Ser Cys Asp Thr Pro Pro Cys Pro Arg Cys Pro Glu Pro
        35                  40                  45

Lys Ser Cys Asp Thr Pro Pro Cys Pro Arg Cys Pro
    50                  55                  60

<210> SEQ ID NO 65
<211> LENGTH: 286
<212> TYPE: PRT
<213> ORGANISM: Artificial Sequence
<220> FEATURE:
<223> OTHER INFORMATION: IgG1 CH2, CH3 Tm and cytoplasmic tail

<400> SEQUENCE: 65

Ala Pro Glu Leu Leu Gly Gly Pro Ser Val Phe Leu Phe Pro Pro Lys
1               5                   10                  15

Pro Lys Asp Thr Leu Met Ile Ser Arg Ala Pro Glu Val Thr Cys Val
            20                  25                  30

Val Val Asp Val Ser His Glu Asp Pro Glu Val Lys Phe Asn Trp Tyr
        35                  40                  45
```

Val Asp Gly Val Glu Val His Asn Ala Lys Thr Lys Pro Arg Glu Glu
         50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Glu Leu Gln Leu Glu Glu Ser Cys Ala
    210                 215                 220

Glu Ala Gln Asp Gly Glu Leu Asp Gly Leu Trp Thr Thr Ile Thr Ile
225                 230                 235                 240

Phe Ile Thr Leu Phe Leu Leu Ser Val Cys Tyr Ser Ala Thr Val Thr
                245                 250                 255

Phe Phe Lys Val Lys Trp Ile Phe Ser Ser Val Val Asp Leu Lys Gln
            260                 265                 270

Thr Ile Ile Pro Asp Tyr Arg Asn Met Ile Gly Gln Gly Ala
        275                 280                 285

<210> SEQ ID NO 66
<211> LENGTH: 578
<212> TYPE: PRT
<213> ORGANISM: Artificial Sequence
<220> FEATURE:
<223> OTHER INFORMATION: Summary (578 ORF2a)

<400> SEQUENCE: 66

Met Glu Phe Gly Leu Ser Trp Val Phe Leu Val Ala Leu Phe Arg Gly
 1               5                  10                  15

Val Gln Cys Gln Val Lys Leu Gln Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Ala Tyr Gly Val Asp Trp Val Arg Gln Pro Pro Gly Lys Gly Leu
    50                  55                  60

Glu Trp Leu Gly Val Ile Trp Gly Gly Gly Arg Thr Asn Tyr Asn Ser
 65                  70                  75                  80

Gly Leu Met Ser Arg Leu Ser Ile Arg Lys Asp Asn Ser Lys Ser Gln
                 85                  90                  95

Val Phe Leu Thr Met Asn Ser Leu Gln Thr Asp Asp Thr Ala Lys Tyr
            100                 105                 110

Tyr Cys Val Lys His Thr Asn Trp Asp Gly Gly Phe Ala Tyr Trp Gly
        115                 120                 125

```
Gln Gly Thr Thr Val Thr Val Ser Ser Pro Ser Val Phe Pro Leu Ala
    130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
210                 215                 220
Lys Val Asp Lys Lys Val Glu Leu Lys Thr Pro Leu Gly Asp Thr Thr
225                 230                 235                 240
His Thr Cys Pro Arg Cys Pro Glu Pro Lys Ser Cys Asp Thr Pro Pro
                245                 250                 255
Pro Cys Pro Arg Cys Pro Glu Pro Lys Ser Cys Asp Thr Pro Pro Pro
            260                 265                 270
Cys Pro Arg Cys Pro Glu Pro Lys Ser Cys Asp Thr Pro Pro Pro Cys
        275                 280                 285
Pro Arg Cys Pro Ala Pro Glu Leu Leu Gly Gly Pro Ser Val Phe Leu
290                 295                 300
Phe Pro Pro Lys Pro Lys Asp Thr Leu Met Ile Ser Arg Ala Pro Glu
305                 310                 315                 320
Val Thr Cys Val Val Val Asp Val Ser His Glu Asp Pro Glu Val Lys
                325                 330                 335
Phe Asn Trp Tyr Val Asp Gly Val Glu Val His Asn Ala Lys Thr Lys
            340                 345                 350
Pro Arg Glu Glu Gln Tyr Asn Ser Thr Tyr Arg Val Val Ser Val Leu
        355                 360                 365
Thr Val Leu His Gln Asp Trp Leu Asn Gly Lys Glu Tyr Lys Cys Lys
370                 375                 380
Val Ser Asn Lys Ala Leu Pro Ala Pro Ile Glu Lys Thr Ile Ser Lys
385                 390                 395                 400
Ala Lys Gly Gln Pro Arg Glu Pro Gln Val Tyr Thr Leu Pro Pro Ser
                405                 410                 415
Arg Asp Glu Leu Thr Lys Asn Gln Val Ser Leu Thr Cys Leu Val Lys
            420                 425                 430
Gly Phe Tyr Pro Ser Asp Ile Ala Val Glu Trp Glu Ser Asn Gly Gln
        435                 440                 445
Pro Glu Asn Asn Tyr Lys Thr Thr Pro Pro Val Leu Asp Ser Asp Gly
450                 455                 460
Ser Phe Phe Leu Tyr Ser Lys Leu Thr Val Asp Lys Ser Arg Trp Gln
465                 470                 475                 480
Gln Gly Asn Val Phe Ser Cys Ser Val Met His Glu Ala Leu His Asn
                485                 490                 495
His Tyr Thr Gln Lys Ser Leu Ser Leu Ser Pro Glu Leu Gln Leu Glu
            500                 505                 510
Glu Ser Cys Ala Glu Ala Gln Asp Gly Glu Leu Asp Gly Leu Trp Thr
        515                 520                 525
Thr Ile Thr Ile Phe Ile Thr Leu Phe Leu Leu Ser Val Cys Tyr Ser
530                 535                 540
```

-continued

```
Ala Thr Val Thr Phe Phe Lys Val Lys Trp Ile Phe Ser Ser Val Val
545                 550                 555                 560

Asp Leu Lys Gln Thr Ile Ile Pro Asp Tyr Arg Asn Met Ile Gly Gln
                565                 570                 575

Gly Ala

<210> SEQ ID NO 67
<211> LENGTH: 4
<212> TYPE: PRT
<213> ORGANISM: Artificial Sequence
<220> FEATURE:
<223> OTHER INFORMATION: Synthetic

<400> SEQUENCE: 67

Ile Arg Glu Ser
1

<210> SEQ ID NO 68
<211> LENGTH: 24
<212> TYPE: PRT
<213> ORGANISM: Artificial Sequence
<220> FEATURE:
<223> OTHER INFORMATION: L1 Signal

<400> SEQUENCE: 68

Met Ala Thr Asp Met Arg Val Pro Ala Gln Leu Leu Gly Leu Leu Leu
1               5                   10                  15

Leu Trp Leu Ser Gly Ala Arg Cys
            20

<210> SEQ ID NO 69
<211> LENGTH: 99
<212> TYPE: PRT
<213> ORGANISM: Artificial Sequence
<220> FEATURE:
<223> OTHER INFORMATION: LC Variable

<400> SEQUENCE: 69

Gly Ser Pro Gly Gln Ser Val Ser Ile Ser Cys Ser Gly Ser Ser Ser
1               5                   10                  15

Asn Ile Gly Asn Asn Tyr Val Tyr Trp Tyr Gln His Leu Pro Gly Thr
                20                  25                  30

Ala Pro Lys Leu Leu Ile Tyr Ser Asp Thr Lys Arg Pro Ser Gly Val
            35                  40                  45

Pro Asp Arg Ile Ser Gly Ser Lys Ser Gly Thr Ser Ala Ser Leu Ala
        50                  55                  60

Ile Ser Gly Leu Gln Ser Glu Asp Glu Ala Asp Tyr Tyr Cys Ala Ser
65                  70                  75                  80

Trp Asp Asp Ser Leu Asp Gly Pro Val Phe Gly Gly Gly Thr Lys Leu
                85                  90                  95

Thr Val Leu

<210> SEQ ID NO 70
<211> LENGTH: 106
<212> TYPE: PRT
<213> ORGANISM: Artificial Sequence
<220> FEATURE:
<223> OTHER INFORMATION: LC Constant Region 1

<400> SEQUENCE: 70

Gly Gln Pro Lys Ala Asn Pro Thr Val Thr Leu Phe Pro Pro Ser Ser
1               5                   10                  15
```

```
Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                    85                  90                  95

Glu Lys Thr Val Ala Pro Thr Glu Cys Ser
            100                 105

<210> SEQ ID NO 71
<211> LENGTH: 229
<212> TYPE: PRT
<213> ORGANISM: Artificial Sequence
<220> FEATURE:
<223> OTHER INFORMATION: Summary (229 ORF2b)

<400> SEQUENCE: 71

Met Ala Thr Asp Met Arg Val Pro Ala Gln Leu Leu Gly Leu Leu Leu
 1               5                  10                  15

Leu Trp Leu Ser Gly Ala Arg Cys Gly Ser Pro Gly Gln Ser Val Ser
            20                  25                  30

Ile Ser Cys Ser Gly Ser Ser Ser Asn Ile Gly Asn Asn Tyr Val Tyr
        35                  40                  45

Trp Tyr Gln His Leu Pro Gly Thr Ala Pro Lys Leu Leu Ile Tyr Ser
 50                  55                  60

Asp Thr Lys Arg Pro Ser Gly Val Pro Asp Arg Ile Ser Gly Ser Lys
 65                  70                  75                  80

Ser Gly Thr Ser Ala Ser Leu Ala Ile Ser Gly Leu Gln Ser Glu Asp
                    85                  90                  95

Glu Ala Asp Tyr Tyr Cys Ala Ser Trp Asp Asp Ser Leu Asp Gly Pro
            100                 105                 110

Val Phe Gly Gly Gly Thr Lys Leu Thr Val Leu Gly Gln Pro Lys Ala
        115                 120                 125

Asn Pro Thr Val Thr Leu Phe Pro Pro Ser Ser Glu Glu Leu Gln Ala
 130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Gly Ser Pro Val Lys Ala Gly Val
                    165                 170                 175

Glu Thr Thr Lys Pro Ser Lys Gln Ser Asn Asn Lys Tyr Ala Ala Ser
            180                 185                 190

Ser Tyr Leu Ser Leu Thr Pro Glu Gln Trp Lys Ser His Arg Ser Tyr
        195                 200                 205

Ser Cys Gln Val Thr His Glu Gly Ser Thr Val Glu Lys Thr Val Ala
 210                 215                 220

Pro Thr Glu Cys Ser
225

<210> SEQ ID NO 72
<211> LENGTH: 17
<212> TYPE: PRT
<213> ORGANISM: Artificial Sequence
```

```
<220> FEATURE:
<223> OTHER INFORMATION: GM-CSF signal sequence

<400> SEQUENCE: 72

Met Trp Leu Gln Ser Leu Leu Leu Leu Gly Thr Val Ala Cys Ser Ile
1               5                   10                  15

Ser

<210> SEQ ID NO 73
<211> LENGTH: 127
<212> TYPE: PRT
<213> ORGANISM: Artificial Sequence
<220> FEATURE:
<223> OTHER INFORMATION: wild type GM-CSF sequence

<400> SEQUENCE: 73

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 74
<211> LENGTH: 4
<212> TYPE: PRT
<213> ORGANISM: Artificial Sequence
<220> FEATURE:
<223> OTHER INFORMATION: Synthetic

<400> SEQUENCE: 74

Ile Arg Glu Ser
1

<210> SEQ ID NO 75
<211> LENGTH: 26
<212> TYPE: PRT
<213> ORGANISM: Artificial Sequence
<220> FEATURE:
<223> OTHER INFORMATION: FLT3L signal

<400> SEQUENCE: 75

Met Ala Thr Val Leu Ala Pro Ala Trp Ser Pro Thr Thr Tyr Leu Leu
1               5                   10                  15

Leu Leu Leu Leu Leu Ser Ser Gly Leu Ser
            20                  25

<210> SEQ ID NO 76
<211> LENGTH: 210
<212> TYPE: PRT
<213> ORGANISM: Artificial Sequence
<220> FEATURE:
```

<223> OTHER INFORMATION: FLT3L

<400> SEQUENCE: 76

```
Gly Thr Gln Asp Cys Ser Phe Gln His Ser Pro Ile Ser Ser Asp Phe
1               5                   10                  15

Ala Val Lys Ile Arg Glu Leu Ser Asp Tyr Leu Leu Gln Asp Tyr Pro
            20                  25                  30

Val Thr Val Ala Ser Asn Leu Gln Asp Glu Glu Leu Cys Gly Gly Leu
        35                  40                  45

Trp Arg Leu Val Leu Ala Gln Arg Trp Met Glu Arg Leu Lys Thr Val
50                  55                  60

Ala Gly Ser Lys Met Gln Gly Leu Leu Glu Arg Val Asn Thr Glu Ile
65                  70                  75                  80

His Phe Val Thr Lys Cys Ala Phe Gln Pro Pro Pro Ser Cys Leu Arg
                85                  90                  95

Phe Val Gln Thr Asn Ile Ser Arg Leu Leu Gln Glu Thr Ser Glu Gln
            100                 105                 110

Leu Val Ala Leu Lys Pro Trp Ile Thr Arg Gln Asn Phe Ser Arg Cys
        115                 120                 125

Leu Glu Leu Gln Cys Gln Pro Asp Ser Ser Thr Leu Pro Pro Pro Trp
130                 135                 140

Ser Pro Arg Pro Leu Glu Ala Thr Ala Pro Thr Ala Pro Gln Pro Pro
145                 150                 155                 160

Leu Leu Leu Leu Leu Leu Pro Val Gly Leu Leu Leu Leu Ala Ala
                165                 170                 175

Ala Trp Cys Leu His Trp Gln Arg Thr Arg Arg Arg Thr Pro Arg Pro
            180                 185                 190

Gly Glu Gln Val Pro Pro Val Pro Ser Pro Gln Asp Leu Leu Leu Val
            195                 200                 205

Glu His
    210
```

<210> SEQ ID NO 77
<211> LENGTH: 144
<212> TYPE: PRT
<213> ORGANISM: Artificial Sequence
<220> FEATURE:
<223> OTHER INFORMATION: Summary (144 ORF3a)

<400> SEQUENCE: 77

```
Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125
```

Asp Phe Leu Leu Val Ile Pro Phe Asp Cys Trp Glu Pro Val Gln Glu
130                 135                 140

<210> SEQ ID NO 78
<211> LENGTH: 236
<212> TYPE: PRT
<213> ORGANISM: Artificial Sequence
<220> FEATURE:
<223> OTHER INFORMATION: Summary (236 ORF3b)

<400> SEQUENCE: 78

Met Ala Thr Val Leu Ala Pro Ala Trp Ser Pro Thr Thr Tyr Leu Leu
1               5                   10                  15

Leu Leu Leu Leu Leu Ser Ser Gly Leu Ser Gly Thr Gln Asp Cys Ser
                20                  25                  30

Phe Gln His Ser Pro Ile Ser Ser Asp Phe Ala Val Lys Ile Arg Glu
            35                  40                  45

Leu Ser Asp Tyr Leu Leu Gln Asp Tyr Pro Val Thr Val Ala Ser Asn
50                  55                  60

Leu Gln Asp Glu Glu Leu Cys Gly Gly Leu Trp Arg Leu Val Leu Ala
65                  70                  75                  80

Gln Arg Trp Met Glu Arg Leu Lys Thr Val Ala Gly Ser Lys Met Gln
                85                  90                  95

Gly Leu Leu Glu Arg Val Asn Thr Glu Ile His Phe Val Thr Lys Cys
            100                 105                 110

Ala Phe Gln Pro Pro Pro Ser Cys Leu Arg Phe Val Gln Thr Asn Ile
            115                 120                 125

Ser Arg Leu Leu Gln Glu Thr Ser Glu Gln Leu Val Ala Leu Lys Pro
130                 135                 140

Trp Ile Thr Arg Gln Asn Phe Ser Arg Cys Leu Glu Leu Gln Cys Gln
145                 150                 155                 160

Pro Asp Ser Ser Thr Leu Pro Pro Trp Ser Pro Arg Pro Leu Glu
                165                 170                 175

Ala Thr Ala Pro Thr Ala Pro Gln Pro Pro Leu Leu Leu Leu Leu Leu
            180                 185                 190

Leu Pro Val Gly Leu Leu Leu Ala Ala Ala Trp Cys Leu His Trp
            195                 200                 205

Gln Arg Thr Arg Arg Arg Thr Pro Arg Pro Gly Glu Gln Val Pro Pro
            210                 215                 220

Val Pro Ser Pro Gln Asp Leu Leu Leu Val Glu His
225                 230                 235

<210> SEQ ID NO 79
<211> LENGTH: 183
<212> TYPE: PRT
<213> ORGANISM: Artificial Sequence
<220> FEATURE:
<223> OTHER INFORMATION: wild type FLT3L sequence with transmembrane
      deleted

<400> SEQUENCE: 79

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

-continued

```
Ser Asp Tyr Leu Leu Gln Asp Tyr Pro Val Thr Val Ala Ser Asn Leu
    50              55                  60

Gln Asp Glu Glu Leu Cys Gly Gly Leu Trp Arg Leu Val Leu Ala Gln
65              70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
130             135                 140

Ile Thr Arg Gln Asn Phe Ser Arg Cys Leu Glu Leu Gln Cys Gln Pro
145             150                 155                 160

Asp Ser Ser Thr Leu Pro Pro Pro Trp Ser Pro Arg Pro Leu Glu Ala
            165                 170                 175

Thr Ala Pro Thr Ala Pro Gln
            180
```

<210> SEQ ID NO 80
<211> LENGTH: 4
<212> TYPE: PRT
<213> ORGANISM: Artificial Sequence
<220> FEATURE:
<223> OTHER INFORMATION: Synthetic

<400> SEQUENCE: 80

```
Ile Arg Glu Ser
1
```

<210> SEQ ID NO 81
<211> LENGTH: 26
<212> TYPE: PRT
<213> ORGANISM: Artificial Sequence
<220> FEATURE:
<223> OTHER INFORMATION: FLT3L signal

<400> SEQUENCE: 81

```
Met Ala Thr Val Leu Ala Pro Ala Trp Ser Pro Thr Thr Tyr Leu Leu
1               5                   10                  15

Leu Leu Leu Leu Leu Ser Ser Gly Leu Ser
            20                  25
```

<210> SEQ ID NO 82
<211> LENGTH: 127
<212> TYPE: PRT
<213> ORGANISM: Artificial Sequence
<220> FEATURE:
<223> OTHER INFORMATION: wild type GM-CSF sequence

<400> SEQUENCE: 82

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
                35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
```

```
                65                  70                  75                  80
Ala Ser His Tyr Lys Gln His Cys Pro Pro Thr Pro Glu Thr Ser Cys
                    85                  90                  95

Ala Thr Gln Ile Ile Thr Phe Glu Ser Phe Lys Glu Asn Leu Lys Asp
                    100                 105                 110

Phe Leu Leu Val Ile Pro Phe Asp Cys Trp Glu Pro Val Gln Glu
                    115                 120                 125

<210> SEQ ID NO 83
<211> LENGTH: 99
<212> TYPE: PRT
<213> ORGANISM: Artificial Sequence
<220> FEATURE:
<223> OTHER INFORMATION: CD8alpha transmembrane and cytoplasmic domain

<400> SEQUENCE: 83

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
                20                  25                  30

Gly Gly Ala Val His Thr Arg Gly Leu Asp Phe Ala Cys Asp Ile Tyr
            35                  40                  45

Ile Trp Ala Pro Leu Ala Gly Thr Cys Gly Val Leu Leu Leu Ser Leu
50                  55                  60

Val Ile Thr Leu Tyr Cys Asn His Arg Asn Arg Arg Val Cys Lys
65                  70                  75                  80

Cys Pro Arg Pro Val Val Lys Ser Gly Asp Lys Pro Ser Leu Ser Ala
                85                  90                  95

Arg Tyr Val

<210> SEQ ID NO 84
<211> LENGTH: 183
<212> TYPE: PRT
<213> ORGANISM: Artificial Sequence
<220> FEATURE:
<223> OTHER INFORMATION: Summary (183 ORF4a)

<400> SEQUENCE: 84

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
                100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
```

145             150             155             160
Asp Ser Ser Thr Leu Pro Pro Pro Trp Ser Pro Arg Pro Leu Glu Ala
                165             170             175
Thr Ala Pro Thr Ala Pro Gln
        180

<210> SEQ ID NO 85
<211> LENGTH: 252
<212> TYPE: PRT
<213> ORGANISM: Artificial Sequence
<220> FEATURE:
<223> OTHER INFORMATION: Summary for CYAGEN (253 ORF4b)

<400> SEQUENCE: 85

Met Ala Thr Val Leu Ala Pro Ala Trp Ser Pro Thr Thr Tyr Leu Leu
1               5                   10                  15
Leu Leu Leu Leu Ser Ser Gly Leu Ser Ala Pro Ala Arg Ser Pro
            20                  25                  30
Ser Pro Ser Thr Gln Pro Trp Glu His Val Asn Ala Ile Gln Glu Ala
        35                  40                  45
Arg Arg Leu Leu Asn Leu Ser Arg Asp Thr Ala Ala Glu Met Asn Glu
    50                  55                  60
Thr Val Glu Val Ile Ser Glu Met Phe Asp Leu Gln Glu Pro Thr Cys
65                  70                  75                  80
Leu Gln Thr Arg Leu Glu Leu Tyr Lys Gln Gly Leu Arg Gly Ser Leu
                85                  90                  95
Thr Lys Leu Lys Gly Pro Leu Thr Met Met Ala Ser His Tyr Lys Gln
            100                 105                 110
His Cys Pro Pro Thr Pro Glu Thr Ser Cys Ala Thr Gln Ile Ile Thr
        115                 120                 125
Phe Glu Ser Phe Lys Glu Asn Leu Lys Asp Phe Leu Leu Val Ile Pro
    130                 135                 140
Phe Asp Cys Trp Glu Pro Val Gln Glu Pro Thr Thr Thr Pro Ala Pro
145                 150                 155                 160
Arg Pro Pro Thr Pro Ala Pro Thr Ile Ala Ser Gln Pro Leu Ser Leu
                165                 170                 175
Arg Pro Glu Ala Cys Arg Pro Ala Ala Gly Gly Ala Val His Thr Arg
            180                 185                 190
Gly Leu Asp Phe Ala Cys Asp Ile Tyr Ile Trp Ala Pro Leu Ala Gly
        195                 200                 205
Thr Cys Gly Val Leu Leu Leu Ser Leu Val Ile Thr Leu Tyr Cys Asn
    210                 215                 220
His Arg Asn Arg Arg Val Cys Lys Cys Pro Arg Pro Val Val Lys
225                 230                 235                 240
Ser Gly Asp Lys Pro Ser Leu Ser Ala Arg Tyr Val
                245                 250

<210> SEQ ID NO 86
<211> LENGTH: 261
<212> TYPE: PRT
<213> ORGANISM: Artificial Sequence
<220> FEATURE:
<223> OTHER INFORMATION: mCD40L modified to stop cleavage

<400> SEQUENCE: 86

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Pro Arg Gly Glu Glu Asp Ser Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
                145                 150                 155                 160

Leu Thr Val Lys Arg Gln Gly Leu Tyr Tyr Ile Tyr Ala Gln Val Thr
            165                 170                 175

Phe Cys Ser Asn Arg Glu Ala Ser Ser Gln Ala Pro Phe Ile Ala Ser
        180                 185                 190

Leu Cys Leu Lys Ser Pro Gly Arg Phe Glu Arg Ile Leu Leu Arg Ala
195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
            245                 250                 255

Gly Leu Leu Lys Leu
            260

<210> SEQ ID NO 87
<211> LENGTH: 261
<212> TYPE: PRT
<213> ORGANISM: Artificial Sequence
<220> FEATURE:
<223> OTHER INFORMATION: Summary (261 ORF5)

<400> SEQUENCE: 87

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

```
Met Pro Arg Gly Glu Glu Asp Ser Gln Ile Ala Ala His Val Ile Ser
            115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 88
<211> LENGTH: 221
<212> TYPE: PRT
<213> ORGANISM: Artificial Sequence
<220> FEATURE:
<223> OTHER INFORMATION: mTNFalpha modified to stop cleavage

<400> SEQUENCE: 88

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
        115                 120                 125

Lys Gly Gln Gly Cys Pro Ser Thr His Val Leu Leu Thr His Thr Ile
130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
            180                 185                 190

Gly Asp Arg Leu Ser Ala Glu Ile Asn Arg Pro Asp Tyr Leu Asp Phe
        195                 200                 205
```

-continued

```
Ala Glu Ser Gly Gln Val Tyr Phe Gly Ile Ile Ala Leu
    210                 215                 220
```

<210> SEQ ID NO 89
<211> LENGTH: 221
<212> TYPE: PRT
<213> ORGANISM: Artificial Sequence
<220> FEATURE:
<223> OTHER INFORMATION: Summary (221 ORF6)

<400> SEQUENCE: 89

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Ala His Val
65                  70                  75                  80

Val Ala Asn Pro Gln Ala Glu Gly Gln Leu Gln Trp Leu Asn Arg Arg
                85                  90                  95

Ala Asn Ala Leu Leu Ala Asn Gly Val Glu Leu Arg Asp Asn Gln Leu
            100                 105                 110

Val Val Pro Ser Glu Gly Leu Tyr Leu Ile Tyr Ser Gln Val Leu Phe
        115                 120                 125

Lys Gly Gln Gly Cys Pro Ser Thr His Val Leu Leu Thr His Thr Ile
    130                 135                 140

Ser Arg Ile Ala Val Ser Tyr Gln Thr Lys Val Asn Leu Leu Ser Ala
145                 150                 155                 160

Ile Lys Ser Pro Cys Gln Arg Glu Thr Pro Glu Gly Ala Glu Ala Lys
                165                 170                 175

Pro Trp Tyr Glu Pro Ile Tyr Leu Gly Gly Val Phe Gln Leu Glu Lys
            180                 185                 190

Gly Asp Arg Leu Ser Ala Glu Ile Asn Arg Pro Asp Tyr Leu Asp Phe
        195                 200                 205

Ala Glu Ser Gly Gln Val Tyr Phe Gly Ile Ile Ala Leu
    210                 215                 220
```

<210> SEQ ID NO 90
<211> LENGTH: 244
<212> TYPE: PRT
<213> ORGANISM: Artificial Sequence
<220> FEATURE:
<223> OTHER INFORMATION: wild-type

<400> SEQUENCE: 90

```
Met Asp Pro Asn Arg Ile Ser Glu Asp Gly Thr His Cys Ile Tyr Arg
1               5                   10                  15

Ile Leu Arg Leu His Glu Asn Ala Asp Phe Gln Asp Thr Thr Leu Glu
            20                  25                  30

Ser Gln Asp Thr Lys Leu Ile Pro Asp Ser Cys Arg Arg Ile Lys Gln
        35                  40                  45

Ala Phe Gln Gly Ala Val Gln Lys Glu Leu Gln His Ile Val Gly Ser
    50                  55                  60

Gln His Ile Arg Ala Glu Lys Ala Met Val Asp Gly Ser Trp Leu Asp
65                  70                  75                  80
```

-continued

```
Leu Ala Lys Arg Ser Lys Leu Glu Ala Gln Pro Phe Ala His Leu Thr
                85                  90                  95
Ile Asn Ala Thr Asp Ile Pro Ser Gly Ser His Lys Val Ser Leu Ser
            100                 105                 110
Ser Trp Tyr His Asp Arg Gly Trp Ala Lys Ile Ser Asn Met Thr Phe
        115                 120                 125
Ser Asn Gly Lys Leu Ile Val Asn Gln Asp Gly Phe Tyr Tyr Leu Tyr
    130                 135                 140
Ala Asn Ile Cys Phe Arg His His Glu Thr Ser Gly Asp Leu Ala Thr
145                 150                 155                 160
Glu Tyr Leu Gln Leu Met Val Tyr Val Thr Lys Thr Ser Ile Lys Ile
                165                 170                 175
Pro Ser Ser His Thr Leu Met Lys Gly Gly Ser Thr Lys Tyr Trp Ser
            180                 185                 190
Gly Asn Ser Glu Phe His Phe Tyr Ser Ile Asn Val Gly Gly Phe Phe
        195                 200                 205
Lys Leu Arg Ser Gly Glu Glu Ile Ser Ile Glu Val Ser Asn Pro Ser
    210                 215                 220
Leu Leu Asp Pro Asp Gln Asp Ala Thr Tyr Phe Gly Ala Phe Lys Val
225                 230                 235                 240
Arg Asp Ile Asp

<210> SEQ ID NO 91
<211> LENGTH: 4
<212> TYPE: PRT
<213> ORGANISM: Artificial Sequence
<220> FEATURE:
<223> OTHER INFORMATION: Synthetic

<400> SEQUENCE: 91

Ile Arg Glu Ser
1

<210> SEQ ID NO 92
<211> LENGTH: 26
<212> TYPE: PRT
<213> ORGANISM: Artificial Sequence
<220> FEATURE:
<223> OTHER INFORMATION: FLT3L signal

<400> SEQUENCE: 92

Met Ala Thr Val Leu Ala Pro Ala Trp Ser Pro Thr Thr Tyr Leu Leu
1               5                   10                  15
Leu Leu Leu Leu Leu Ser Ser Gly Leu Ser
            20                  25

<210> SEQ ID NO 93
<211> LENGTH: 5
<212> TYPE: PRT
<213> ORGANISM: Artificial Sequence
<220> FEATURE:
<223> OTHER INFORMATION: Linker

<400> SEQUENCE: 93

Gly Gly Gly Gly Ser
1               5

<210> SEQ ID NO 94
<211> LENGTH: 14
<212> TYPE: PRT
```

<213> ORGANISM: Artificial Sequence
<220> FEATURE:
<223> OTHER INFORMATION: V5 epitope tag for flow detection

<400> SEQUENCE: 94

Gly Lys Pro Ile Pro Asn Pro Leu Leu Gly Leu Asp Ser Thr
1               5                   10

<210> SEQ ID NO 95
<211> LENGTH: 118
<212> TYPE: PRT
<213> ORGANISM: Artificial Sequence
<220> FEATURE:
<223> OTHER INFORMATION: anti-biotin murine vH with inserted Cys for
      intralinkage

<400> SEQUENCE: 95

Gln Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Ala Tyr
            20                  25                  30

Gly Val Asp Trp Val Arg Gln Pro Pro Gly Lys Cys Leu Glu Trp Leu
        35                  40                  45

Gly Val Ile Trp Gly Gly Gly Arg Thr Asn Tyr Asn Ser Gly Leu Met
    50                  55                  60

Ser Arg Leu Ser Ile Arg Lys Asp Asn Ser Lys Ser Gln Val Phe Leu
65                  70                  75                  80

Thr Met Asn Ser Leu Gln Thr Asp Asp Thr Ala Lys Tyr Tyr Cys Val
                85                  90                  95

Lys His Thr Asn Trp Asp Gly Gly Phe Ala Tyr Trp Gly Gln Gly Thr
            100                 105                 110

Thr Val Thr Val Ser Ser
        115

<210> SEQ ID NO 96
<211> LENGTH: 15
<212> TYPE: PRT
<213> ORGANISM: Artificial Sequence
<220> FEATURE:
<223> OTHER INFORMATION: Linker

<400> SEQUENCE: 96

Gly Gly Gly Gly Ser Gly Gly Gly Gly Ser Gly Gly Gly Gly Ser
1               5                   10                  15

<210> SEQ ID NO 97
<211> LENGTH: 99
<212> TYPE: PRT
<213> ORGANISM: Artificial Sequence
<220> FEATURE:
<223> OTHER INFORMATION: LC Variable

<400> SEQUENCE: 97

Gly Ser Pro Gly Gln Ser Val Ser Ile Ser Cys Ser Gly Ser Ser Ser
1               5                   10                  15

Asn Ile Gly Asn Asn Tyr Val Tyr Trp Tyr Gln His Leu Pro Gly Thr
            20                  25                  30

Ala Pro Lys Leu Leu Ile Tyr Ser Asp Thr Lys Arg Pro Ser Gly Val
        35                  40                  45

Pro Asp Arg Ile Ser Gly Ser Lys Ser Gly Thr Ser Ala Ser Leu Ala
    50                  55                  60

Ile Ser Gly Leu Gln Ser Glu Asp Glu Ala Asp Tyr Tyr Cys Ala Ser
65                  70                  75                  80

Trp Asp Asp Ser Leu Asp Gly Pro Val Phe Gly Cys Gly Thr Lys Leu
                85                  90                  95

Thr Val Leu

<210> SEQ ID NO 98
<211> LENGTH: 99
<212> TYPE: PRT
<213> ORGANISM: Artificial Sequence
<220> FEATURE:
<223> OTHER INFORMATION: CD8alpha transmembrane and cytoplasmic domain

<400> SEQUENCE: 98

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
                20                  25                  30

Gly Gly Ala Val His Thr Arg Gly Leu Asp Phe Ala Cys Asp Ile Tyr
            35                  40                  45

Ile Trp Ala Pro Leu Ala Gly Thr Cys Gly Val Leu Leu Leu Ser Leu
50                  55                  60

Val Ile Thr Leu Tyr Cys Asn His Arg Asn Arg Arg Val Cys Lys
65                  70                  75                  80

Cys Pro Arg Pro Val Val Lys Ser Gly Asp Lys Pro Ser Leu Ser Ala
                85                  90                  95

Arg Tyr Val

<210> SEQ ID NO 99
<211> LENGTH: 244
<212> TYPE: PRT
<213> ORGANISM: Artificial Sequence
<220> FEATURE:
<223> OTHER INFORMATION: Summary (244 ORF7a)

<400> SEQUENCE: 99

Met Asp Pro Asn Arg Ile Ser Glu Asp Gly Thr His Cys Ile Tyr Arg
1               5                   10                  15

Ile Leu Arg Leu His Glu Asn Ala Asp Phe Gln Asp Thr Thr Leu Glu
                20                  25                  30

Ser Gln Asp Thr Lys Leu Ile Pro Asp Ser Cys Arg Arg Ile Lys Gln
            35                  40                  45

Ala Phe Gln Gly Ala Val Gln Lys Glu Leu Gln His Ile Val Gly Ser
50                  55                  60

Gln His Ile Arg Ala Glu Lys Ala Met Val Asp Gly Ser Trp Leu Asp
65                  70                  75                  80

Leu Ala Lys Arg Ser Lys Leu Glu Ala Gln Pro Phe Ala His Leu Thr
                85                  90                  95

Ile Asn Ala Thr Asp Ile Pro Ser Gly Ser His Lys Val Ser Leu Ser
            100                 105                 110

Ser Trp Tyr His Asp Arg Gly Trp Ala Lys Ile Ser Asn Met Thr Phe
        115                 120                 125

Ser Asn Gly Lys Leu Ile Val Asn Gln Asp Gly Phe Tyr Tyr Leu Tyr
    130                 135                 140

Ala Asn Ile Cys Phe Arg His His Glu Thr Ser Gly Asp Leu Ala Thr
145                 150                 155                 160

Glu Tyr Leu Gln Leu Met Val Tyr Val Thr Lys Thr Ser Ile Lys Ile

```
                165                 170                 175
Pro Ser Ser His Thr Leu Met Lys Gly Gly Ser Thr Lys Tyr Trp Ser
            180                 185                 190

Gly Asn Ser Glu Phe His Phe Tyr Ser Ile Asn Val Gly Gly Phe Phe
            195                 200                 205

Lys Leu Arg Ser Gly Glu Glu Ile Ser Ile Glu Val Ser Asn Pro Ser
            210                 215                 220

Leu Leu Asp Pro Asp Gln Asp Ala Thr Tyr Phe Gly Ala Phe Lys Val
225                 230                 235                 240

Arg Asp Ile Asp

<210> SEQ ID NO 100
<211> LENGTH: 381
<212> TYPE: PRT
<213> ORGANISM: Artificial Sequence
<220> FEATURE:
<223> OTHER INFORMATION: Summary  (381aa ORF7b)

<400> SEQUENCE: 100

Met Ala Thr Val Leu Ala Pro Ala Trp Ser Pro Thr Thr Tyr Leu Leu
1               5                   10                  15

Leu Leu Leu Leu Ser Ser Gly Leu Ser Gly Gly Gly Ser Gly
            20                  25                  30

Lys Pro Ile Pro Asn Pro Leu Leu Gly Leu Asp Ser Thr Gly Gly Gly
            35                  40                  45

Gly Ser Gln Val Lys Leu Gln Glu Ser Gly Pro Gly Leu Val Ala Pro
        50                  55                  60

Ser Gln Ser Leu Ser Ile Thr Cys Thr Val Ser Gly Phe Ser Leu Thr
65                  70                  75                  80

Ala Tyr Gly Val Asp Trp Val Arg Gln Pro Pro Gly Lys Cys Leu Glu
                85                  90                  95

Trp Leu Gly Val Ile Trp Gly Gly Gly Arg Thr Asn Tyr Asn Ser Gly
            100                 105                 110

Leu Met Ser Arg Leu Ser Ile Arg Lys Asp Asn Ser Lys Ser Gln Val
            115                 120                 125

Phe Leu Thr Met Asn Ser Leu Gln Thr Asp Asp Thr Ala Lys Tyr Tyr
        130                 135                 140

Cys Val Lys His Thr Asn Trp Asp Gly Gly Phe Ala Tyr Trp Gly Gln
145                 150                 155                 160

Gly Thr Thr Val Thr Val Ser Ser Gly Gly Gly Gly Ser Gly Gly Gly
                165                 170                 175

Gly Ser Gly Gly Gly Gly Ser Gly Ser Pro Gly Gln Ser Val Ser Ile
            180                 185                 190

Ser Cys Ser Gly Ser Ser Ser Asn Ile Gly Asn Asn Tyr Val Tyr Trp
            195                 200                 205

Tyr Gln His Leu Pro Gly Thr Ala Pro Lys Leu Leu Ile Tyr Ser Asp
        210                 215                 220

Thr Lys Arg Pro Ser Gly Val Pro Asp Arg Ile Ser Gly Ser Lys Ser
225                 230                 235                 240

Gly Thr Ser Ala Ser Leu Ala Ile Ser Gly Leu Gln Ser Glu Asp Glu
                245                 250                 255

Ala Asp Tyr Tyr Cys Ala Ser Trp Asp Asp Ser Leu Asp Gly Pro Val
            260                 265                 270

Phe Gly Cys Gly Thr Lys Leu Thr Val Leu Pro Thr Thr Thr Pro Ala
            275                 280                 285
```

```
Pro Arg Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
                340                 345                 350

Asn His Arg Asn Arg Arg Val Cys Lys Cys Pro Arg Pro Val Val
                355                 360                 365

Lys Ser Gly Asp Lys Pro Ser Leu Ser Ala Arg Tyr Val
    370                 375                 380

<210> SEQ ID NO 101
<211> LENGTH: 11
<212> TYPE: PRT
<213> ORGANISM: Artificial Sequence
<220> FEATURE:
<223> OTHER INFORMATION: Synthetic peptide

<400> SEQUENCE: 101

Gln Met Gln Gly Val Asn Cys Thr Val Ser Ser
1               5                   10

<210> SEQ ID NO 102
<211> LENGTH: 30
<212> TYPE: DNA
<213> ORGANISM: Artificial Sequence
<220> FEATURE:
<223> OTHER INFORMATION: CpG
<220> FEATURE:
<221> NAME/KEY: misc_feature
<222> LOCATION: (1)..(2)
<223> OTHER INFORMATION: n is a G-phosphorothioate
<220> FEATURE:
<221> NAME/KEY: misc_feature
<222> LOCATION: (25)..(29)
<223> OTHER INFORMATION: n is a G-phosphorothioate

<400> SEQUENCE: 102
nnaaccgtat cggcgatatc ggttnnnnng                                    30

<210> SEQ ID NO 103
<211> LENGTH: 30
<212> TYPE: DNA
<213> ORGANISM: Artificial Sequence
<220> FEATURE:
<223> OTHER INFORMATION: CpG
<220> FEATURE:
<221> NAME/KEY: misc_feature
<222> LOCATION: (1)..(2)
<223> OTHER INFORMATION: n is a G-phosphorothioate
<220> FEATURE:
<221> NAME/KEY: misc_feature
<222> LOCATION: (25)..(29)
<223> OTHER INFORMATION: n is a G-phosphorothioate

<400> SEQUENCE: 103
nnaaccgtat gcggcatatc ggttnnnnng                                    30

<210> SEQ ID NO 104
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 104

Val Arg Ser Ser Ser Arg Thr Pro Ser Asp Lys Pro
1               5                   10
```